US008263594B2

(12) United States Patent
Lindstrom et al.

(10) Patent No.: US 8,263,594 B2
(45) Date of Patent: *Sep. 11, 2012

(54) ARYLOXY AND ARYLALKYLENEOXY SUBSTITUTED IMIDAZOQUINOLINES

(75) Inventors: Kyle J. Lindstrom, Houlton, WI (US); Hugues M. H. Martin, Ingre (FR); Bryon A. Merrill, River Falls, WI (US); Michael J. Rice, Oakdale, MN (US); Joshua R. Wurst, North St. Paul, MN (US); Chad A. Haraldson, Apple Valley, MN (US); Philip D. Heppner, Forest Lake, MN (US); Shri Niwas, Maple Grove, MN (US); Matthew R. Radmer, Robbinsdale, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 12 days.

This patent is subject to a terminal disclaimer.

(21) Appl. No.: 13/008,453

(22) Filed: Jan. 18, 2011

(65) Prior Publication Data

US 2011/0144099 A1    Jun. 16, 2011

Related U.S. Application Data

(63) Continuation of application No. 10/595,103, filed as application No. PCT/US2004/028021 on Aug. 27, 2004, now Pat. No. 7,897,597.

(60) Provisional application No. 60/498,270, filed on Aug. 27, 2003, provisional application No. 60/581,254, filed on Jun. 18, 2004.

(51) Int. Cl.
*A61K 31/5377* (2006.01)
*A61K 31/437* (2006.01)
*A61K 31/497* (2006.01)
*C07D 471/04* (2006.01)
*C07D 413/14* (2006.01)
*A61P 31/12* (2006.01)
*A61P 35/00* (2006.01)

(52) U.S. Cl. ............... 514/232.8; 514/293; 514/255.05; 546/82; 544/126; 544/405

(58) Field of Classification Search ............... 514/232.8, 514/293, 255.05; 546/82; 544/405, 126
See application file for complete search history.

(56) References Cited

U.S. PATENT DOCUMENTS

| | | |
|---|---|---|
| 3,314,941 A | 4/1967 | Littell et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gester |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Lindstrom et al. |
| 5,482,936 A | 1/1996 | Lindstrom |
| 5,494,916 A | 2/1996 | Lindstrom et al. |
| 5,525,612 A | 6/1996 | Gerster |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,741,908 A | 4/1998 | Gerster et al. |
| 5,756,747 A | 5/1998 | Gerster et al. |
| 5,886,006 A | 3/1999 | Nikolaides et al. |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,200,592 B1 | 3/2001 | Tomai et al. |
| 6,245,776 B1 | 6/2001 | Skwierczynski et al. |
| 6,331,539 B1 | 12/2001 | Crooks et al. |
| 6,365,166 B2 | 4/2002 | Beaurline et al. |
| 6,376,669 B1 | 4/2002 | Rice et al. |

(Continued)

FOREIGN PATENT DOCUMENTS

JP          0 394 026          10/1990

(Continued)

OTHER PUBLICATIONS

Wozniak et al., "The Amination of 3-nitro-1, Permanganatet[1,2]. A New and Convenient Chemical Society, 102, pp. 511-513, Dec. 5-naphthyridines by Liquid Ammonia/Potassium Amination Method.", *Journal of the Royal Netherlands Chemical Society*, 102, pp. 511-513, Dec. 12, 1983. Brennan et al., "Automated Bioassay of Interferons in Micro-test Plates.", 78, 1983. *Biotechniques*, Jun./Jul., 78, 1983.

Testerman et al., "Cytokine Induction by the Immunomodulators Imiquimod and S-27609.", *Journal of Leukocyte Biology*, vol. 58, pp. 365-372, Sep. 1995.

Bachman et al., "Synthesis of Substituted Quinolylamines. Derivatives of 4-Amino-7-Chloroquinoline.", *J. Org. Chem.* 15, pp. 1278-1284 (1950).

(Continued)

*Primary Examiner* — Niloofar Rahmani

(57) ABSTRACT

Imidazoquinoline compounds with an aryloxy or arylalkyleneoxy substituent at the 6, 7, 8, or 9-position, pharmaceutical compositions containing the compounds, intermediates, and methods of use of these compounds as immunomodulators, for modulating cytokine biosynthesis in animals and in the treatment of diseases including viral and neoplastic diseases, are disclosed.

27 Claims, No Drawings

U.S. PATENT DOCUMENTS

| | | |
|---|---|---|
| 6,440,992 B1 | 8/2002 | Gerster et al. |
| 6,451,810 B1 | 9/2002 | Coleman et al. |
| 6,486,168 B1 | 11/2002 | Skwierczynski et al. |
| 6,514,985 B1 | 2/2003 | Gerster et al. |
| 6,518,265 B1 | 2/2003 | Kato et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,610,319 B2 | 8/2003 | Tomai et al. |
| 6,627,638 B2 | 9/2003 | Gerster et al. |
| 6,627,640 B2 | 9/2003 | Gerster et al. |
| 6,630,588 B2 | 10/2003 | Rice et al. |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,797,718 B2 | 9/2004 | Dellaria et al. |
| 6,800,624 B2 | 10/2004 | Crooks et al. |
| 6,809,203 B2 | 10/2004 | Gerster et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,878,719 B2 | 4/2005 | Lindstrom et al. |
| 6,888,000 B2 | 5/2005 | Crooks et al. |
| 6,894,060 B2 | 5/2005 | Slade |
| 6,897,221 B2 | 5/2005 | Crooks et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,255 B2 | 9/2005 | Lee et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,523 B2 | 7/2006 | Crooks et al. |
| 7,091,214 B2 | 8/2006 | Hays et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,132,438 B2 | 11/2006 | Frenkel et al. |
| 7,148,232 B2 | 12/2006 | Gerster et al. |
| 7,157,453 B2 | 1/2007 | Crooks et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,301,027 B2 | 11/2007 | Colombo et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,485,432 B2 | 2/2009 | Fink et al. |
| 7,544,697 B2 | 6/2009 | Hays et al. |
| 7,576,068 B2 | 8/2009 | Averett |
| 7,578,170 B2 | 8/2009 | Mayer et al. |
| 7,579,359 B2 | 8/2009 | Krepski et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 7,655,672 B2 | 2/2010 | Statham et al. |
| 7,687,628 B2 | 3/2010 | Gutman et al. |
| 7,696,159 B2 | 4/2010 | Owens et al. |
| 7,699,057 B2 | 4/2010 | Miller et al. |
| 7,731,967 B2 | 6/2010 | O'Hagan et al. |
| 7,799,800 B2 | 9/2010 | Wightman |
| 7,879,849 B2 | 2/2011 | Hays et al. |
| 7,884,207 B2 | 2/2011 | Stoermer et al. |
| 7,888,349 B2 | 2/2011 | Kshirsagar et al. |
| 7,897,597 B2 * | 3/2011 | Lindstrom et al. ......... 514/227.8 |
| 7,897,609 B2 | 3/2011 | Niwas et al. |
| 7,897,767 B2 | 3/2011 | Kshirsagar et al. |
| 7,902,209 B2 | 3/2011 | Statham et al. |
| 7,902,210 B2 | 3/2011 | Statham et al. |
| 7,902,211 B2 | 3/2011 | Statham et al. |
| 7,902,212 B2 | 3/2011 | Statham et al. |
| 7,902,213 B2 | 3/2011 | Statham et al. |
| 7,902,214 B2 | 3/2011 | Statham et al. |
| 7,902,215 B2 | 3/2011 | Statham et al. |
| 7,902,216 B2 | 3/2011 | Statham et al. |
| 7,902,242 B2 | 3/2011 | Statham et al. |
| 7,902,243 B2 | 3/2011 | Statham et al. |
| 7,902,244 B2 | 3/2011 | Statham et al. |
| 7,902,245 B2 | 3/2011 | Statham et al. |
| 7,902,246 B2 | 3/2011 | Statham et al. |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2003/0133913 A1 | 7/2003 | Tomai et al. |
| 2003/0139364 A1 | 7/2003 | Krieg et al. |
| 2004/0014779 A1 | 1/2004 | Gorden et al. |
| 2004/0132079 A1 | 7/2004 | Gupta et al. |
| 2004/0175336 A1 | 9/2004 | Egging et al. |
| 2004/0180919 A1 | 9/2004 | Lee et al. |
| 2004/0191833 A1 | 9/2004 | Fink et al. |
| 2004/0197865 A1 | 10/2004 | Gupta et al. |
| 2004/0202720 A1 | 10/2004 | Wightman et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0048072 A1 | 3/2005 | Kedl et al. |
| 2005/0059072 A1 | 3/2005 | Birmachu et al. |
| 2005/0070460 A1 | 3/2005 | Hammerbeck et al. |
| 2005/0096259 A1 | 5/2005 | Tomai et al. |
| 2005/0106300 A1 | 5/2005 | Chen et al. |
| 2005/0158325 A1 | 7/2005 | Hammerbeck et al. |
| 2005/0165043 A1 | 7/2005 | Miller et al. |
| 2005/0171072 A1 | 8/2005 | Tomai et al. |
| 2005/0239735 A1 | 10/2005 | Miller et al. |
| 2005/0245562 A1 | 11/2005 | Garcia-Echeverria et al. |
| 2006/0045885 A1 | 3/2006 | Kedl et al. |
| 2006/0045886 A1 | 3/2006 | Kedl |
| 2006/0051374 A1 | 3/2006 | Miller et al. |
| 2006/0088542 A1 | 4/2006 | Braun |
| 2006/0142202 A1 | 6/2006 | Alkan et al. |
| 2006/0142235 A1 | 6/2006 | Miller et al. |
| 2006/0195067 A1 | 8/2006 | Wolter et al. |
| 2006/0216333 A1 | 9/2006 | Miller et al. |
| 2007/0060754 A1 * | 3/2007 | Lindstrom et al. ............... 546/82 |
| 2007/0066639 A1 | 3/2007 | Kshirsagar et al. |
| 2007/0072893 A1 | 3/2007 | Krepski et al. |
| 2007/0099901 A1 | 5/2007 | Krepski et al. |
| 2007/0123559 A1 | 5/2007 | Statham et al. |
| 2007/0155767 A1 | 7/2007 | Radmer et al. |
| 2007/0166384 A1 | 7/2007 | Zarraga |

| | | |
|---|---|---|
| 2007/0167479 A1 | 7/2007 | Busch et al. |
| 2007/0208052 A1 | 9/2007 | Prince et al. |
| 2007/0213355 A1 | 9/2007 | Capraro et al. |
| 2007/0213356 A1 | 9/2007 | Merrill et al. |
| 2007/0219196 A1 | 9/2007 | Krepski et al. |
| 2007/0243215 A1 | 10/2007 | Miller et al. |
| 2007/0259881 A1 | 11/2007 | Dellaria et al. |
| 2007/0259907 A1 | 11/2007 | Prince |
| 2007/0287725 A1 | 12/2007 | Moser et al. |
| 2007/0292456 A1 | 12/2007 | Hammerbeck et al. |
| 2008/0015184 A1 | 1/2008 | Kshirsagar et al. |
| 2008/0039533 A1 | 2/2008 | Sahouani et al. |
| 2008/0063714 A1 | 3/2008 | Sahouani et al. |
| 2008/0070907 A1 | 3/2008 | Griesgraber et al. |
| 2008/0085895 A1 | 4/2008 | Griesgraber et al. |
| 2008/0119508 A1 | 5/2008 | Slade et al. |
| 2008/0188513 A1 | 8/2008 | Skwierczynski et al. |
| 2008/0193468 A1 | 8/2008 | Levy et al. |
| 2008/0193474 A1 | 8/2008 | Griesgraber et al. |
| 2008/0207674 A1 | 8/2008 | Stoesz et al. |
| 2008/0213308 A1 | 9/2008 | Valiante et al. |
| 2008/0262021 A1 | 10/2008 | Capraro et al. |
| 2008/0262022 A1 | 10/2008 | Lee et al. |
| 2008/0269192 A1 | 10/2008 | Griesgraber et al. |
| 2008/0275077 A1 | 11/2008 | Skwierczynski et al. |
| 2008/0306252 A1 | 12/2008 | Crooks et al. |
| 2008/0306266 A1 | 12/2008 | Martin et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0023720 A1 | 1/2009 | Kshirsagar et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0035323 A1 | 2/2009 | Stoermer et al. |
| 2009/0062272 A1 | 3/2009 | Bonk et al. |
| 2009/0062328 A1 | 3/2009 | Kshirsagar et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0124652 A1 | 5/2009 | Ach et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0202443 A1 | 8/2009 | Miller et al. |
| 2009/0221551 A1 | 9/2009 | Kshirsagar et al. |
| 2009/0221556 A1 | 9/2009 | Kshirsagar et al. |
| 2009/0240055 A1 | 9/2009 | Krepski et al. |
| 2009/0246174 A1 | 10/2009 | Rook et al. |
| 2009/0253695 A1 | 10/2009 | Kshirsagar et al. |
| 2009/0270443 A1 | 10/2009 | Stoermer et al. |
| 2009/0298821 A1 | 12/2009 | Kshirsagar et al. |
| 2009/0306388 A1 | 12/2009 | Zimmerman et al. |
| 2010/0028381 A1 | 2/2010 | Gorski et al. |
| 2010/0056557 A1 | 3/2010 | Benninghoff et al. |
| 2010/0096287 A1 | 4/2010 | Stoesz et al. |
| 2010/0113565 A1 | 5/2010 | Gorden et al. |
| 2010/0152230 A1 | 6/2010 | Dellaria et al. |
| 2010/0158928 A1 | 6/2010 | Stoermer et al. |
| 2010/0173906 A1 | 7/2010 | Griesgraber |
| 2010/0180902 A1 | 7/2010 | Miller et al. |
| 2010/0240693 A1 | 9/2010 | Lundquist et al. |

FOREIGN PATENT DOCUMENTS

| | | |
|---|---|---|
| JP | 9-208584 | 8/1997 |
| JP | 11-080156 A | 3/1999 |
| JP | 11-222432 | 8/1999 |
| JP | 2000-247884 | 9/2000 |
| JP | 1 104 764 | 6/2001 |
| WO | WO 02/36592 | 5/2002 |
| WO | 20050324846 * | 4/2005 |
| WO | WO 2006/028451 | 3/2006 |
| WO | WO 2006/063072 | 6/2006 |
| WO | WO 2006/121528 | 11/2006 |
| WO | WO 2007/030775 | 3/2007 |

OTHER PUBLICATIONS

Jain et al., "Chemical and Pharmacological Investigations of Some (0-Substituted Alkylamino-3-aminopyridines.", *J. Med. Chem.*, 11, pp. 87-92 (1968).

Baranov et al., "Pyrazoles, Imidazoles, and Other 5-Membered Rings.", *Chem. Abs.* 85, 94362, (1976).

Berényi et al., "Ring Transformation of Condensed Dihydro-as-triazines.", *J. Heterocyclic Chem.*, Chollet et al., "Development of a Topically Active Imiquimod Formulation.", *Pharmaceutical Development and Technology*, 4(1), pp. 35-43 (1999).

Izumi et al., "1*H*-Imidazo[4,5-*c*]quinoline Derivatives as Novel Potent TNF-α Suppressors: Synthesis and Structure-Activity Relationship of 1-, 2- and 4-Substituted 1*H*-imidazo[4,5-*c*]pyridines.", *Bioorganic & Medicinal Chemistry*, 11, pp. 2541-2550 (2003).

* cited by examiner

ARYLOXY AND ARYLALKYLENEOXY SUBSTITUTED IMIDAZOQUINOLINES

RELATED APPLICATIONS

This application is a continuation of U.S. patent application Ser. No. 10/595,103, filed Feb. 14, 2006, now U.S. Pat. No. 7,897,597 which is the National Stage of International Application No. PCT/US2004/028021, filed Aug. 27, 2004, which claims priority to U.S. Provisional Application Ser. No. 60/498,270, filed Aug. 27, 2003, and U.S. Provisional Application Ser. No. 60/581,254, filed Jun. 18, 2004, both of which are incorporated herein by reference.

BACKGROUND

There has been a major effort in recent years to find compounds that modulate the immune system. Examples of such compounds, which have demonstrated cytokine inducing and immunomodulating activity that render them useful in the treatment of a variety of disorders, include certain 1H-imidazo[4,5-c]quinolin-4-amine, 1H-imidazo[4,5-c]pyridin-4-amine, tetrahydroquinolin-4-amine, naphthyridin-4-amine, and tetrahydronaphthyridin-4-amine compounds as well as certain analogous thiazolo and oxazolo compounds.

But despite important progress in the effort to find immunomodulating compounds, there is still a critical scientific and medical need for additional compounds that have an ability to modulate aspects of the immune response, by induction or inhibition of cytokine biosynthesis or other mechanisms.

SUMMARY

A new class of compounds useful for modulating cytokine biosynthesis has now been found. In one aspect, the present invention provides such compounds, which are of the following Formula I:

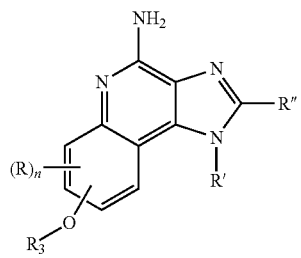

wherein R, n, R', R" and $R_3$ are as defined below; and pharmaceutically acceptable salts thereof.

The compounds and/or salts of Formula I are useful as immune response modifiers (IRMs) due to their ability to modulate cytokine biosynthesis (e.g., induce or inhibit the biosynthesis or production of one or more cytokines) and otherwise modulate the immune response when administered to animals. This makes the compounds or salts useful in the treatment of a variety of conditions such as viral diseases and neoplastic diseases that are responsive to such changes in the immune response.

In another aspect, the present invention provides pharmaceutical compositions containing an effective amount of a compound or salt of the invention, and methods of modulating (e.g., inducing or inhibiting) cytokine biosynthesis in an animal, treating a viral disease in an animal, and treating a neoplastic disease in an animal, by administering an effective amount of one or more compounds of Formula I and/or pharmaceutically acceptable salts thereof to the animal.

In another aspect, the present invention provides methods of synthesizing compounds of Formula I and intermediate compounds useful in the synthesis of these compounds. Certain of these intermediate compounds, for example, compounds of the Formula VII described below, have also been found to be useful as immune response modifiers as described above. Accordingly, the present invention provides pharmaceutical compositions containing an effective amount of one or more of these compounds and/or salts thereof, and methods of inducing cytokine biosynthesis in an animal, treating a viral disease in an animal, and treating a neoplastic disease in an animal, by administering an effective amount of one or more of these compounds and/or pharmaceutically acceptable salts thereof to the animal.

As used herein, "a," "an," "the," "at least one," and "one or more" are used interchangeably.

The terms "comprising" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. Guidance is also provided herein through lists of examples, which can be used in various combinations. In each instance, the recited list serves only as a representative group and should not be interpreted as an exclusive list.

DETAILED DESCRIPTION OF ILLUSTRATIVE EMBODIMENTS OF THE INVENTION

In one aspect, the present invention provides compounds of the formula (I):

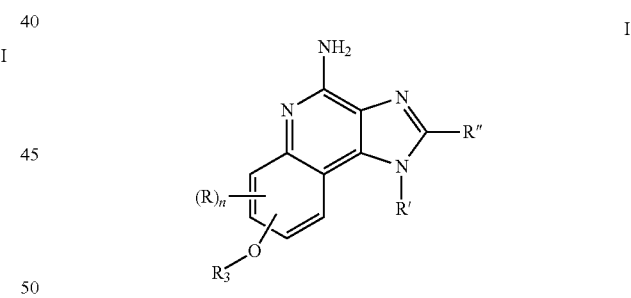

wherein:
$R_3$ is selected from the group consisting of:
—Z—Ar,
—Z—Ar'—Y—$R_4$,
—Z—Ar'—X—Y—$R_4$,
—Z—Ar'—$R_5$, and
—Z—Ar'—X—$R_5$;
Z is selected from the group consisting of a bond, alkylene, alkenylene, and alkynylene wherein alkylene, alkenylene, and alkynylene are optionally interrupted with —O—;
Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

X is selected from the group consisting of alkylene, alkenylene, alkynylene, arylene, heteroarylene, and heterocyclylene wherein the alkylene, alkenylene, and alkynylene groups can be optionally interrupted by arylene, heteroarylene or heterocyclylene or by one or more —O— groups.

Y is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

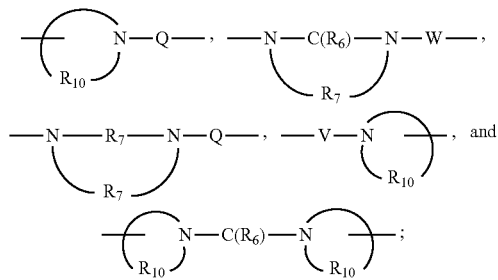

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino) alkyleneoxy, and in the case of alkyl, alkenyl, alkynyl, and heterocyclyl, oxo;

R$_5$ is selected from the group consisting of:

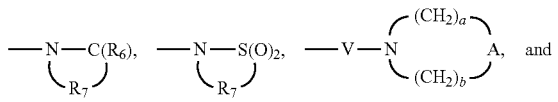

each R$_6$ is independently selected from the group consisting of =O and =S;
each R$_7$ is independently C$_{2-7}$ alkylene;
R$_8$ is selected from the group consisting of hydrogen, alkyl, alkoxyalkylenyl, and arylalkylenyl;
R$_9$ is selected from the group consisting of hydrogen and alkyl;
each R$_{10}$ is independently C$_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7;
R is selected from the group consisting of alkyl, alkoxy, hydroxy, halogen, and trifluoromethyl;
R' and R" are independently selected from the group consisting of hydrogen and non-interfering substitutents; and
n is 0 or 1;
or a pharmaceutically acceptable salt thereof.

In one embodiment, the present invention provides a compound of the formula (II):

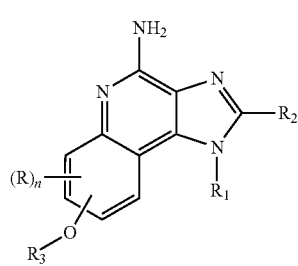

wherein:
R$_3$ is selected from the group consisting of:
—Z—Ar,
—Z—Ar'—Y—R$_4$,
—Z—Ar'—X—Y—R$_4$,
—Z—Ar'—R$_5$, and
—Z—Ar'—X—R$_5$;
Z is selected from the group consisting of a bond, alkylene, alkenylene, and alkynylene wherein alkylene, alkenylene, and alkynylene are optionally interrupted with —O—;
Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

R is selected from the group consisting of alkyl, alkoxy, hydroxy, halogen, and trifluoromethyl;

n is 0 or 1;

$R_1$ is selected from the group consisting of:
—$R_4$,
—X—$R_4$,
—X—Y—$R_4$,
—X—Y—X—Y—$R_4$, and
—X—$R_5$;

$R_2$ is selected from the group consisting of:
—$R_4$,
—X—$R_4$,
—X—Y—$R_4$, and
—X—$R_5$;

each X is independently selected from the group consisting of alkylene, alkenylene, alkynylene, arylene, heteroarylene, and heterocyclylene wherein the alkylene, alkenylene, and alkynylene groups can be optionally interrupted by arylene, heteroarylene or heterocyclylene or by one or more —O— groups;

each Y is independently selected from the group consisting of:
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(OR$_9$)—,

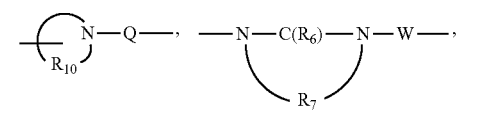
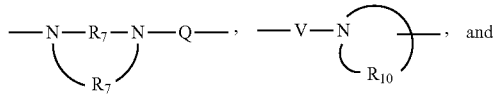
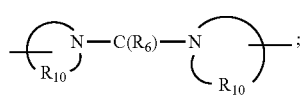

each $R_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

each $R_5$ is independently selected from the group consisting of:

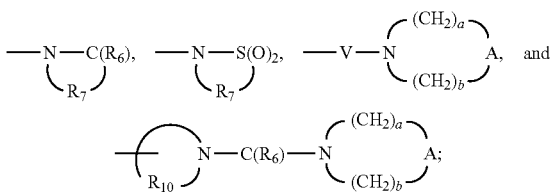

each $R_6$ is independently selected from the group consisting of =O and =S;
each $R_7$ is independently $C_{2-7}$ alkylene;
each $R_8$ is independently selected from the group consisting of hydrogen, alkyl, alkoxyalkylenyl, and arylalkylenyl;
each $R_9$ is independently selected from the group consisting of hydrogen and alkyl;
each $R_{10}$ is independently $C_{3-8}$ alkylene;
each A is independently selected from the group consisting of —O—, —C(O)—, —S(O)$_{0-2}$—, —CH$_2$—, and —N($R_4$)—;
each Q is independently selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(OR$_9$)—;
each V is independently selected from the group consisting of —C($R_6$)—, —O—C($R_6$)—, —N($R_8$)—C($R_6$)—, and —S(O)$_2$—;
each W is independently selected from the group consisting of a bond, —C(O)—, and —S(O)$_2$—; and
a and b are independently integers from 1 to 6 with the proviso that a+b is ≦7;
or a pharmaceutically acceptable salt thereof.

In another embodiment, the present invention provides a compound of the formula (III):

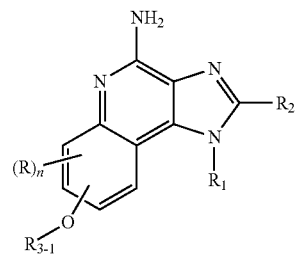

wherein:
$R_{3-1}$ is —Z—Ar;
Z is selected from the group consisting of a bond, alkylene, alkenylene, and alkynylene wherein alkylene, alkenylene, and alkynylene are optionally interrupted with —O—;
Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

R is selected from the group consisting of alkyl, alkoxy, hydroxy, halogen, and trifluoromethyl;

n is 0 or 1;

$R_1$ is selected from the group consisting of:
—$R_4$,
—X—$R_4$,
—X—Y—$R_4$,
X—Y—X—Y—$R_4$, and
—X—$R_5$;

$R_2$ is selected from the group consisting of:
—$R_4$,
—X—$R_4$,
—X—Y—$R_4$, and
—X—$R_5$;

X' is selected from the group consisting of alkylene, alkenylene, alkynylene, arylene, heteroarylene, and heterocyclylene wherein the alkylene, alkenylene, and alkynylene groups can be optionally interrupted by an arylene, heteroarylene or heterocyclylene group;

each Y is independently selected from the group consisting of:
—$S(O)_{0-2}$—,
—$S(O)_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

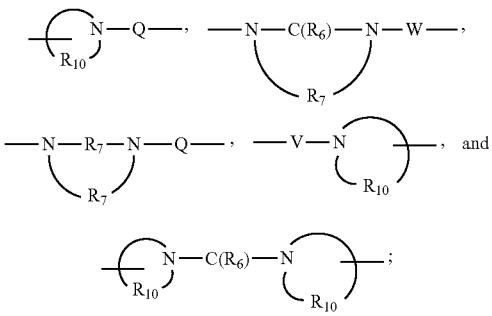

Y' is selected from the group consisting of:
—$S(O)_2$—N($R_8$)—,
—C($R_6$)—,
—C($R_6$)—O—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

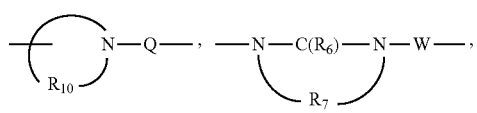

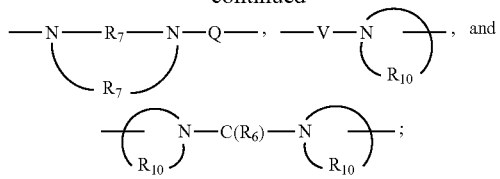

each $R_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

each $R_5$ is independently selected from the group consisting of:

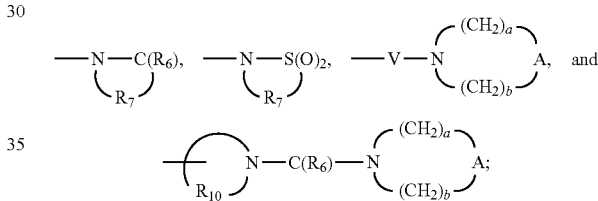

each $R_6$ is independently selected from the group consisting of =O and =S;

each $R_7$ is independently $C_{2-7}$ alkylene;

each $R_8$ is independently selected from the group consisting of hydrogen, alkyl, alkoxyalkylenyl, and arylalkylenyl;

each $R_9$ is independently selected from the group consisting of hydrogen and alkyl;

each $R_{10}$ is independently $C_{3-8}$ alkylene;

each A is independently selected from the group consisting of —O—, —C(O)—, —$S(O)_{0-2}$—, —$CH_2$—, and —N($R_4$)—;

each Q is independently selected from the group consisting of a bond, —C($R_6$)—, —C($R_6$)—C($R_6$)—, —$S(O)_2$—, —C($R_6$)—N($R_8$)—W—, —$S(O)_2$—N($R_8$)—, —C($R_6$)—O—, and —C($R_6$)—N(O$R_9$)—;

each V is independently selected from the group consisting of —C($R_6$)—, —O—C($R_6$)—, —N($R_8$)—C($R_6$)—, and —$S(O)_2$—;

each W is independently selected from the group consisting of a bond, —C(O)—, and —$S(O)_2$—; and a and b are independently integers from 1 to 6 with the proviso that a+b is ≦7;

or a pharmaceutically acceptable salt thereof.

In another aspect, the present invention provides intermediate compounds of Formulas VII, IX, and XI.

In one embodiment, the present invention provides a compound of the following formula (VII):

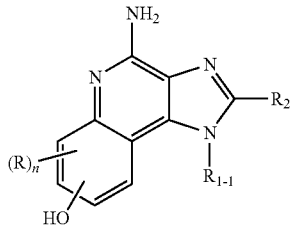

VII wherein:
R is selected from the group consisting of alkyl, alkoxy, hydroxy, halogen, and trifluoromethyl;
n is 0 or 1;
$R_{1-1}$ is selected from the group consisting of:
—$R_{4-1}$,
—X'—$R_{4-1}$,
—X'—Y'—$R_4$,
X'—Y'—X—Y—$R_4$, and
—X'—$R_5$;
$R_2$ is selected from the group consisting of:
—$R_4$,
—X—$R_4$,
—X—Y—$R_4$, and
—X—$R_5$;
each X is independently selected from the group consisting of alkylene, alkenylene, alkynylene, arylene, heteroarylene, and heterocyclylene wherein the alkylene, alkenylene, and alkynylene groups can be optionally interrupted by arylene, heteroarylene or heterocyclylene or by one or more —O— groups;
X' is selected from the group consisting of alkylene, alkenylene, alkynylene, arylene, heteroarylene, and heterocyclylene wherein the alkylene, alkenylene, and alkynylene groups can be optionally interrupted by an arylene, heteroarylene or heterocyclylene group;
each Y is independently selected from the group consisting of:
—$S(O)_{0-2}$—,
—$S(O)_2$—$N(R_8)$—,
—$C(R_6)$—,
—$C(R_6)$—O—,
—O—$C(R_6)$—,
—O—C(O)—O—,
—$N(R_8)$-Q-,
—$C(R_6)$—$N(R_8)$—,
—O—$C(R_6)$—$N(R_8)$—,
—$C(R_6)$—$N(OR_9)$—,

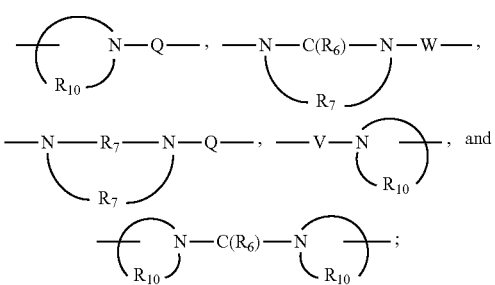

Y' is selected from the group consisting of:
—$S(O)_2$—$N(R_8)$—,
—$C(R_6)$—,
—$C(R_6)$—O—,
—O—C(O)—O—,
—$N(R_8)$-Q-,
—$C(R_6)$—$N(R_8)$—,
—O—$C(R_6)$—$N(R_8)$—,
—$C(R_6)$—$N(OR_9)$—,

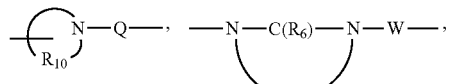

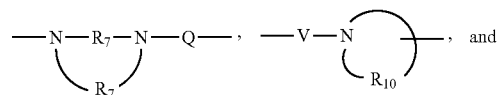

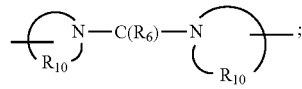

each $R_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
$R_{4-1}$ is selected from the group consisting of hydrogen, alkyl, alkenyl, alkynyl, aryl, arylalkylenyl, alkylarylenyl, heteroaryl, heteroarylalkylenyl, alkylheteroarylenyl, and heterocyclyl wherein the alkyl, alkenyl, alkynyl, aryl, arylalkylenyl, alkylarylenyl, heteroaryl, heteroarylalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, heteroaryl, heterocyclyl, amino, alkylamino, dialkylamino, (dialkylamino)alkyleneoxy, and in the case of alkyl, alkenyl, alkynyl, and heterocyclyl, oxo;
each $R_5$ is independently selected from the group consisting of:

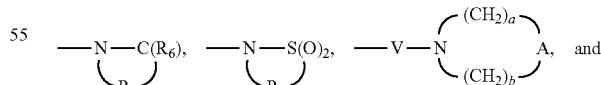

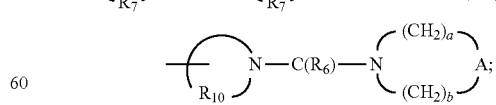

each $R_6$ is independently selected from the group consisting of =O and =S;
each $R_7$ is independently $C_{2-7}$ alkylene;
each $R_8$ is independently selected from the group consisting of hydrogen, alkyl, alkoxyalkylenyl, and arylalkylenyl;

each $R_9$ is independently selected from the group consisting of hydrogen and alkyl;

each $R_{10}$ is independently $C_{3-8}$ alkylene;

each A is independently selected from the group consisting of —O—, —C(O)—, —S(O)$_{0-2}$—, —CH$_2$—, and —N($R_4$)—;

each Q is independently selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—;

each V is independently selected from the group consisting of —C($R_6$)—, —O—C($R_6$)—, —N($R_8$)—C($R_6$)—, and —S(O)$_2$—;

each W is independently selected from the group consisting of a bond, —C(O)—, and —S(O)$_2$—; and a and b are independently integers from 1 to 6 with the proviso that a+b is ≦7;

or a pharmaceutically acceptable salt thereof; with the proviso that when $R_{1-1}$ is hydrogen or 2-methylpropyl, $R_2$ is other than hydrogen, and with the further proviso that when $R_{1-1}$ is 2-methylpropenyl or 2-hydroxy-2-methylpropyl, $R_2$ is other than methyl, ethoxymethyl, and hydroxymethyl.

In another embodiment, the present invention provides a compound of the following formula (IX):

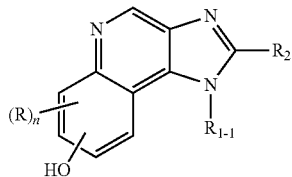

IX wherein:

R is selected from the group consisting of alkyl, alkoxy, hydroxy, halogen, and trifluoromethyl;

n is 0 or 1;

$R_{1-1}$ is selected from the group consisting of:
—$R_{4-1}$,
—X'—$R_{4-1}$,
—X'—Y'—$R_4$,
X'—Y'—X—Y—$R_4$, and
—X'—$R_5$;

$R_2$ is selected from the group consisting of:
—$R_4$,
—X—$R_4$,
—X—Y—$R_4$, and
—X—$R_5$;

each X is independently selected from the group consisting of alkylene, alkenylene, alkynylene, arylene, heteroarylene, and heterocyclylene wherein the alkylene, alkenylene, and alkynylene groups can be optionally interrupted by arylene, heteroarylene or heterocyclylene or by one or more —O— groups;

X' is selected from the group consisting of alkylene, alkenylene, alkynylene, arylene, heteroarylene, and heterocyclylene wherein the alkylene, alkenylene, and alkynylene groups can be optionally interrupted by an arylene, heteroarylene or heterocyclylene group;

each Y is independently selected from the group consisting of:
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

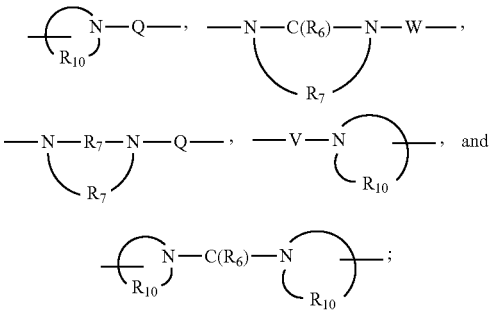

Y' is selected from the group consisting of:
—S(O)$_2$—N($R_8$)—,
—C($R_6$)—,
—C($R_6$)—O—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

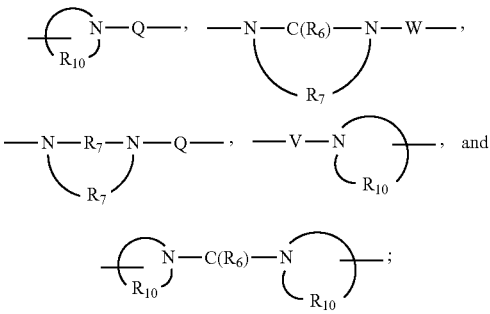

each $R_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_{4-1}$ is selected from the group consisting of hydrogen, alkyl, alkenyl, alkynyl, aryl, arylalkylenyl, alkylarylenyl, heteroaryl, heteroarylalkylenyl, alkylheteroarylenyl, and heterocyclyl wherein the alkyl, alkenyl, alkynyl, aryl, arylalkylenyl, alkylarylenyl, heteroaryl, heteroarylalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, heteroaryl, heterocyclyl, amino, alkylamino, dialkylamino, (dialkylamino)alkyleneoxy, and in the case of alkyl, alkenyl, alkynyl, and heterocyclyl, oxo;

each $R_5$ is independently selected from the group consisting of:

$$-N(R_7)-C(R_6)-,\quad -N(R_7)-S(O)_2-,\quad -V-N\binom{(CH_2)_a}{(CH_2)_b}A,\text{ and}$$

$$-\binom{}{R_{10}}N-C(R_6)-N\binom{(CH_2)_a}{(CH_2)_b}A;$$

each $R_6$ is independently selected from the group consisting of =O and =S;

each $R_7$ is independently $C_{2-7}$ alkylene;

each $R_8$ is independently selected from the group consisting of hydrogen, alkyl, alkoxyalkylenyl, and arylalkylenyl;

each $R_9$ is independently selected from the group consisting of hydrogen and alkyl;

each $R_{10}$ is independently $C_{3-8}$ alkylene;

each A is independently selected from the group consisting of —O—, —C(O)—, —S(O)$_{0-2}$—, —CH$_2$—, and —N(R$_4$)—;

each Q is independently selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

each V is independently selected from the group consisting of —C(R$_6$)—, —O—C(R$_6$)—, —N(R$_8$)—C(R$_6$)—, and —S(O)$_2$—;

each W is independently selected from the group consisting of a bond, —C(O)—, and —S(O)$_2$—; and a and b are independently integers from 1 to 6 with the proviso that a+b is ≦7;

or a pharmaceutically acceptable salt thereof.

In another embodiment, the present invention provides a compound of the following formula (XI):

XI wherein:

$R_3$ is selected from the group consisting of:
—Z—Ar,
—Z—Ar'—Y—R$_4$,
—Z—Ar'—X—Y—R$_4$,
—Z—Ar'—R$_5$, and
—Z—Ar'—X—R$_5$;

Z is selected from the group consisting of a bond, alkylene, alkenylene, and alkynylene wherein alkylene, alkenylene, and alkynylene are optionally interrupted with —O—;

Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

R is selected from the group consisting of alkyl, alkoxy, hydroxy, halogen, and trifluoromethyl;

n is 0 or 1;

$R_1$ is selected from the group consisting of:
—R$_4$,
—X—R$_4$,
—X—Y—R$_4$,
X—Y—X—Y—R$_4$, and
—X—R$_5$;

$R_2$ is selected from the group consisting of:
—R$_4$,
—X—R$_4$,
—X—Y—R$_4$, and
—X—R$_5$;

each X is independently selected from the group consisting of alkylene, alkenylene, alkynylene, arylene, heteroarylene, and heterocyclylene wherein the alkylene, alkenylene, and alkynylene groups can be optionally interrupted by arylene, heteroarylene or heterocyclylene or by one or more —O— groups;

each Y is independently selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—, $$-\binom{}{R_{10}}N-Q-,\quad -N(R_7)-C(R_6)-N(R_7)-W-,$$

$$-N(R_7)-R_7-N(R_7)-Q-,\quad -V-N\binom{}{R_{10}},\text{ and}$$

$$-\binom{}{R_{10}}N-C(R_6)-N\binom{}{R_{10}};$$

each $R_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

each $R_5$ is independently selected from the group consisting of:

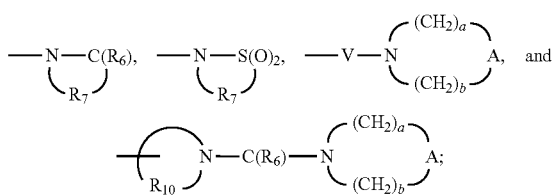

each $R_6$ is independently selected from the group consisting of =O and =S;

each $R_7$ is independently $C_{2-7}$ alkylene;

each $R_8$ is independently selected from the group consisting of hydrogen, alkyl, alkoxyalkylenyl, and arylalkylenyl;

each $R_9$ is independently selected from the group consisting of hydrogen and alkyl;

each $R_{10}$ is independently $C_{3-8}$ alkylene;

each A is independently selected from the group consisting of —O—, —C(O)—, —S(O)$_{0-2}$—, —CH$_2$—, and —N(R$_4$)—;

each Q is independently selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

each V is independently selected from the group consisting of —C(R$_6$)—, —O—C(R$_6$)—, —N(R$_8$)—C(R$_6$)—, and —S(O)$_2$—;

each W is independently selected from the group consisting of a bond, —C(O)—, and —S(O)$_2$—; and a and b are independently integers from 1 to 6 with the proviso that a+b is ≦7;

or a pharmaceutically acceptable salt thereof.

As used herein, the terms "alkyl," "alkenyl," "alkynyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene," "-alkylene-", "alkenylene", "-alkenylene-", "alkynylene", and "-alkynylene-" are the divalent forms of the "alkyl", "alkenyl", and "alkynyl" groups defined above. The terms "alkylenyl", "alkenylenyl", and "alkynylenyl" are used when "alkylene", "alkenylene", and "alkynylene", respectively, are substituted. For example, an arylalkylenyl group comprises an "alkylene" moiety to which an aryl group is attached.

The term "haloalkyl" is inclusive of alkyl groups that are substituted by one or more halogen atoms, including perfluorinated groups. This is also true of other groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

The term "heteroatom" refers to the atoms O, S, or N.

The term "heteroaryl" includes aromatic rings or ring systems that contain at least one ring heteroatom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on. Also, suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, tetrahydropyranyl, quinuclidinyl, homopiperidinyl, homopiperazinyl, and the like. Also, exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, tetrahydropyranyl, and the like.

The terms "arylene", "heteroarylene", and "heterocyclylene" are the divalent forms of the "aryl", "heteroaryl", and "heterocyclyl" groups defined above. The terms "arylenyl," "heteroarylenyl," and "heterocyclylenyl" are used when "arylene", "heteroarylene", and "heterocyclylene", respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula —N(R$_8$)—C(R$_6$)—N(R$_8$)— each R$_8$ group is independently selected. In another example, when an R$_2$ and an R$_3$ group both contain an R$_4$ group, each R$_4$ group is independently selected. In a further example, when more than one Y group is present (i.e., R$_2$ and R$_3$ both contain a Y group) and each Y group contains one or more R$_8$ groups, then each Y group is independently selected, and each R$_8$ group is independently selected.

The invention is inclusive of the compounds described herein and salts thereof in any of their pharmaceutically acceptable forms, including isomers such as diastereomers and enantiomers, solvates, polymorphs, and the like. In particular, if a compound is optically active, the invention specifically includes each of the compound's enantiomers as well as racemic mixtures of the enantiomers.

For any of the compounds presented herein, each one of the following variables (e.g., R, R', R'', $R_1$, $R_2$, $R_3$, n, A, X, Z, and so on) in any of its embodiments can be combined with any one or more of the other variables in any of their embodiments as would be understood by one of skill in the art. Each of the resulting combinations of variables is an embodiment of the present invention.

In some embodiments, $R_3$ is selected from the group consisting of —Z—Ar, —Z—Ar'—Y—$R_4$, —Z—Ar'—X—Y—$R_4$, —Z—Ar'—$R_5$, and —Z—Ar'—X—$R_5$. In some embodiments, $R_3$ is selected from the group consisting of —Z—Ar, —Z—Ar'—X—Y—$R_4$, and —Z—Ar'—Y—$R_4$. In some embodiments, $R_3$ or $R_{3-1}$ is —Z—Ar. In some embodiments, Ar is phenyl or heteroaryl which is unsubstituted or substituted by one or more substituents independently selected from the group consisting of alkyl, alkoxy, nitro, cyano, carboxy, halogen, hydroxyalkyl, amino, alkylamino, dialkylamino, trifluoromethyl, trifluoromethoxy, and thienyl. In certain of these embodiments heteroaryl is selected from the group consisting of benzothiazolyl, furanyl, imidazolyl, indolyl, isoxazolyl, oxadiazolyl, pyrazinyl, pyridinyl, pyrrolyl, thiazolyl, and thienyl. In some of these embodiments, Z is a bond, alkylene, or alkylene interrupted by —O—. In certain of these embodiments Z is $C_{1-3}$ alkylene. In certain of these embodiments Z is a bond.

In some embodiments, $R_3$ or $R_{3-1}$ is benzyl, pyridin-3-ylmethyl, 4-chlorobenzyl, 4-fluorobenzyl, or 3-pyridin-3-ylpropyl.

In some embodiments, $R_3$ is —Z—Ar'—Y—$R_4$, or —Z—Ar'—X—Y—$R_4$. In certain of these embodiments, X is $C_{1-2}$ alkylene; Y is —N($R_8$)—S(O)$_2$—, —S(O)$_2$—, —C($R_6$)—, or —C($R_6$)—O—; and $R_4$ is alkyl or phenyl. In certain of these embodiments, X is $C_{1-2}$ alkylene; Y is —NH—S(O)$_2$—, —S(O)$_2$—, —C(O)—, or —C(O)—O—; and $R_4$ is $C_{1-4}$ alkyl or phenyl. In some of these embodiments, Z is a bond, alkylene, or alkylene interrupted by —O—. In certain of these embodiments Z is $C_{1-3}$ alkylene. In certain of these embodiments Z is a bond.

In some embodiments, $R_3$ is —Z—Ar'—Y—$R_4$. In certain of these embodiments, Y is selected from the group consisting of —S(O)$_2$— and —C(O)O—, and $R_4$ is $C_{1-4}$ alkyl, for example, methyl. In certain of these embodiments, Ar' is phenylene which is unsubstituted or substituted by one or more substituents independently selected from the group consisting of alkyl, alkoxy, nitro, cyano, halogen, amino, alkylamino, dialkylamino, trifluoromethyl, and trifluoromethoxy.

In some embodiments, each of R, R', and R'' is independently a non-interfering substituent. For certain embodiments, each R' and R'' is independently selected from the group consisting of hydrogen and non-interfering substituents. Herein, "non-interfering" means that the immunomodulator activity (for example, the ability to induce the biosynthesis of one or more cytokines, or to inhibit the biosynthesis of one or more cytokines) of the compound is not destroyed.

In some embodiments, R is selected from the group consisting of alkyl, alkoxy, hydroxy, halogen, and trifluoromethyl.

In some embodiments, n is 0.

In some embodiments, n is 0 or 1.

In some embodiments, R' is selected from the group consisting of hydrogen and a non-interfering substitutent.

In some embodiments, R' is selected from the group consisting of —$R_4$, —X—$R_4$, —X—Y—$R_4$, X—Y—X—Y—$R_4$, and —X—$R_5$.

In some embodiments, R' is selected from the group consisting of alkyl, arylalkylenyl, aryloxyalkylenyl, hydroxyalkyl, dihydroxyalkyl, alkylsulfonylalkylenyl, heterocyclylalkylenyl wherein heterocyclyl is optionally substituted by one or more alkyl groups, —X—Y—$R_4$, and —X—$R_5$; wherein X is alkylene, Y is —N($R_8$)—C(O)—, —N($R_8$)—S(O)$_2$—, —N($R_8$)—C($R_6$)—N($R_8$)—, or

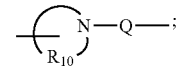

$R_4$ is alkyl, aryl, arylalkylenyl, or heteroaryl, each of which is optionally substituted by one or more substituents selected from the group consisting of alkyl, alkoxy, halogen, or dialkylamino; and $R_5$ is

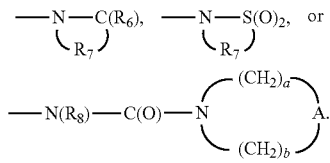

In some embodiments, R' is selected from the group consisting of 2-hydroxy-2-methylpropyl, 2-methylpropyl, propyl, 2,3-dihydroxypropyl, 4-[(methylsulfonyl)amino]butyl, 2-methyl-2-[(methylsulfonyl)amino]propyl, 2-[(cyclohexylcarbonyl)amino]-2-methylpropyl, 4-(1,1-dioxidoisothiazolidin-2-yl)butyl, tetrahydro-2H-pyran-4-ylmethyl, and (2,2-dimethyl-1,3-dioxolan-4-yl)methyl.

In some embodiments R' is selected from the group consisting of propyl, 2,3-dihydroxypropyl, 4-[(methylsulfonyl)amino]butyl, 2-methyl-2-[(methylsulfonyl)amino]propyl, 2-[(cyclohexylcarbonyl)amino]-2-methylpropyl, 4-(1,1-dioxidoisothiazolidin-2-yl)butyl, tetrahydro-2H-pyran-4-ylmethyl, and (2,2-dimethyl-1,3-dioxolan-4-yl)methyl.

In some embodiments, $R_1$ is selected from the group consisting of —$R_4$, —X—$R_4$, —X—Y—$R_4$, X—Y—X—Y—$R_4$, and —X—$R_5$.

In some embodiments, $R_1$ is selected from the group consisting of alkyl, arylalkylenyl, aryloxyalkylenyl, hydroxyalkyl, dihydroxyalkyl, alkylsulfonylalkylenyl, heterocyclylalkylenyl wherein heterocyclyl is optionally substituted by one or more alkyl groups, —X—Y—$R_4$, and —X—$R_5$; wherein X is alkylene, Y is —N($R_8$)—C(O)—, —N($R_8$)—S(O)$_2$—, —N($R_8$)—C($R_6$)—N($R_8$)—, or

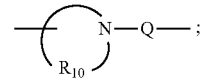

$R_4$ is alkyl, aryl, arylalkylenyl, or heteroaryl, each of which is optionally substituted by one or more substituents selected from the group consisting of alkyl, alkoxy, halogen, or dialkylamino; and $R_5$ is

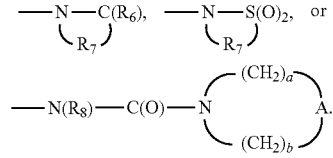

In some embodiments, $R_1$ is selected from the group consisting of 2-hydroxy-2-methylpropyl, 2-methylpropyl, propyl, 2,3-dihydroxypropyl, 4-[(methylsulfonyl)amino]butyl, 2-methyl-2-[(methylsulfonyl)amino]propyl, 2-[(cyclohexylcarbonyl)amino]-2-methylpropyl, 4-(1,1-dioxidoisothiazolidin-2-yl)butyl, tetrahydro-2H-pyran-4-ylmethyl, and (2,2-dimethyl-1,3-dioxolan-4-yl)methyl.

In some embodiments, $R_1$ is selected from the group consisting of propyl, 2,3-dihydroxypropyl, 4-[(methylsulfonyl)amino]butyl, 2-methyl-2-[(methylsulfonyl)amino]propyl, 2-[(cyclohexylcarbonyl)amino]-2-methylpropyl, 4-(1,1-dioxidoisothiazolidin-2-yl)butyl, tetrahydro-2H-pyran-4-ylmethyl, and (2,2-dimethyl-1,3-dioxolan-4-yl)methyl.

In some embodiments, $R_{1-1}$ is selected from the group consisting of —$R_{4-1}$, —X'—$R_{4-1}$, —X'—Y'—$R_4$, X'—Y'—X—Y—$R_4$, and —X'—$R_5$;

In some embodiments, $R_{1-1}$ is selected from the group consisting of alkyl, arylalkylenyl, hydroxyalkyl, dihydroxyalkyl, heterocyclylalkylenyl wherein heterocyclyl is optionally substituted by one or more alkyl groups, —X'—Y'—$R_4$, and —X'—$R_5$. In certain of these embodiments, X' is alkylene; Y' is —N($R_8$)-Q-; Q is —C($R_6$)—, —S(O)$_2$—, or —C($R_6$)—N($R_8$)—W—; $R_4$ is alkyl, aryl, arylalkylenyl, or heteroaryl, each of which is optionally substituted by one or more substituents selected from the group consisting of alkyl, alkoxy, halogen, or dialkylamino; and $R_5$ is

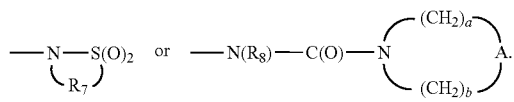

In some embodiments, $R_{1-1}$ is selected from the group consisting of 2-hydroxy-2-methylpropyl, 2-methylpropyl, propyl, 2,3-dihydroxypropyl, 4-[(methylsulfonyl)amino]butyl, 2-methyl-2-[(methylsulfonyl)amino]propyl, 2-[(cyclohexylcarbonyl)amino]-2-methylpropyl, 4-(1,1-dioxidoisothiazolidin-2-yl)butyl, tetrahydro-2H-pyran-4-ylmethyl, and (2,2-dimethyl-1,3-dioxolan-4-yl)methyl.

In some embodiments $R_{1-1}$ is selected from the group consisting of propyl, 2,3-dihydroxypropyl, 4-[(methylsulfonyl)amino]butyl, 2-methyl-2-[(methylsulfonyl)amino]propyl, 2-[(cyclohexylcarbonyl)amino]-2-methylpropyl, 4-(1,1-dioxidoisothiazolidin-2-yl)butyl, tetrahydro-2H-pyran-4-ylmethyl, and (2,2-dimethyl-1,3-dioxolan-4-yl)methyl.

In some embodiments, R" is hydrogen or a non-interfering substituent.

In some embodiments, R" is selected from the group consisting of —$R_4$, —X—$R_4$, —X—Y—$R_4$, and —X—$R_5$.

In some embodiments, R" is selected from the group consisting of hydrogen, alkyl, alkoxyalkylenyl, and —X—N($R_8$)—C($R_6$)—N($R_8$)—$R_4$. In certain of these embodiments, X is $C_{1-4}$ alkylene, and $R_4$ is $C_{1-4}$ alkyl. In some of these embodiments X is $C_{1-2}$ alkylene.

In some embodiments, R" is selected from the group consisting of hydrogen, methyl, ethyl, propyl, butyl, ethoxymethyl, methoxymethyl, 2-methoxyethyl, and methylaminocarbonylaminomethyl. In some of these embodiments, R" is selected from the group consisting of ethyl, propyl, ethoxymethyl, 2-methoxyethyl, and methoxymethyl. In some of these embodiments, R" is selected from the group consisting of ethyl, propyl, 2-methoxyethyl, and methoxymethyl.

In some embodiments, $R_2$ is selected from the group consisting of —$R_4$, —X—$R_4$, —X—Y—$R_4$, and —X—$R_5$.

In some embodiments, $R_2$ is selected from the group consisting of hydrogen, alkyl, alkoxyalkylenyl, and —X—N($R_8$)—C($R_6$)—N($R_8$)—$R_4$. In certain of these embodiments, X is $C_{1-4}$ alkylene, and $R_4$ is $C_{1-4}$ alkyl. In some of these embodiments X is $C_{1-2}$ alkylene. Also, in some embodiments, $R_2$ is selected from the group consisting of hydrogen, alkyl, and alkoxyalkylenyl.

In some embodiments, $R_2$ is selected from the group consisting of hydrogen, methyl, ethyl, propyl, butyl, ethoxymethyl, methoxymethyl, 2-methoxyethyl, and methylaminocarbonylaminomethyl. In some of these embodiments, $R_2$ is selected from the group consisting of ethyl, propyl, ethoxymethyl, 2-methoxyethyl, and methoxymethyl. In some of these embodiments, $R_2$ is selected from the group consisting of ethyl, propyl, 2-methoxyethyl, and methoxymethyl.

In some embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo. Also in some embodiments, $R_4$ is selected from the group consisting of hydrogen, alkyl, alkenyl, alkynyl, aryl, arylalkylenyl, aryloxyalkylenyl, alkylarylenyl, heteroaryl, alkylheteroarylenyl, and heterocyclyl wherein the alkyl, alkenyl, alkynyl, aryl, arylalkylenyl, aryloxyalkylenyl, alkylarylenyl, heteroaryl, alkylheteroarylenyl, and heterocyclyl groups can be unsubstituted or substituted by one or more substituents independently selected from the group consisting of acetyl, alkyl, alkoxy, alkylthio, alkylsulfonyl, alkanoyloxy, alkoxycarbonyl, hydroxyalkyl, haloalkyl, haloalkoxy, halogen, nitro, hydroxy, mercapto, cyano, carboxy, formyl, aryl, aryloxy, arylthio, arylsulfonyl, arylalkyleneoxy, aroylamino, heteroaryl, heteroaryloxy, heteroarylalkyleneoxy, heterocyclyl, heterocyclylalkylenyl, amino, alkylamino, dialkylamino, (dialkylamino)alkyleneoxy, aminosulfonyl, and in the case of alkyl, alkenyl, alkynyl, and heterocyclyl, oxo. In some embodiments, $R_4$ is alkyl, aryl, arylalkylenyl, or heteroaryl, each of which is optionally substituted by one or more substituents selected from the group consisting of alkyl, alkoxy, halogen, or dialkylamino. In some embodiments, $R_4$ is alkyl or phenyl. In some embodiments, $R_4$ is $C_{1-4}$ alkyl or phenyl. In some embodiments, $R_4$ is $C_{1-4}$ alkyl.

In some embodiments, $R_{4-1}$ is selected from the group consisting of hydrogen, alkyl, alkenyl, alkynyl, aryl, arylalkylenyl, alkylarylenyl, heteroaryl, heteroarylalkylenyl, alkylheteroarylenyl, and heterocyclyl wherein the alkyl, alkenyl, alkynyl, aryl, arylalkylenyl, alkylarylenyl, heteroaryl, heteroarylalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, heteroaryl, heterocyclyl, amino, alkylamino, dialkylamino, (dialkylamino)alkyleneoxy, and in the case of alkyl, alkenyl, alkynyl, and heterocyclyl, oxo. In some embodiments, $R_{4-1}$ is alkyl, aryl, arylalkylenyl, or heteroaryl, each of which is optionally substituted by one or more substituents selected from the group consisting of alkyl, alkoxy, halogen, or dialkylamino. In some embodiments, $R_{4-1}$ is alkyl or phenyl. In some embodiments, $R_{4-1}$ is $C_{1-4}$ alkyl or phenyl. In some embodiments, $R_{4-1}$ is $C_{1-4}$ alkyl.

In some embodiments, $R_5$ is selected from the group consisting of:

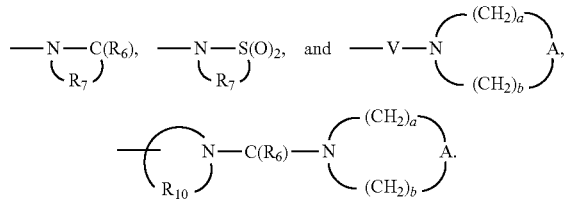

In some embodiments, $R_5$ is

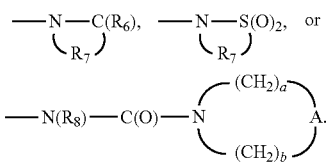

In some embodiments, $R_5$ is

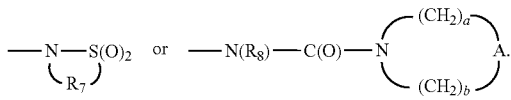

In some embodiments, $R_5$ is

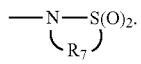

In some embodiments, $R_6$ is selected from the group consisting of =O and =S. In some embodiments, $R_6$ is =O. In some embodiments, $R_6$ is =S.

In some embodiments, $R_7$ is $C_{2-7}$ alkylene. In some embodiments, $R_7$ is $C_{3-4}$ alkylene. In some embodiments, $R_7$ is propylene.

In some embodiments, $R_8$ is selected from the group consisting of hydrogen, alkyl, alkoxyalkylenyl, and arylalkylenyl. In some embodiments, $R_8$ is hydrogen or alkyl. In some embodiments, $R_8$ is hydrogen.

In some embodiments, $R_9$ is selected from the group consisting of hydrogen and alkyl.

In some embodiments, $R_{10}$ is independently $C_{3-8}$ alkylene.

In some embodiments, Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino. In some embodiments, Ar is phenyl or heteroaryl which is unsubstituted or substituted by one or more substituents independently selected from the group consisting of alkyl, alkoxy, nitro, cyano, carboxy, halogen, hydroxyalkyl, amino, alkylamino, dialkylamino, trifluoromethyl, trifluoromethoxy, and thienyl. In certain of these embodiments heteroaryl is selected from the group consisting of benzothiazolyl, furanyl, imidazolyl, indolyl, isoxazolyl, oxadiazolyl, pyrazinyl, pyridinyl, pyrrolyl, thiazolyl, and thienyl. Also, in some embodiments, Ar is phenyl which is unsubstituted or substituted with one or more substitutents independently selected from the group consisting of alkyl, alkoxy, nitro, cyano, halogen, amino, alkylamino, dialkylamino, trifluoromethyl, and trifluoromethoxy. In some embodiments, Ar is phenyl.

In some embodiments, Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino. In some embodiments, Ar' is phenylene which is unsubstituted or substituted by one or more substituents independently selected from the group consisting of alkyl, alkoxy, nitro, cyano, halogen, amino, alkylamino, dialkylamino, trifluoromethyl, and trifluoromethoxy.

In some embodiments, A is selected from the group consisting of —O—, —C(O)—, —S(O)$_{0-2}$—, —CH$_2$—, and —N(R$_4$)—. In some embodiments, A is —O—.

In some embodiments, Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—. In some embodiments, Q is —C(R$_6$)—, —S(O)$_2$—, or —C(R$_6$)—N(R$_8$)—W—. In some embodiments, Q is —S(O)$_2$—. In some embodiments, Q is —C(R$_6$)—N(R$_8$)—W—.

In some embodiments, V is selected from the group consisting of —C(R$_6$)—, —O—C(R$_6$)—, —N(R$_8$)—C(R$_6$)—, and —S(O)$_2$—.

In some embodiments, W is selected from the group consisting of a bond, —C(O)—, and —S(O)$_2$—. In some embodiments, W is a bond.

In some embodiments, X is selected from the group consisting of alkylene, alkenylene, alkynylene, arylene, heteroarylene, and heterocyclylene wherein the alkylene, alkenylene, and alkynylene groups can be optionally interrupted by arylene, heteroarylene or heterocyclylene or by one or more —O— groups. In some embodiments, X is alkylene. In some embodiments, X is $C_{1-4}$ alkylene. In some embodiments, X is $C_{1-2}$ alkylene.

In some embodiments, X' is selected from the group consisting of alkylene, alkenylene, alkynylene, arylene, heteroarylene, and heterocyclylene wherein the alkylene, alkenylene, and alkynylene groups can be optionally interrupted by an arylene, heteroarylene or heterocyclylene group. In some embodiments, X' is alkylene. In some embodiments, X' is $C_{1-4}$ alkylene. In some embodiments, X' is $C_{1-2}$ alkylene.

In some embodiments, Y is selected from the group consisting of —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—,

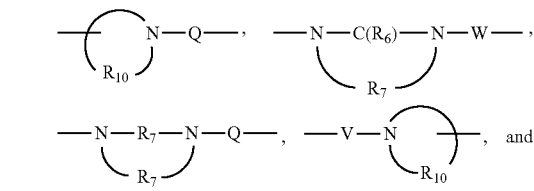

-continued

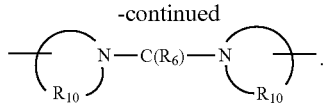

In some embodiments, Y is —N($R_8$)—C(O)—, —N($R_8$)—S(O)$_2$—, —N($R_8$)—C($R_6$)—N($R_8$)—, or

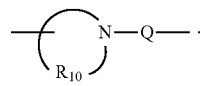

In some embodiments, Y is —N($R_8$)—C(O)—, —N($R_8$)—S(O)$_2$—, or —N($R_8$)—C($R_6$)—N($R_8$)—. In some embodiments, Y is —N($R_8$)—S(O)$_2$—, —S(O)$_2$—, —C($R_6$)—, or —C($R_6$)—O—. In some embodiments, Y is —NH—S(O)$_2$—, —S(O)$_2$—, —C(O)—, or —C(O)—O—. In some embodiments, Y is —S(O)$_2$— or —C(O)O—.

In some embodiments, Y' is selected from the group consisting of —S(O)$_2$—N($R_8$)—, —C($R_6$)—, —C($R_6$)—O—, —O—C(O)—O—, —N($R_8$)-Q-, —C($R_6$)—N($R_8$)—, —O—C($R_6$)—N($R_8$)—, —C($R_6$)—N(O$R_9$)—,

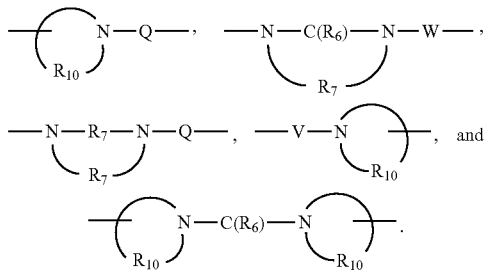

In some embodiments, Y' is —N($R_8$)—C($R_6$)—, —N($R_8$)—S(O)$_2$—, or —N($R_8$)—C($R_6$)—N($R_8$)—W—. In some embodiments, Y' is —N($R_8$)—C(O)—. In some embodiments, Y' is —N($R_8$)—S(O)$_2$—. In some embodiments, Y' is —N($R_8$)—C($R_6$)—N($R_8$)—.

In some embodiments, Z is selected from the group consisting of a bond, alkylene, alkenylene, and alkynylene wherein alkylene, alkenylene, and alkynylene are optionally interrupted with —O—. In some embodiments, Z is a bond, alkylene, or alkylene interrupted by —O—. Also, in some embodiments, Z is a bond or alkylene. In certain embodiments Z is $C_{1-3}$ alkylene. In certain embodiments Z is a bond.

In some embodiments, a and b are independently integers from 1 to 6 with the proviso that a+b is ≦7. In some embodiments, a and b are each the integer 2.

In some embodiments of Formulas I-III and XI, $R_3$—O— or $R_{3-1}$—O— is at the 7- or 8-position. In some embodiments $R_3$—O— or $R_{3-1}$—O— is at the 7-position. In some embodiments $R_3$—O— or $R_{3-1}$—O— is at the 8-position.

In some embodiments of Formulas VII and IX, HO— is at the 7- or 8-position. In some embodiments HO— is at the 7-position. In some embodiments HO— is at the 8-position.

In some embodiments, compounds of the invention induce the biosynthesis of one or more cytokines (for example IFN-α and or TNF-α). Compounds of the invention include, for example, compounds of Formulas I, II, III, and VII, as well as any of the embodiments thereof described herein.

In some embodiments, compounds of Formulas I, II, III, or embodiments thereof described herein inhibit the biosynthesis of one or more cytokines (for example TNF-a).

Preparation of Compounds

Compounds of the invention can be prepared according to Reaction Scheme I where R, $R_1$, $R_2$, and n are as defined above. In step (1) of Reaction Scheme I, a benzyloxyaniline of Formula XV is treated with the condensation product generated from 2,2-dimethyl-1,3-dioxane-4,6-dione (Meldrum's acid) and triethyl orthoformate to provide an imine of Formula XVI. The reaction is conveniently carried out by adding a solution of a benzyloxyaniline of Formula XV to a heated mixture of Meldrum's acid and triethyl orthoformate and heating the reaction at an elevated temperature such as 45° C. The product can be isolated using conventional methods.

In step (2) of Reaction Scheme I, an imine of Formula XVI undergoes thermolysis and cyclization to provide a benzyloxyquinolin-4-ol of Formula XVII. The reaction is conveniently carried out in a medium such as DOWTHERM A heat transfer fluid at a temperature between 200 and 250° C. The product can be isolated using conventional methods.

In step (3) of Reaction Scheme I, the benzyloxyquinolin-4-ol of Formula XVII is nitrated under conventional nitration conditions to provide a benzyloxy-3-nitroquinolin-4-ol of Formula XVIII. The reaction is conveniently carried out by adding nitric acid to the benzyloxyquinolin-4-ol of Formula XVII in a suitable solvent such as propionic acid and heating the mixture at an elevated temperature such as 125° C. The product can be isolated using conventional methods.

In step (4) of Reaction Scheme I, a benzyloxy-3-nitroquinolin-4-ol of Formula XVIII is chlorinated using conventional chlorination chemistry to provide a benzyloxy-4-chloro-3-nitroquinoline of Formula XIX. The reaction is conveniently carried out by treating the benzyloxy-3-nitroquinolin-4-ol of Formula XVIII with phosphorous oxychloride in a suitable solvent such as N,N-dimethylformamide (DMF). The reaction can be carried out at an elevated temperature such as 100° C., and the product can be isolated using conventional methods.

In step (5) of Reaction Scheme I, a benzyloxy-4-chloro-3-nitroquinoline of Formula XIX is treated with an amine of Formula $R_1$—$NH_2$ to provide a benzyloxy-3-nitroquinolin-4-amine of Formula XX. Several amines of Formula $R_1$—$NH_2$ are commercially available; others can be prepared by known synthetic methods. The reaction is conveniently carried out by adding the amine of Formula $R_1$—$NH_2$ to a solution of the benzyloxy-4-chloro-3-nitroquinoline of Formula XIX in a suitable solvent such as dichloromethane or methanol in the presence of a tertiary amine such as triethylamine The reaction can be carried out at ambient temperature or at an elevated temperature such as, for example, the reflux temperature of the solvent. The reaction product can be isolated using conventional methods.

In step (6) of Reaction Scheme I, a benzyloxy-3-nitroquinolin-4-amine of Formula XX is reduced to provide a benzyloxyquinoline-3,4-diamine of Formula XXI. The reaction can be carried out by hydrogenation using a heterogeneous hydrogenation catalyst such as platinum on carbon. The hydrogenation is conveniently carried out in a Parr apparatus in a suitable solvent such as toluene, methanol, or acetonitrile. The reaction can be carried out at ambient temperature or at an elevated temperature such as 55° C., and the product can be isolated using conventional methods.

Alternatively, the reduction in step (6) can be carried out using nickel boride, prepared in situ from sodium borohydride and nickel(II) chloride. The reduction is conveniently carried out by adding a solution of a benzyloxy-3-nitroquinolin-4-amine of Formula XX in a suitable solvent or solvent mixture such as dichloromethane/methanol to a mixture of excess sodium borohydride and catalytic nickel(II) chloride in methanol. The reaction can be carried out at ambient temperature. The product can be isolated using conventional methods.

In step (7) of Reaction Scheme I, a benzyloxyquinoline-3,4-diamine of Formula XXI is treated with a carboxylic acid equivalent to provide a benzyloxy-1H-imidazo[4,5-c]quinoline of Formula XXII. Suitable carboxylic acid equivalents include orthoesters of Formula $R_2C(O-alkyl)_3$, 1,1-dialkoxyalkyl alkanoates of Formula $R_2C(O\text{-alkyl})_2(O—C(O)\text{-alkyl})$, and acid chlorides of Formula $R_2C(O)Cl$. The selection of the carboxylic acid equivalent is determined by the desired substituent at $R_2$. For example, triethyl orthoformate will provide a compound where $R_2$ is hydrogen, and trimethyl orthovalerate will provide a compound where $R_2$ is a butyl group. The reaction is conveniently carried out by adding the carboxylic acid equivalent to a benzyloxyquinoline-3,4-diamine of Formula XXI in a suitable solvent such as toluene or xylenes. Optionally, catalytic pyridine hydrochloride can be added. The reaction is carried out at a temperature high enough to drive off alcohol or water formed during the reaction. Conveniently, a Dean-Stark trap can be used to collect the volatiles.

Alternatively, step (7) can be carried out in two steps when an acid chloride of Formula $R_2C(O)Cl$ is used as the carboxylic acid equivalent. Part (i) of step (7) is conveniently carried out by adding the acid chloride to a solution of a benzyloxyquinoline-3,4-diamine of Formula XXI in a suitable solvent such as dichloromethane or acetonitrile to afford an amide. Optionally, a tertiary amine such as triethylamine, pyridine, or 4-dimethylaminopyridine can be added. The reaction can be carried out at ambient temperature or at an elevated temperature. The amide product can be isolated and optionally purified using conventional techniques. Part (ii) of step (7) involves heating the amide prepared in part (i) to provide a benzyloxy-1H-imidazo[4,5-c]quinoline of Formula XXII. The reaction is conveniently carried out in a suitable solvent such as toluene at a temperature sufficient to drive off water formed during the reaction. In part (ii) of step (7), the imidazo ring forming reaction can also be carried out in a solvent such as ethanol or methanol in the presence of a base such as triethylamine or aqueous sodium hydroxide. The benzyloxy-1H-imidazo[4,5-c]quinoline of Formula XXII can be isolated using conventional methods.

In one embodiment, the present invention provides a process comprising the steps of (1) providing a 3-amido-4-aminoquinoline substituted at the 5-, 6-, 7-, or 8-position with one benzyloxy group and optionally with one R group, wherein amido is —NH—C(O)—$R_2$, amino is —NH—$R_1$, and R, $R_1$, and $R_2$ are as defined above; (2) preparing a mixture comprising an alcohol and the compound provided in step (1); and (3) contacting the mixture of step (2) with a base to provide a 1-H-imidazo[4,5-c]quinoline substituted at the 1-position with $R_1$, at the 2-position with $R_2$; and at the 5-, 6-, 7-, or 8-position with one benzyloxy group and optionally with one R group; wherein the base is aqueous sodium hydroxide or triethylamine. In certain embodiments, the alcohol is methanol, ethanol, or a mixture thereof. In certain embodiments, the base is aqueous sodium hydroxide.

In step (8) of Reaction Scheme I, a benzyloxy-1H-imidazo[4,5-c]quinoline of Formula XXII is oxidized to provide a benzyloxy-1H-imidazo[4,5-c]quinoline-5N-oxide of Formula XXIII using a conventional oxidizing agent capable of forming N-oxides. The reaction is conveniently carried out by adding 3-chloroperoxybenzoic acid to a solution of a compound of Formula XXII in a solvent such as dichloromethane or chloroform. The reaction can be carried out at ambient temperature, and the product can be isolated using conventional methods.

In step (9) of Reaction Scheme I, a benzyloxy-1H-imidazo[4,5-c]quinoline-5N-oxide of Formula XXIII is aminated to provide a benzyloxy-1H-imidazo[4,5-c]quinolin-4-amine of Formula XXIV, a subgenus of Formulas I, II, and III. Step (9) can be carried out by the activation of an N-oxide of Formula XXIII by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide to a solution of the N-oxide of Formula XXIII in a suitable solvent such as dichloromethane or chloroform and then adding p-toluenesulfonyl chloride. The reaction can be carried out at ambient temperature. The reaction may be carried out by adding ammonium hydroxide and p-toluenesulfonyl chloride to the reaction mixture from step (8) without isolating the N-oxide of Formula XXIII. The product or pharmaceutically acceptable salt thereof can be isolated using conventional methods.

Alternatively step (9) can be carried out by the reaction of a benzyloxy-1H-imidazo[4,5-c]quinoline-5N-oxide of Formula XXIII with trichloroacetyl isocyanate followed by hydrolysis of the resulting intermediate to provide a benzyloxy-1H-imidazo[4,5-c]quinolin-4-amine of Formula XXIV. The reaction is conveniently carried out in two steps by (i) adding trichloroacetyl isocyanate to a solution of the N-oxide of Formula XXIII in a solvent such as dichloromethane and stirring at ambient temperature to provide an isolable amide intermediate. In step (ii), a solution of the intermediate in methanol is treated with a base such as sodium methoxide or ammonium hydroxide at ambient temperature. The product or pharmaceutically acceptable salt thereof can be isolated using conventional methods.

Reaction Scheme I

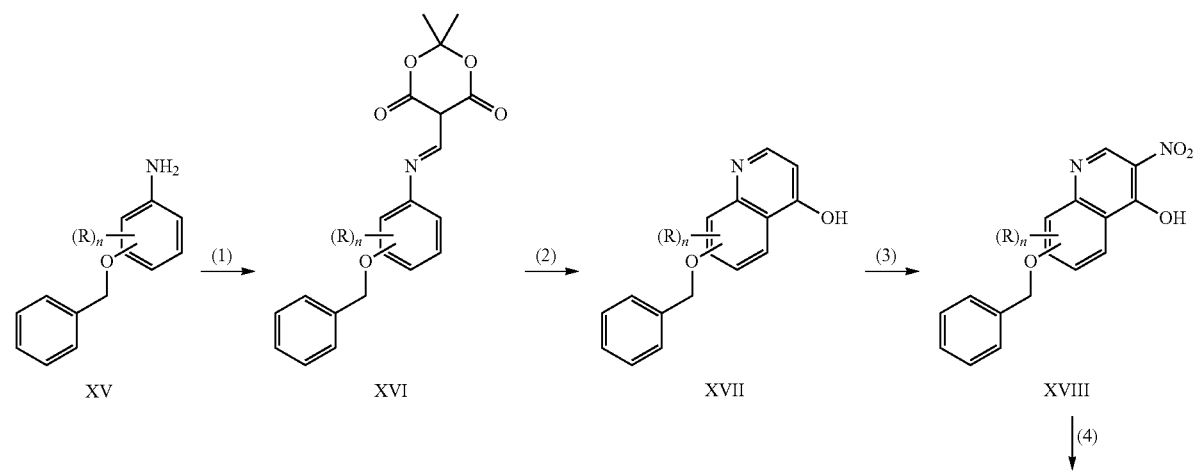

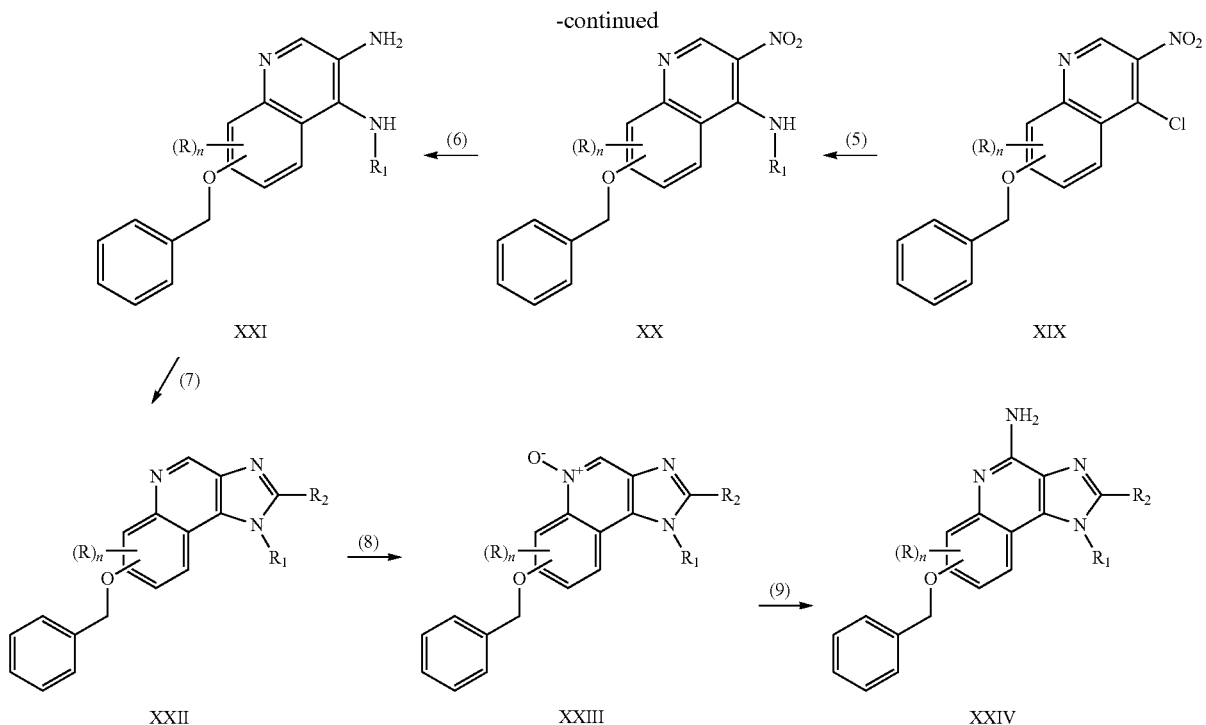

For some embodiments, compounds shown in Reaction Scheme I can be further elaborated using conventional synthetic methods. For example, an amine of Formula $R_1$—$NH_2$, where $R_1$ is $R_4$, may be substituted by a hydroxy or second amino group, which can be further functionalized before step (6) of Reaction Scheme I. For example, a benzyloxy-3-nitroquinolin-4-amine of Formula XX, in which $R_1$ is $R_4$ having a hydroxy substituent, can be chlorinated using conventional chlorinating agents and subsequently reacted with a thioalkoxide salt to provide a benzyloxy-3-nitroquinolin-4-amine of Formula XX in which $R_1$ is —X—Y—$R_4$, where X and $R_4$ are defined as above and Y is —S—. The chlorination reaction is conveniently carried out by adding thionyl chloride to a solution of a benzyloxy-3-nitroquinolin-4-amine of Formula XX, in which $R_1$ is $R_4$ having a hydroxy substituent, in a solvent such as dichloromethane and heating the reaction at an elevated temperature. The thioether group is conveniently introduced by adding thioalkoxide salt, such as sodium thiomethoxide, to a solution of a benzyloxy-3-nitroquinolin-4-amine of Formula XX, in which $R_1$ is $R_4$ having a chloro substituent, in a solvent such as DMF. The reaction may be carried out at ambient temperature or at an elevated temperature. The thioether group thus introduced may be oxidized to a sulfone group with excess oxidizing agent in step (8) of Reaction Scheme I to provide a benzyloxy-1H-imidazo[4,5-c]quinoline-5N-oxide of Formula XXIII in which $R_1$ is —X—Y—$R_4$, where Y is —$S(O)_2$—.

A benzyloxy-3-nitroquinolin-4-amine of Formula XX, in which $R_1$ is $R_4$ having an amino substituent, may also be functionalized before step (6) of Reaction Scheme I using conventional methods. For example, a benzyloxy-3-nitroquinolin-4-amine of Formula XX, in which $R_1$ is $R_4$ having an amino substituent, can react with a sulfonyl chloride of Formula $R_4$—$S(O)_2$Cl or a sulfonic anhydride of Formula ($R_4$—$S(O)_2)_2$O to provide a compound of Formula XX in which $R_1$ is —X—Y—$R_4$, where Y is —N($R_8$)—$S(O)_2$—, wherein $R_8$ is defined as above. Numerous sulfonyl chlorides and sulfonic anhydrides are commercially available; others can be readily prepared using known synthetic methods. The reaction can be conveniently carried out by adding the sulfonyl anhydride to a solution of a benzyloxy-3-nitroquinolin-4-amine of Formula XX, in which $R_1$ is $R_4$ having an amino substituent, and a base such as triethylamine in a suitable solvent such as dichloromethane. The reaction can be carried out at ambient temperature. The product can then be treated according to steps (6)-(9) of Reaction Scheme I.

In some embodiments, further elaboration at $R_1$ is introduced according to Reaction Scheme II where R, $R_2$, $R_4$, $R_5$, X, Q, and n are defined as above. In step (1) of Reaction Scheme II, a benzyloxy-4-chloro-3-nitroquinoline of Formula XIX is treated with a Boc-protected diamine of Formula $(CH_3)_3CO$—C(O)—NH—X—$NH_2$ to provide a benzyloxy-3-nitroquinolin-4-amine of Formula XXV. Several Boc-protected diamines of Formula $(CH_3)_3CO$—C(O)—NH—X—$NH_2$ are commercially available; others can be prepared by known synthetic methods. The reaction is conveniently carried out by adding the Boc-protected diamine of Formula $(CH_3)_3CO$—C(O)—NH—X—$NH_2$ to a cooled solution of the benzyloxy-4-chloro-3-nitroquinoline of Formula XIX in a suitable solvent such as dichloromethane or water in the presence of a tertiary amine such as triethylamine. The reaction can be carried out at ambient temperature or at an elevated temperature such as, for example, the reflux temperature of the solvent. The product can be isolated using conventional methods.

In steps (2)-(5) of Reaction Scheme II, a benzyloxy-3-nitroquinolin-4-amine of Formula XXV is first reduced to provide a benzyloxyquinoline-3,4-diamine of Formula XXVI, which is converted to benzyloxy-1H-imidazo[4,5-c]quinoline of Formula XXVII by reaction with a carboxylic acid equivalent. The benzyloxy-1H-imidazo[4,5-c]quinoline of Formula XXVII is then oxidized to afford a benzyloxy-1H-imidazo[4,5-c]quinoline-5N-oxide of Formula XXVIII, which is aminated to provide a benzyloxy-1H-imidazo[4,5-c]quinolin-4-amine of Formula XXIX, a subgenus of Formulas I, II, and III. Steps (2), (3), (4), and (5) of Reaction Scheme II can be carried out as described for steps (6), (7), (8), and (9), respectively, of Reaction Scheme I to provide a benzyloxy-1H-imidazo[4,5-c]quinolin-4-amine of Formula XXIX as the product formed after step (5). In step (5), the preferred conditions for amination are the activation of an N-oxide of Formula XXVIII by conversion to an ester and then reacting the ester with an aminating agent. Step (5) is conveniently carried out by adding ammonium hydroxide to a solution of the N-oxide of Formula XXVIII in a suitable solvent such as dichloromethane or dichloroethane and then adding p-toluenesulfonyl chloride and stirring at ambient temperature. The product can be isolated using conventional methods.

In step (6) of Reaction Scheme II, the Boc-protecting group of a benzyloxy-1H-imidazo[4,5-c]quinolin-4-amine of Formula XXIX is removed to provide a benzyloxy-1H-imidazo[4,5-c]quinolin-4-amine of Formula XXX, which represents a subgenus of Formulas I, II, and III. The reaction is conveniently carried out by adding a solution of hydrochloric acid in ethanol to a benzyloxy-1H-imidazo[4,5-c]quinolin-4-amine of Formula XXIX. The reaction can be carried out at an elevated temperature, for example, the reflux temperature of the solvent. The product or pharmaceutically acceptable salt thereof can be isolated by conventional methods.

In step (7) of Reaction Scheme II, a benzyloxy-1H-imidazo[4,5-c]quinolin-4-amine of Formula XXX is converted to a benzyloxy-1H-imidazo[4,5-c]quinolin-1-yl compound of Formula XXXI using conventional methods. For example, a benzyloxy-1H-imidazo[4,5-c]quinolin-4-amine of Formula XXX can react with an acid chloride of Formula $R_4C(O)Cl$ to provide a compound of Formula XXXI in which Q is —C(O)—. In addition, a benzyloxy-1H-imidazo[4,5-c]quinolin-4-amine of Formula XXX can react with sulfonyl chloride of Formula $R_4S(O)_2Cl$ or a sulfonic anhydride of Formula $(R_4S(O)_2)_2O$ to provide a compound of Formula XXXI in which Q is —S(O)$_2$—. Numerous acid chlorides of Formula $R_4C(O)Cl$, sulfonyl chlorides of Formula $R_4S(O)_2Cl$, and sulfonic anhydrides of Formula $(R_4S(O)_2)_2O$ are commercially available; others can be readily prepared using known synthetic methods. The reaction can be conveniently carried out by adding the acid chloride of Formula $R_1C(O)Cl$, sulfonyl chloride of Formula $R_1S(O)_2Cl$, or sulfonic anhydride of Formula $(R_4S(O)_2)_2O$ to a cooled solution of a benzyloxy-1H-imidazo[4,5-c]quinolin-4-amine of Formula XXX and a base such as triethylamine in a suitable solvent such as chloroform, dichloromethane, or acetonitrile. The reaction can be carried out at ambient temperature or a sub-ambient temperature such as 0° C. The product or pharmaceutically acceptable salt thereof can be isolated using conventional methods.

Ureas of Formula XXXI, where Q is —C(R$_6$)—N(R$_8$)—W—, in which R$_6$ is =O, R$_8$ is defined as above, and W is a bond, can be prepared by reacting a benzyloxy-1H-imidazo[4,5-c]quinolin-4-amine of Formula XXX with isocyanates of Formula $R_4N$=C=O or carbamoyl chlorides of Formula $R_4N$—(R$_8$)—C(O)Cl. Numerous isocyanates of Formula $R_4N$=C=O and carbamoyl chlorides of Formula $R_4N$—(R$_8$)—C(O)Cl are commercially available; others can be readily prepared using known synthetic methods. The reaction can be conveniently carried out by adding the isocyanate or carbamoyl chloride to a cooled solution of a benzyloxy-1H-imidazo[4,5-c]quinolin-4-amine of Formula XXX and a base such as triethylamine in a suitable solvent such as dichloromethane or chloroform. The reaction can be carried out at ambient temperature or a sub-ambient temperature such as 0° C. Alternatively, a compound of Formula XXX can be treated with an isocyanate of Formula $R_4(CO)N$=C=O, a thioisocyanate of Formula $R_4N$=C=S, or a sulfonyl isocyanate of Formula $R_4S(O)_2N$=C=O to provide a compound of Formula XXXI, where Q is —C(R$_6$)—N(R$_8$)—W—, in which R$_6$, R$_8$, and W are defined as above. The product or pharmaceutically acceptable salt thereof can be isolated using conventional methods.

A benzyloxy-1H-imidazo[4,5-c]quinolin-4-amine of Formula XXX can also be converted to a benzyloxy-1H-imidazo[4,5-c]quinolin-1-yl compound of Formula XXXIa, wherein R$_5$ is

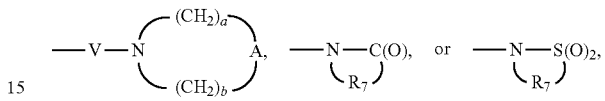

where V is —N(R$_8$)—C(R$_6$)—, and a, b, R$_6$, R$_7$, R$_8$, and A are as defined above, as shown in step (7a) of Reaction Scheme II.

A compound of Formula XXX can be treated with a carbamoyl chloride of Formula

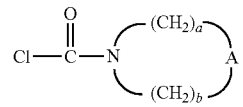

under the conditions described in step (7) to provide a compound of Formula XXXIa, wherein R$_5$ is

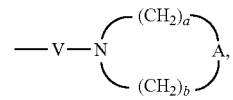

where V is —NH—C(O)—, and A is as defined above. The product or pharmaceutically acceptable salt thereof can be isolated using conventional methods.

In step (7a), a compound of Formula XXX can also react with a chloroalkanesulfonyl chloride of Formula Cl—R$_7$S(O)$_2$Cl or a chloroalkanoyl chloride of Formula C$_1$—R$_7$C(O)Cl, wherein R$_7$ is as defined above. The reaction is conveniently carried out by adding the chloroalkanesulfonyl chloride or chloroalkanoyl chloride to a solution of amine in a suitable solvent such as chloroform or dichloromethane in the presence of a base such as triethylamine at ambient temperature. The isolable intermediate chloroalkanesulfonamide or chloroalkanamide can then be treated with a base such as 1,8-diazabicyclo[5.4.0]undec-7-ene at ambient temperature in a suitable solvent such as DMF to effect the cyclization to afford a compound of Formula XXXIa in which R$_5$ is

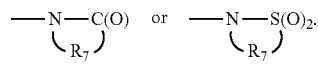

The product or pharmaceutically acceptable salt thereof can be isolated using conventional methods.

It may be desirable in some instances to carry out the steps of Reaction Scheme II in a different order. For example, a compound of Formula XXVII may be deprotected according to step (6), and the resulting amine may be functionalized as in step (7) or (7a) prior to the oxidation and amination steps (4) and (5), respectively.

Reaction Scheme II

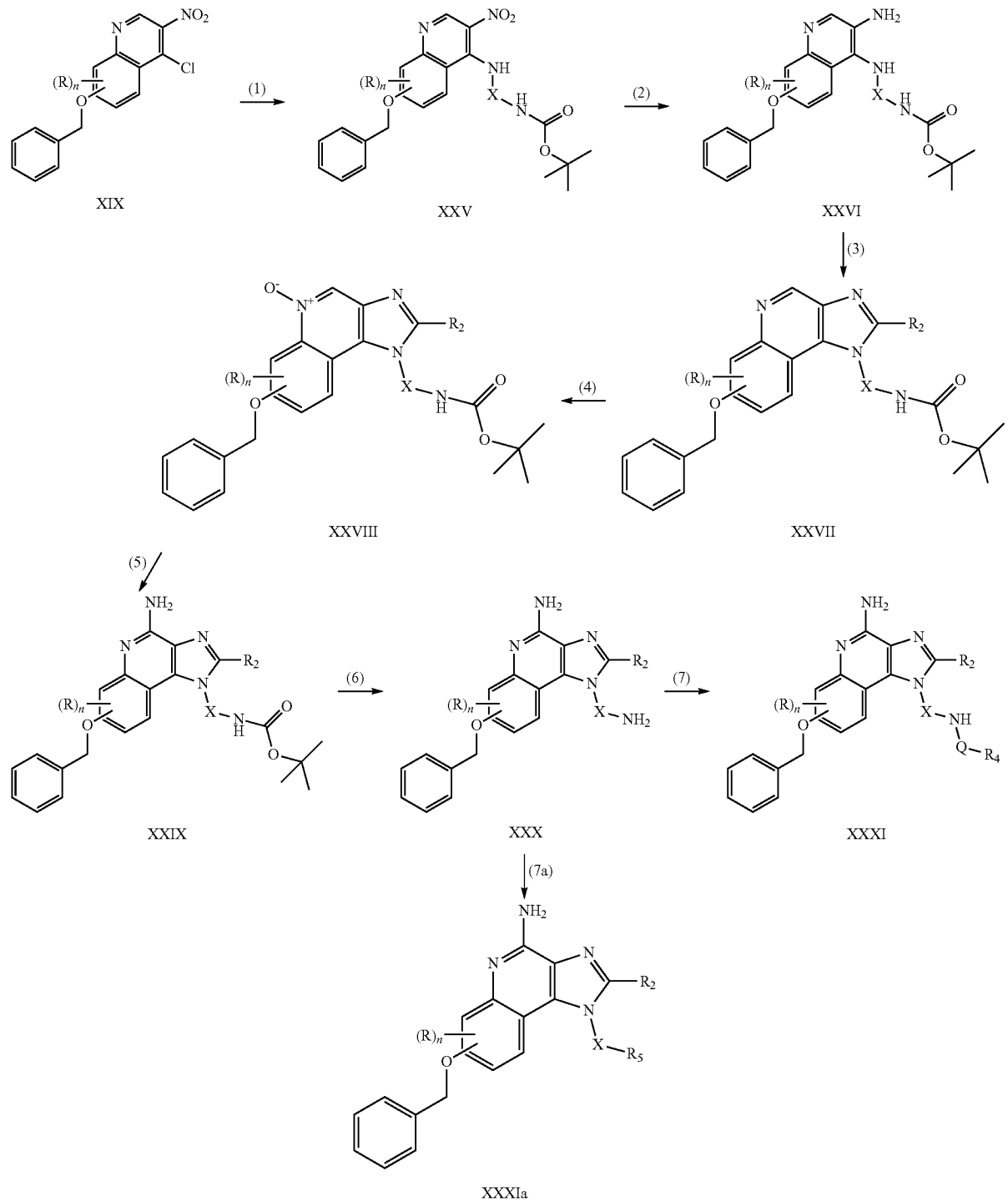

Synthetic transformations similar to those described in steps (7) and (7a) of Reaction Scheme II can also be made at $R_2$ of a benzyloxy-1H-imidazo[4,5-c]quinoline of Formula XXIV if, for example, an acid chloride used in step (7) of Reaction Scheme I contains a protected hydroxy or amino group or a halogen. Several acid chlorides of this type, for example acetoxyacetyl chloride and chloroacetyl chloride, are commercially available; others such as 5-(tert-butoxycarbonylamino)valeryl chloride can be prepared using known synthetic methods. An $R_2$ functional group introduced in this manner can then be manipulated to reveal an amino group, which can be converted into a variety of functional groups according to the methods described in steps (7) and (7a) of Reaction Scheme II. For example, chloroacetyl chloride can be used in step (7) of Reaction Scheme I to introduce a chloromethyl-substituted benzyloxy-1H-imidazo[4,5-c]

quinoline, which can be oxidized and aminated according to steps (8) and (9) of Reaction Scheme I. The resulting chloromethyl-substituted benzyloxy-1H-imidazo[4,5-c]quinolin-4-amine can be treated with ammonia in a suitable solvent such as methanol to provide an aminomethyl-substituted benzyloxy-1H-imidazo[4,5-c]quinolin-4-amine, which can then treated according to the methods described in step (7) or (7a) of Reaction Scheme II to provide a variety of compounds.

Compounds of the invention can be prepared according to Reaction Scheme III where R, $R_1$, $R_2$, and n are defined as above and $R_3$ is —Z—Ar, —Z—Ar'—Y—$R_4$, or —Z—Ar'—X—Y—$R_4$ where Z, Ar, Ar', X, Y, and $R_4$ are defined as above. In step (1) of Reaction Scheme III, the benzyl group of a benzyloxy-1H-imidazo[4,5-c]quinolin-4-amine of Formula XXIV is cleaved to provide a 1H-imidazo[4,5-c]quinolinol of Formula XXXII. The cleavage is conveniently carried out on a Parr apparatus out under hydrogenolysis conditions using a suitable heterogeneous catalyst such as palladium on carbon in a solvent such as ethanol. The product or pharmaceutically acceptable salt thereof can be isolated using conventional methods.

In step (2) of Reaction Scheme III a 1H-imidazo[4,5-c]quinolinol of Formula XXXII is converted to an ether-substituted 1H-imidazo[4,5-c]quinolin-4-amine of Formula II using a Williamson-type ether synthesis. The reaction is effected by treating a 1H-imidazo[4,5-c]quinolinol of Formula XXXII with an alkyl or aryl halide of Formula Halide-Z—Ar, Halide-Z—Ar'—Y—$R_4$, or Halide-Z—Ar'—X—Y—$R_4$ in the presence of a base. Numerous alkyl or aryl halides of these formulas are commercially available, including substituted benzyl bromides and chlorides, substituted or unsubstituted arylalkylenyl bromides and chlorides, and substituted fluorobenzenes. Other alkyl or aryl halides of these formulas can be prepared using conventional synthetic methods. The reaction is conveniently carried out by combining a reagent of Formula Halide-Z—Ar, Halide-Z—Ar'—Y—$R_4$, or Halide-Z—Ar'—X—Y—$R_4$ with a 1H-imidazo[4,5-c]quinolinol of Formula XXXII in a solvent such as DMF in the presence of a suitable base such as cesium carbonate or potassium carbonate. Optionally, catalytic tetrabutylammonium bromide can be added. The reaction can be carried out at ambient temperature or at an elevated temperature, for example 65° C. or 85° C., depending on the reactivity of the reagent of Formula Halide-Z—Ar, Halide-Z—Ar'—Y—$R_4$, or Halide-Z—Ar'—X—Y—$R_4$. The product or pharmaceutically acceptable salt thereof can be isolated using conventional methods.

Alternatively, step (2) may be carried out using the Ullmann ether synthesis, in which an alkali metal aryloxide of a 1-H-imidazo[4,5-c]quinolinol of Formula XXXII reacts with an aryl halide in the presence of copper salts, to provide compounds of Formula II, where $R_3$ is —Z—Ar or —Z—Ar'—Y—$R_4$, and Z is a bond.

Step (2) of Reaction Scheme III can alternatively be carried out by treating a 1H-imidazo[4,5-c]quinolinol of Formula XXXII with an alcohol of Formula HO—Z—Ar under Mitsunobu reaction conditions. Some alcohols of this formula, such as 3-pyridylcarbinol and 3-furanmethanol, are commercially available, and others can be prepared using conventional synthetic methods. The reaction is conveniently carried out by out by adding triphenylphosphine and an alcohol of Formula HO—Z—Ar to a solution of a 1H-imidazo[4,5-c]quinolinol of Formula XXXII in a suitable solvent such as tetrahydrofuran and then slowly adding diisopropyl azodicarboxylate. The reaction can be carried out at ambient temperature or at a sub-ambient temperature, such as 0° C. The product can be isolated using conventional methods.

Reaction Scheme III

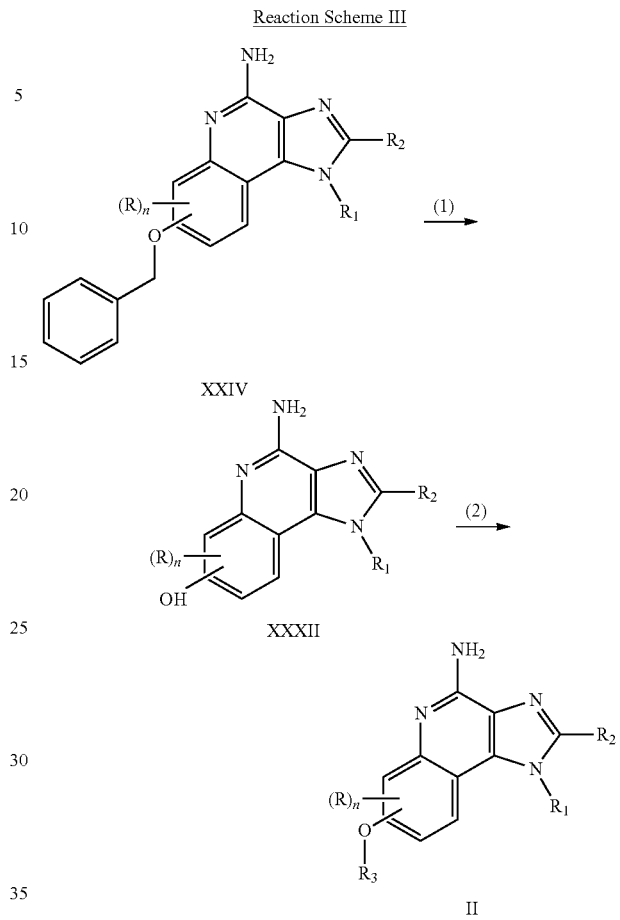

Compounds of the invention can be prepared according to Reaction Scheme IV, where R, $R_1$, $R_2$, and n are defined as above and $R_3$ is —Z—Ar, —Z—Ar'—Y—$R_4$, —Z—Ar'—X—Y—$R_4$, where Z, Ar, Ar', X, Y, and $R_4$ are defined as above. In step (1) of Reaction Scheme IV, the benzyl group of a benzyloxy-1H-imidazo[4,5-c]quinoline of Formula XXII is cleaved to provide a 1H-imidazo[4,5-c]quinolinol of Formula XXXIII. The reaction can be carried out as described in step (1) of Reaction Scheme III, or the reaction can be carried out by transfer hydrogenation in the presence of a suitable hydrogenation catalyst. The transfer hydrogenation is conveniently carried out by adding ammonium formate to a solution of a benzyloxy-1H-imidazo[4,5-c]quinoline of Formula XXII in a suitable solvent such as ethanol in the presence of a catalyst such as palladium on carbon. The reaction is carried out at an elevated temperature, for example, the refluxing temperature of the solvent.

In step (2) of Reaction Scheme IV, a 1H-imidazo[4,5-c]quinolinol of Formula XXXIII is treated with an alkyl or aryl halide of Formula Halide-Z—Ar, Halide-Z—Ar'—Y—$R_4$, or Halide-Z—Ar'—X—Y—$R_4$ to afford an ether-substituted 1H-imidazo[4,5-c]quinoline of Formula XI. The reaction can be carried out as described in step (2) of Reaction Scheme III.

In steps (3) and (4) of Reaction Scheme IV, an ether-substituted 1H-imidazo[4,5-c]quinoline of Formula XI is oxidized to afford a 1H-imidazo[4,5-c]quinoline-5N-oxide of Formula X, which is aminated to provide a 1H-imidazo[4,5-c]quinolin-4-amine of Formula II. Steps (3) and (4) can be carried out as described in steps (8) and (9), respectively, of Reaction Scheme I. The product or pharmaceutically acceptable salt thereof can be isolated using conventional methods.

Reaction Scheme IV

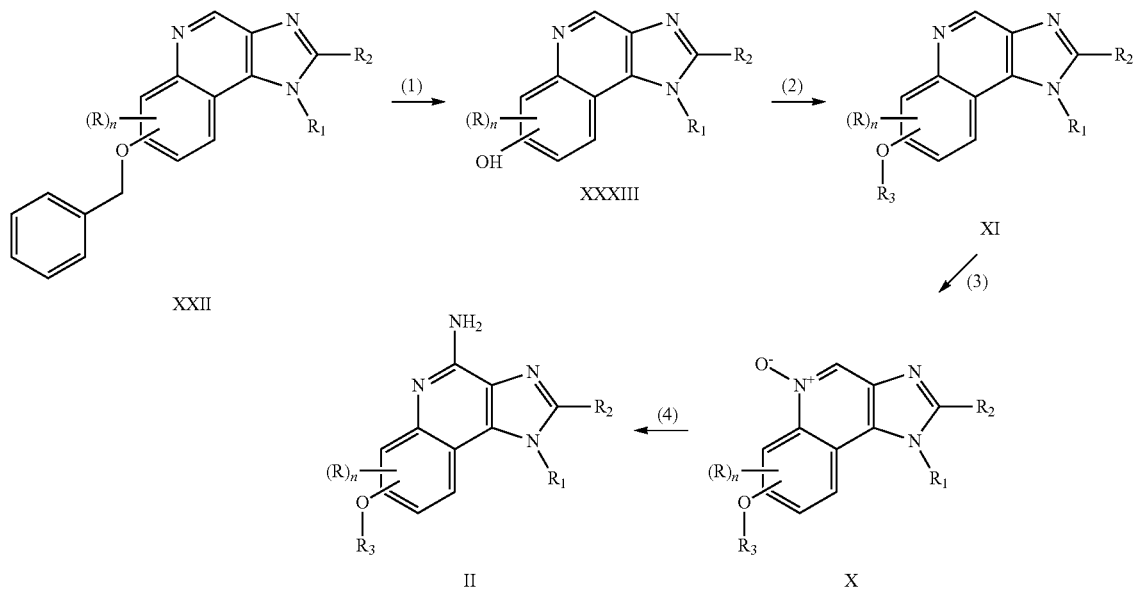

Further synthetic elaboration of ether-substituted 1H-imidazo[4,5-c]quinolin-4-amines of Formula II, prepared in Reaction Scheme III or IV, or ether-substituted 1H-imidazo[4,5-c]quinolines of Formula XI, intermediates in Reaction Scheme IV, is possible. For example, a nitro substituent on the aryl or heteroaryl group on a compound of Formula II, where $R_3$ is —Z—Ar, can be reduced to an amino group using conventional methods. The reduction can be carried out using the methods described in step (6) of Reaction Scheme I. The resulting amino substituent on the aryl or heteroaryl group on a compound of Formula II or XI, where $R_3$ is —Z—Ar, can be further elaborated as described below.

An amino substituent on the aryl or heteroaryl group on a compound of Formula II or XI, where $R_3$ is —Z—Ar, can be reacted with an aldehyde to provide an imine that can be reduced using conventional methods to provide a compound of Formula II or XI, wherein $R_3$ is —Z—Ar'—N($R_8$)—H, and $R_8$ is as defined above, or a pharmaceutically acceptable salt thereof. A compound of Formula II or XI, where $R_3$ is —Z—Ar'—N($R_8$)—H can be treated according to the methods described in step (7) or (7a) of Reaction Scheme II to provide a compound of Formula II or XI in which $R_3$ is —Z—Ar'—N($R_8$)-Q-$R_4$ or —Z—Ar'—$R_5$, wherein Q, $R_4$, and $R_8$ are as defined above and $R_5$ is

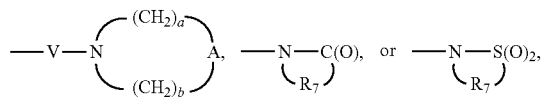

wherein V is —N($R_8$)—C($R_6$)—, and a, b, $R_6$, $R_7$, $R_8$, and A are as defined above. A compound of Formula XI, in which $R_3$ is —Z—Ar'-N($R_8$)-Q-$R_4$ or —Z—Ar'—$R_5$, can be converted into compound of Formula II or a pharmaceutically acceptable salt thereof using the chemistry described in steps (3) and (4) in Reaction Scheme IV.

Compounds of Formula II, where R, $R_1$, $R_2$, and n are defined as above and $R_3$ is —Z—Ar or —Z—Ar'—Y—$R_4$, where Z is a bond, and Ar, Ar', Y, and $R_4$ are defined as above, may alternatively be prepared as shown in Reaction Scheme V and Reaction Scheme VI wherein Hal is halogen. Step (1) of Reaction Scheme V and Reaction Scheme VI may be carried out using the Ullmann ether synthesis, in which an alkali metal aryloxide of an aryl alcohol of Formula ArOH or HOAr—Y—$R_4$ reacts with a halogen-substituted 1H-imidazo[4,5-c]quinolin-4-amine of Formula XXXIV or a halogen-substituted 1H-imidazo[4,5-c]quinoline of Formula XXXV in the presence of copper salts. Many compounds of Formulae XXXIV and XXXV are known. See, for example, U.S. Pat. Nos. 4,689,338; 4,929,624; 5,268,376; 5,346,905; 5,389,640; 5,756,746; 6,331,539; 6,451,810; 6,541,485; 6,545,016; 6,660,747; 6,683,088; 6,656,938; 6,664,264; and 6,664,260; European Patent Application 1 104 764; and Japanese Patent Application 9-255926. Others can be readily prepared using known synthetic methods. See, for example, U.S. Pat. Nos. 4,988,815; 5,175,296; 5,367,076; 5,395,937; and 5,741,908. Several aryl alcohols of Formulae ArOH or HOAr—Y—$R_4$ are known; others can be prepared using known synthetic methods. In Reaction Scheme I, the reaction of a halogen-substituted 1H-imidazo[4,5-c]quinolin-4-amine of Formula XXXIV under Ullmann conditions would provide an ether-substituted 1H-imidazo[4,5-c]quinolin-4-amine of Formula II.

Reaction Scheme V

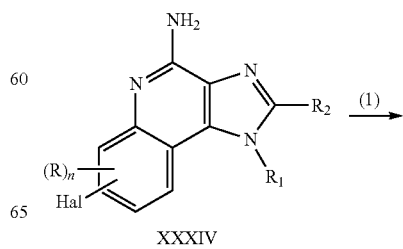

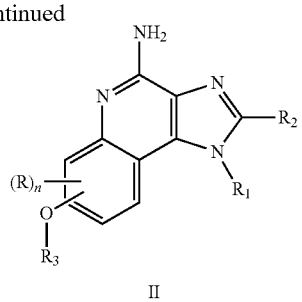

In Reaction Scheme VI the reaction of halogen-substituted 1H-imidazo[4,5-c]quinoline of Formula XXXV would provide an ether-substituted 1H-imidazo[4,5-c]quinoline of Formula XI. In steps (2) and (3) of Reaction Scheme VI an ether-substituted 1H-imidazo[4,5-c]quinoline of Formula XI can be oxidized to afford a 1H-imidazo[4,5-c]quinoline-5N-oxide of Formula X, which can be aminated to provide a 1H-imidazo[4,5-c]quinolin-4-amine of Formula II. Steps (2) and (3) of Reaction Scheme VI can be carried out as described in steps (3) and (4) of Reaction Scheme IV.

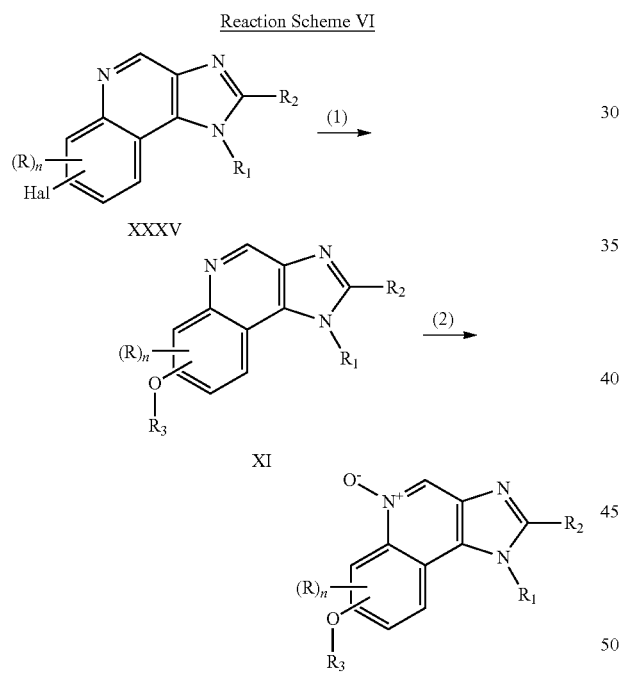

Compounds of the invention can be prepared according to Reaction Scheme VII, where Ar, R, $R_1$, $R_2$, and n are as defined above.

In step (1) of Reaction Scheme VII, a 1H-imidazo[4,5-c]quinolinol of Formula XXXII is alkylated with a bromide of the Formula Br—$(CH_2)_m$—C≡CH to provide a 1H-imidazo[4,5-c]quinolinyl ether of Formula XXXVI. The compound of Formula XXXII and the bromide are combined in a suitable solvent such as DMF in the presence of cesium carbonate. The reaction can be run at ambient temperature.

In step (2) of Reaction Scheme VII, a 1H-imidazo[4,5-c]quinoline of Formula XXXVI is coupled with a halide of the Formula halide-Ar using Sonogashira reaction conditions to provide a 1H-imidazo[4,5-c]quinoline of Formula IIa, which is a subgenus of Formula II. A compound of the Formula XXXVI is combined with the halide in the presence of copper (I) iodide, dichlorobis(triphenylphosphine)palladium(II), and excess triethylamine in a suitable solvent such as DMF. The reaction is preferably carried out at an elevated temperature (60-80° C.).

In step (3) of Reaction Scheme VII, the alkyne bond of a 1H-imidazo[4,5-c]quinoline of Formula IIa is reduced to provide a 1H-imidazo[4,5-c]quinoline of Formula IIb, which is a subgenus of Formula II. The reduction can be carried out by hydrogenation using a conventional heterogeneous hydrogenation catalyst such as palladium on carbon. The hydrogenation is conveniently carried out in a Parr apparatus in a suitable solvent such as ethanol. The reaction can be run at ambient temperature. The product or a pharmaceutically acceptable salt thereof can be isolated using conventional methods.

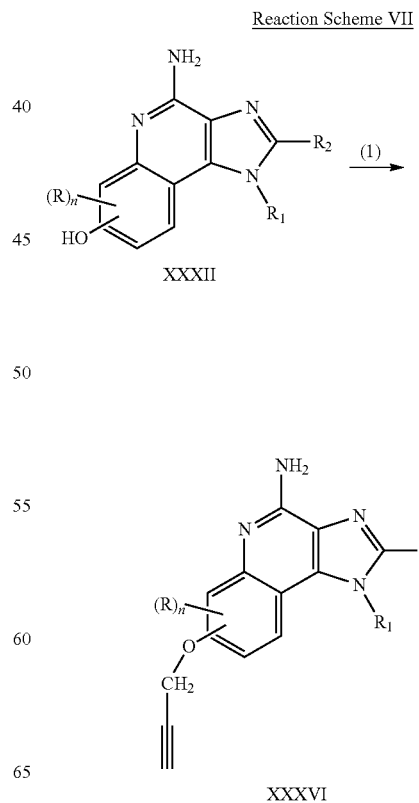

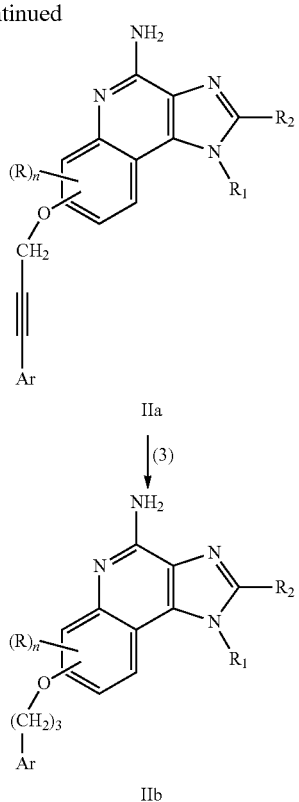

IIa

IIb

Pharmaceutical Compositions and Biological Activity

Pharmaceutical compositions of the invention contain a therapeutically effective amount of a compound of the invention as described above in combination with a pharmaceutically acceptable carrier.

The term "a therapeutically effective amount" or "effective amount" means an amount of the compound sufficient to induce a therapeutic or prophylactic effect, such as cytokine induction, cytokine inhibition, immunomodulation, antitumor activity, and/or antiviral activity. Although the exact amount of active compound used in a pharmaceutical composition of the invention will vary according to factors known to those of skill in the art, such as the physical and chemical nature of the compound, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (μg/kg) to about 5 mg/kg, of the compound to the subject. A variety of dosage forms may be used, such as tablets, lozenges, capsules, parenteral formulations, syrups, creams, ointments, aerosol formulations, transdermal patches, transmucosal patches and the like.

The compounds of the invention can be administered as the single therapeutic agent in the treatment regimen, or the compounds of the invention may be administered in combination with one another or with other active agents, including additional immune response modifiers, antivirals, antibiotics, antibodies, proteins, peptides, oligonucleotides, etc.

Compounds of the invention have been shown to induce, and certain compounds of the invention may inhibit, the production of certain cytokines in experiments performed according to the tests set forth below. These results indicate that the compounds are useful as immune response modifiers that can modulate the immune response in a number of different ways, rendering them useful in the treatment of a variety of disorders.

Cytokines whose production may be induced by the administration of compounds according to the invention generally include interferon-α (IFN-α) and/or tumor necrosis factor-α (TNF-α) as well as certain interleukins (IL). Cytokines whose biosynthesis may be induced by compounds of the invention include IFN-α, TNF-α, IL-1, IL-6, IL-10 and IL-12, and a variety of other cytokines. Among other effects, these and other cytokines can inhibit virus production and tumor cell growth, making the compounds useful in the treatment of viral diseases and neoplastic diseases. Accordingly, the invention provides a method of inducing cytokine biosynthesis in an animal comprising administering an effective amount of a compound or composition of the invention to the animal. The animal to which the compound or composition is administered for induction of cytokine biosynthesis may have a disease as described infra, for example a viral disease or a neoplastic disease, and administration of the compound may provide therapeutic treatment. Alternatively, the compound may be administered to the animal prior to the animal acquiring the disease so that administration of the compound may provide a prophylactic treatment.

In addition to the ability to induce the production of cytokines, compounds of the invention may affect other aspects of the innate immune response. For example, natural killer cell activity may be stimulated, an effect that may be due to cytokine induction. The compounds may also activate macrophages, which in turn stimulate secretion of nitric oxide and the production of additional cytokines. Further, the compounds may cause proliferation and differentiation of B-lymphocytes.

Compounds of the invention can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds.

Other cytokines whose production may be inhibited by the administration of certain compounds according to the invention include tumor necrosis factor-α (TNF-α). Among other effects, inhibition of TNF-α production can provide prophylaxis or therapeutic treatment of diseases in animals in which TNF is mediated, making the compounds useful in the treatment of, for example, autoimmune diseases. Accordingly, the invention provides a method of inhibiting TNF-α biosynthesis in an animal comprising administering an effective amount of a compound or composition of the invention to the animal. The animal to which the compound or composition is administered for inhibition of TNF-α biosynthesis may have a disease as described infra, for example an autoimmune disease, and administration of the compound may provide therapeutic treatment. Alternatively, the compound may be administered to the animal prior to the animal acquiring the disease so that administration of the compound may provide a prophylactic treatment.

Whether for prophylaxis or therapeutic treatment of a disease, and whether for effecting innate or acquired immunity, the compound or composition may be administered alone or in combination with one or more active components as in, for example, a vaccine adjuvant. When administered with other components, the compound and other component or components may be administered separately; together but independently such as in a solution; or together and associated with one another such as (a) covalently linked or (b) non-covalently associated, e.g., in a colloidal suspension.

Conditions for which IRMs identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV), a coronavirus (e.g., SARS), a papovavirus, (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases, such as, for example, diseases resulting from infection by bacteria of, for example, the genus *Escherichia, Enterobacter, Salmonella*, Staphylococci, *Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella*;

(c) other infectious diseases, such as chlamydia, fungal diseases, such as, for example, candidiasis, aspergillosis, histoplasmonsis, cryptococcal meningitis, or parasitic diseases, such as, for example, malaria, pneumocystis carnii pneomonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell leukemia, Karposi's sarcoma, melanoma, renal cell carcinoma, leukemias, such as, for example, myelogeous leukemia, chronic lymphocytic leukemia, and multiple myeloma, non-Hodgkin's lymphoma, cutaneous T-cell lymphoma, B-cell lymphoma, hairy cell leukemia, and other cancers; and (e) $T_H2$-mediated, atopic, and autoimmune diseases, such as atopic dermatitis or eczema, eosinophilia, asthma, allergy, allergic rhinitis, systemic lupus erythematosis, essential thrombocythaemia, multiple sclerosis, Ommen's syndrome, discoid lupus, alopecia greata, inhibition of keloid formation and other types of scarring, and enhancing wound healing, including chronic wounds.

IRMs identified herein also may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; recombinant proteins; and the like, for use in connection with, for example, BCG, cholera, plague, typhoid, hepatitis A, hepatitis B, and hepatitis C, influenza A and influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

IRMs may also be particularly helpful in individuals having compromised immune function. For example, IRM compounds may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention or a combination thereof to the animal. An animal may also be vaccinated by administering an effective amount of a compound or salt of the invention or a combination thereof to the animal as a vaccine adjuvant.

An amount of a compound effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased over the background level of such cytokines. The precise amount will vary according to factors known in the art but is expected to be a dose of about 100 ng/kg to about 50 mg/kg, preferably about 10 µg/kg to about 5 mg/kg. The invention also provides a method of treating a viral infection in an animal and a method of treating a neoplastic disease in an animal comprising administering an effective amount of a compound or composition of the invention to the animal.

An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 ng/kg to about 5 mg/kg. An amount of a compound effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 ng/kg to about 5 mg/kg.

In certain embodiments, there is provided a method of inducing cytokine biosynthesis in an animal comprising administering an effective amount of a compound or salt described herein to the animal. In another embodiment, there is provided a method of treating a viral disease in an animal comprising administering a therapeutically effective amount of a compound or salt described herein to the animal. In another embodiment, there is provided a method of treating a neoplastic disease in an animal comprising administering a therapeutically effective amount of a compound or salt described herein to the animal.

EXAMPLES

Example 1

7-Benzyloxy-1-(2-methylpropyl)-2-propyl-1H-imidazo[4,5-c]quinolin-4-amine

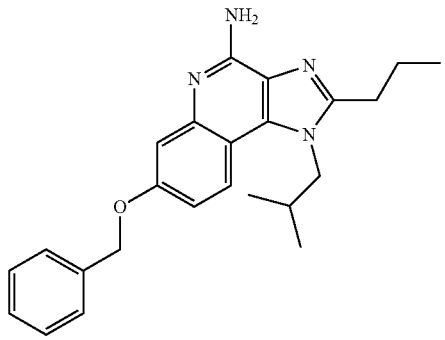

Part A

A mixture of triethyl orthoformate (92 mL, 0.55 mol) and 2,2-dimethyl-[1,3]-dioxane-4,6-dione (75.3 g, 0.522 mol) (Meldrum's acid) was heated at 55° C. for 90 minutes and then cooled to 45° C. A solution of 3-benzyloxyaniline (100.2 g, 0.5029 mol) in methanol (200 mL) was slowly added to the reaction over a period 45 minutes while maintaining the reaction temperature below 50° C. The reaction was then heated at 45° C. for one hour, allowed to cool to room temperature, and stirred overnight. The reaction mixture was cooled to 1° C., and the product was isolated by filtration and washed with cold ethanol (~400 mL) until the filtrate was colorless. 5-{[(3-Benzyloxy)phenylimino]methyl}-2,2-dimethyl-[1,3]-dioxane-4,6-dione (170.65 g) was isolated as a tan, powdery solid.

$^1$H NMR (300 MHz, DMSO-$d_6$): δ 11.21 (d, J=14.2 Hz, 1H), 8.61 (d, J=14.2 Hz, 1H), 7.49-7.30 (m, 7H), 7.12 (dd, J=8.1, 1.96 Hz, 1H), 6.91 (dd, J=8.4, 2.1 Hz, 1H), 5.16 (s, 2H), 1.68 (s, 6H).

Part B

A mixture of 5-{[(3-benzyloxy)phenylimino]methyl}-2,2-dimethyl-[1,3]-dioxane-4,6-dione (170.65 g, 0.483 mol) and DOWTHERM A heat transfer fluid (800 mL) was heated to 100° C. and then slowly added to a flask containing DOWTHERM A heat transfer fluid (1.3 L, heated at 210° C.) over a period of 40 minutes. During the addition, the reaction temperature was not allowed to fall below 207° C. Following the addition, the reaction was stirred at 210° C. for one hour, and then allowed to cool to ambient temperature. A precipitate formed, which was isolated by filtration, washed with diethyl ether (1.7 L) and acetone (0.5 L), and dried in an oven to provide 76.5 g of 7-benzyloxyquinolin-4-ol as a tan powder.

$^1$H NMR (300 MHz, DMSO-$d_6$): δ 11.53 (s, 1H), 7.99 (dd, J=2.4, 7.4 Hz, 1H), 7.79 (d, J=7.4 Hz, 1H), 7.50-7.32 (m, 5H), 7.00 (s, 1H), 6.98 (dd, J=2.5, 7.4 Hz, 1H), 5.93 (d, J=7.5 Hz, 1H), 5.20 (s, 2H).

Part C

A mixture of 7-benzyloxyquinolin-4-ol (71.47 g, 0.2844 mol) and propionic acid (700 mL) was heated to 125° C. with vigorous stirring. Nitric acid (23.11 mL of 16 M) was slowly added over a period of 30 minutes while maintaining the reaction temperature between 121° C. and 125° C. After the addition, the reaction was stirred at 125° C. for 1 hour then allowed to cool to ambient temperature. The resulting solid was isolated by filtration, washed with water, and dried in an oven for 1.5 days to provide 69.13 g of 7-benzyloxy-3-nitroquinolin-4-ol as a grayish powder.

$^1$H NMR (300 MHz, DMSO-$d_6$): δ 12.77 (s, 1H), 9.12 (s, 1H), 8.17 (dd, J=3.3, 6.3 Hz, 1H), 7.51-7.33 (m, 5H), 7.21-7.17 (m, 2H), 5.25 (s, 2H).

Part D

N,N-Dimethylformamide (100 mL) (DMF) was cooled to 0° C., and phosphorous oxychloride (27.5 mL, 0.295 mol) was added dropwise. The resulting solution was stirred for 25 minutes and then added dropwise to a mixture of 7-benzyloxy-3-nitroquinolin-4-ol (72.87 g, 0.2459 mol) in DMF (400 mL). Following the addition, the reaction was heated at 100° C. for 5 minutes, cooled to ambient temperature, and poured into ice water with stirring. A tan precipitate formed, which was isolated by filtration and dissolved in dichloromethane. The resulting solution was dried over magnesium sulfate, filtered, and concentrated under reduced pressure to yield 72.9 g of 7-benzyloxy-4-chloro-3-nitroquinoline as a light brown solid.

$^1$H NMR (300 MHz, DMSO-$d_6$): δ 9.34 (s, 1H), 8.36 (d, J=8.7 Hz, 1H), 7.71 (d, J=2.4 Hz, 1H), 7.66 (dd, J=2.4, 9.3 Hz, 1H), 7.56-7.51 (m, 2H), 7.46-7.34 (m, 3H), 5.40 (s, 2H).

Part E

Triethylamine (38.6 mL, 0.277 mol) was added to a solution of 7-benzyloxy-4-chloro-3-nitroquinoline (72.9 g, 0.232 mol) in dichloromethane (1200 mL). Isobutylamine (25.24 mL, 0.2540 mol) was then added, and the reaction mixture was stirred for 18 hours at ambient temperature. The reaction mixture was diluted with dichloromethane, washed sequentially with water (2×) and brine, dried over anhydrous sodium sulfate, filtered, and concentrated under reduced pressure to yield 67.4 g of (7-benzyloxy-3-nitroquinolin-4-yl)-(2-methylpropyl)amine as a brown solid.

$^1$H NMR (300 MHz, DMSO-$d_6$): δ 9.29 (t, J=4.8 Hz, 1H), 9.07 (s, 1H), 8.42 (d, J=9.4 Hz, 1H), 7.53-7.49 (m, 2H), 7.45-7.32 (m, 4H), 7.27 (dd, J=2.6, 9.3 Hz, 1H), 5.32 (s, 2H), 3.60 (t, J=6.0 Hz, 2H), 2.00 (septet, J=6.7 Hz, 1H), 0.96 (d, J=6.3 Hz, 6H).

Part F

Sodium borohydride (29.0 g, 0.767 mol) was added in small portions to a solution of nickel(II)chloride (22.8 g, 0.096 mol) in methanol (1.25 L). A solution of (7-benzyloxy-3-nitroquinolin-4-yl)-(2-methylpropyl)amine (67.4 g, 0.192 mol) in methanol (300 mL) and dichloromethane (300 mL) was added to the resulting mixture. A precipitate was present and was dissolved by the addition of dichloromethane (500 mL). Additional sodium borohydride (~10 g) was added in small portions until the (7-benzyloxy-3-nitroquinolin-4-yl)-(2-methylpropyl)amine was consumed. The reaction mixture was filtered through a layer of CELITE filter aid, and the filter cake was washed with 50:50 dichloromethane:methanol. The filtrate was concentrated under reduced pressure, and the black, oily residue was treated with water and dichloromethane. The organic solution was washed with water and brine, dried over magnesium sulfate, and filtered. The filtrate was treated with activated charcoal, filtered, and concentrated under reduced pressure to yield 55.4 g of 7-benzyloxy-$N^4$-(2-methylpropyl)quinoline-3,4-diamine as an oily brown solid.

$^1$H NMR (300 MHz, DMSO-$d_6$): δ 8.26 (s, 1H), 7.94 (d, J=9.4 Hz, 1H), 7.51-7.48 (m, 2H), 7.43-7.30 (m, 3H), 7.21 (d, J=3.2 Hz, 1H), 7.10 (dd, J=9.5, 2.4 Hz, 1H), 5.18 (s, 2H), 4.92 (t, J=7.0 Hz, 1H), 4.70 (s, 2H), 3.04 (t, J=6.9 Hz, 2H), 1.75 (septet, J=6.8 Hz, 1H), 0.89 (d, J=6.3 Hz, 6H).

Part G

Trimethyl orthobutyrate (29.75 mL, 0.1859 mol) was added in three portions to a solution of 7-benzyloxy-$N^4$-(2-methylpropyl)quinoline-3,4-diamine (54.6 g, 0.170 mol) in toluene (795 mL). Pyridine hydrochloride (1.96 g) was then added, and the reaction was heated at 105° C. and stirred for four hours. Additional trimethyl orthobutyrate (7 mL, 40 mmol) was then added, and the reaction was stirred for three hours. The reaction was allowed to cool to ambient temperature, and the solvent was removed under reduced pressure. The oily residue was treated with chloroform, which was removed under reduced pressure to remove residual toluene, and then again diluted with chloroform (1.2 L). The resulting solution was washed with 5% aqueous sodium bicarbonate, water, and brine; dried over magnesium sulfate; filtered; and concentrated under reduced pressure to yield 60.3 g of 7-benzyloxy-1-(2-methylpropyl)-2-propyl-1H-imidazo[4,5-c]quinoline as an oily brown solid, containing a small amount of toluene (0.93 equivalents).

$^1$H NMR (300 MHz, DMSO-$d_6$): δ 9.15 (s, 1H), 8.25 (d, J=8.8 Hz, 1H), 7.68 (d, J=2.6 Hz, 1H), 7.53-7.12 (m, 6H), 5.31 (s, 2H), 4.42 (d, J=7.5 Hz, 2H), 2.94 (t, J=7.5 Hz, 2H), 2.25-2.09 (m, 1H), 1.90 (sextet, J=7.4 Hz, 2H), 1.04 (t, J=7.5 Hz, 3H), 0.89 (d, J=6.3 Hz, 6H).

Part H

3-Chloroperoxybenzoic acid (60% pure, 22.9 g, 79.6 mmol) (mCPBA) was added in portions to a solution of 7-benzyloxy-1-(2-methylpropyl)-2-propyl-1H-imidazo[4,5- c]quinoline (27.0 g, 72.3 mmol) in dichloromethane (1 L), and the reaction was stirred for 30 minutes. Water (1 L) was added, and the resulting mixture was stirred for 30 minutes. The organic layer was washed with 1% aqueous sodium carbonate (2×200 mL), dried over magnesium sulfate, filtered, and concentrated under reduced pressure.

Part I

The material from Part H was dissolved in dichloromethane (800 mL), and concentrated ammonium hydroxide (300 mL) was added. p-Toluenesulfonyl chloride (16.6 g, 86.8 mmol) was added in small portions to the resulting mixture, and the reaction was stirred for 30 minutes and then diluted with water. The organic layer was dried over magnesium sulfate, filtered, and concentrated under reduced pressure. The crude product was recrystallized from acetonitrile to provide 21.4 g of 7-benzyloxy-1-(2-methylpropyl)-2-propyl-1H-imidazo[4,5-c]quinolin-4-amine as feathery off-white crystals, mp 206.2-208.2° C.

$^1$H NMR (300 MHz, DMSO-$d_6$): δ 7.87 (d, J=9.1 Hz, 1H), 7.52-7.28 (m, 5H), 7.12 (d, J=2.4 Hz, 1H), 6.97 (dd, J=2.8, 8.9 Hz, 1H), 6.38 (s, 2H), 5.20 (s, 2H), 4.28 (d, J=6.8 Hz, 2H), 2.86 (t, J=7.5 Hz, 2H), 2.21-2.08 (m, 1H), 1.83 (sextet, J=7.3 Hz, 2H), 1.01 (t, J=7.5 Hz, 3H), 0.91 (d, J=7.0 Hz, 6H).

MS (CI) m/z 420.2042 (420.2036 calcd for $C_{24}H_{28}N_4O$, M+H).

Anal. Calcd. for $C_{24}H_{28}N_4O$: % C, 74.20; % H, 7.26; % N, 14.42. Found: % C, 74.21; % H, 7.09; % N, 14.48.

Material from a smaller scale run of Parts H and I was used to obtain these characterization data.

Example 2

7-Benzyloxy-2-ethoxymethyl-1-(2-methylpropyl)-1H-imidazo[4,5-c]quinolin-4-amine

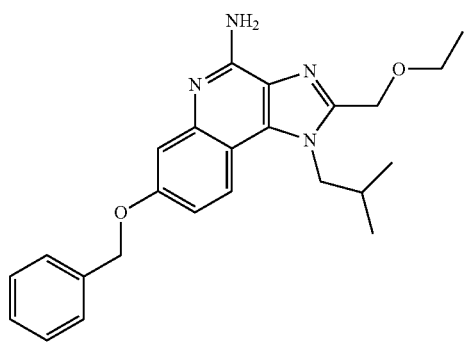

Part A

The preparation of 7-benzyloxy-$N^4$-(2-methylpropyl) quinoline-3,4-diamine is described in Parts A-F of Example 1. A concentrated solution of ethoxyacetyl chloride (12.2 g, 99.2 mmol) was added dropwise to a solution of 7-benzyloxy-$N^4$-(2-methylpropyl)quinoline-3,4-diamine (29 g, 90 mmol) in 50:50 toluene:pyridine. The temperature of the reaction reached 40° C., and a precipitate formed. Triethylamine (15-20 g) and pyridine were added to help dissolve the precipitate. The reaction was heated at reflux for three hours and then allowed to cool to ambient temperature overnight. The solvents were removed under reduced pressure, and the black residue was dissolved in dichloromethane. The resulting solution was washed several times with aqueous sodium carbonate (150 mL), dried over magnesium sulfate, filtered, and concentrated under reduced pressure to provide 29.2 g of 7-benzyloxy-2-ethoxymethyl-1-(2-methylpropyl)-1H-imidazo[4,5-c]quinoline as a tan solid.

Part B

The general methods described in Parts H and I of Example 1 were followed using 7-benzyloxy-2-ethoxymethyl-1-(2-methylpropyl)-1H-imidazo[4,5-c]quinoline (29.2 g, 78.2 mmol) in lieu of 7-benzyloxy-1-(2-methylpropyl)-2-propyl-1H-imidazo[4,5-c]quinoline. The crude product was triturated with acetonitrile, isolated by filtration, and dried for 18 hours in a vacuum oven at 68° C. to provide 16.3 g of 7-benzyloxy-2-ethoxymethyl-1-(2-methylpropyl)-1H-imidazo[4,5-c]quinolin-4-amine as an off-white solid, mp 201.0-203.0° C.

$^1$H NMR (300 MHz, DMSO-$d_6$) δ 7.91 (d, J=9.1 Hz, 1H), 7.51-7.31 (m, 5H), 7.12 (d, J=2.7 Hz, 1H), 6.99 (dd, J=9.0, 2.7 Hz, 1H), 6.54 (br s, 2H), 5.21 (s, 2H), 4.73 (s, 2H), 4.39 (d, J=7.6 Hz, 2H), 3.55 (q, J=7.0 Hz, 2H), 2.27-2.18 (m, 1H), 1.15 (t, J=7.0 Hz, 3H), 0.91 (d, J=6.7 Hz, 6H);

$^{13}$C NMR (75 MHz, DMSO-$d_6$) δ 157.1, 152.2, 148.4, 146.9, 137.2, 133.4, 128.3, 127.6, 127.4, 125.0, 121.6, 111.7, 108.9, 108.6, 67.0, 65.2, 64.1, 51.6, 28.4, 19.2, 14.8;

MS (APCI) m/z 405 (M+H)$^+$;

Anal. Calcd. for $C_{24}H_{28}N_4O_2$: % C, 71.26; % H, 6.98; % N, 13.85. Found: % C, 71.12; % H, 7.11; % N, 13.76.

Example 3

7-Benzyloxy-2-methyl-1-(2-methylpropyl)-1H-imidazo[4,5-c]quinolin-4-amine

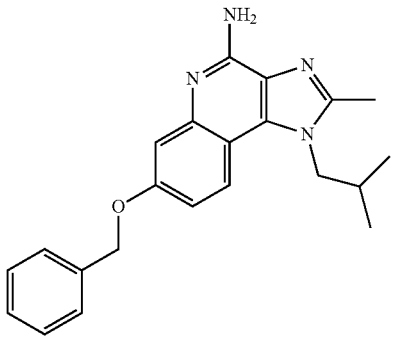

Part A

The preparation of 7-benzyloxy-$N^4$-(2-methylpropyl) quinoline-3,4-diamine is described in Parts A-F of Example 1. Under a nitrogen atmosphere, triethyl orthoacetate (4.59 mL, 25.0 mmol) was added to a solution of 7-benzyloxy-$N^4$-(2-methylpropyl)quinoline-3,4-diamine (8.05 g, 25.0 mmol) in xylenes (130 mL), and the resulting solution was heated at reflux (160° C.) overnight. The solvent volume was reduced to 70 mL using a Dean-Stark trap. Over a period of a few days, a precipitate formed. Diethyl ether was added, and the precipitate was isolated by filtration and washed with diethyl ether to provide 6.81 g of 7-benzyloxy-2-methyl-1-(2-methylpropyl)-1H-imidazo[4,5-c]quinoline as a light-brown powder.

Part B mCPBA (65% pure, 2.31 g, 8.70 mmol) was added in two portions with stirring to a solution of 7-benzyloxy-2-methyl-1-(2-methylpropyl)-1H-imidazo[4,5-c]quinoline (3.01 g, 8.71 mmol) in chloroform (100 mL), and the reaction was stirred for four hours. An analysis by thin layer chromatography (TLC) indicated the reaction was incomplete, and additional mCPBA was added. The solution was stirred until the reaction was complete as determined by TLC and then washed with saturated aqueous sodium bicarbonate, dried over magnesium sulfate, filtered, and concentrated under reduced pressure. The residue was used without purification.
Part C Under a nitrogen atmosphere, trichloroacetyl isocyanate (1.60 mL, 13.4 mmol) was added dropwise to a solution of the material from Part B in dichloromethane (100 mL), and the reaction was stirred for one hour. The solvent was removed under reduced pressure. The residue was diluted with methanol, and a solution of sodium methoxide (3.06 mL, 13.4 mmol, 25% in methanol) was slowly added. The reaction was stirred overnight, and a precipitate formed. The precipitate was isolated by filtration, washed with cold hexanes (3×), recrystallized from acetonitrile, and dried for two days at 60° C. to provide 1.15 g of 7-benzyloxy-2-methyl-1-(2-methylpropyl)-1H-imidazo[4,5-c]quinolin-4-amine as a white solid, mp 171.9° C.

$^1$H NMR (300 MHz, DMSO-$d_6$) δ 7.87 (d, J=9.0 Hz, 1H), 7.51-7.48 (m, 2H), 7.42-7.29 (m, 3H), 7.23 (d, J=2.7 Hz, 1H), 7.08 (dd, J=9.3, 2.7 Hz, 1H), 5.19 (s, 2H), 4.25 (d, J=7.5 Hz, 2H), 2.62 (s, 3H), 2.27 (heptet, J=6.9 Hz, 1H), 1.00 (d, J=6.6 Hz, 6H);

MS (ESI) m/z 361.2030 (calcd for $C_{22}H_{24}N_4O$ 361.2028, M+H);

Anal. Calcd. for $C_{22}H_{24}N_4O$: % C, 73.31; % H, 6.71; % N, 15.54. Found: % C, 73.29; % H, 6.67; % N, 15.54.

Example 4

7-Benzyloxy-2-ethyl-1-(2-methylpropyl)-1H-imidazo[4,5-c]quinolin-4-amine

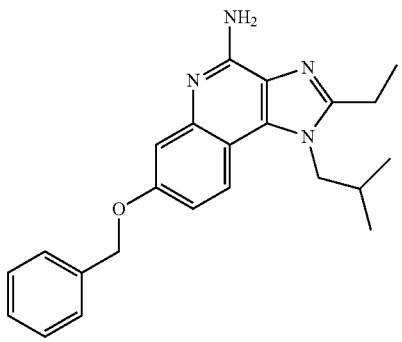

Part A

The general method described in Part A of Example 3 was followed. Triethyl orthopropionate (7.66 mL, 58.11 mmol) was added in lieu of triethyl orthoacetate to a solution of 7-benzyloxy-$N^1$-(2-methylpropyl)quinoline-3,4-diamine (18.68 g, 58.11 mmol) in xylenes (200 mL). At the end of the reaction, the precipitate was collected in three crops to provide 7.16 g of 7-benzyloxy-2-ethyl-1-(2-methylpropyl)-1H-imidazo[4,5-c]quinoline as a light-brown solid, mp 127° C.

Anal. Calcd. for $C_{23}H_{25}N_3O$: % C, 76.85; % H, 7.01; % N, 11.69. Found: % C, 76.86; % H, 7.10; % N, 11.77.
Part B A modification of the general method described in Part B of Example 3 was followed using 7-benzyloxy-2-ethyl-1-(2-methylpropyl)-1H-imidazo[4,5-c]quinoline as the starting material; the reaction was complete in four hours. The reaction product was dried under high vacuum overnight to provide 1.38 g of 7-benzyloxy-2-ethyl-1-(2-methylpropyl)-5-oxido-1H-imidazo[4,5-c]quinoline as a foamy, orange solid.
Part C The general method described in Part C of Example 3 was used to convert 7-benzyloxy-2-ethyl-1-(2-methylpropyl)-5-oxido-1H-imidazo[4,5-c]quinoline (1.38 g, 3.67 mmol) to 0.460 g of 7-benzyloxy-2-ethyl-1-(2-methylpropyl)-1H-imidazo[4,5-c]quinolin-4-amine, which was obtained as a white solid, mp 193.2-193.5° C.

$^1$H NMR (300 MHz, DMSO-$d_6$) δ 7.86 (d, J=8.7 Hz, 1H), 7.50 (dd, J=8.7, 1.8 Hz, 2H), 7.43-7.30 (m, 3H), 7.11 (d, J=2.4 Hz, 1H), 6.99 (dd, J=9.0, 2.7 Hz, 1H), 6.38 (s, 2H), 5.20 (s, 2H), 4.26 (d, J=7.5 Hz, 2H), 2.90 (q, J=6.9 Hz, 2H), 2.15 (septet, J=6.9, 1H), 1.35 (t, J=7.5 Hz, 3H), 0.89 (d, J=6.9 Hz, 6H);

MS (ESI) m/z 375.2179 (calcd for $C_{23}H_{26}N_4O$ 375.2185, M+H);

Anal. Calcd. for $C_{23}H_{26}N_4O$: % C, 73.77; % H, 7.00; % N, 14.96. Found: % C, 73.54; % H, 6.93; % N, 15.00.

Example 5

4-Amino-1-(2-methylpropyl)-2-propyl-1H-imidazo[4,5-c]quinolin-7-ol

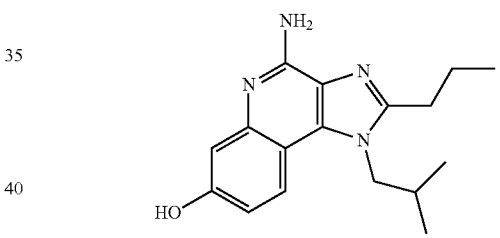

7-Benzyloxy-1-(2-methylpropyl)-2-propyl-1H-imidazo[4,5-c]quinolin-4-amine (21.4 g, 55.1 mmol), prepared as described in Example 1, was dissolved in refluxing ethanol (2 L), and 10% palladium on carbon (5.4 g, 5.1 mmol) was added to the warm solution. The reaction was placed under hydrogen pressure (50 psi, 3.4×10$^5$ Pa) overnight. The catalyst was removed by filtration and washed with hot ethanol (500 mL) and methanol (400 mL). The filtrate was concentrated under reduced pressure to yield 14.5 g of an off-white solid. A small portion of the solid was recrystallized from 2-propanol to provide 4-amino-1-(2-methylpropyl)-2-propyl-1H-imidazo[4,5-c]quinolin-7-ol as white crystals, mp>265° C.

$^1$H NMR (300 MHz, DMSO-$d_6$) δ 9.44 (br s, 1H), 7.78 (d, J=8.9 Hz, 1H), 6.95 (d, J=2.5 Hz, 1H), 6.79 (dd, J=8.9, 2.6 Hz, 1H), 6.29 (br s, 2H), 4.26 (d, J=7.4 Hz, 2H), 2.84 (t, J=7.4 Hz, 2H), 2.14 (septet, J=7.1 Hz, 1H), 1.88-1.77 (m, 2H), 1.01 (t, J=7.3 Hz, 3H), 0.91 (d, J=6.6 Hz, 6H);

$^{13}$C NMR (75 MHz, DMSO-$d_6$) δ 156.1, 152.3, 151.9, 146.9, 133.1, 126.5, 121.2, 111.9, 109.9, 108.4, 51.3, 28.8, 28.7, 21.0, 19.3, 13.9;

MS (APCI) m/z 299 (M+H)$^+$;

Anal. Calcd. for $C_{17}H_{22}N_4O$: % C, 68.43; % H, 7.43; % N, 18.78. Found: % C, 68.38; % H, 7.27; % N, 18.74.

Example 6

4-Amino-2-ethoxymethyl-1-(2-methylpropyl)-1H-imidazo[4,5-c]quinolin-7-ol

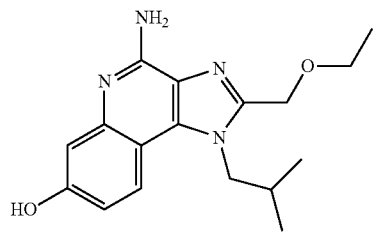

7-Benzyloxy-2-ethoxymethyl-1-(2-methylpropyl)-1H-imidazo[4,5-c]quinolin-4-amine (16.3 g, 40.3 mmol), prepared as described in Example 2, was dissolved in refluxing ethanol (1.5 L), and 10% palladium on carbon (4.3 g, 4.0 mmol) was added to the warm solution. A precipitate formed upon cooling to ambient temperature. The reaction mixture was placed under hydrogen pressure (50 psi, $3.4 \times 10^5$ Pa) overnight. The catalyst was removed by filtration and washed with hot ethanol (500 mL) and boiling DMF. The filtrate was concentrated under reduced pressure to yield 11.5 g of an off-white solid. A small portion of the solid was recrystallized from 2-propanol to provide 4-amino-2-ethoxymethyl-1-(2-methylpropyl)-1H-imidazo[4,5-c]quinolin-7-ol as white crystals, mp>265° C.

$^1$H NMR (300 MHz, DMSO-$d_6$) δ 9.50 (br s, 1H), 7.82 (d, J=8.8 Hz, 1H), 6.95 (d, J=2.5 Hz, 1H), 6.80 (dd, J=8.9, 2.6 Hz, 1H), 6.44 (br s, 2H), 4.72 (s, 2H), 4.36 (d, J=7.7 Hz, 2H), 3.55 (q, J=7.0 Hz, 2H), 2.30-2.15 (m, 1H), 1.15 (t, J=7.0 Hz, 3H), 0.91 (d, J=6.6 Hz, 6H); $^{13}$C NMR (75 MHz, DMSO-$d_6$) δ 156.3, 152.0, 148.0, 147.1, 133.6, 124.6, 121.5, 111.8, 109.7, 107.9, 65.1, 64.5, 51.6, 28.4, 19.2, 14.8;

MS (APCI) m/z 315 (M+H)$^+$;

Anal. Calcd. for $C_{17}H_{22}N_4O_2$: % C, 64.95; % H, 7.05; % N, 17.82. Found: % C, 64.73; % H, 6.99; % N, 17.62.

Examples 7-20

A warm solution of 4-amino-1-(2-methylpropyl)-2-propyl-1H-imidazo[4,5-c]quinolin-7-ol (1 g, 3 mmol), prepared as described in Example 5, in DMF (25-50 mL) was cooled to approximately 0° C. Solid cesium carbonate (2 equivalents) was added, and the reaction became pale yellow in color. The benzyl halide (1.1 equivalents) indicated in the table below was slowly added, and the reaction was allowed to warm to room temperature and was stirred overnight or until it was judged to be complete by a high-performance liquid chromatography (HPLC) analysis. The reaction was poured into deionized water (500-750 mL) and stirred for several minutes. A precipitate formed and was isolated by filtration. For each example, the purification and characterization of the product is described below the table.

| Example | Benzyl Halide | R |
|---|---|---|
| 7 | 3-Methylbenzyl bromide | |
| 8 | 4-Chlorobenzyl bromide | |
| 9 | 4-Methylbenzyl bromide | |
| 10 | 3,4-Dichlorobenzyl bromide | |
| 11 | 3-Chlorobenzyl bromide | |
| 12 | 4-Nitrobenzyl bromide | |
| 13 | 4-(tert-Butyl)benzyl bromide | |
| 14 | 4-Fluorobenzyl bromide | |
| 15 | 4-(Trifluoromethyl)benzyl bromide | |
| 16 | 3-Nitrobenzyl bromide | |
| 17 | 2-Methylbenzyl bromide | |

-continued

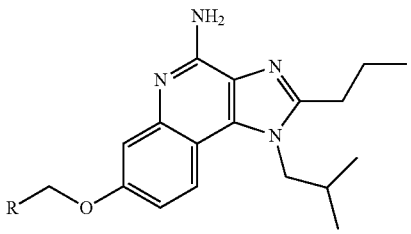

| Example | Benzyl Halide | R |
|---|---|---|
| 18 | 2-Chlorobenzyl bromide | 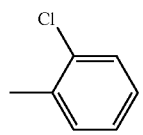 |
| 19 | 2-Methoxybenzyl chloride | 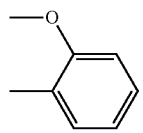 |
| 20 | 4-Methoxybenzyl chloride | 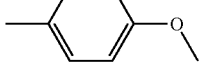 |

Example 7

7-(3-Methylbenzyloxy)-1-(2-methylpropyl)-2-propyl-1H-imidazo[4,5-c]quinolin-4-amine The product was recrystallized from acetonitrile, isolated by filtration, and washed with a small volume of acetonitrile to provide 750 mg of 7-(3-methylbenzyloxy)-1-(2-methylpropyl)-2-propyl-1H-imidazo[4,5-c]quinolin-4-amine as a white solid, mp 200-203° C. $^1$H NMR (300 MHz, DMSO-$d_6$) δ 7.87 (d, J=9.1 Hz, 1H), 7.29-7.27 (m, 3H), 7.15-7.13 (m, 2H), 6.98 (dd, J=9.0; 2.7 Hz, 1H), 6.43 (br s, 2H), 5.16 (s, 2H), 4.28 (d, J=7.5 Hz, 2H), 2.86 (t, J=7.4 Hz, 2H), 2.32 (s, 3H), 2.21-2.07 (m, 1H), 1.89-1.77 (m, 2H), 1.02 (t, J=7.4 Hz, 3H), 0.91 (d, J=6.6 Hz, 6H);

MS (APCI) m/z 403 (M+H)$^+$;

Anal. Calcd. for $C_{25}H_{30}N_4O$: % C, 74.60; % H, 7.51; % N, 13.92. Found: % C, 74.32; % H, 7.54; % N, 13.97.

Example 8

7-(4-Chlorobenzyloxy)-1-(2-methylpropyl)-2-propyl-1H-imidazo[4,5-c]quinolin-4-amine The product was purified by column chromatography on silica gel (eluting with 98:2 chloroform:methanol), triturated with hot acetonitrile, isolated by filtration, washed with a small volume of acetonitrile, and dried for two hours in a vacuum oven at 65° C. to provide 1.16 g of 7-(4-chlorobenzyloxy)-1-(2-methylpropyl)-2-propyl-1H-imidazo[4,5-c]quinolin-4-amine as bright white crystals, mp 215-217° C.

$^1$H NMR (300 MHz, DMSO-$d_6$) δ 7.89 (d, J=9.0 Hz, 1H), 7.49 (d, J=8.5 Hz, 2H), 7.42 (d, J=8.4 Hz, 2H), 7.16 (s, 1H), 6.99 (dd, J=8.9; 2.6 Hz, 1H), 6.10 (br s, 2H), 5.19 (s, 2H), 4.27 (d, J=7.5 Hz, 2H), 2.85 (t, J=7.2 Hz, 2H), 2.18 (septet, J=6.7 Hz, 1H), 1.92-1.82 (m, 2H), 1.03 (t, J=7.4 Hz, 3H), 0.92 (d, J=6.7 Hz, 6H);

$^{13}$C NMR (125 MHz, DMSO-$d_6$) δ 157.7, 153.6, 152.8, 147.3, 137.4, 133.8, 133.2, 130.0, 129.2, 126.3, 122.0, 112.7, 110.6, 110.4, 69.6, 52.3, 29.6, 29.5, 21.5, 20.0, 14.5;

MS (APCI) m/z 423 (M+H)$^+$;

Anal. Calcd. for $C_{24}H_{27}ClN_4O$: % C, 68.15; % H, 6.43; % N, 13.25. Found: % C, 67.84; % H, 6.39; % N, 13.14.

Example 9

7-(4-Methylbenzyloxy)-1-(2-methylpropyl)-2-propyl-1H-imidazo[4,5-c]quinolin-4-amine The product was purified by column chromatography on silica gel (eluting sequentially with 99:1 and 98:2 chloroform:methanol), recrystallized from acetonitrile (36 mL/g), isolated by filtration, washed with a small volume of acetonitrile, and finally dried for two days in a vacuum oven at 65° C. to provide 1.12 g of 7-(4-methylbenzyloxy)-1-(2-methylpropyl)-2-propyl-1H-imidazo[4,5-c]quinolin-4-amine as bright white crystals, mp 205-207° C.

$^1$H NMR (300 MHz, DMSO-$d_6$) δ 7.85 (d, J=9.0 Hz, 1H), 7.36 (d, J=8.0 Hz, 2H), 7.20 (d, J=7.8 Hz, 2H), 7.10 (d, J=2.6 Hz, 1H), 6.96 (dd, J=9.0, 2.7 Hz, 1H), 6.39 (br s, 2H), 5.15 (s, 2H), 4.28 (d, J=7.2 Hz, 2H), 2.85 (t, J=7.4 Hz, 2H), 2.30 (s, 3H), 2.14 (septet, J=6.8 Hz, 1H), 1.87-1.77 (m, 2H), 1.01 (t, J=7.3 Hz, 3H), 0.91 (d, J=6.8 Hz, 6H);

$^{13}$C NMR (75 MHz, DMSO-$d_6$) δ 157.2, 153.0, 152.3, 146.8, 137.3, 134.6, 133.1, 129.3, 128.0, 125.5, 121.6, 112.1, 109.5, 109.0, 69.3, 51.6, 29.1, 28.9, 21.3, 21.1, 19.5, 14.2;

MS (APCI) m/z 403 (M+H)$^+$;

Anal. Calcd. for $C_{25}H_{30}N_4O$: % C, 74.60; % H, 7.51; % N, 13.92. Found: % C, 74.57; % H, 7.42; % N, 13.89.

Example 10

7-(3,4-Dichlorobenzyloxy)-1-(2-methylpropyl)-2-propyl-1H-imidazo[4,5-c]quinolin-4-amine The product was purified by column chromatography on silica gel (eluting with chloroform:methanol ranging in ratios from 99.5:0.5 to 98:2), recrystallized from 2-propanol, isolated by filtration, and dried overnight in a vacuum oven at 60° C. to provide 1.11 g of 7-(3,4-dichlorobenzyloxy)-1-(2-methylpropyl)-2-propyl-1H-imidazo[4,5-c]quinolin-4-amine as a white solid, mp 183-184° C.

$^1$H NMR (300 MHz, DMSO-$d_6$) δ 7.89 (d, J=9.0 Hz, 1H), 7.76 (d, J=1.9 Hz, 1H), 7.67 (d, J=8.3 Hz, 1H), 7.49 (dd, J=8.3, 2.0 Hz, 1H), 7.11 (d, J=2.7 Hz, 1H), 6.99 (dd, J=9.0; 2.7 Hz, 1H), 6.42 (br s, 2H), 5.23 (s, 2H), 4.29 (d, J=7.3 Hz, 2H), 2.86 (t, J=7.3 Hz, 2H), 2.22-2.07 (m, 1H), 1.89-1.79 (m, 2H), 1.01 (t, J=7.4 Hz, 3H), 0.91 (d, J=6.6 Hz, 6H);

$^{13}$C NMR (75 MHz, DMSO-$d_6$) δ 156.7, 153.0, 152.4, 146.7, 139.0, 133.1, 131.4, 131.0, 130.5, 129.6, 128.0, 125.6, 121.7, 112.0, 109.7, 109.1, 67.8, 51.5, 29.1, 28.9, 21.2, 19.5, 14.1; MS (APCI) m/z 458 (M+H)$^+$;

Anal. Calcd. for $C_{24}H_{26}Cl_2N_4O$: % C, 63.02; % H, 5.73; % N, 12.25. Found: % C, 62.77; % H, 5.71; % N, 12.17.

Example 11

7-(3-Chlorobenzyloxy)-1-(2-methylpropyl)-2-propyl-1H-imidazo[4,5-c]quinolin-4-amine The product was purified as described in Example 10 to provide 1.00 g of 7-(3-chlorobenzyloxy)-1-(2-methylpropyl)-2-propyl-1H-imidazo[4,5-c]quinolin-4-amine as white crystals, mp 182-183° C.

¹H NMR (300 MHz, DMSO-d₆) δ 7.88 (d, J=9.0 Hz, 1H), 7.55 (s, 1H), 7.47-7.39 (m, 3H), 7.12 (d, J=2.6 Hz, 1H), 6.99 (dd, J=9.0, 2.7 Hz, 1H), 6.42 (br s, 2H), 5.23 (s, 2H), 4.29 (d, J=7.4 Hz, 2H), 2.86 (t, J=7.6 Hz, 2H), 2.14 (septet, J=6.5 Hz, 1H), 1.89-1.79 (m, 2H), 1.01 (t, J=7.4 Hz, 3H), 0.91 (d, J=6.6 Hz, 6H);

¹³C NMR (75 MHz, DMSO-d₆) δ 156.9, 153.0, 152.4, 146.8, 140.3, 133.4, 133.1, 130.7, 128.0, 127.4, 126.3, 125.5, 121.6, 112.0, 109.7, 109.1, 68.5, 51.5, 29.1, 28.9, 21.2, 19.5, 14.1; MS (APCI) m/z 423 (M+H)⁺;

Anal. Calcd. for $C_{24}H_{27}ClN_4O$: % C, 68.15; % H, 6.43; % N, 13.25. Found: % C, 67.89; % H, 6.43; % N, 13.08.

Example 12

1-(2-Methylpropyl)-7-(4-nitrobenzyloxy)-2-propyl-1H-imidazo[4,5-c]quinolin-4-amine The general procedure described for Examples 7-20 was followed with the exception that after the reaction was stirred overnight, it was cooled and additional 4-nitrobenzyl bromide and cesium carbonate were added. The reaction was stirred for four hours and poured into deionized water (~450 mL) to form a brown, milky precipitate. The precipitate was isolated by filtration; an analysis by HPLC indicated that the filtrate contained starting material. The product was purified as described in Example 10 and then dried a second time for 1.5 days in a vacuum oven at 70° C. to provide 320 mg of 1-(2-methylpropyl)-7-(4-nitrobenzyloxy)-2-propyl-1H-imidazo[4,5-c]quinolin-4-amine as a bright yellow solid.

¹H NMR (300 MHz, DMSO-d₆) δ 8.28 (d, J=8.8 Hz, 2H), 7.90 (d, J=9.0 Hz, 1H), 7.76 (d, J=8.7 Hz, 2H), 7.12 (d, J=2.6 Hz, 1H), 7.01 (dd, J=9.0, 2.7 Hz, 1H), 6.42 (br s, 2H), 5.39 (s, 2H), 4.29 (d, J=7.4 Hz, 2H), 2.86 (t, J=7.6 Hz, 2H), 2.21-2.07 (m, 1H), 1.89-1.79 (m, 2H), 1.01 (t, J=7.3 Hz, 3H), 0.91 (d, J=6.6 Hz, 6H); ¹³C NMR (75 MHz, DMSO-d₆) δ 156.2, 152.6, 151.9, 146.8, 146.2, 145.2, 132.6, 127.9, 125.1, 123.5, 121.2, 111.5, 109.3, 108.6, 67.8, 51.1, 28.6, 28.4, 20.8, 19.0, 13.7;

MS (APCI) m/z 434 (M+H)⁺;

Anal. Calcd. for $C_{24}H_{27}N_5O_3$: % C, 66.50; % H, 6.28; % N, 16.15. Found: % C, 66.48; % H, 6.34; % N, 15.91.

Example 13

7-[4-(tert-Butyl)benzyloxy]-1-(2-methylpropyl)-2-propyl-1H-imidazo[4,5-c]quinolin-4-amine The product was purified as described in Example 10 to provide 820 mg of 7-[4-(tert-butyl)benzyloxy]-1-(2-methylpropyl)-2-propyl-1H-imidazo[4,5-c]quinolin-4-amine as a white solid, mp 203.5-205.0° C.

¹H NMR (300 MHz, DMSO-d₆) δ 7.87 (d, J=9.1 Hz, 1H), 7.42-7.39 (m, 4H), 7.13 (d, J=2.7 Hz, 1H), 6.97 (dd, J=9.0, 2.7 Hz, 1H), 6.44 (br s, 2H), 5.16 (s, 2H), 4.28 (d, J=7.3 Hz, 2H), 2.86 (t, J=7.3 Hz, 2H), 2.22-2.07 (m, 1H), 1.89-1.79 (m, 2H), 1.28 (s, 9H), 1.01 (t, J=7.3 Hz, 3H), 0.91 (d, J=6.6 Hz, 6H);

¹³C NMR (75 MHz, DMSO-d₆) δ 156.7, 152.4, 151.8, 150.0, 146.2, 134.1, 132.6, 127.3, 125.06, 125.04, 121.1, 111.6, 109.0, 108.4, 68.7, 51.1, 34.1, 31.0, 28.6, 28.4, 20.7, 19.0, 13.7; MS (APCI) m/z 445 (M+H)⁺;

Anal. Calcd. for $C_{28}H_{36}N_4O$: % C, 75.64; % H, 8.16; % N, 12.60. Found: % C, 75.37; % H, 8.36; % N, 12.56.

Example 14

7-(4-Fluorobenzyloxy)-1-(2-methylpropyl)-2-propyl-1H-imidazo[4,5-c]quinolin-4-amine The product was purified as described in Example 10 to provide 900 mg of 7-(4-fluorobenzyloxy)-1-(2-methylpropyl)-2-propyl-1H-imidazo[4,5-c]quinolin-4-amine as white, flaky crystals, mp 198.0-199.7° C.

¹H NMR (300 MHz, DMSO-d₆) δ 7.88 (d, J=9.1 Hz, 1H), 7.56-7.52 (m, 2H), 7.26-7.20 (m, 2H), 7.14 (d, J=2.7 Hz, 1H), 6.98 (dd, J=9.0; 2.7 Hz, 1H), 6.43 (br s, 2H), 5.19 (s, 2H), 4.28 (d, J=7.4 Hz, 2H), 2.86 (t, J=7.4 Hz, 2H), 2.14 (septet, J=6.8 Hz, 1H), 1.89-1.79 (m, 2H), 1.02 (t, J=7.4 Hz, 3H), 0.91 (d, J=6.6 Hz, 6H);

MS (APCI) m/z 407 (M+H)⁺;

Anal. Calcd. for $C_{24}H_{27}FN_4O$: % C, 70.91; % H, 6.69; % N, 13.78. Found: % C, 70.66; % H, 6.72; % N, 13.79.

Example 15

1-(2-Methylpropyl)-2-propyl-7-[4-(trifluoromethyl)benzyloxy]-1H-imidazo[4,5-c]quinolin-4-amine The product was purified as described in Example 10 to provide 1.14 g of 1-(2-methylpropyl)-2-propyl-7-[4-(trifluoromethyl)benzyloxy]-1H-imidazo[4,5-c]quinolin-4-amine as white, flaky crystals, mp 191.8-193.5° C.

¹H NMR (300 MHz, DMSO-d₆) δ 7.89 (d, J=9.0 Hz, 1H), 7.78 (d, J=8.5 Hz, 2H), 7.71 (d, J=8.4 Hz, 2H), 7.13 (d, J=2.7 Hz, 1H), 7.01 (dd, J=9.0, 2.7 Hz, 1H), 6.46 (br s, 2H), 5.34 (s, 2H), 4.29 (d, J=7.2 Hz, 2H), 2.86 (t, J=7.2 Hz, 2H), 2.14 (septet, J=6.8 Hz, 1H), 1.89-1.79 (m, 2H), 1.02 (t, J=7.4 Hz, 3H), 0.91 (d, J=6.5 Hz, 6H);

MS (APCI) m/z 457 (M+H)⁺;

Anal. Calcd. for $C_{25}H_{27}F_3N_4O$: % C, 65.78; % H, 5.96; % N, 12.27. Found: % C, 65.76; % H, 5.94; % N, 12.18.

Example 16

1-(2-Methylpropyl)-7-(3-nitrobenzyloxy)-2-propyl-1H-imidazo[4,5-c]quinolin-4-amine The product was purified as described in Example 10 to provide 1.15 mg of 1-(2-methylpropyl)-7-(3-nitrobenzyloxy)-2-propyl-1H-imidazo[4,5-c]quinolin-4-amine as a bright yellow solid, mp 175-176° C.

¹H NMR (300 MHz, DMSO-d₆) δ 8.35 (dd, J=1.9, 1.9 Hz, 1H), 8.22-8.17 (m, 1H), 7.98-7.94 (m, 1H), 7.90 (d, J=9.1 Hz, 1H), 7.72 (t, J=8.0 Hz, 1H), 7.16 (d, J=2.7 Hz, 1H), 7.03 (dd, J=9.0, 2.7 Hz, 1H), 6.50 (br s, 2H), 5.38 (s, 2H), 4.29 (d, J=7.4 Hz, 2H), 2.86 (t, J=7.7 Hz, 2H), 2.14 (septet, J=6.7 Hz, 1H), 1.89-1.79 (m, 2H), 1.02 (t, J=7.4 Hz, 3H), 0.91 (d, J=6.6 Hz, 6H);

¹³C NMR (75 MHz, DMSO-d₆) δ 156.3, 152.6, 151.8, 147.7, 146.0, 139.6, 133.8, 132.6, 129.9, 125.0, 122.5, 121.7, 121.3, 111.6, 109.2, 108.4, 67.7, 51.1, 28.6, 28.4, 20.7, 19.0, 13.7; MS (APCI) m/z 434 (M+H)⁺;

Anal. Calcd. for $C_{24}H_{27}N_5O_3$: % C, 66.50; % H, 6.28; % N, 16.15. Found: % C, 66.23; % H, 6.38; % N, 16.03.

Example 17

7-(2-Methylbenzyloxy)-1-(2-methylpropyl)-2-propyl-1H-imidazo[4,5-c]quinolin-4-amine The product was purified by column chromatography on silica gel (eluting with chloroform:methanol ranging in ratios from 99.5:0.5 to 98:2), triturated with hot 2-propanol, isolated by filtration, and dried overnight in a vacuum oven at 60° C. to provide 980 mg of 7-(2-methylbenzyloxy)-1-(2-methylpropyl)-2-propyl-1H-imidazo[4,5-c]quinolin-4-amine as a white powder, mp 227.5-228.5° C.

$^1$H NMR (300 MHz, DMSO-$d_6$) δ 7.89 (d, J=9.0 Hz, 1H), 7.43 (d, J=6.3 Hz, 1H), 7.23-7.17 (m, 4H), 6.99 (dd, J=9.0, 2.7 Hz, 1H), 6.04 (br s, 2H), 5.18 (s, 2H), 4.28 (d, J=7.5 Hz, 2H), 2.85 (t, J=7.5 Hz, 2H), 2.37 (s, 3H), 2.19 (septet, J=6.8 Hz, 1H), 1.92-1.82 (m, 2H), 1.03 (t, J=7.4 Hz, 3H), 0.93 (d, J=6.7 Hz, 6H);

$^{13}$C NMR (75 MHz, DMSO-$d_6$) δ 156.6, 152.1, 151.3, 146.0, 135.8, 134.7, 132.4, 129.5, 127.8, 127.2, 125.1, 124.9, 120.5, 111.2, 109.1, 108.9, 67.7, 50.9, 28.2, 28.1, 20.1, 18.6, 17.7, 13.0;

MS (APCI) m/z 403 (M+H)$^+$;

Anal. Calcd. for $C_{25}H_{30}N_4O$: % C, 74.60; % H, 7.51; % N, 13.92. Found: % C, 74.42; % H, 7.81; % N, 13.99.

Example 18

7-(2-Chlorobenzyloxy)-1-(2-methylpropyl)-2-propyl-1H-imidazo[4,5-c]quinolin-4-amine The product was purified as described in Example 10 to provide 1.16 g of 7-(2-chlorobenzyloxy)-1-(2-methylpropyl)-2-propyl-1H-imidazo[4,5-c]quinolin-4-amine as a white powder, mp 216.0-217.5° C.

$^1$H NMR (300 MHz, DMSO-$d_6$) δ 7.90 (d, J=9.1 Hz, 1H), 7.63-7.57 (m, 1H), 7.52-7.45 (m, 1H), 7.39-7.33 (m, 2H), 7.17 (d, J=2.6 Hz, 1H), 7.00 (dd, J=9.0, 2.8 Hz, 1H), 6.06 (br s, 2H), 5.26 (s, 2H), 4.28 (d, J=7.5 Hz, 2H), 2.85 (t, J=7.5 Hz, 2H), 2.26-2.12 (m, 1H), 1.93-1.80 (m, 2H), 1.03 (t, J=7.3 Hz, 3H), 0.93 (d, J=6.7 Hz, 6H);

$^{13}$C NMR (75 MHz, DMSO-$d_6$) δ 156.3, 152.2, 146.0, 151.4, 134.1, 132.4, 131.9, 129.2, 129.0, 128.7, 126.6, 120.6, 124.9, 111.1, 108.9, 109.3, 66.5, 50.9, 28.2, 28.1, 20.1, 18.6, 13.0; MS (APCI) m/z 423 (M+H)$^+$;

Anal. Calcd. for $C_{24}H_{22}ClN_4O$: % C, 68.15; % H, 6.43; % N, 13.25. Found: % C, 68.14; % H, 6.42; % N, 13.13.

Example 19

7-(2-Methoxybenzyloxy)-1-(2-methylpropyl)-2-propyl-1H-imidazo[4,5-c]quinolin-4-amine The general procedure for Examples 7-20 was followed with the following modification. After the dropwise addition of 2-methoxybenzyl chloride (578 mg, 3.69 mmol), tetrabutylammonium bromide (110 mg, 0.34 mmol) was added. The reaction was stirred overnight. The product was purified by column chromatography on silica gel (eluting sequentially with 99:1 and 98:2 chloroform:methanol), recrystallized from 2-propanol (28 mL/g), isolated by filtration, and dried for two days in a vacuum oven at 65° C. to provide 950 mg of 7-(2-methoxybenzyloxy)-1-(2-methylpropyl)-2-propyl-1H-imidazo[4,5-c]quinolin-4-amine as white crystals, mp 205.0-206.0° C.

$^1$H NMR (300 MHz, DMSO-$d_6$) δ 7.88 (d, J=9.0 Hz, 1H), 7.41-7.30 (m, 2H), 7.15-7.13 (m, 1H), 7.05 (d, J=8.3 Hz, 1H), 6.99-6.93 (m, 2H), 6.04 (br s, 2H), 5.16 (s, 2H), 4.28 (d, J=7.6 Hz, 2H), 3.85 (s, 3H), 2.85 (t, J=7.4 Hz, 2H), 2.19 (septet, J=6.5 Hz, 1H), 1.92-1.82 (m, 2H), 1.03 (t, J=7.4 Hz, 3H), 0.92 (d, J=6.7 Hz, 6H);

$^{13}$C NMR (75 MHz, DMSO-$d_6$) δ 156.7, 156.5, 152.1, 151.3, 146.1, 132.4, 128.5, 128.2, 124.88, 124.86, 120.5, 119.8, 111.3, 110.8, 109.0, 108.8, 64.3, 55.2, 50.9, 28.2, 28.1, 20.1, 18.6, 13.1;

MS (APCI) m/z 419 (M+H)$^+$;

Anal. Calcd. for $C_{25}H_{30}N_4O_2$: % C, 71.74; % H, 7.22; % N, 13.39. Found: % C, 71.80; % H, 7.25; % N, 13.36.

Example 20

7-(4-Methoxybenzyloxy)-1-(2-methylpropyl)-2-propyl-1H-imidazo[4,5-c]quinolin-4-amine The modification described in Example 19 was followed with 4-methoxybenzyl chloride (551 mg, 3.52 mmol) used in lieu of 2-methoxybenzyl bromide. The reaction was stirred for six hours, and a small additional amount of 4-methoxybenzyl bromide was added. Following the purification, 750 mg of 7-(4-methoxybenzyloxy)-1-(2-methylpropyl)-2-propyl-1H-imidazo[4,5-c]quinolin-4-amine were obtained as a white powder, mp 186.5-188.0° C.

$^1$H NMR (300 MHz, DMSO-$d_6$) δ 7.86 (d, J=9.1 Hz, 1H), 7.41 (d, J=8.5 Hz, 2H), 7.13 (d, J=2.6 Hz, 1H), 6.97-6.93 (m, 3H), 6.40 (br s, 2H), 5.11 (s, 2H), 4.28 (d, J=7.4 Hz, 2H), 3.76 (s, 3H), 2.86 (t, J=7.6 Hz, 2H), 2.21-2.07 (m, 1H), 1.89-1.79 (m, 2H), 1.01 (t, J=7.6 Hz, 3H), 0.91 (d, J=6.6 Hz, 6H);

$^{13}$C NMR (75 MHz, DMSO-$d_6$) δ 158.8, 156.7, 152.4, 151.8, 146.3, 132.6, 129.2, 129.0, 125.0, 121.0, 113.7, 111.7, 109.0, 108.5, 68.7, 54.9, 51.1, 28.6, 28.4, 20.8, 19.0, 13.7;

MS (APCI) m/z 419 (M+H)$^+$;

Anal. Calcd. for $C_{25}H_{30}N_4O_2$: % C, 71.74; % H, 7.22; % N, 13.39. Found: % C, 71.66; % H, 7.17; % N, 13.32.

Example 21

7-(3-Aminobenzyloxy)-1-(2-methylpropyl)-2-propyl-1H-imidazo[4,5-c]quinolin-4-amine

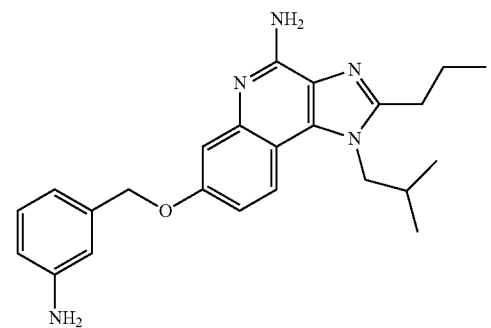

1-(2-Methylpropyl)-7-(3-nitrobenzyloxy)-2-propyl-1H-imidazo[4,5-c]quinolin-4-amine (700 mg, 1.6 mmol), prepared as described in Example 16, was mixed with acetonitrile (35 mL), and catalytic 5% platinum on carbon was added. The reaction was placed under hydrogen pressure (50 psi, 3.4×10$^5$ Pa) for three hours. The reaction mixture was filtered through a layer of CELITE filter aid, and the filter cake was washed with hot methanol. The filtrate was concentrated under reduced pressure to yield 600 mg of a solid. The solid was purified by column chromatography on silica gel (eluting with chloroform:methanol ranging in ratios from 99.5:0.5 to 98:2), recrystallized from 75:25 acetonitrile:2-propanol, isolated by filtration, and dried in a vacuum oven to provide 270 mg of 7-(3-aminobenzyloxy)-1-(2-methylpropyl)-2-propyl-1H-imidazo[4,5-c]quinolin-4-amine as off-white crystals, mp 228.0-230.0° C.

$^1$H NMR (300 MHz, CDCl$_3$) δ 7.78 (d, J=9.0 Hz, 1H), 7.33 (d, J=2.6 Hz, 1H), 7.19-7.14 (m, 1H), 7.03 (dd, J=9.0; 2.7 Hz, 1H), 6.87-6.83 (m, 2H), 6.66-6.62 (m, 1H), 5.43 (br s, 2H), 5.09 (s, 2H), 4.2 (d, J=7.5 Hz, 2H), 3.73 (br s, 2H), 2.86 (t, J=8.3 Hz, 2H), 2.34 (septet, J=6.7 Hz, 1H), 1.97-1.87 (m, 2H), 1.08 (t, J=7.4 Hz, 3H), 1.00 (d, J=6.7 Hz, 6H);

$^{13}$C NMR (75 MHz, CDCl$_3$) δ 157.8, 153.0, 151.4, 146.6, 146.4, 138.1, 133.8, 129.5, 125.5, 120.7, 117.6, 114.6, 114.1, 113.5, 109.8, 108.7, 70.0, 52.4, 29.6, 29.0, 21.4, 19.7, 14.0;

MS (APCI) m/z 404 (M+H)$^+$;

Anal. Calcd. for C$_{24}$H$_{29}$N$_5$O: % C, 71.44; % H, 7.24; % N, 17.36. Found: % C, 71.67; % H, 7.08; % N, 17.22.

Examples 22-32

The general method described for Examples 7-20 was followed with the following modifications. A warm solution of 4-amino-2-ethoxymethyl-1-(2-methylpropyl)-1H-imidazo[4,5-c]quinolin-7-ol (1 g, 3 mmol), prepared as described in Example 6, in DMF (50 mL) was allowed to cool to room temperature before the addition of cesium carbonate (2 equivalents). A halide (1.1 equivalents) selected from the table below was used. The purification methods described in Example 10 were used unless otherwise indicated below the table. For each example, the characterization data for the product is included below the table.

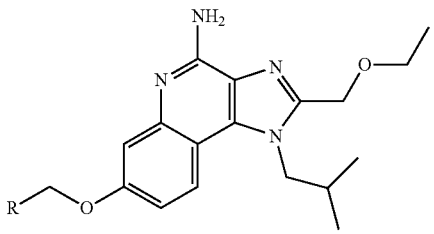

| Example | Halide | R |
|---|---|---|
| 22 | 4-Methylbenzyl bromide | ⟨4-methylphenyl⟩ |
| 23 | 3-Methylbenzyl bromide | ⟨3-methylphenyl⟩ |
| 24 | 4-(Trifluoromethyl)benzyl bromide | ⟨4-CF$_3$-phenyl⟩ |
| 25 | 3-Methoxybenzyl bromide | ⟨3-OMe-phenyl⟩ |
| 26 | 3-(Trifluoromethyl)benzyl bromide | ⟨3-CF$_3$-phenyl⟩ |
| 27 | 3-Nitrobenzyl bromide | ⟨3-NO$_2$-phenyl⟩ |
| 28 | 3,5-Dimethoxybenzyl bromide | ⟨3,5-diOMe-phenyl⟩ |
| 29 | 1-(3-Bromopropyl)pyrrole | ⟨propyl-pyrrole⟩ |
| 30 | 2-Chlorobenzyl chloride | ⟨2-Cl-phenyl⟩ |
| 31 | 4-Methoxybenzyl chloride | ⟨4-OMe-phenyl⟩ |
| 32 | 2-Methoxybenzyl chloride | ⟨2-OMe-phenyl⟩ |

Example 22

2-Ethoxymethyl-7-(4-methylbenzyloxy)-1-(2-methylpropyl)-1H-imidazo[4,5-c]quinolin-4-amine The general method described for Examples 22-32 was used with the following modifications. After the addition of 4-methylbenzyl bromide (630 mg, 3.40 mmol), the reaction was stirred for six hours. The reaction was incomplete as determined by HPLC analysis, and a small additional amount of 4-methylbenzyl bromide was added. The product was purified by column chromatography on silica gel (eluting with chloroform and then chloroform:methanol in ratios ranging from 99:1 to 97:3), recrystallized from 2-propanol, isolated by filtration, and dried for two days in a vacuum oven at 65° C. to provide 1.06 g of 2-ethoxymethyl-7-(4-methylbenzyloxy)-1-(2-methylpropyl)-1H-imidazo[4,5-c]quinolin-4-amine as an off-white solid, mp 209.0-210.2° C.

$^1$H NMR (300 MHz, DMSO-d$_6$) δ 7.91 (d, J=9.0 Hz, 1H), 7.37 (d, J=8.0 Hz, 2H), 7.21 (d, J=8.2 Hz, 2H), 7.12 (d, J=2.6

Hz, 1H), 6.97 (dd, J=8.9, 2.7 Hz, 1H), 6.57 (br s, 2H), 5.16 (s, 2H), 4.73 (s, 2H), 4.38 (d, J=7.7 Hz, 2H), 3.55 (q, J=7.0 Hz, 2H), 2.31 (s, 3H), 2.28-2.15 (m, 1H), 1.15 (t, J=7.0 Hz, 3H), 0.91 (d, J=6.6 Hz, 6H);
$^{13}$C NMR (75 MHz, DMSO-d$_6$) δ 157.6, 152.6, 148.9, 147.3, 137.3, 134.5, 133.8, 129.3, 128.0, 125.4, 122.0, 112.2, 109.3, 109.1, 69.3, 65.6, 64.6, 52.0, 28.9, 21.1, 19.6, 15.2;
MS (APCI) m/z 419 (M+H)$^+$;
Anal. Calcd. for C$_{25}$H$_{30}$N$_4$O$_2$: % C, 71.74; % H, 7.22; % N, 13.39. Found: % C, 71.59; % H, 7.21; % N, 13.17.

Example 23

2-Ethoxymethyl-7-(3-methylbenzyloxy)-1-(2-methylpropyl)-1H-imidazo[4,5-c]quinolin-4-amine The general method described for Examples 22-32 was followed using the following modifications. 4-Amino-2-ethoxymethyl-1-(2-methylpropyl)-1H-imidazo[4,5-c]quinolin-7-ol (310 mg, 0.97 mmol) was dissolved in DMF (15 mL) with heating but precipitated from the solution as it cooled to room temperature. A solution of 3-methylbenzyl bromide (197 mg, 1.07 mmol) in DMF (0.5 mL) was added followed by solid cesium carbonate (643 mg, 1.97 mmol). N-Methylpyrrolidone (1 mL) was added to the reaction, and the reaction was stirred overnight. The crude product was purified by column chromatography on silica gel (eluting with chloroform:methanol), triturated with acetonitrile, and isolated by filtration to provide 175 mg of 2-ethoxymethyl-7-(3-methylbenzyloxy)-1-(2-methylpropyl)-1H-imidazo[4,5-c]quinolin-4-amine as a white solid, mp 207.0-208.0° C.
$^1$H NMR (300 MHz, DMSO-d$_6$) δ 7.92 (d, J=9.0 Hz, 1H), 7.29-7.27 (m, 3H), 7.15-7.13 (m, 2H), 6.99 (dd, J=9.0, 2.6 Hz, 1H), 6.61 (br s, 2H), 5.17 (s, 2H), 4.74 (s, 2H), 4.39 (d, J=7.5 Hz, 2H), 3.55 (q, J=7.0 Hz, 2H), 2.32 (s, 3H), 2.28-2.16 (m, 1H), 1.15 (t, J=7.0 Hz, 3H), 0.91 (d, J=6.6 Hz, 6H);
$^{13}$C NMR (75 MHz, DMSO-d$_6$) δ 157.1, 152.2, 148.4, 146.8, 137.4, 137.0, 133.3, 128.2, 128.2, 127.9, 124.9, 124.5, 121.5, 111.6, 108.8, 108.5, 69.0, 65.1, 64.1, 51.5, 28.4, 20.9, 19.1, 14.8;
MS (APCI) m/z 419 (M+H)$^+$;
Anal. Calcd. for C$_{25}$H$_{30}$N$_4$O$_2$: % C, 71.74; % H, 7.22; % N, 13.39. Found: % C, 71.41; % H, 7.43; % N, 13.27.

Example 24

2-Ethoxymethyl-1-(2-methylpropyl)-7-[4-(trifluoromethyl)benzyloxy]-1H-imidazo[4,5-c]quinolin-4-amine The product (1.07 g) was obtained as an off-white solid, mp 181.3-182.7° C.
$^1$H NMR (300 MHz, DMSO-d$_6$) δ 7.83 (d, J=9.1 Hz, 1H), 7.65 (d, J=8.4 Hz, 2H), 7.59 (d, J=8.2 Hz, 2H), 7.30 (d, J=2.6 Hz, 1H), 7.06 (dd, J=9.0, 2.7 Hz, 1H), 5.50 (br s, 2H), 5.24 (s, 2H), 4.81 (s, 2H), 4.39 (d, J=7.6 Hz, 2H), 3.60 (q, J=7.0 Hz, 2H), 2.39 (septet, J=6.8 Hz, 1H), 1.24 (t, J=7.0 Hz, 3H), 1.01 (d, J=6.7 Hz, 6H);
MS (APCI) m/z 473 (M+H)$^+$;
Anal. Calcd. for C$_{25}$H$_{27}$F$_3$N$_4$O$_2$: % C, 63.55; % H, 5.76; % N, 11.86. Found: % C, 63.43; % H, 5.68; % N, 11.79.

Example 25

2-Ethoxymethyl-7-(3-methoxybenzyloxy)-1-(2-methylpropyl)-1H-imidazo[4,5-c]quinolin-4-amine The product (710 mg) was obtained as an off-white solid, mp 144.0-145.0° C. $^1$H NMR (300 MHz, DMSO-d$_6$) δ 7.81 (d, J=9.1 Hz, 1H), 7.34-7.26 (m, 2H), 7.08-7.03 (m, 3H), 6.89-6.84 (m, 1H), 5.50 (br s, 2H), 5.16 (s, 2H), 4.80 (s, 2H), 4.38 (d, J=7.6 Hz, 2H), 3.82 (s, 3H), 3.59 (q, J=7.0 Hz, 2H), 2.39 (septet, J=6.8 Hz, 1H), 1.24 (t, J=7.0 Hz, 3H), 1.00 (d, J=6.7 Hz, 6H);
$^{13}$C NMR (75 MHz, DMSO-d$_6$) 159.8, 158.1, 151.7, 148.7, 146.9, 138.4, 134.6, 129.5, 125.5, 121.2, 119.7, 113.6, 113.5, 112.9, 109.8, 108.8, 69.8, 66.1, 65.3, 55.2, 52.7, 28.9, 19.7, 15.0;
MS (APCI) m/z 435 (M+H)$^+$;
Anal. Calcd. for C$_{25}$H$_{30}$N$_4$O$_3$: % C, 69.10; % H, 6.96; % N, 12.89. Found: % C, 69.26; % H, 6.82; % N, 12.93.

Example 26

2-Ethoxymethyl-1-(2-methylpropyl)-7-[3-(trifluoromethyl)benzyloxy]-1H-imidazo[4,5-c]quinolin-4-amine The product (990 mg) was obtained as an off-white solid, mp 151.0-152.0° C.
$^1$H NMR (300 MHz, DMSO-d$_6$) δ 7.83 (d, J=9.1 Hz, 1H), 7.76 (s, 1H), 7.67-7.48 (m, 3H), 7.33 (d, J=2.6 Hz, 1H), 7.07 (dd, J=9.0, 2.7 Hz, 1H), 5.59 (br s, 2H), 5.22 (s, 2H), 4.81 (s, 2H), 4.39 (d, J=7.6 Hz, 2H), 3.60 (q, J=7.0 Hz, 2H), 2.39 (septet, J=6.8 Hz, 1H), 1.24 (t, J=7.0 Hz, 3H), 1.01 (d, J=6.7 Hz, 6H);
MS (APCI) m/z 473 (M+H)$^+$;
Anal. Calcd. for C$_{25}$H$_{27}$F$_3$N$_4$O$_2$: % C, 63.55; % H, 5.76; % N, 11.86. Found: % C, 63.50; % H, 5.69; % N, 11.74.

Example 27

2-Ethoxymethyl-1-(2-methylpropyl)-7-(3-nitrobenzyloxy)-1H-imidazo[4,5-c]quinolin-4-amine The general method described for Examples 22-32 was followed with the following modification. The cesium carbonate was added before the solution of 4-amino-2-ethoxymethyl-1-(2-methylpropyl)-1H-imidazo[4,5-c]quinolin-7-ol in DMF had cooled to room temperature. The product, 2-ethoxymethyl-1-(2-methylpropyl)-7-(3-nitrobenzyloxy)-1H-imidazo[4,5-c]quinolin-4-amine (1.00 g), was obtained as a pale yellow solid, mp 162.5-164.5° C.
$^1$H NMR (300 MHz, DMSO-d$_6$) δ 8.35 (s, 1H), 8.18 (d, J=8.2 Hz, 1H), 7.85-7.77 (m, 2H), 7.56 (t, J=8.2 Hz, 1H), 7.30 (d, J=2.6 Hz, 1H), 7.08 (dd, J=9.0, 2.7 Hz, 1H), 5.63 (br s, 2H), 5.26 (s, 2H), 4.81 (s, 2H), 4.39 (d, J=7.6 Hz, 2H), 3.60 (q, J=7.0 Hz, 2H), 2.39 (septet, J=6.7 Hz, 1H), 1.24 (t, J=7.0 Hz, 3H), 1.01 (d, J=6.7 Hz, 6H);
$^{13}$C NMR (75 MHz, DMSO-d$_6$) δ 157.4, 151.9, 148.9, 148.4, 146.9, 139.1, 134.5, 133.0, 129.4, 125.6, 122.8, 122.0, 121.4, 113.3, 110.1, 108.7, 68.4, 66.1, 65.2, 52.7, 28.9, 19.7, 14.9; MS (APCI) m/z 450 (M+H)$^+$;
Anal. Calcd. for C$_{24}$H$_{27}$N$_5$O$_4$: % C, 64.13; % H, 6.05; % N, 15.58. Found: % C, 64.19; % H, 5.88; % N, 15.56.

Example 28

7-(3,5-Dimethoxybenzyloxy)-2-ethoxymethyl-1-(2-methylpropyl)-1H-imidazo[4,5-c]quinolin-4-amine The reaction was carried out at half the scale of the general method described for Examples 22-32. The product (370 mg) was obtained as an off-white solid, mp 130.0-131.0° C.
$^1$H NMR (300 MHz, CDCl$_3$) δ 7.81 (d, J=9.1 Hz, 1H), 7.33 (d, J=2.6 Hz, 1H), 7.06 (dd, J=9.0, 2.7 Hz, 1H), 6.64 (d, J=2.3

Hz, 2H), 6.42 (t, J=2.3 Hz, 1H), 5.47 (br s, 2H), 5.13 (s, 2H), 4.80 (s, 2H), 4.39 (d, J=7.6 Hz, 2H), 3.80 (s, 6H), 3.59 (q, J=7.0 Hz, 2H), 2.39 (septet, J=6.8 Hz, 1H), 1.24 (t, J=6.8 Hz, 3H), 1.01 (d, J=6.7 Hz, 6H);
$^{13}$C NMR (75 MHz, CDCl$_3$) δ 160.9, 158.1, 151.7, 148.8, 146.9, 139.2, 134.6, 125.5, 121.2, 113.6, 109.8, 108.9, 105.2, 99.9, 69.9, 66.1, 65.3, 55.3, 52.7, 28.9, 19.8, 15.0;
MS (APCI) m/z 465 (M+H)$^+$;
Anal. Calcd. for $C_{26}H_{32}N_4O_4$: % C, 67.22; % H, 6.94; % N, 12.06. Found: % C, 67.17; % H, 7.27; % N, 11.91.

Example 29

2-Ethoxymethyl-1-(2-methylpropyl)-7-[3-(pyrrol-1-yl)propoxy]-1H-imidazo[4,5-c]quinolin-4-amine The general method described for Examples 22-32 was followed with the following modifications. The reaction mixture in deionized water was decanted from the flask to leave the crude product, which was rinsed with water and allowed to dry. Following chromatographic purification, the product was recrystallized from acetonitrile. After the product was dried, 730 mg of 2-ethoxymethyl-1-(2-methylpropyl)-7-[3-(pyrrol-1-yl)propoxy]-1H-imidazo[4,5-c]quinolin-4-amine were obtained as an off-white solid, mp 160.0-162.0° C. $^1$H NMR (300 MHz, DMSO-d$_6$) δ 7.80 (d, J=9.1 Hz, 1H), 7.22 (d, J=2.6 Hz, 1H), 6.99 (dd, J=9.0, 2.6 Hz, 1H), 6.67 (t, J=2.1 Hz, 2H), 6.13 (t, J=2.1 Hz, 2H), 5.51 (br s, 2H), 4.80 (s, 2H), 4.39 (d, J=7.6 Hz, 2H), 4.14 (t, J=6.8 Hz, 2H), 4.03 (t, J=5.9 Hz, 2H), 3.59 (q, J=7.0 Hz, 2H), 2.46-2.21 (m, 3H), 1.24 (t, J=7.0 Hz, 3H), 1.01 (d, J=6.7 Hz, 6H);
$^{13}$C NMR (75 MHz, DMSO-d$_6$) δ 158.0, 151.7, 148.7, 146.9, 134.6, 125.5, 121.2, 120.6, 113.2, 109.8, 108.5, 108.1, 66.1, 65.3, 64.3, 52.7, 46.0, 31.2, 28.9, 19.7, 15.0;
MS (APCI) m/z 422 (M+H)$^+$;
Anal. Calcd. for $C_{24}H_{31}N_5O_2$: % C, 68.38; % H, 7.41; % N, 16.61. Found: % C, 68.35; % H, 7.35; % N, 16.66.

Example 30

7-(2-Chlorobenzyloxy)-2-ethoxymethyl-1-(2-methylpropyl)-1H-imidazo[4,5-c]quinolin-4-amine The general method described for Examples 22-32 was followed with the following modification. The cesium carbonate (1.55 g, 4.77 mmol) was added before the solution of 4-amino-2-ethoxymethyl-1-(2-methylpropyl)-1H-imidazo [4,5-c]quinolin-7-ol (0.750 g, 2.39 mmol) in DMF (50 mL) had cooled to room temperature. The product, 7-(2-chlorobenzyloxy)-2-ethoxymethyl-1-(2-methylpropyl)-1H-imidazo[4,5-c]quinolin-4-amine (810 mg), was obtained as an off-white solid, mp 211.0-212.0° C.
$^1$H NMR (300 MHz, DMSO-d$_6$) δ 7.83 (d, J=9.1 Hz, 1H), 7.62-7.58 (m, 1H), 7.43-7.23 (m, 4H), 7.09 (dd, J=9.0, 2.7 Hz, 1H), 5.45 (br s, 2H), 5.29 (s, 2H), 4.81 (s, 2H), 4.39 (d, J=7.6 Hz, 2H), 3.59 (q, J=7.0 Hz, 2H), 2.40 (septet, J=6.8 Hz, 1H), 1.24 (t, J=7.0 Hz, 3H), 1.01 (d, J=6.7 Hz, 6H);
$^{13}$C NMR (75 MHz, DMSO-d$_6$) δ 157.9, 151.7, 148.8, 146.9, 134.6, 134.67, 132.63, 129.3, 128.8, 128.6, 126.8, 125.5, 121.2, 113.4, 110.0, 109.0, 67.2, 66.1, 65.3, 52.7, 28.9, 19.8, 15.0; MS (APCI) m/z 439 (M+H)$^+$;
Anal. Calcd. for $C_{24}H_{27}ClN_4O_2$: % C, 65.67; % H, 6.20; % N, 12.76. Found: % C, 65.82; % H, 6.38; % N, 12.69.

Example 31

2-Ethoxymethyl-7-(4-methoxybenzyloxy)-1-(2-methylpropyl)-1H-imidazo[4,5-c]quinolin-4-amine The modification described in Example 19 was followed using 4-methoxybenzyl chloride (548 mg, 3.50 mmol) in lieu of 2-methoxybenzyl chloride. The product (1.04 g) was obtained as an off-white solid, mp 181.0-182.5° C.
$^1$H NMR (300 MHz, DMSO-d$_6$) δ 7.80 (d, J=9.1 Hz, 1H), 7.41 (d, J=8.7 Hz, 2H), 7.35 (d, J=2.6 Hz, 1H), 7.03 (dd, J=9.0, 2.6 Hz, 1H), 6.93 (d, J=8.7 Hz, 2H), 5.57 (br s, 2H), 5.10 (s, 2H), 4.80 (s, 2H), 4.38 (d, J=7.6 Hz, 2H), 3.81 (s, 3H), 3.59 (q, J=7.0 Hz, 2H), 2.39 (septet, J=6.8 Hz, 1H), 1.24 (t, J=7.0 Hz, 3H), 1.00 (d, J=6.7 Hz, 6H);
$^{13}$C NMR (75 MHz, DMSO-d$_6$) δ 159.3, 158.1, 151.7, 148.6, 146.9, 134.6, 129.2, 128.8, 125.4, 121.1, 113.9, 113.6, 109.7, 108.7, 69.6, 66.0, 65.2, 55.2, 52.6, 28.8, 19.7, 14.9;
MS (APCI) m/z 435 (M+H)$^+$;
Anal. Calcd. for $C_{25}H_{30}N_4O_3$: % C, 69.10; % H, 6.96; % N, 12.89. Found: % C, 69.20; % H, 6.95; % N, 12.83.

Example 32

2-Ethoxymethyl-7-(2-methoxybenzyloxy)-1-(2-methylpropyl)-1H-imidazo[4,5-c]quinolin-4-amine The modification described in Example 19 was followed with the exception that the reaction was allowed to stir over two nights. The purification methods described for Example 10 were followed to provide 820 mg of 2-ethoxymethyl-7-(2-methoxybenzyloxy)-1-(2-methylpropyl)-1H-imidazo[4,5-c] quinolin-4-amine as an off-white solid, mp 206.0-207.0° C.
$^1$H NMR (300 MHz, DMSO-d$_6$) δ 7.81 (d, J=9.1 Hz, 1H), 7.50 (dd, J=7.5, 1.6 Hz, 1H), 7.38 (d, J=2.6 Hz, 1H), 7.30 (dt, J=8.1, 1.7 Hz, 1H), 7.08 (dd, J=9.0, 2.7 Hz, 1H), 6.98 (dt, J=7.5, 1.0 Hz, 1H), 6.92 (dd, J=8.2, 0.6 Hz, 1H), 5.44 (br s, 2H), 5.25 (s, 2H), 4.80 (s, 2H), 4.38 (d, J=7.6 Hz, 2H), 3.87 (s, 3H), 3.59 (q, J=7.0 Hz, 2H), 2.40 (septet, J=6.8 Hz, 1H), 1.24 (t, J=6.8 Hz, 3H), 1.00 (d, J=6.7 Hz, 6H);
$^{13}$C NMR (75 MHz, DMSO-d$_6$) δ 158.4, 156.8, 151.6, 148.7, 146.9, 134.7, 128.8, 128.4, 125.4, 125.2, 121.1, 120.5, 113.7, 110.2, 109.7, 108.9, 66.1, 65.3, 65.2, 55.3, 52.7, 28.9, 19.7, 15.0;
MS (APCI) m/z 435 (M+H)$^+$;
Anal. Calcd. for $C_{25}H_{30}N_4O_3$: % C, 69.10; % H, 6.96; % N, 12.89. Found: % C, 69.14; % H, 7.26; % N, 12.82.

Example 33

7-(3-Aminobenzyloxy)-2-ethoxymethyl-1-(2-methylpropyl)-1H-imidazo[4,5-c]quinolin-4-amine

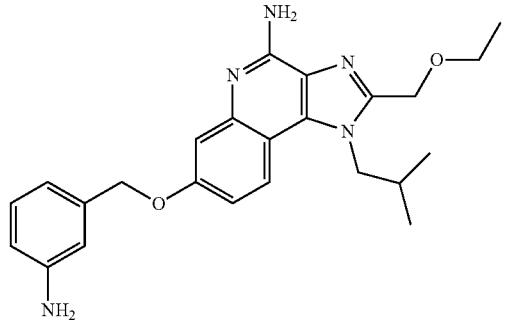

2-Ethoxymethyl-1-(2-methylpropyl)-7-(3-nitrobenzyloxy)-1H-imidazo[4,5-c]quinolin-4-amine (980 mg, 2.2 mmol), prepared as described in Example 27, was mixed with acetonitrile (30 mL), and 5% platinum on carbon (~25 mg) was added. The reaction was placed under hydrogen pressure (50 psi, 3.4×10$^5$ Pa) overnight. An analysis by liquid chromatography/mass spectrometry (LC/MS) indicated the presence of starting material; additional 5% platinum on carbon (~25 mg) was added. The reaction was placed under hydrogen pressure (50 psi, 3.4×10$^5$ Pa) for an additional three hours. An analysis by LC/MS again indicated that the reaction was incomplete; methanol (100 mL) and 5% platinum on carbon (200 mg) were added. The reaction was placed under hydrogen pressure (50 psi, $3.4 \times 10^5$ Pa) overnight. The reaction mixture was filtered through a layer of CELITE filter aid, the filter cake washed with hot methanol, and the filtrate concentrated under reduced pressure to yield a solid. The solid was purified by column chromatography on silica gel (45 g, eluting with chloroform:methanol ranging in ratios from 99:1 to 95:5) to provide two products. The first product was recrystallized from 2-propanol to provide 90 mg of 7-(3-aminobenzyloxy)-2-ethoxymethyl-1-(2-methylpropyl)-1H-imidazo[4,5-c]quinolin-4-amine as off-white crystals, mp 228.0-230.0° C.

$^1$H NMR (300 MHz, DMSO-$d_6$) δ 7.91 (d, J=9.1 Hz, 1H), 7.10 (d, J=2.7 Hz, 1H), 7.05-6.95 (m, 2H), 6.67-6.48 (m, 5H), 5.11 (br s, 2H), 5.05 (s, 2H), 4.73 (s, 2H), 4.38 (d, J=7.6 Hz, 2H), 3.55 (q, J=7.0 Hz, 2H), 2.23 (septet, J=6.7 Hz, 1H), 1.15 (t, J=7.0 Hz, 3H), 0.91 (d, J=6.7 Hz, 6H);

$^{13}$C NMR (75 MHz, DMSO-$d_6$) δ 157.7, 152.6, 149.1, 148.8, 147.3, 138.2, 133.8, 129.2, 125.4, 122.0, 115.1, 113.6, 112.9, 112.1, 109.2, 109.0, 69.9, 65.6, 64.6, 52.0, 28.9, 19.6, 15.3; MS (APCI) m/z 419 (M+H)$^+$;

Anal. Calcd. for $C_{24}H_{29}N_5O_2$: % C, 68.71; % H, 6.97; % N, 16.69. Found: % C, 68.70; % H, 7.02; % N, 16.52.

Example 34

2-Ethoxymethyl-7-(3-ethylaminobenzyloxy)-1-(2-methylpropyl)-1H-imidazo[4,5-c]quinolin-4-amine

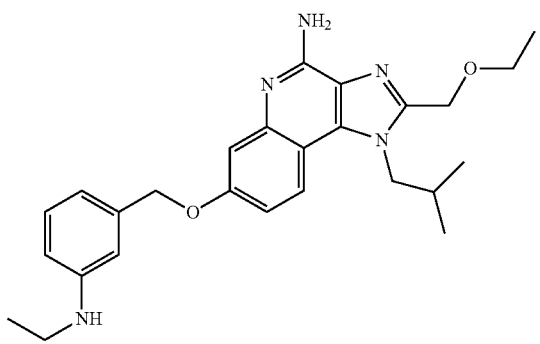

The second product obtained from Example 33 after chromatographic purification was isolated as a tan solid, mp 60.0-65.0° C.

$^1$H NMR (300 MHz, DMSO-$d_6$) δ 7.91 (d, J=9.1 Hz, 1H), 7.11-7.05 (m, 2H), 6.98 (dd, J=9.0, 2.7 Hz, 1H), 6.65-6.60 (m, 4H), 6.49 (dd, J=8.0, 1.3 Hz, 1H), 5.57 (t, J=5.0 Hz, 1H), 5.08 (s, 2H), 4.73 (s, 2H), 4.39 (d, J=7.6 Hz, 2H), 3.55 (q, J=7.0 Hz, 2H), 3.07-2.97 (m, 2H), 2.29-2.15 (m, 1H), 1.17-1.11 (m, 6H), 0.91 (d, J=6.7 Hz, 6H);

$^{13}$C NMR (75 MHz, DMSO-$d_6$) δ 157.8, 152.5, 149.4, 148.9, 147.0, 138.1, 133.9, 129.3, 125.3, 122.0, 114.9, 112.2, 111.5, 111.2, 109.2, 108.9, 70.0, 65.6, 64.5, 52.0, 37.6, 28.9, 19.6, 15.3, 14.7;

MS (APCI) m/z 448 (M+H)$^+$.

Examples 35-40

Part A

7-Benzyloxy-1-(2-methylpropyl)-2-propyl-1H-imidazo[4,5-c]quinoline (60.3 g, 0.188 mol), prepared as described in Parts A-G of Example 1, and 10% palladium on carbon (10 g) were mixed with ethanol (500 mL). Ammonium formate (101.53 g, 1.61 mol) and ethanol (500 mL) were then added, and the reaction mixture was heated at reflux for two hours. The mixture was allowed to cool to ambient temperature slowly and stirred overnight. The reaction mixture was filtered through a layer of CELITE filter aid, and the filter cake was washed with ethanol (1 L), methanol (2 L) and dichloromethane (2 L). The combined filtrates were concentrated under reduced pressure to provide a tan solid, which was triturated with cold ethanol and isolated by filtration to yield 30 g of 1-(2-methylpropyl)-2-propyl-1H-imidazo[4,5-c]quinolin-7-ol as a tan, granular solid.

$^1$H NMR (300 MHz, DMSO-$d_6$): δ 9.89 (s, 1H), 9.00 (s, 1H), 8.12 (d, J=9.3 Hz, 1H), 7.41 (d, J=2.5 Hz, 1H), 7.23 (dd, J=9.3, 2.5 Hz, 1H), 4.36 (d, J=7.4 Hz, 2H), 2.91 (t, J=7.5 Hz, 2H), 2.25-2.10 (m, 1H), 1.88 (sextet, J=7.4 Hz, 2H), 1.03 (t, J=7.5 Hz, 3H), 0.92 (d, J=7.1 Hz, 6H).

Part B 1-(2-Methylpropyl)-2-propyl-1H-imidazo[4,5-c]quinolin-7-ol (1 equivalent) and cesium carbonate (1.6 equivalents) were stirred in DMF. The fluorobenzene (1.6 equivalents) indicated in the table below was added in one portion, and the reaction was heated at 65° C. for 16 hours. The solvent was removed under reduced pressure, and the residue was partitioned between water and dichloromethane. The aqueous layer was extracted with dichloromethane. The combined organic fractions were washed sequentially with water (2×) and brine, dried over magnesium sulfate, filtered, and concentrated under reduced pressure to provide a black oil. The oil was purified by column chromatography on silica gel (eluting with 50:50 ethyl acetate:hexanes) to provide a solid.

Part C mCPBA (1.2 equivalents) was added to a solution of the material from Part B in chloroform. The reaction was stirred for one hour and then poured into saturated aqueous sodium carbonate and stirred for 20 minutes. The aqueous layer was extracted with chloroform. The combined organic solutions were washed sequentially with water and brine, dried over magnesium sulfate, filtered, and concentrated under reduced pressure.

Part D

The residue from Part C was dissolved in dichloromethane Ammonium hydroxide was added, followed by p-toluenesulfonyl chloride (1.5 equivalents). The reaction was stirred for 16 hours and then diluted with dichloromethane. The organic layer was washed with aqueous ammonium hydroxide (100 mL). The combined aqueous fractions were extracted with dichloromethane. The combined organic fractions were washed sequentially with water and brine, dried over magnesium sulfate, filtered, and concentrated under reduced pressure. For each example, the purification and characterization of the product is described below the table.

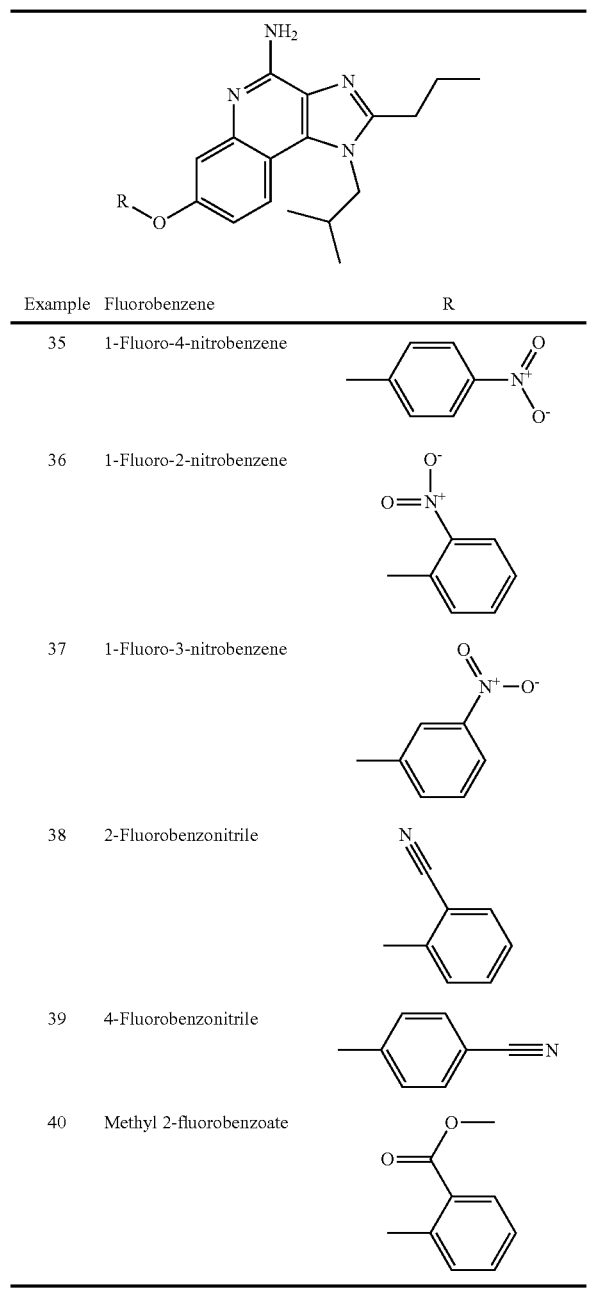

Example 35

1-(2-Methylpropyl)-7-(4-nitrophenoxy)-2-propyl-1H-imidazo[4,5-c]quinolin-4-amine Part B of the general methods described for Examples 35-40 was followed using 2.00 g of 1-(2-methylpropyl)-2-propyl-1H-imidazo[4,5-c]quinolin-7-ol to provide 2.33 g of 1-(2-methylpropyl)-7-(4-nitrophenoxy)-2-propyl-1H-imidazo[4,5-c]quinoline as a yellow solid. Parts C and D of the general methods described for Examples 35-40 were replaced by the following procedure. mCPBA (0.853 g, 2.97 mmol) was added in one portion to a solution of 1-(2-methylpropyl)-7-(4-nitrophenoxy)-2-propyl-1H-imidazo[4,5-c]quinoline (1.00 g, 2.47 mmol) in chloroform (17 mL), and the reaction was stirred for 30 minutes Ammonium hydroxide (17 mL) was then added, followed by p-toluenesulfonyl chloride (0.710 g, 3.70 mmol). The reaction was stirred for 16 hours and then diluted with dichloromethane. The aqueous layer was extracted with dichloromethane. The combined organic solutions were washed sequentially with water and brine, dried over magnesium sulfate, filtered, and concentrated under reduced pressure to provide a brown solid. The solid was recrystallized from acetonitrile to provide 0.680 g of 1-(2-methylpropyl)-7-(4-nitrophenoxy)-2-propyl-1H-imidazo[4,5-c]quinolin-4-amine as a reddish-brown, crystalline solid, mp 209-211° C.

$^1$H NMR (300 MHz, DMSO-$d_6$): δ 8.29-8.24 (m, 2H), 8.07 (d, J=9.2 Hz, 1H), 7.29 (d, J=3.3 Hz, 1H), 7.23-7.17 (m, 2H), 7.08 (dd, J=9.0, 2.8 Hz, 1H), 6.63 (s, 2H), 4.35 (d, J=7.4 Hz, 2H), 2.90 (t, J=7.5 Hz, 2H), 2.24-2.10 (m, 1H), 1.86 (sextet, J=7.5 Hz, 2H), 1.03 (t, J=7.4 Hz, 3H), 0.94 (d, J=6.6 Hz, 6H).

MS (ESI) m/z 420.2042 (420.2036 calcd for $C_{23}H_{25}N_5O_3$, M+H).

Anal. Calcd. for $C_{23}H_{25}N_5O_3$: % C, 65.86; % H, 6.01; % N, 16.70. Found: % C, 65.47; % H, 5.79; % N, 17.00.

Example 36

1-(2-Methylpropyl)-7-(2-nitrophenoxy)-2-propyl-1H-imidazo[4,5-c]quinolin-4-amine The crude product was purified by flash chromatography using a 35 g silica gel cartridge (RediSep, ISCO, 230-400 mesh, 13.5 cm×2.7 cm diameter) attached to a gradient pump system, 254 nm UV detector and fraction collector (ISCO COMBIFLASH Sg100c system). The column was equilibrated with dichloromethane and the reaction mixture was injected onto the column. The mixture was eluted at 35 mL/minute with a linear gradient program consisting of 100% dichloromethane to 2% methanol/dichloromethane over five minutes, holding at 2% methanol/dichloromethane for five minutes, and then eluting with 7% methanol/dichloromethane until no compound could be detected. Fractions were examined by TLC and those containing the desired compound were combined and concentrated. Following chromatographic purification, the product was recrystallized from acetonitrile to provide 0.079 g of 1-(2-methylpropyl)-7-(2-nitrophenoxy)-2-propyl-1H-imidazo[4,5-c]quinolin-4-amine as yellow needles, mp 207-208.5° C.

$^1$H NMR (300 MHz, DMSO-$d_6$): δ 8.09 (dd, J=8.1, 1.8 Hz, 1H), 8.01 (d, J=9.4 Hz, 1H), 7.75-7.69 (m, 1H), 7.43-7.37 (m, 1H), 7.26 (dd, J=8.0, 1.3 Hz, 1H), 7.08 (d, J=2.4 Hz, 1H), 7.02 (dd, J=8.9, 2.7 Hz, 1H), 6.56 (s, 2H), 4.32 (ad, J=7.5 Hz, 2H), 2.89 (t, J=7.5 Hz, 2H), 2.16 (septet, J=6.9 Hz, 1H), 1.85 (sextet, J=7.4 Hz, 2H), 1.02 (t, J=7.2 Hz, 3H), 0.92 (d, J=6.0 Hz, 6H).

$^{13}$C NMR (75 MHz, DMSO-$d_6$): δ 154.2, 153.3, 152.4, 149.0, 146.2, 141.4, 134.9, 132.3, 126.0, 125.5, 124.3, 122.1, 121.5, 113.5, 112.6, 111.7, 51.2, 28.7, 28.5, 20.8, 19.1, 13.7.

MS (ESI) m/z 420.2028 (420.2036 calcd for $C_{23}H_{25}N_5O_3$, M+H).

Anal. Calcd. for $C_{23}H_{25}N_5O_3$: % C, 65.86; % H, 6.01; % N, 16.70. Found: % C, 65.74; % H, 5.83; % N, 16.78.

Example 37

1-(2-Methylpropyl)-7-(3-nitrophenoxy)-2-propyl-1H-imidazo[4,5-c]quinolin-4-amine The crude product was recrystallized from acetonitrile to provide 1-(2-methylpropyl)-7-(3-nitrophenoxy)-2-propyl-1H-imidazo[4,5-c]quinolin-4-amine as a yellow, crystalline solid, mp 198-200° C.

$^1$H NMR (300 MHz, DMSO-$d_6$): δ 8.05 (d, J=8.9 Hz, 1H), 8.02-7.98 (m, 1H), 7.77 (t, J=2.2 Hz, 1H), 7.70 (t, J=8.1 Hz, 1H), 7.58-7.54 (m, 1H), 7.23 (d, J=2.5 Hz, 1H), 7.07 (dd, J=9.1, 2.8 Hz, 1H), 6.60 (s, 2H), 4.34 (d, J=7.5 Hz, 2H), 2.90 (t, J=7.5 Hz, 2H), 2.17 (septet, J=6.5 Hz, 1H), 1.86 (sextet, J=7.4 Hz, 2H), 1.03 (t, J=7.2 Hz, 3H), 0.93 (d, J=6.9 Hz, 6H).
$^{13}$C NMR (75 MHz, DMSO-$d_6$): δ 157.8, 153.5, 153.3, 152.4, 148.8, 146.4, 132.4, 131.3, 126.1, 124.8, 122.3, 117.9, 115.1, 113.5, 112.2, 112.1, 51.2, 28.8, 28.6, 20.9, 19.1, 13.8.

MS (ESI) m/z 420.2052 (420.2036 calcd for $C_{23}H_{25}N_5O_3$, M+H).

Anal. Calcd. for $C_{23}H_{25}N_5O_3$: % C, 65.86; % H, 6.01; % N, 16.70. Found: % C, 65.61; % H, 5.91; % N, 16.60.

Example 38

2-[4-Amino-1-(2-methylpropyl)-2-propyl-1H-imidazo[4,5-c]quinolin-7-yloxy]benzonitrile The crude product was recrystallized from ethanol to yield 2-[4-amino-1-(2-methylpropyl)-2-propyl-1H-imidazo[4,5-c]quinolin-7-yloxy]benzonitrile as tan crystals, mp 230-232° C.

$^1$H NMR (300 MHz, DMSO-$d_6$): δ 8.04 (d, J=9.4 Hz, 1H), 7.93 (dd, J=7.8, 1.6 Hz, 1H), 7.72-7.65 (m, 1H), 7.32 (at, J=7.5 Hz, 1H), 7.19 (d, J=2.6 Hz, 1H), 7.10-7.05 (m, 2H), 6.61 (s, 2H), 4.34 (ad, J=7.4 Hz, 2H), 2.89 (t, J=7.5 Hz, 2H), 2.17 (septet, J=6.7 Hz, 1H), 1.85 (sextet, J=7.4 Hz, 2H), 1.03 (t, J=7.2 Hz, 3H), 0.93 (d, J=6.1 Hz, 6H).
$^{13}$C NMR (125 MHz, DMSO-$d_6$): δ 158.7, 153.4, 153.3, 152.4, 146.3, 135.2, 134.1, 132.3, 126.1, 123.8, 122.2, 118.2, 115.9, 114.6, 113.2, 112.1, 103.1, 51.2, 28.7, 28.5, 20.8, 19.1, 13.7.

MS (ESI) m/z 400.2143 (400.2137 calcd for $C_{24}H_{25}N_5O$, M+H).

Anal. Calcd. for $C_{24}H_{25}N_5O$: % C, 72.16; % H, 6.31; % N, 17.53. Found: % C, 71.93; % H, 6.35; % N, 17.61.

Example 39

4-[4-Amino-1-(2-methylpropyl)-2-propyl-1H-imidazo[4,5-c]quinolin-7-yloxy]benzonitrile The crude product was recrystallized from ethanol to provide 4-[4-amino-1-(2-methylpropyl)-2-propyl-1H-imidazo[4,5-c]quinolin-7-yloxy]benzonitrile as tan crystals, mp 223-225° C.

$^1$H NMR (300 MHz, DMSO-$d_6$): δ 8.05 (d, J=9.1 Hz, 1H), 7.91-7.82 (m, 2H), 7.24 (d, J=2.5 Hz, 1H), 7.22-7.14 (m, 2H), 7.05 (dd, J=9.3, 2.5 Hz, 1H), 6.61 (s, 2H), 4.34 (d, J=7.5 Hz, 2H), 2.90 (t, J=7.8 Hz, 2H), 2.17 (septet, J=6.7 Hz, 1H), 1.86 (sextet, J=7.5 Hz, 2H), 1.03 (t, J=7.4 Hz, 3H), 0.93 (d, J=6.2 Hz, 6H).
$^{13}$C NMR (125 MHz, DMSO-$d_6$): δ 161.1, 153.4, 152.7, 152.4, 146.3, 134.5, 132.3, 126.1, 122.2, 118.7, 118.2, 115.7, 113.8, 112.3, 105.0, 51.2, 28.7, 28.5, 20.8, 19.1, 13.7.

MS (ESI) m/z 400.2138 (400.2137 calcd for $C_{24}H_{25}N_5O$, M+H).

Anal. Calcd. for $C_{24}H_{25}N_5O$: % C, 72.16; % H, 6.31; % N, 17.53. Found: % C, 71.90; % H, 6.32; % N, 17.37.

Example 40

Methyl 2-[4-amino-1-(2-methylpropyl)-2-propyl-1H-imidazo[4,5-c]quinolin-7-yloxy]benzoate The crude product was purified by column chromatography on silica gel (eluting with dichloromethane:methanol ranging in ratios from 98:2 to 95:5) and then recrystallized from acetonitrile to provide methyl 2-[4-amino-1-(2-methylpropyl)-2-propyl-1H-imidazo[4,5-c]quinolin-7-yloxy]benzoate as tan crystals, mp 167-168.5° C.

$^1$H NMR (300 MHz, DMSO-$d_6$): δ 7.97-7.94 (m, 1H), 7.87 (dd, J=7.6, 1.8 Hz, 1H), 7.63 (ddd, J=7.8, 7.8, 1.8 Hz, 1H), 7.32 (ddd, J=7.4, 7.4, 1.3 Hz, 1H), 7.14 (dd, J=7.7, 1.2 Hz, 1H), 6.95-6.92 (m, 2H), 6.48 (s, 2H), 4.31 (d, J=7.5 Hz, 2H), 3.71 (s, 3H), 2.88 (t, J=7.5 Hz, 2H), 2.15 (septet, J=7.0 Hz, 1H), 1.84 (sextet, J=7.4 Hz, 2H), 1.02 (t, J=7.5 Hz, 3H), 0.92 (d, J=6.8 Hz, 6H).
$^{13}$C NMR (75 MHz, DMSO-$d_6$): δ 155.9, 154.9, 153.0, 152.2, 146.2, 134.0, 132.5, 131.3, 125.7, 124.1, 123.3, 121.7, 121.5, 112.5, 110.8, 52.0, 51.2, 28.7, 28.5, 20.9, 19.1, 13.8.

MS (ESI) m/z 433.2238 (433.2240 calcd for $C_{25}H_{28}N_4O_3$, M+H).

Anal. Calcd. for $C_{25}H_{28}N_4O_3 \cdot 0.6H_2O$: % C, 67.73; % H, 6.64; % N, 12.64. Found: % C, 67.75; % H, 6.40; % N, 12.66.

Example 41

7-(4-Aminophenoxy)-1-(2-methylpropyl)-2-propyl-1H-imidazo[4,5-c]quinolin-4-amine

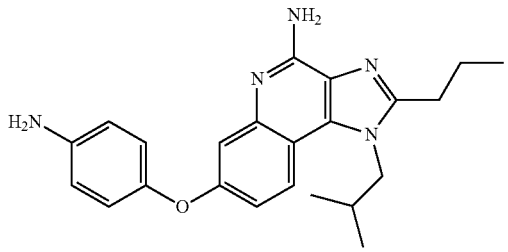

Nickel(II)chloride (0.044 g, 0.34 mmol) was added to a solution of 1-(2-methylpropyl)-7-(4-nitrophenoxy)-2-propyl-1H-imidazo[4,5-c]quinolin-4-amine (0.436 g, 1.04 mmol), prepared as described in Example 35, in 20:80 dichloromethane:methanol (30 mL). Sodium borohydride (0.300 g) was added in small portions to the resulting solution, and the reaction was stirred for 25 minutes. A solid formed in the reaction and was removed by filtration, and the filtrate was concentrated under reduced pressure. The residue was dissolved in chloroform, and the resulting solution was washed with water. The organic solution was stirred with AMBERLITE IRA-756 ion exchange resin for 30 minutes, and the resin was then removed by filtration. The filtrate was concentrated under reduced pressure to provide a brown oil, which was purified by flash chromatography using a 10 g silica gel cartridge (RediSep, ISCO, 230-400 mesh) attached to a gradient pump system, 254 nm UV detector and fraction collector (ISCO COMBIFLASH Sg100c system). The column was equilibrated with 1% methanol in dichloromethane and the reaction mixture was injected onto the column. The mixture was eluted at 35 mL/minute, with a linear gradient program consisting of 1% methanol/dichloromethane to 5% methanol/dichloromethane over five minutes and holding at 5% methanol/dichloromethane to elute the desired compound. Fractions were examined by TLC and those containing the desired compound were combined and concentrated. The product was then recrystallized from acetonitrile to yield 0.242 g of 7-(4-aminophenoxy)-1-(2-methylpropyl)-2-propyl-1H-imidazo[4,5-c]quinolin-4-amine as a tan, crystalline solid, mp 190-191° C.

$^1$H NMR (300 MHz, DMSO-$d_6$): δ 7.89 (d, J=8.7 Hz, 1H), 6.9-6.79 (m, 4H), 6.64-6.59 (m, 2H), 6.39 (s, 2H), 4.98 (s, 2H), 4.28 (d, J=7.6 Hz, 2H), 2.86 (t, J=7.5 Hz, 2H), 2.21-2.07 (m, 1H), 1.84 (sextet, J=7.4 Hz, 2H), 1.01 (t, J=7.6 Hz, 3H), 0.91 (d, J=6.6 Hz, 6H).

MS (ESI) m/z 390.2290 (390.2294 calcd for $C_{23}H_{27}N_5O$, M+H).

Anal. Calcd. for $C_{23}H_{27}N_5O$: % C, 70.93; % H, 6.99; % N, 17.98. Found: % C, 70.70; % H, 6.81; % N, 17.88.

Example 42

7-(2-Aminophenoxy)-1-(2-methylpropyl)-2-propyl-1H-imidazo[4,5-c]quinolin-4-amine

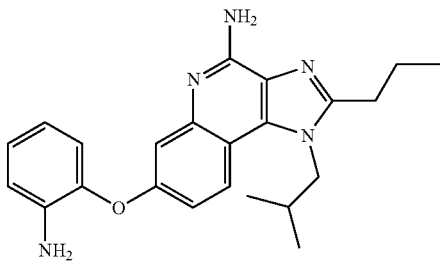

A modification of the general method described in Example 41 was followed using 1-(2-methylpropyl)-7-(2-nitrophenoxy)-2-propyl-1H-imidazo[4,5-c]quinolin-4-amine, prepared as described in Example 36, in lieu of 1-(2-methylpropyl)-7-(4-nitrophenoxy)-2-propyl-1H-imidazo[4,5-c]quinolin-4-amine. When the reaction was complete, the reaction mixture was filtered through a layer of CELITE filter aid, and the filter cake was washed with methanol and methanol:dichloromethane. Following treatment with the ion exchange resin, the crude product was purified by column chromatography on silica gel (eluting with dichloromethane:methanol ranging in ratios from 98:2 to 94:6). The white, waxy solid was recrystallized from acetonitrile to yield 0.150 g of 7-(2-aminophenoxy)-1-(2-methylpropyl)-2-propyl-1H-imidazo[4,5-c]quinolin-4-amine as tan crystals, mp 197-199° C.

$^1$H NMR (300 MHz, DMSO-$d_6$): δ 7.92 (d, J=8.8 Hz, 1H), 6.98-6.82 (m, 5H), 6.58 (ddd, J=7.5, 7.5, 1.8 Hz, 1H), 6.41 (s, 2H), 4.89 (s, 2H), 4.29 (d, J=7.5 Hz, 2H), 2.86 (t, J=7.5 Hz, 2H), 2.15 (septet, J=6.6 Hz, 1H), 1.84 (sextet, J=7.5 Hz, 2H), 1.02 (t, J=7.5 Hz, 3H), 0.91 (d, J=6.0 Hz, 6H).

MS (APCI) m/z 390 (M+H)$^+$.

Anal. Calcd. for $C_{23}H_{27}N_5O$: % C, 70.93; % H, 6.99; % N, 17.98. Found: % C, 70.91; % H, 7.06; % N, 17.70.

Example 43

7-(3-Ethylaminophenoxy)-1-(2-methylpropyl)-2-propyl-1H-imidazo[4,5-c]quinolin-4-amine

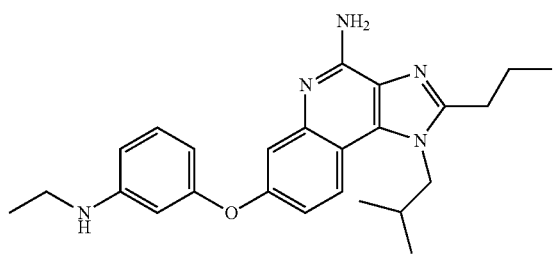

1-(2-Methylpropyl)-7-(3-nitrophenoxy)-2-propyl-1H-imidazo[4,5-c]quinolin-4-amine (0.254 g, 0.606 mmol), prepared as described in Example 37, was stirred in ethanol (10 mL), and 5% platinum on carbon (0.025 g) was added. The reaction was placed under a positive pressure of hydrogen and stirred for one hour. The reaction mixture was filtered through a layer of CELITE filter aid, and the filter cake was washed with methanol. The filtrate was concentrated under reduced pressure, and the residue was purified by column chromatography on silica gel (eluting with dichloromethane:methanol ranging in ratios from 98:2 to 95:5). The product was recrystallized from acetonitrile to provide 0.032 g of 7-(3-ethylaminophenoxy)-1-(2-methylpropyl)-2-propyl-1H-imidazo[4,5-c]quinolin-4-amine as square, orange crystals, mp 168-174° C.

$^1$H NMR (300 MHz, DMSO-$d_6$): δ 7.94 (d, J=9.3 Hz, 1H), 7.10-7.04 (m, 2H), 6.95 (dd, J=2.4, 8.6 Hz, 1H), 6.46 (s, 2H), 6.37-6.33 (m, 1H), 6.24 (m, 2H), 5.71-5.68 (m, 1H), 4.30 (d, J=7.6 Hz, 2H), 3.03-2.94 (m, 2H), 2.87 (t, J=7.5 Hz, 2H), 2.22-2.08 (m, 1H), 1.84 (sextet, J=7.5 Hz, 2H), 1.13 (t, J=7.1 Hz, 3H), 1.02 (t, J=7.5 Hz, 3H), 0.92 (d, J=6.3 Hz, 6H).

MS (ESI) m/z 418.2614 (418.2607 calcd for $C_{25}H_{31}N_5O$, M+H).

Anal. Calcd. for $C_{25}H_{31}N_5O$: % C, 71.91; % H, 7.48; % N, 16.77. Found: % C, 71.80; % H, 7.49; % N, 16.89.

Example 44

7-Benzyloxy-2-ethoxymethyl-1-propyl-1H-imidazo[4,5-c]quinolin-4-amine

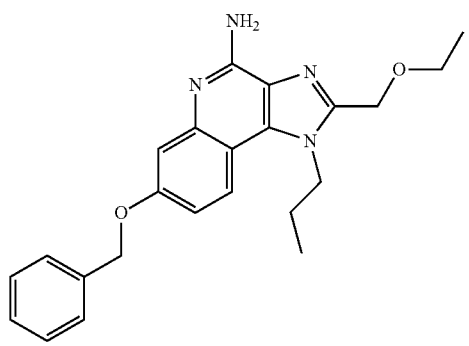

The general methods described in Example 1 were followed. Propylamine was used in lieu of isobutylamine in Part E, and ethoxyacetyl chloride was used in lieu of trimethyl orthobutyrate in Part G. The crude product was recrystallized from acetonitrile to provide 7-benzyloxy-2-ethoxymethyl-1-propyl-1H-imidazo[4,5-c]quinolin-4-amine as a flocculent, white solid, mp 188-189° C.

$^1$H NMR (300 MHz, DMSO-$d_6$): δ 7.91 (d, J=9.1 Hz, 1H), 7.52-7.30 (m, 5H), 7.13 (d, J=2.7 Hz, 1H), 7.00 (dd, J=8.9, 2.6 Hz, 1H), 6.53 (s, 2H), 5.21 (s, 2H), 4.74 (s, 2H), 4.49-4.44 (m, 2H), 3.54 (q, J=7.0 Hz, 2H), 1.92-1.78 (m, 2H), 1.15 (t, J=6.9 Hz, 3H), 1.00 (t, J=7.4 Hz, 3H).

$^{13}$C NMR (75 MHz, DMSO-$d_6$): δ 157.3, 152.3, 148.1, 146.9, 137.2, 133.4, 128.4, 127.7, 127.6, 124.9, 121.3, 111.9, 108.9, 108.7, 69.1, 65.3, 64.2, 46.6, 23.0, 14.9, 10.7.

MS (ESI) m/z 391.2134 (391.2117 calcd for $C_{23}H_{26}N_4O_2$,

Anal. Calcd. for $C_{23}H_{26}N_4O_2$: % C, 70.75; % H, 6.71; % N, 14.35. Found: % C, 70.49; % H, 6.57; % N, 14.22. M+H$^+$).

Example 45

4-Amino-2-ethoxymethyl-1-propyl-1H-imidazo[4,5-c]quinolin-7-ol

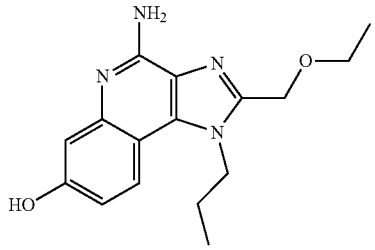

7-Benzyloxy-2-ethoxymethyl-1-propyl-1H-imidazo[4,5-c]quinolin-4-amine (3.9 g, 9.99 mmol), prepared in Example 44, was mixed with ethanol and added to a Parr flask charged with 10% palladium on carbon (0.390 g) in ethanol. The flask was placed under hydrogen pressure and shaken for 18 hours. The reaction mixture was filtered through a layer of CELITE filter aid, and the filter cake was washed with warm DMF. The filtrate was concentrated under reduced pressure, and the residue was recrystallized from methanol to yield 2.4 g of 4-amino-2-ethoxymethyl-1-propyl-1H-imidazo[4,5-c]quinolin-7-ol as a white solid, mp>250° C.

$^1$H NMR (300 MHz, DMSO-$d_6$): δ 9.50 (s, 1H), 7.82 (d, J=8.9 Hz, 1H), 6.96 (d, J=2.5 Hz, 1H), 6.81 (dd, J=8.8, 2.6 Hz, 1H), 6.45 (s, 2H), 4.73 (s, 2H), 4.47-4.41 (m, 2H), 3.54 (q, J=7.0 Hz, 2H), 1.92-1.78 (m, 2H), 1.15 (t, J=6.9 Hz, 3H), 1.00 (t, J=7.4 Hz, 3H);

$^{13}$C NMR (75 MHz, DMSO-$d_6$): δ 156.4, 152.1, 147.7, 147.1, 133.6, 124.5, 121.2, 112.0, 109.8, 107.9, 65.2, 64.2, 46.6, 23.0, 14.9, 10.7;

Anal. Calcd. for $C_{16}H_{20}N_4O_2$: % C, 63.98; % H, 6.71; % N, 18.65. Found: % C, 63.71; % H, 6.48; % N, 18.53.

Example 46

7-Benzyloxy-1-(2-phenoxyethyl)-1H-imidazo[4,5-c]quinolin-4-amine

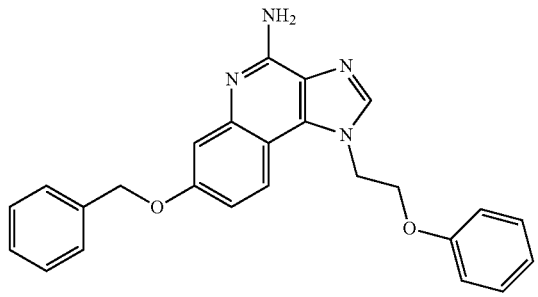

Part A

Triethylamine (8.93 mL, 64.1 mmol) was added to a solution of 7-benzyloxy-4-chloro-3-nitroquinoline (13.45 g, 42.7 mmol), prepared in Parts A-D of Example 1, in dichloromethane (250 mL). 2-Phenoxyethylamine (6.15 mL, 47.0 mmol) was added dropwise over a period of ten minutes, and the reaction mixture was stirred for three hours at ambient temperature. Distilled water (200 mL) was added to the solution, and the aqueous layer was washed with dichloromethane (2×200 mL). The combined organic solutions were dried over magnesium sulfate, filtered, and concentrated under reduced pressure to provide a solid. The solid was washed with hexanes, isolated by filtration, and dried under reduced pressure to provide 17.14 g of (7-benzyloxy-3-nitroquinolin-4-yl)-(2-phenoxyethyl)amine as a yellow solid.

Part B (7-Benzyloxy-3-nitroquinolin-4-yl)-(2-phenoxyethyl)amine (14.24 g, 34.28 mmol) was dissolved in toluene (900 mL) with heating and added to a Parr vessel charged with 5% platinum on carbon (6.7 g, 34.28 mmol) and toluene (100 mL). The vessel was placed under hydrogen pressure (35 psi, 2.4×10$^5$ Pa) and shaken for two hours. The catalyst was removed by filtration and washed with hexanes and dichloromethane. The filtrate was concentrated under reduced pressure, and the residue was recrystallized from methanol, isolated by filtration, washed with hexanes, and dried under high vacuum to provide 13.82 g of 7-benzyloxy-$N^4$-(2-phenoxyethyl)quinoline-3,4-diamine as a solid.

Part C

Under a nitrogen atmosphere, diethoxymethyl acetate (3.0 mL, 18 mmol) was added dropwise to a solution of 7-benzyloxy-$N^4$-(2-phenoxyethyl)quinoline-3,4-diamine (3.0 g, 7.8 mmol) in toluene (30 mL), and the reaction was heated at reflux for three hours. The reaction mixture was concentrated under reduced pressure until a small volume of solvent remained. Hexanes were added, and the resulting mixture was cooled for 20 minutes in a refrigerator. A precipitate formed which was isolated by filtration, washed with hexanes, and dried overnight under reduced pressure to provide 3.12 g of 7-benzyloxy-1-(2-phenoxyethyl)-1H-imidazo[4,5-c]quinoline as a solid.

Part D

A modification of the general method described in Part B of Example 3 was followed. mCPBA (1.5 g, 5.1 mmol, 60% pure) was added in portions over a period of 30 minutes to a solution of 7-benzyloxy-1-(2-phenoxyethyl)-1H-imidazo[4,5-c]quinoline (2.0 g, 5.1 mmol) in chloroform (80 mL), and the reaction was stirred for 24 hours. Following the work-up 1.59 g of 7-benzyloxy-5-oxido-1-(2-phenoxyethyl)-1H-imidazo[4,5-c]quinoline were obtained.

Part E

A modification of the general method described in Part C of Example 3 was used to treat 7-benzyloxy-5-oxido-1-(2-phenoxyethyl)-1H-imidazo[4,5-c]quinoline (1.59 g, 3.86 mmol). Chloroform (10 mL) was added to help keep the starting material in solution. The reaction with trichloroacetyl isocyanate (0.6 mL, 5 mmol) was stirred for 4.5 hours. Following the reaction with sodium methoxide, a tan precipitate formed, which was isolated by filtration, washed with hexanes, and dried overnight in a vacuum oven. The solid was then stirred with water overnight, isolated by filtration, and dried in a vacuum oven to provide 0.94 g of 7-benzyloxy-1-(2-phenoxyethyl)-1H-imidazo[4,5-c]quinolin-4-amine as a tan powder, mp 200.3-200.9° C.

$^1$H NMR (300 MHz, DMSO-$d_6$) δ 8.14 (s, 1H), 8.10 (d, J=9.0 Hz, 1H), 7.50 (m, 2H), 7.43-7.33 (m, 3H), 7.23 (m, 2H), 7.16 (d, J=2.7 Hz, 1H), 6.98 (dd, J=9.0, 2.7 Hz, 1H), 6.93-6.82 (m, 3H), 6.53 (s, 2H), 5.22 (s, 2H), 5.00 (t, J=5.1 Hz, 2H), 4.41 (t, J=5.1 Hz, 2H);

$^{13}$C NMR (500 MHz, DMSO-$d_6$) 158.2, 157.7, 152.8, 147.1, 142.9, 137.6, 132.8, 129.9, 128.8, 128.1, 128.0, 127.0, 122.2, 121.4, 114.8, 112.1, 109.5, 108.9, 69.5, 66.7, 46.3;

MS (EI) 410.1749 (410.1743 calcd for $C_{25}H_{22}N_4O_2$);

Anal. Calcd. for C$_{25}$H$_{22}$N$_4$O$_2$·0.25 H$_2$O: % C, 72.36; % H, 5.47; % N, 13.50. Found: % C, 72.26; % H, 5.35; % N, 13.47.

Example 47

7-Benzyloxy-2-butyl-1-(2-phenoxyethyl)-1H-imidazo[4,5-c]quinolin-4-amine

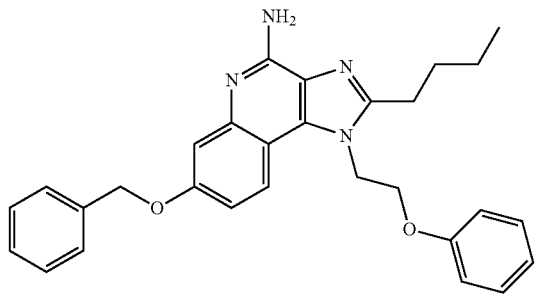

Part A

Under a nitrogen atmosphere, trimethyl orthovalerate (2.7 mL, 16 mmol) was added dropwise to a solution of 7-benzyloxy-N$^4$-(2-phenoxyethyl)quinoline-3,4-diamine (3.0 g, 7.8 mmol), prepared as described in Parts A and B of Example 46, in xylenes (30 mL), and the reaction was heated at reflux for 24 hours. The reaction mixture was allowed to cool to ambient temperature; a precipitate formed, which was isolated by filtration, washed with hexanes, and dried for two hours in a vacuum oven to provide 2.96 g of 7-benzyloxy-2-butyl-1-(2-phenoxyethyl)-1H-imidazo[4,5-c]quinoline.

Part B

The general method described in Part D of Example 46 was used to convert 7-benzyloxy-2-butyl-1-(2-phenoxyethyl)-1H-imidazo[4,5-c]quinoline (1.0 g, 2.2 mmol) to 1.0 g of 7-benzyloxy-2-butyl-5-oxido-1-(2-phenoxyethyl)-1H-imidazo[4,5-c]quinoline.

Part C

A modification of the general method described in Part C of Example 3 was used to treat 7-benzyloxy-2-butyl-5-oxido-1-(2-phenoxyethyl)-1H-imidazo[4,5-c]quinoline (1.0 g, 2.1 mmol). An analysis by TLC indicated that the reaction with trichloroacetyl isocyanate (1.35 mL, 11.3 mmol) was incomplete after two hours, and additional trichloroacetyl isocyanate (1 mL) was added and stirred for one hour. Following the reaction with sodium methoxide, a tan precipitate formed, and the mixture was stirred over two days. The precipitate was isolated by filtration, recrystallized from ethanol, isolated by filtration, washed with hexanes, and dried overnight in a vacuum oven to provide 0.63 g of 7-benzyloxy-2-butyl-1-(2-phenoxyethyl)-1H-imidazo[4,5-c]quinolin-4-amine as a white, crystalline solid, mp 188.0-189.0° C.

$^1$H NMR (300 MHz, DMSO-d$_6$) δ 8.06 (d, J=9.1 Hz, 1H), 7.51-7.19 (m, 7H), 7.14 (d, J=2.7 Hz, 1H), 6.98-6.87 (m, 4H), 6.36 (s, 2H), 5.20 (s, 2H), 4.91 (t, J=4.8 Hz, 2H), 4.40 (t, J=4.8 Hz, 2H), 2.96 (m, 2H), 1.84 (m, 2H), 1.46 (m, 2H), 0.96 (t, J=7.4 Hz, 3H);

$^{13}$C NMR (125 MHz, DMSO-d$_6$) 158.2, 157.3, 153.5, 152.3, 146.9, 137.7, 133.3, 129.9, 128.8, 128.1, 128.0, 125.4, 121.7, 121.4, 114.6, 112.1, 109.5, 109.0, 69.5, 66.7, 44.6, 29.8, 26.6, 22.4, 14.2;

MS (EI) m/z 466.2362 (466.2369 calcd for C$_{29}$H$_{30}$N$_4$O$_2$).

Anal. Calcd for C$_{29}$H$_{30}$N$_4$O$_2$·0.2 H$_2$O: % C, 74.08; % H, 6.52; % N, 11.92. Found: % C, 74.11; % H, 6.43; % N, 11.88.

Example 48

7-Benzyloxy-2-methoxymethyl-1-phenethyl-1H-imidazo[4,5-c]quinolin-4-amine

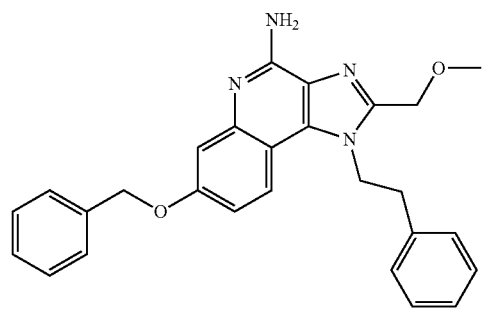

Part A

The general method described in Part A of Example 46 was followed using phenethylamine (9.8 g, 81 mmol) in lieu of 2-phenoxyethylamine. The reaction was stirred for six hours, and after the work-up, 9.9 g of (7-benzyloxy-3-nitroquinolin-4-yl)(phenethyl)amine were obtained.

Part B

The general method described in Part B of Example 46 was used to convert (7-benzyloxy-3-nitroquinolin-4-yl)(phenethyl)amine (6.2 g, 16 mmol) to 7-benzyloxy-N$^4$-(phenethyl)quinoline-3,4-diamine Part C Under a nitrogen atmosphere, a solution of the material from Part B in dichloromethane (150 mL) was cooled to ~0° C.; pyridine (10 mL) was added. A solution of methoxyacetyl chloride (1.67 g, 15.4 mmol) in dichloromethane (40 mL) was then added dropwise, and the reaction was allowed to warm to room temperature and stirred until analysis by TLC indicated the disappearance of starting material. The solvent was removed under reduced pressure, and the residue was mixed with toluene and heated at reflux in a flask equipped with a Dean-Stark trap until an analysis by TLC indicated the reaction was complete. The toluene was removed under reduced pressure, and the residue was partitioned between dichloromethane (300 mL) and water (100 mL). The organic layer was concentrated under reduced pressure. The crude product was purified by column chromatography on silica gel (eluting with ethyl acetate:methanol 95:5 containing a small amount of triethylamine) to provide 4.1 g of 7-benzyloxy-2-methoxymethyl-1-phenethyl-1H-imidazo[4,5-c]quinoline.

Part D

A modification of the general method described in Part B of Example 3 was followed to convert 7-benzyloxy-2-methoxymethyl-1-phenethyl-1H-imidazo[4,5-c]quinoline (4.1 g, 9.7 mmol) to 7-benzyloxy-2-methoxymethyl-5-oxido-1-phenethyl-1H-imidazo[4,5-c]quinoline. Dichloromethane (50 mL) was used as the solvent, and the reaction was terminated after four hours. The material was used without purification.

Part E

The general method described in Part C of Example 3 was followed using the material from Part D. The precipitate from the reaction was isolated by filtration, washed with methanol, and recrystallized from methanol to provide 1.7 g of 7-benzyloxy-2-methoxymethyl-1-phenethyl-1H-imidazo[4,5-c]quinolin-4-amine as a white solid, mp 195-197° C.

$^1$H NMR (300 MHz, DMSO-$d_6$) δ 8.06 (d, J=9.0 Hz, 1H), 7.52 (m, 2H), 7.44-7.26 (m, 6H), 7.18-7.14 (m, 3H), 7.06 (dd, J=9.0, 2.5 Hz, 1H), 6.62 (s, 2H), 5.23 (s, 2H), 4.75 (t, J=7.2 Hz, 2H), 4.32 (s, 2H), 3.28 (s, 3H), 3.12 (t, J=7.2 Hz, 2H);

MS (APCI) m/z 439 (M+H)$^+$;

Anal. Calcd. for $C_{27}H_{26}N_4O_2$: % C, 73.95; % H, 5.98; % N, 12.78. Found: % C, 74.05; % H, 5.80; % N, 12.64.

Example 49

N-{4-[4-Amino-7-benzyloxy-1-(2-phenoxyethyl)-1H-imidazo[4,5-c]quinolin-2-yl]butyl}-N'-phenylurea

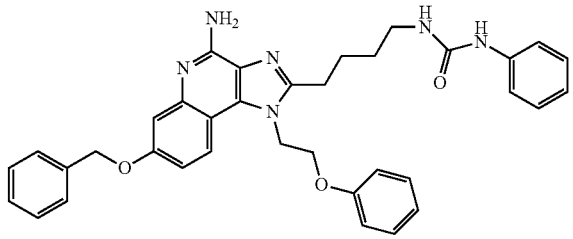

Part A

Under a nitrogen atmosphere, a solution of 5-(tert-butoxycarbonylamino)valeric acid (1.50 g, 6.91 mmol) in dichloroethane (30 mL) was cooled to −25° C. Triethylamine (2.40 mL, 17.2 mmol) and pivaloyl chloride (0.85 mL, 6.91 mmol) were added, and the reaction was stirred for three hours, during which time the temperature rose to −10° C. 7-Benzyloxy-$N^4$-(2-phenoxyethyl)quinoline-3,4-diamine (0.850 g, 2.20 mmol), prepared as described in Parts A-B of Example 46, was added in one portion followed by a small scoop of 4-dimethylaminopyridine. The reaction was allowed to warm to room temperature and stirred overnight and then heated at reflux for three hours. The reaction solution was washed with saturated sodium bicarbonate, water (2×), and brine, dried over sodium sulfate, filtered, and concentrated under reduced pressure. The crude product was purified by column chromatography on silica gel (eluting with sequentially with 98:2 and 95:5 chloroform:methanol) to yield a solid. The solid was treated with diethyl ether and concentrated under reduced pressure to provide 1.03 g of tert-butyl{4-[7-benzyloxy-1-(2-phenoxyethyl)-1H-imidazo[4,5-c]quinolin-2-yl]butyl}carbamate as a white powder.

Part B mCPBA (77% pure, 0.36 g, 1.6 mmol) was added to a solution of tert-butyl{4-[7-benzyloxy-1-(2-phenoxyethyl)-1H-imidazo[4,5-c]quinolin-2-yl]butyl}carbamate (0.89 g, 1.6 mmol) in dichloromethane (50 mL), and the reaction was stirred for 2.5 hours under a nitrogen atmosphere. Additional mCPBA (150 mg) was added, and the reaction was stirred over two nights. The solution was washed with water, saturated aqueous sodium bicarbonate, water, and brine, dried over sodium sulfate, and concentrated under reduced pressure to provide 0.90 g of tert-butyl{4-[7-benzyloxy-5-oxido-1-(2-phenoxyethyl)-1H-imidazo[4,5-c]quinolin-2-yl]butyl}carbamate as a tan foam.

Part C

The general method described in Part I of Example 1 was followed using tert-butyl {4-[7-benzyloxy-5-oxido-1-(2-phenoxyethyl)-1H-imidazo[4,5-c]quinolin-2-yl]butyl}carbamate (0.890 g, 1.53 mmol) as the starting material. Following the work-up, tert-butyl{4-[4-amino-7-benzyloxy-1-(2-phenoxyethyl)-1H-imidazo[4,5-c]quinolin-2-yl]butyl}carbamate (823 mg) was obtained and used without purification.

Part D

A solution of hydrochloric acid (5 mL of 1.5 M in ethanol) was added to a mixture of tert-butyl{4-[4-amino-7-benzyloxy-1-(2-phenoxyethyl)-1H-imidazo[4,5-c]quinolin-2-yl]butyl}carbamate (823 mg, 1.41 mmol) and ethanol. The reaction was heated at reflux for 30 minutes and became homogeneous. The solvent was removed under reduced pressure. The residue was recrystallized from methanol, isolated by filtration, washed with diethyl ether, and dried under reduced pressure to provide 534 mg of 2-(4-aminobutyl)-7-benzyloxy-1-(2-phenoxyethyl)-1H-imidazo[4,5-c]quinolin-4-amine as yellow crystals.

Part E

Under a nitrogen atmosphere, a mixture of 2-(4-aminobutyl)-7-benzyloxy-1-(2-phenoxyethyl)-1H-imidazo[4,5-c]quinolin-4-amine (0.40 g, 0.83 mmol) and pyridine (10 mL) was cooled to 0° C., and phenyl isocyanate (91 μL, 0.84 mmol) was added. The reaction was stirred for one hour and additional phenyl isocyanate (10 μL) was added. The reaction was stirred for one hour and then concentrated under reduced pressure. The residue was purified by column chromatography on silica gel (eluting with 95:5 chloroform:methanol), recrystallized from toluene, and dried in a vacuum oven to provide 150 mg of N-{4-[4-amino-7-benzyloxy-1-(2-phenoxyethyl)-1H-imidazo[4,5-c]quinolin-2-yl]butyl}-N'-phenylurea as a white crystalline solid, mp 186.3-186.9° C.

$^1$H NMR (300 MHz, DMSO-$d_6$) δ 8.41 (s, 1H), 8.08 (d, J=9.1 Hz, 1H), 7.49 (m, 2H), 7.43-7.30 (m, 5H), 7.23-7.18 (m, 4H), 7.13 (d, J=2.6 Hz, 1H), 6.88 (m, 2H), 6.80 (d, J=7.9 Hz, 2H), 6.42 (s, 2H), 6.19 (t, J=5.5 Hz, 1H), 5.20 (s, 2H), 4.93 (s, 2H), 4.39 (m, 2H), 3.18 (m, 2H), 3.01 (m, 2H), 1.90 (m, 2H), 1.62 (m, 2H);

MS (CI) m/z 601.2935 (calcd for $C_{36}H_{36}N_6O_3$ 601.2927, M+H).

Example 50

N-{4-[4-Amino-7-benzyloxy-2-(2-methoxyethyl)-1H-imidazo[4,5-c]quinolin-1-yl]butyl}methanesulfonamide

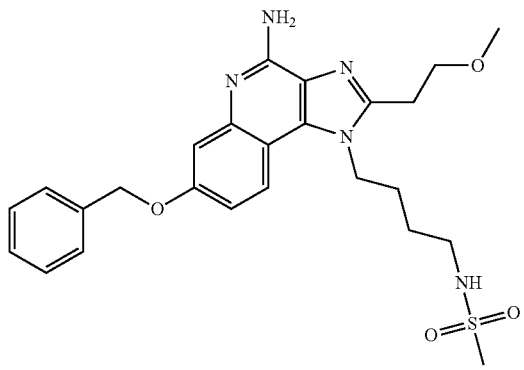

Part A tert-Butyl N-(4-aminobutyl)carbamate (22.01 g, 116.9 mmol) was added to a solution of 7-benzyloxy-4-chloro-3- nitroquinoline (36.80 g, 116.9 mmol), prepared in Parts A-D of Example 1, in distilled water. The reaction was heated at 80° C. for 1.5 hours and then stirred at room temperature for four hours. The reaction was not complete, and triethylamine (16 mL, 115 mmol) was added. The reaction was stirred overnight at room temperature. A precipitate formed, which was isolated by filtration and washed with hexanes to provide 39.92 g of tert-butyl[4-(7-benzyloxy-3-nitroquinolin-4-ylamino)butyl]carbamate as a yellow solid.

Part B tert-Butyl[4-(7-benzyloxy-3-nitroquinolin-4-ylamino)butyl]carbamate (39.92 g, 85.57 mmol) was dissolved in toluene (1700 mL) and added to a Parr vessel charged with 5% platinum on carbon (3.9 g) and a small volume of toluene. The vessel was placed under hydrogen pressure (50 psi, $3.4 \times 10^5$ Pa). The hydrogen was replaced three times, and the reaction was shaken overnight. The reaction mixture was filtered through a layer of CELITE filter aid, and the filter cake was washed with ethanol (700 mL). The filtrate was concentrated under reduced pressure to provide 28.62 g of tert-butyl{4-[3-amino-7-(benzyloxy)quinolin-4-ylamino]butyl}carbamate as a brown solid.

Part C

Under a nitrogen atmosphere, a solution of tert-butyl{4-[3-amino-7-(benzyloxy)quinolin-4-ylamino]butyl}carbamate (28.62 g, 65.5 mmol) in dichloromethane (1 L) was cooled to ~0° C.; triethylamine (10.0 mL, 72.1 mmol) was added. Methoxypropionyl chloride (8.57 mL, 78.6 mmol) was added dropwise, and the reaction was stirred at ambient temperature for two hours. The volatiles were removed under reduced pressure, and the residue was dissolved in ethanol (840 mL). Triethylamine (33 mL) was added, and the reaction was heated at reflux overnight and allowed to cool to ambient temperature. The volatiles were removed under reduced pressure to provide 30.77 g of tert-butyl{4-[7-benzyloxy-2-(2-methoxyethyl)-1H-imidazo[4,5-c]quinolin-1-yl]butyl}carbamate as a brown oil, which was used without purification.

Part D

A modification of the general method described in Part B of Example 3 was followed using tert-butyl{4-[7-benzyloxy-2-(2-methoxyethyl)-1H-imidazo[4,5-c]quinolin-1-yl]butyl}carbamate (9.08 g, 17.9 mmol) in lieu of 7-benzyloxy-2-methyl-1-(2-methylpropyl)-1H-imidazo[4,5-c]quinoline. Over a period of 28 hours, three equivalents of mCPBA were added. Following the work-up procedure, 8.07 g of ten-butyl{4-[7-benzyloxy-2-(2-methoxyethyl)-5-oxido-1H-imidazo[4,5-c]quinolin-1-yl]butyl}carbamate were obtained.

Part E

The general method described in Part I of Example 1 was followed using tert-butyl {4-[7-benzyloxy-2-(2-methoxyethyl)-5-oxido-1H-imidazo[4,5-c]quinolin-1-yl]butyl}carbamate (8.07 g, 15.5 mmol) as the starting material. Following the work-up, tert-butyl{4-[4-amino-7-benzyloxy-2-(2-methoxyethyl)-1H-imidazo[4,5-c]quinolin-1-yl]butyl}carbamate (8.00 g) was obtained as a clear, brown oil and used without purification.

Part F

A solution of hydrochloric acid (9.25 mL of 2 M) in ethanol was added to tert-butyl {4-[4-amino-7-benzyloxy-2-(2-methoxyethyl)-1H-imidazo[4,5-c]quinolin-1-yl]butyl}carbamate (2 g, 4 mmol), and the reaction was heated at 70° C. for 5 hours. The reaction was allowed to cool to ambient temperature, and nitrogen gas was bubbled through the solution overnight. The solvent was removed under reduced pressure, and the residue was triturated with diethyl ether to provide a sticky solid, which was dissolved in water and treated with concentrated ammonium hydroxide until pH 11 was achieved. The solution was extracted with dichloromethane several times, and the combined extracts were concentrated under reduced pressure to provide 1-(4-aminobutyl)-7-benzyloxy-2-(2-methoxyethyl)-1H-imidazo[4,5-c]quinolin-4-amine as a dark-brown oil.

Part G

Triethylamine (0.89 mL, 6.4 mmol) was added to a solution of 1-(4-aminobutyl)-7-benzyloxy-2-(2-methoxyethyl)-1H-imidazo[4,5-c]quinolin-4-amine (2.55 g, 6.07 mmol) in anhydrous acetonitrile (255 mL), and the mixture was heated until it became homogeneous. The reaction was allowed to cool to ambient temperature, and methanesulfonic anhydride (1.11 g, 6.38 mmol) was slowly added. The reaction was stirred at ambient temperature for four hours, and the solvent was removed under reduced pressure. The residue was dissolved in ethyl acetate, and the resulting solution was washed with aqueous sodium bicarbonate. The aqueous solution was washed once with ethyl acetate, and the combined organic solutions were dried over magnesium sulfate, filtered, and concentrated under reduced pressure. The crude product was recrystallized from ethanol and dried for 24 hours in a vacuum oven at 85° C. to provide 0.350 g of N-{4-[4-amino-7-benzyloxy-2-(2-methoxyethyl)-1H-imidazo[4,5-c]quinolin-1-yl]butyl}methanesulfonamide as a brown solid, mp 144.5-147.6° C.

$^1$H NMR (300 MHz, DMSO-$d_6$) δ 7.96 (d, J=9.3 Hz, 1H), 7.50 (d, J=6.9 Hz, 2H), 7.38 (m, 3H), 7.13 (d, J=3.0 Hz, 1H), 7.00 (m, 2H), 6.47 (s, 2H), 5.20 (s, 2H), 4.48 (t, J=7.5 Hz, 2H), 3.81 (t, J=6.9 Hz, 2H), 3.34 (s, 3H), 3.16 (t, J=6.9 Hz, 2H), 2.97 (q, J=6.6 Hz, 2H), 2.86 (s, 3H), 1.81 (pentet, J=7.8 Hz, 2H), 1.59 (pentet, J=7.5 Hz, 2H);

$^{13}$C NMR (75 MHz, DMSO-$d_6$) δ 157.4, 152.2, 150.2, 146.7, 137.6, 133.0, 128.8, 128.1, 127.9, 125.4, 121.5, 112.3, 109.3, 108.8, 70.5, 69.4, 58.4, 44.8, 42.4, 39.5, 27.4, 27.3, 26.7;

MS (ESI) m/z 498.2159 (calcd. for $C_{25}H_{31}N_5O_4S$ 498.2175, M+H);

Anal. Calcd. for $C_{25}H_{31}N_5O_4S$: % C, 60.34; % H, 6.28; % N, 14.07. Found: % C, 60.45; % H, 6.16; % N, 13.69.

Example 51

N-{4-[4-Amino-7-benzyloxy-2-(2-methoxyethyl)-1H-imidazo[4,5-c]quinolin-1-yl]butyl}urea

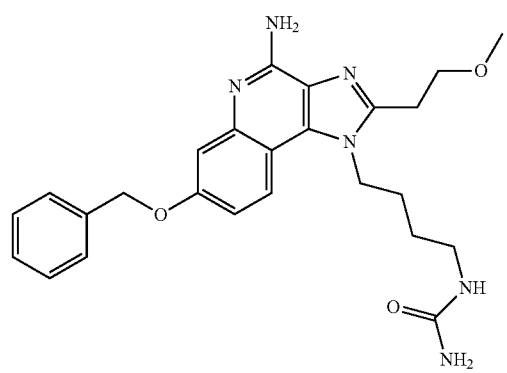

The general method described in Part C of Example 3 was followed using tert-butyl {4-[7-benzyloxy-2-(2-methoxyethyl)-5-oxido-1H-imidazo[4,5-c]quinolin-1-yl]butyl}carbamate (17.18 g, 33.00 mmol), prepared as described in Parts A-D of Example 50, as the starting material. Following the reaction with sodium methoxide, the reaction precipitate was isolated by filtration to provide 0.267 g of N-{4-[4-amino-7-benzyloxy-2-(2-methoxyethyl)-1H-imidazo[4,5-c]quinolin-1-yl]butyl}urea as a yellow powder, mp 169.6-170.70° C.

$^1$H NMR (300 MHz, DMSO-d$_6$) δ 7.91 (d, J=9 Hz, 1H), 7.51-7.48 (m, 2H), 7.43-7.30 (m, 3H), 7.127 (d, J=2.7 Hz, 1H), 7.00 (dd, J=9; 2.7 Hz, 1H), 6.45 (s, 2H), 5.94 (t, J=5.7 Hz, 1H), 5.39 (br s, 2H), 5.20 (s, 2H), 4.47 (t, J=6.6 Hz, 2H), 3.80 (t, J=6.9 Hz, 2H), 3.35 (br s, 3H), 3.15 (t, J=6.9 Hz, 2H), 3.00 (q, J=6.6 Hz, 2H), 1.75 (pentet, J=7.2 Hz, 2H), 1.49 (pentet, J=8.1 Hz, 2H);

$^{13}$C NMR (75 MHz, DMSO) δ59.0, 157.3, 152.3, 150.2, 146.8, 137.7, 133.0, 128.8, 128.1, 127.9, 125.4, 121.4, 112.3, 109.3, 108.9, 70.5, 69.4, 58.4, 44.9, 27.5, 27.5;

MS (APCI) m/z 463 (M+H)$^+$;

Anal. Calcd. for C$_{25}$H$_{30}$N$_6$O$_3$: % C, 64.92; % H, 6.54; % N, 18.17. Found: % C, 64.26; % H, 6.52; % N, 17.66.

Example 52

N-[2-(4-Amino-2-ethoxymethyl-7-hydroxy-1H-imidazo[4,5-c]quinolin-1-yl)-1,1-dimethylethyl]methanesulfonamide

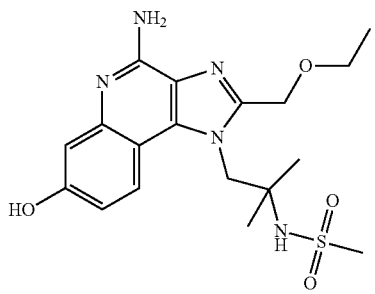

Part A

7-Benzyloxy-4-chloro-3-nitroquinoline (14.5 g, 46.0 mmol) was treated using the general method described in Part E of Example 1. 1,2-Diamino-2-methylpropane (5.29 mL, 50.6 mmol) was used in lieu of isobutylamine. After the work-up, the crude product was passed through a layer of silica gel (eluting sequentially with chloroform and 96:4 chloroform:methanol) to provide 12.4 g of (2-amino-2-methylpropyl)-(7-benzyloxy-3-nitroquinolin-4-yl)amine as a yellow solid.

Part B

Under a nitrogen atmosphere, a solution of (2-amino-2-methylpropyl)-(7-benzyloxy-3-nitroquinolin-4-yl)amine (12.4 g, 33.9 mmol) in dichloromethane (400 mL) was cooled to 0° C. Triethylamine (9.43 mL, 67.8 mmol) and methanesulfonic anhydride (5.90 g, 33.9 mmol) were sequentially added, and the reaction was stirred at ambient temperature for two hours. An analysis by HPLC indicated that the reaction was incomplete, and additional methanesulfonic anhydride (1.4 g, 8.0 mmol) was added. The reaction was stirred for an additional 90 minutes, and additional methanesulfonic anhydride (0.7 g, 4 mmol) was added. The reaction was stirred for an additional three hours, and saturated aqueous sodium bicarbonate (200 mL) was added. A precipitate began to form in the organic layer, which was separated and concentrated under reduced pressure to provide a yellow solid. The solid was triturated with water (200 mL) with heating, isolated by filtration, washed with water (3×100 mL) and diethyl ether (3×50 mL), and dried overnight under vacuum to provide 14.8 g of N-[1,1-dimethyl-2-(3-nitro-7-benzyloxyquinolin-4-ylamino)ethyl]methanesulfonamide as a yellow powder.

Part C

N-[1,1-Dimethyl-2-(3-nitro-7-benzyloxyquinolin-4-ylamino)ethyl]methanesulfonamide (14.8 g, 33.3 mmol) was mixed with acetonitrile (300 mL) and added to a Parr flask; 5% platinum on carbon (2 g) was added. The reaction was flushed with nitrogen and placed under hydrogen pressure (40 psi, 2.8×10$^5$ Pa) for 5.5 hours with the hydrogen replaced after two hours. An analysis by TLC indicated the presence of starting material. Additional acetonitrile (200 mL) and 5% platinum on carbon (2 g) were added, and the reaction was placed under hydrogen pressure overnight. The reaction mixture was filtered through a layer of CELITE filter aid, and the filter cake was washed with acetonitrile. The filtrate was concentrated under reduced pressure. Toluene and dichloromethane were added and removed under reduced pressure twice to yield 12.6 g of N-[2-(3-amino-7-benzyloxyquinolin-4-ylamino)-1,1-dimethylethyl]methanesulfonamide as a foam.

Part D

A modification of the general method described in Part C of Example 50 was followed using N-[2-(3-amino-7-benzyloxyquinolin-4-ylamino)-1,1-dimethylethyl]methanesulfonamide (12.6 g, 30.4 mmol) in lieu of tert-butyl{-4-[3-amino-7-(benzyloxy)quinolin-4-ylamino]butyl}carbamate and ethoxyacetyl chloride (3.33 mL, 30.4 mmol) in lieu of methoxypropionyl chloride. The crude product was dissolved in dichloromethane (300 mL), and the resulting solution was washed with water (2×100 mL) and brine, dried over sodium sulfate, filtered, and concentrated under reduced pressure to provide a brown oil. The oil was purified by column chromatography on silica gel (eluting with 97.5:2.5 chloroform:methanol) to provide 12.4 g of N-[2-(7-benzyloxy-2-ethoxymethyl-1H-imidazo[4,5-c]quinolin-1-yl)-1,1-dimethylethyl]methanesulfonamide as a beige foam.

Part E

A modification of the general method described in Part B of Example 49 was followed using N-[2-(7-benzyloxy-2-ethoxymethyl-1H-imidazo[4,5-c]quinolin-1-yl)-1,1-dimethylethyl]methanesulfonamide (1.71 g, 3.55 mmol) in lieu of tert-butyl{-4-[7-benzyloxy-1-(2-phenoxyethyl)-1H-imidazo[4,5-c]quinolin-2-yl]butyl}carbamate. The reaction was complete in 2.5 hours and provided 1.75 g of N-[2-(7-benzyloxy-2-ethoxymethyl-5-oxido-1H-imidazo[4,5-c]quinolin-1-yl)-1,1-dimethylethyl]methanesulfonamide as a light-brown solid.

Part F

Concentrated ammonium hydroxide (3 to 4 mL) was added to a solution of N-[2-(7-benzyloxy-2-ethoxymethyl-5-oxido-1H-imidazo[4,5-c]quinolin-1-yl)-1,1-dimethylethyl]methanesulfonamide (1.75 g, 3.51 mmol) in dichloromethane (35 mL) with rapid stirring. p-Toluenesulfonyl chloride (670 mg, 3.51 mmol) was added. The reaction was stirred for one hour; a precipitate formed. Water (100 mL) was added, and the dichloromethane was removed under reduced pressure. Dichloromethane (5 mL) was then added with rapid stirring, and the resulting powder was isolated by filtration and dissolved in 90:10 chloroform:methanol (200 mL). The resulting solution was concentrated under reduced pressure, and the residue was triturated with hot propyl acetate (50 mL), isolated by filtration, and dried under reduced pressure to provide 1.45 g of N-[2-(4-amino-7-benzyloxy-2-ethoxymethyl-1H-imidazo[4,5-c]quinolin-1-yl)-1,1-dimethylethyl]methanesulfonamide as a tan powder.

Part G

The general method described in Example 5 was followed using N-[2-(4-amino-7-benzyloxy-2-ethoxymethyl-1H-imidazo[4,5-c]quinolin-1-yl)-1,1-dimethylethyl]methanesulfonamide (1.00 g, 2.01 mmol) in lieu of 7-benzyloxy-1-(2-methylpropyl)-2-propyl-1H-imidazo[4,5-c]quinolin-4-amine. The crude product was recrystallized from methanol (20 mL). The crystals were collected in three crops and washed with methanol and ethyl acetate. The crops were combined and purified by column chromatography on silica gel (eluting with 89.1:9.9:1 chloroform:methanol:ammonium hydroxide) to provide 330 mg of N-[2-(4-amino-2-ethoxymethyl-7-hydroxy-1H-imidazo[4,5-c]quinolin-1-yl)-1,1-dimethylethyl]methanesulfonamide as a white powder, mp 255-256° C. $^1$H NMR (300 MHz, DMSO-$d_6$ 350K) δ 9.18 (br s, 1H), 8.09 (d, J=8.9 Hz, 1H), 7.00 (br s, 1H), 6.96 (d, J=2.5 Hz, 1H), 6.77 (dd, J=8.9, 2.5 Hz, 1H), 6.11 (s, 2H), 4.84 (s, 2H), 4.81 (s, 2H), 3.56 (q, J=7.0 Hz, 2H), 2.97 (s, 3H), 1.29 (s, 6H), 1.15 (t, J=7.0 Hz, 3H);

$^{13}$C NMR (125 MHz, DMSO-$d_6$) δ 156.6, 152.5, 149.6, 147.8, 135.0, 125.0, 122.5, 111.7, 110.1, 108.7, 65.7, 65.1, 57.7, 54.5, 44.7, 25.8, 15.3;

MS (APCI) m/z 408 (M+H)$^+$;

Anal. Calcd. for $C_{18}H_{25}N_5O_4S$: % C, 52.43; % H, 6.11; % N, 16.94. Found: % C, 52.34; % H, 6.03; % N, 16.79.

Example 53

7-(4-Methanesulfonylphenoxy)-2-(2-methoxyethyl)-1-propyl-1H-imidazo[4,5-c]quinolin-4-amine

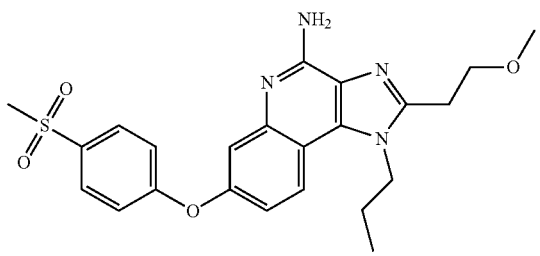

The general methods described in Parts A-G of Example 1 were used to prepare 7-benzyloxy-2-(2-methoxyethyl)-1-propyl-1H-imidazo[4,5-c]quinoline. Propylamine was used in lieu of isobutylamine in Part E, and methoxypropionyl chloride was used in lieu of trimethyl orthobutyrate in Part G. 7-Benzyloxy-2-(2-methoxyethyl)-1-propyl-1H-imidazo[4,5-c]quinoline was treated according to the general methods described in Parts A-D of Examples 35-40. In Part B, the fluorobenzene used was 4-fluorophenyl methyl sulfone. Following chromatographic purification, the product was recrystallized from acetonitrile to provide 0.890 g of 7-(4-methanesulfonylphenoxy)-2-(2-methoxyethyl)-1-propyl-1H-imidazo[4,5-c]quinolin-4-amine as dark tan needles, mp 210-212° C.

$^1$H NMR (300 MHz, DMSO-$d_6$): δ 8.09 (d, J=9.0 Hz, 1H), 7.96-7.91 (m, 2H), 7.26-7.21 (m, 3H), 7.06 (dd, J=8.8, 2.5 Hz, 1H), 6.62 (s, 2H), 4.51-4.46 (m, 2H), 3.83 (t, J=6.7 Hz, 2H), 3.30 (s, 3H), 3.21-3.17 (m, 5H), 1.90-1.77 (m, 2H), 0.99 (t, J=7.4 Hz, 3H);

MS (CI) m/z 455.1746 (455.1753 calcd for $C_{23}H_{26}N_4O_4S$, M+H);

Anal. Calcd. for $C_{23}H_{26}N_4O_4S$: % C, 60.78; % H, 5.77; % N, 12.33; % S, 7.05. Found: % C, 60.43; % H, 5.73; % N, 12.48; % S, 7.00.

Example 54

1-[4-Amino-7-benzyloxy-2-(hydroxymethyl)-1H-imidazo[4,5-c]quinolin-1-yl]-2-methylpropan-2-ol

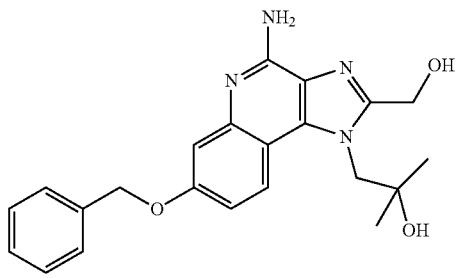

Part A

Triethylamine (81.3 g, 0.803 mol) was added to a solution of 230.0 g (0.731 mol) of 7-benzyloxy-4-chloro-3-nitroquinoline (230.0 g, 0.731 mmol), prepared in Parts A-D of Example 1, in methanol (1.84 L). Hydroxyisobutylamine (71.6 g, 0.803 mol) was then added over a period of five minutes; the temperature rose from 30° C. to 39° C. during the addition. The reaction mixture was heated at reflux for four hours and then allowed to cool to room temperature. The solid product was isolated by filtration, washed with ethanol (1 L), and dried under vacuum at 55° C. to provide 261.2 g of 1-[(7-benzyloxy-3-nitroquinolin-4-yl)amino]-2-methylpropan-2-ol.

Part B

A solution of 1-[(7-benzyloxy-3-nitroquinolin-4-yl)amino]-2-methylpropan-2-ol (245.0 g, 0.667 mol) in methanol (3 L) was added to a pressure vessel containing 5% platinum on carbon (7.35 g). The vessel was placed under hydrogen pressure (30 psi, 2.1×10$^5$ Pa) at 55° C. for five hours. The reaction was allowed to cool to 40° C., and dichloromethane (2.5 L) was added. The reaction mixture was then filtered through CLARCEL filter aid at 30-40° C., and the filter cake was washed with methanol. The filtrate was concentrated to a volume of 1.5 L, cooled to 5-10° C., and stirred for two hours. A solid formed and was isolated by filtration, washed with a small amount of methanol, and dried under vacuum at 50° C. to provide 199.4 g of 1-{[3-amino-7-(benzyloxy)quinolin-4-yl]amino}-1-2-methylpropan-2-ol.

Part C

Under a nitrogen atmosphere, a mixture of 1-{[3-amino-7-(benzyloxy)quinolin-4-yl]amino}-1-2-methylpropan-2-ol (45.0 g, 0.133 mol) and acetonitrile (180 mL) was heated to 40° C. Acetoxyacetyl chloride (21.8 g, 0.160 mol) was added to the resulting gray suspension over a period of 15 minutes while maintaining the temperature at 55±5° C. during the addition. Following the addition, a precipitate formed, and the reaction was heated at 55° C. for 15 minutes. The reaction mixture was then cooled to ~0° C., and the product was isolated by filtration, washed sequentially with a small amount of acetonitrile and acetone, and dried under vacuum at 50° C. to provide 57.6 g of 2-({7-benzyloxy-4-[(2-hydroxy-2-methylpropyl)amino]quinolin-3-yl}amino)-2-oxoethyl acetate hydrochloride.

Part D

A mixture of 2-({7-benzyloxy-4-[(2-hydroxy-2-methylpropyl)amino]quinolin-3-yl}amino)-2-oxoethyl acetate hydrochloride (54.0 g, 0.114 mol) in methanol (270 mL) was heated to 55° C., at which point a solution was obtained. A solution of sodium hydroxide (9.2 g, 0.23 mol) in water (90 mL) was then added over a period of five minutes while heating the reaction mixture at reflux. Following the addition, the addition funnel was rinsed with water (10 mL), and the reaction mixture was heated at reflux for one hour. The reaction mixture was then cooled to ~0° C., and the solid product was isolated by filtration, washed with methanol, deionized water, and a small volume of acetone, and dried under vacuum at 50° C. to provide 42.1 g of 1-[7-benzyloxy-2-(hydroxymethyl)-1H-imidazo[4,5-c]quinolin-1-yl]-2-methylpropan-2-ol as an off-white solid.

Part E

A mixture of 1-[7-benzyloxy-2-(hydroxymethyl)-1H-imidazo[4,5-c]quinolin-1-yl]-2-methylpropan-2-ol (39.0 g, 0.133 mol), pyridine (390 mL), and acetic anhydride (195 mL) was heated at 35±5° C. for one hour in a reaction flask fitted with a calcium chloride drying tube. The reaction mixture was poured into a mixture of ice (2.5 kg) and deionized water and stirred for approximately 15 minutes. A precipitate formed and was isolated by filtration, washed with deionized water (500 mL), and dried under vacuum at 50° C. to provide 41.8 g of [7-benzyloxy-1-(2-hydroxy-2-methylpropyl)-1H-imidazo[4,5-c]quinolin-2-yl]methyl acetate.

Part F

Hydrogen fluoride (7.5 g of 48%, 0.18 mol) was added to a solution of [7-benzyloxy-1-(2-hydroxy-2-methylpropyl)-1H-imidazo[4,5-c]quinolin-2-yl]methyl acetate (40.0 g, 0.0953 mol) in DMF (910 mL) and methanol (300 mL). mCPBA (60.6 g, 0.200 mol, 57% pure) was then added in one portion, and the reaction was stirred at ambient temperature for 5.5 hours. A mixture of ice and deionized water (4 L) was then added to the reaction mixture, and the resulting mixture was stirred vigorously for 30 minutes. The solid product was isolated by filtration, washed with deionized water, and dried under vacuum at 50° C. The solid was then triturated with diethyl ether (500 mL) for one hour, isolated by filtration, washed with diethyl ether (400 mL), and dried under vacuum at 40° C. to provide 41.7 g of [7-benzyloxy-1-(2-hydroxy-2-methylpropyl)-5-oxido-1H-imidazo[4,5-c]quinolin-2-yl]methyl acetate.

Part G

A solution of [7-benzyloxy-1-(2-hydroxy-2-methylpropyl)-5-oxido-1H-imidazo[4,5-c]quinolin-2-yl]methyl acetate (40.0 g, 0.0918 mol) in dichloromethane (650 mL) was cooled to 0° C.; ammonium hydroxide (250 mL of 28%) was added. A solution of p-toluenesulfonyl chloride (29.1 g, 0.153 mol) in dichloromethane (200 mL) was added over a period of 12 minutes while maintaining the reaction temperature below 5.5° C. The reaction mixture was then allowed to warm to room temperature and stirred for one hour. The reaction mixture was diluted with dichloromethane (100 mL), and the organic layer was washed with deionized water (2×400 mL), dried over magnesium sulfate, and filtered. The solution was then treated with activated charcoal for one hour, filtered through a layer of CELITE filter aid, concentrated under reduced pressure, and further dried under vacuum at 60° C. to provide 40.1 g of [4-amino-7-benzyloxy-1-(2-hydroxy-2-methylpropyl)-1H-imidazo[4,5-c]quinolin-2-yl]methyl acetate.

Part H

A solution of [4-amino-7-benzyloxy-1-(2-hydroxy-2-methylpropyl)-1H-imidazo[4,5-c]quinolin-2-yl]methyl acetate (34.0 g, 0.0782 mol) in methanol (150 mL) was heated at reflux, and a solution of aqueous sodium hydroxide (50 mL of 1.7 M) was added over a period of five minutes. A white precipitate formed, and the reaction was heated at reflux for one hour. The reaction mixture was allowed to cool to room temperature and stirred for about three hours. The precipitate was isolated by filtration, washed with deionized water and methanol, and then dried under vacuum at 50° C. to provide 24.9 g of the crude product. The crude product (6.0 g) was recrystallized from a mixture of 2-propanol:acetic acid 9:1 (470 mL); the hot solution was treated with activated charcoal and filtered through a layer of CELITE filter aid. The crystals were isolated by filtration, washed with a small volume of 2-propanol:acetic acid, and dried under vacuum at 50° C. The product was stirred with aqueous sodium hydroxide (200 mL of 0.15 M) for three hours, isolated by filtration, washed with deionized water, stirred with methanol (100 mL) for one hour, isolated by filtration, washed with methanol, and dried under vacuum at 60° C. Finally, the product (4.5 g) was recrystallized from DMF, isolated by filtration, and dried under vacuum to provide 1-[4-amino-7-benzyloxy-2-(hydroxymethyl)-1H-imidazo[4,5-c]quinolin-1-yl]-2-methylpropan-2-ol as a white solid, mp 284.5-285.5° C.

Anal. Calcd. for $C_{22}H_{24}N_4O_3$: % C, 67.33; % H, 6.16; % N, 14.28. Found: % C, 66.58; % H, 6.33; % N, 14.25.

Example 55

(4-Amino-7-benzyloxy-1H-imidazo[4,5-c]quinolin-1-yl)-2-methylpropan-2-ol

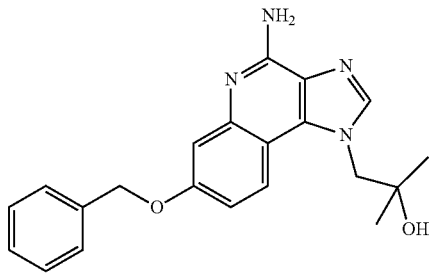

1-{[3-Amino-7-(benzyloxy)quinolin-4-yl]amino}-2-methylpropan-2-ol, prepared as described in Parts A and B of Example 54, was treated according to the general method of Part G of Example 1 with triethyl orthoformate used in lieu of trimethyl orthobutyrate. The product, (7-benzyloxy-1H-imidazo[4,5-c]quinolin-1-yl)-2-methylpropan-2-ol, was treated according to the general methods of Parts H and I of Example 1 to provide (4-amino-7-benzyloxy-1H-imidazo[4,5-c]quinolin-1-yl)-2-methylpropan-2-ol as a white powder, mp 254-257° C.

Anal. Calcd. for $C_{21}H_{22}N_4O_2 \cdot 0.5H_2O$: % C, 67.91; % H, 6.24; % N, 15.08. Found: % C, 68.38; % H, 5.98; % N, 15.15.

Example 56

(4-Amino-7-benzyloxy-2-ethoxymethyl-1H-imidazo[4,5-c]quinolin-1-yl)-2-methylpropan-2-ol

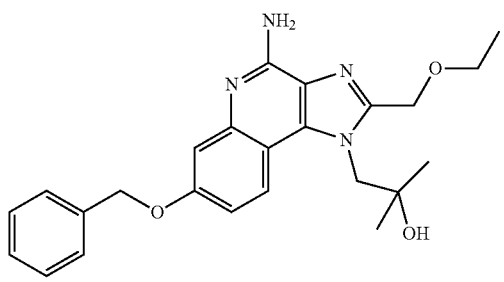

1-{[3-Amino-7-(benzyloxy)quinolin-4-yl]amino}-2-methylpropan-2-ol, prepared as described in Parts A and B of Example 54, was treated according to the general methods described in Parts C and D of Example 54 with ethoxyacetyl chloride used in lieu of acetoxyacetyl chloride in Part C. The product, (7-benzyloxy-2-ethoxymethyl-1H-imidazo[4,5-c]quinolin-1-yl)-2-methylpropan-2-ol, was treated according to the general methods of Parts F and G of Example 54 to provide (4-amino-7-benzyloxy-2-ethoxymethyl-1H-imidazo[4,5-c]quinolin-1-yl)-2-methylpropan-2-ol as a white powder, mp 215.1-215.5° C.

Anal. Calcd. for $C_{24}H_{28}N_4O_3$: % C, 68.55; % H, 6.71; % N, 13.32. Found: % C, 68.52; % H, 6.71; % N, 13.30.

Example 57

8-Benzyloxy-2-ethyl-1-methyl-1H-imidazo[4,5-c]quinolin-4-amine

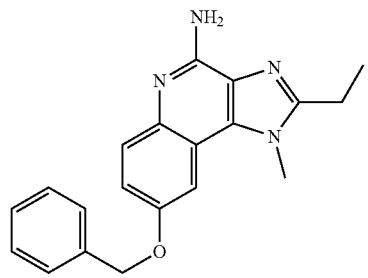

Part A

The general procedure described in Part A of Example 1 was used with the following modification. A solution of 4-benzyloxyaniline (100 g, 0.5 mol) in methanol (150 mL) was used in lieu of a solution of 3-benzyloxyaniline. The addition of this solution was carried out over a period of one hour while maintaining the temperature between 57-60° C. The reaction product, 5-{[(4-benzyloxy)phenylimino)]methyl}-2,2-dimethyl-[1,3]dioxane-4,6-dione (136.7 g) was isolated as a yellow powder.

$^1$H NMR (300 MHz, DMSO-$d_6$): δ 11.23 (d, J=15.2 Hz, 1H), 8.46 (d, J=14.3 Hz, 1H), 7.53-7.30 (m, 7H), 7.10-7.04 (m, 2H), 5.13 (s, 2H), 1.66 (s, 6H).

Part B

A solution of 5-{[(4-benzyloxy)phenylimino)]methyl}-2,2-dimethyl-[1,3]dioxane-4,6-dione (127.2 g, 0.360 mol) and DOWTHERM A heat transfer fluid (500 mL) was heated to 100° C. and then slowly added to a flask containing DOWTHERM A heat transfer fluid (1 L, heated at 250° C.) over a period of 90 minutes. During the addition, the reaction temperature was not allowed to fall below 245° C. Following the addition, the reaction was stirred at 250° C. for 30 minutes, and then allowed to cool to ambient temperature. A precipitate formed, which was isolated by filtration, washed with diethyl ether (1 L) and acetone (250 mL), and dried for two hours under vacuum in to provide 65.7 g of 6-benzyloxyquinolin-4-ol as a yellow powder.

$^1$H NMR (300 MHz, DMSO-$d_6$): δ 11.72 (s, 1H), 7.84 (d, J=7.3 Hz, 1H), 7.59 (m, 8H), 5.98 (d, J=7.0 Hz, 1H), 5.18 (s, 2H).

Part C

The general method described in Part C of Example 1 was followed using 6-benzyloxyquinolin-4-ol (65.7 g, 0.261 mol) in lieu of 7-benzyloxyquinolin-4-ol. The reaction precipitate was isolated by filtration; washed with propionic acid (600 mL), isopropanol (500 mL) and diethyl ether (500 mL); and dried for two days under vacuum to provide 46.01 g of 6-benzyloxy-3-nitroquinolin-4-ol as a tan powder, containing 5% 6-benzyloxyquinolin-4-ol.

$^1$H NMR (300 MHz, DMSO-$d_6$): δ 12.98 (s, 1H), 9.12 (s, 1H), 7.75 (d, J=3.3 Hz, 1H), 7.70 (d, J=8.6 Hz, 1H), 7.53-7.30 (m, 6H), 5.25 (s, 2H).

Part D

The general method described in Part D of Example 1 was used to convert 6-benzyloxy-3-nitroquinolin-4-ol (13.26 g, 44.7 mmol) to 13.74 g of 6-benzyloxy-4-chloro-3-nitroquinoline, which was isolated as a tan solid.

$^1$H NMR (500 MHz, DMSO-$d_6$): δ 9.23 (s, 1H), 8.16 (d, J=9.1 Hz, 1H), 7.80 (dd, J=9.1, 2.8 Hz, 1H), 7.76 (d, J=2.7 Hz, 1H), 7.57-7.53 (m, 2H), 7.45-7.34 (m, 3H), 5.39 (s, 2H).

Part E

Methylamine (available as a 40% solution in water, 21 mL, 0.25 mol) was added to a suspension of 6-benzyloxy-4-chloro-3-nitroquinoline (13.74 g, 43.65 mmol) in distilled water (300 mL), and the reaction was stirred at 100° C. for 1.5 hours. The reaction was allowed to cool to ambient temperature and stirred for three hours. A precipitate formed, which was isolated by filtration, washed with distilled water (3×), and recrystallized from 2-propanol (44.2 mL/g). The crystals were isolated by filtration and washed with cold hexanes (2×100 mL) to provide 11.36 g of N-(6-benzyloxy-3-nitroquinolin-4-yl)-N-methylamine as orange crystals.

Part F

The general method described in Part B of Example 46 was followed using N-(6-benzyloxy-3-nitroquinolin-4-yl)-N-methylamine (11.36 g, 36.7 mmol) in lieu of (7-benzyloxy-3-nitroquinolin-4-yl)-(2-phenoxyethyl)amine. 6-Benzyloxy-$N^4$-methylquinoline-3,4-diamine (7.91 g) was obtained as a dark yellow oil and used without purification.

Part G

The general method described in Part A of Example 47 was followed using 6-benzyloxy-$N^4$-methylquinoline-3,4-diamine (7.91 g, 28.3 mmol) in lieu of 7-benzyloxy-$N^4$-(2-phenoxyethyl)quinoline-3,4-diamine and triethyl orthopropionate (12.69 mL, 56.6 mmol) in lieu of trimethyl orthovalerate. The precipitate from the reaction was isolated in two crops to provide 7.56 g of 8-benzyloxy-2-ethyl-1-methyl-1H-imidazo[4,5-c]quinoline as a yellow solid, mp 168.2-169.0° C.

Part H

A modification of the general method described in Part B of Example 3 was followed. mCPBA (60% pure, 1.39 g, 47.3 mmol) was added in portions to a solution of 8-benzyloxy-2- ethyl-1-methyl-1H-imidazo[4,5-c]quinoline (1.5 g, 47 mmol) in chloroform (75 mL), and the reaction was stirred for 5.5 hours. During the work-up, the combined aqueous washings were extracted with dichloromethane, and the product precipitated from solution. The combined dichloromethane and chloroform solutions were concentrated under reduced pressure until crystals formed and then allowed to stand overnight. The crystals were isolated by filtration. The aqueous solution was extracted with chloroform, and the combined extracts were washed with water (2×) and concentrated under reduced pressure to a small volume. Hexanes were added, and the resulting crystals were isolated by filtration. The mother liquor was concentrated under reduced pressure to afford a solid that was recrystallized from 2-propanol. The three batches of crystals were combined to yield 1.30 g of 8-benzyloxy-2-ethyl-1-methyl-5-oxido-1H-imidazo[4,5-c]quinoline.

Part I

A modification of the general method of Part C of Example 3 was used. Chloroform (10 mL) was added to the solution of 8-benzyloxy-2-ethyl-1-methyl-5-oxido-1H-imidazo[4,5-c]quinoline (1.30 g, 3.90 mmol) in dichloromethane (35 mL) to improve the solubility. After the addition of trichloroacetyl isocyanate (0.633 mL, 5.31 mmol), the reaction was stirred for 3.5 hours. In the second step, chloroform (10 mL) was also added to the suspension in methanol (30 mL). After the reaction with sodium methoxide, the reaction was stirred over two nights, and the precipitate was isolated by filtration, washed with hexanes, recrystallized from methanol (278 mL/g), isolated by filtration, washed with hexanes, and dried for two days in a vacuum oven. A second crop of crystals from the mother liquor was combined with the first to provide 0.95 g of 8-benzyloxy-2-ethyl-1-methyl-1H-imidazo[4,5-c]quinolin-4-amine as a white crystalline solid, mp 238.4-238.9° C.

$^1$H NMR (300 MHz, DMSO-$d_6$) δ 7.66 (d, J=2.7 Hz, 1H), 7.53 (m, 3H), 7.44-7.34 (m, 3H), 7.17 (dd, J=9.1, 2.7 Hz, 1H), 6.17 (s, 2H) 5.24 (s, 2H), 4.07 (s, 3H), 2.94 (q, J=7.5 Hz, 2H), 1.33 (t, J=7.5 Hz, 3H);

$^{13}$C NMR (75 MHz, DMSO-$d_6$) δ 154.5, 153.0, 150.6, 140.0, 137.8, 133.4, 128.8, 128.1, 127.7, 126.8, 116.9, 115.6, 103.5, 70.1, 20.4, 12.2;

MS (EI) m/z 332.1630 (332.1637 calcd for $C_{20}H_{20}N_4O$);

Anal. Calcd. for $C_{20}H_{20}N_4O \cdot 0.4 H_2O$: % C, 70.73; % H, 6.16; % N, 16.50. Found: % C, 70.56; % H, 6.12; % N, 16.44.

Example 58

8-Benzyloxy-2-(2-methoxyethyl)-1-methyl-1H-imidazo[4,5-c]quinolin-4-amine

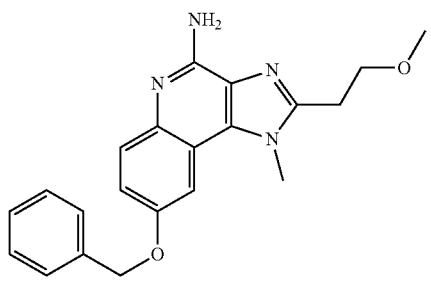

Part A

Under a nitrogen atmosphere, a solution of 6-benzyloxy-$N^4$-methylquinoline-3,4-diamine (7.88 g, 28.2 mmol), prepared as described in Parts A-F of Example 57, in dichloromethane (300 mL) was cooled to ~0° C.; triethylamine (4.2 mL, 30.3 mmol) was added. Methoxypropionyl chloride (3.3 mL, 30.6 mmol) was added dropwise over a period of five minutes, and the reaction was stirred at ambient temperature for 90 minutes. The volatiles were removed under reduced pressure, and the residue was dissolved in ethanol (300 mL) and triethylamine (13 mL) and heated at 75° C. over two nights. The volatiles were removed under reduced pressure, and the residue was dissolved in chloroform. The resulting solution was washed with deionized water (3×200 mL) and concentrated under reduced pressure. Small volumes of hexanes and dichloromethane were added, and a white precipitate formed, which was isolated by filtration and washed with hexanes to provide 3.76 g of 8-benzyloxy-2-(2-methoxyethyl)-1-methyl-1H-imidazo[4,5-c]quinoline as a white solid.

Part B

The general method described in Part B of Example 3 was used to convert 8-benzyloxy-2-(2-methoxyethyl)-1-methyl-1H-imidazo[4,5-c]quinoline (2.0 g, 5.8 mmol) to 8-benzyloxy-2-(2-methoxyethyl)-1-methyl-5-oxido-1H-imidazo[4,5-c]quinoline, which was obtained as a light-orange solid and used without purification.

Part C

The general method described in Part C of Example 3 was used to convert 8-benzyloxy-2-(2-methoxyethyl)-1-methyl-5-oxido-1H-imidazo[4,5-c]quinoline (2.09 g, 5.76 mmol) to 8-benzyloxy-2-(2-methoxyethyl)-1-methyl-1H-imidazo[4,5-c]quinolin-4-amine. The crude product (1.6 g) was recrystallized from methyl acetate (3 L). The solution was concentrated under reduced pressure to a volume of 600 mL, and the resulting first crop of crystals was isolated by filtration and dried in a vacuum oven. The mother liquor was concentrated under reduced pressure to a volume of 300 mL, and the resulting second crop of crystals was isolated by filtration. The combined crops provided 0.91 g of 8-benzyloxy-2-(2-methoxyethyl)-1-methyl-1H-imidazo[4,5-c]quinolin-4-amine as an off-white powder, mp 192-194° C.

$^1$H NMR (300 MHz, DMSO-$d_6$) δ 7.67 (d, J=2.7 Hz, 1H), 7.57-7.51 (m, 3H), 7.44-7.34 (m, 3H), 7.18 (dd, J=9.1, 2.7 Hz, 1H), 6.27 (s, 2H), 5.25 (s, 2H), 4.09 (s, 3H), 3.78 (t, J=6.7 Hz, 2H), 3.29 (s, 3H), 3.19 (t, J=6.7 Hz, 2H);

$^{13}$C NMR (300 MHz, DMSO-$d_6$) 152.7, 151.0, 150.0, 139.2, 137.4, 133.0, 128.4, 127.7, 127.6, 127.1, 126.5, 116.7, 115.1, 103.1, 70.0, 69.6, 58.0, 33.1, 27.2;

MS (EI) m/z 362.1734 (362.1743 calcd for $C_{21}H_{22}N_4O_2$);

Anal. Calcd. for $C_{21}H_{22}N_4O_2 \cdot 0.4 H_2O$: % C, 68.24; % H, 6.22; % N, 15.16. Found: % C, 68.40; % H, 6.13; % N, 15.06.

Example 59

8-Benzyloxy-2-butyl-1-methyl-1H-imidazo[4,5-c]quinolin-4-amine

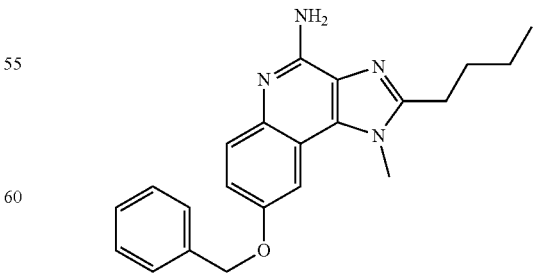

Part A

The general method described in Part A of Example 47 was followed using 6-benzyloxy-$N^4$-methylquinoline-3,4-diamine (1.53 g, 5.48 mmol), prepared as described in Parts A-F of Example 57, in lieu of 7-benzyloxy-$N^4$-(2-phenoxyethyl)quinoline-3,4-diamine. The reaction was heated at reflux for three days. The precipitate from the reaction was isolated by filtration, and the filtrate was concentrated under reduced pressure. The residue was purified by column chromatography on silica gel (eluting sequentially with 98:2 dichloromethane:methanol and 97:3 dichloromethane:methanol). The reaction precipitate and chromatographed product together yielded 0.89 g of 8-benzyloxy-2-butyl-1-methyl-1H-imidazo[4,5-c]quinoline as a brown solid.

Part B

A modification of the general method described in Part B of Example 3 was followed to convert 8-benzyloxy-2-butyl-1-methyl-1H-imidazo[4,5-c]quinoline (0.500 g, 1.44 mmol) to 0.50 g of 8-benzyloxy-2-butyl-1-methyl-5-oxido-1H-imidazo[4,5-c]quinoline. The reaction was complete in one hour, and the product was dried overnight under high vacuum.

Part C

The general method described in Part C of Example 3 was used to aminate 8-benzyloxy-2-butyl-1-methyl-5-oxido-1H-imidazo[4,5-c]quinoline (0.50 g, 1.4 mmol). The solid isolated from the reaction was recrystallized from methanol to provide 0.32 g of 8-benzyloxy-2-butyl-1-methyl-1H-imidazo[4,5-c]quinolin-4-amine as a white solid, mp 197.9-199.1° C.

$^1$H NMR (300 MHz, DMSO-$d_6$) δ 7.65 (d, J=2.7 Hz, 1H), 7.55 (d, J=9.3 Hz, 1H), 7.52 (d, J=7.2 Hz, 2H), 7.41-7.31 (m, 3H), 7.19 (dd, J=9.0, 2.7 Hz, 1H), 6.28 (s, 2H), 5.24 (s, 2H), 4.06 (s, 3H), 2.91 (t, J=7.2 Hz, 2H), 1.73 (pentet, J=7.5 Hz, 2H), 1.42 (sextet, J=7.5 Hz, 2H), 0.94 (t, J=7.5 Hz, 3H);

$^{13}$C NMR (75 MHz, DMSO-$d_6$) δ 53.6, 153.0, 150.5, 139.7, 137.8, 133.4, 128.8, 128.14, 128.08, 127.5, 126.8, 116.9, 115.5, 103.5, 70.0, 33.3, 29.8, 26.6, 22.2, 14.1;

MS (EI) m/z 360.1960 (calcd for $C_{22}H_{24}N_4O$ 360.1950);

Anal. Calcd. for $C_{22}H_{24}N_4O$: % C, 73.31; % H, 6.71; % N, 15.54. Found: % C, 73.08; % H, 6.62; % N, 15.33.

Example 60

8-Benzyloxy-2-[2-methoxy(ethoxymethyl)]-1-methyl-1H-imidazo[4,5-c]quinolin-4-amine

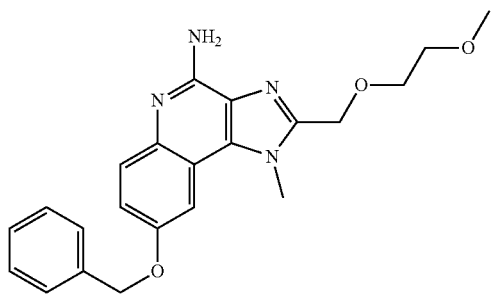

Part A

The method described in Part B of Example 46 was used to convert N-(6-benzyloxy-3-nitroquinolin-4-yl)-N-methylamine (9.9 g, 32 mmol), prepared as described in Parts A-E of Example 57, to 6-benzyloxy-$N^4$-methylquinoline-3,4-diamine with the exception that ethanol was used as the solvent.

Part B

Under a nitrogen atmosphere, a solution of the material from Part A and triethylamine (5.02 g, 49.6 mmol) in dichloromethane was cooled to ~0° C., and methoxyethoxyacetyl chloride (6.99 g, 45.8 mmol) was slowly added. The reaction was allowed to warm to room temperature and stirred until analysis by TLC indicated the disappearance of starting material. The solvent was removed under reduced pressure, and the residue was mixed with toluene and heated at reflux using a Dean-Stark trap. The toluene was removed under reduced pressure, and the residue was partitioned between dichloromethane and water. The organic layer was washed with water (2×100 mL) and brine (200 mL), dried over magnesium sulfate, filtered, and concentrated under reduced pressure. The crude product was purified by column chromatography on silica gel (eluting with 95:5 ethyl acetate:methanol). The reaction was found to be incomplete, and the product mixture was dissolved in toluene. Pyridine hydrochloride was added, and the reaction was heated at reflux until analysis by TLC indicated the reaction was complete. The work-up and purification described above was repeated to provide 6.3 g of 8-benzyloxy-2-[2-methoxy(ethoxymethyl)]-1-methyl-1H-imidazo[4,5-c]quinoline as a solid, mp 128-132° C.

Part C

A modification of the general method described in Part B of Example 3 was followed using 8-benzyloxy-2-[2-methoxy(ethoxymethyl)]-1-methyl-1H-imidazo[4,5-c]quinoline (5.4 g, 14 mmol) in lieu of 7-benzyloxy-2-methyl-1-(2-methylpropyl)-1H-imidazo[4,5-c]quinoline. Dichloromethane (100 mL) was used as the solvent, and after three hours an analysis by TLC indicated the reaction was incomplete. Additional mCPBA (0.5 equivalents) was added, and the reaction was terminated after one additional hour. After the work-up the product was purified by column chromatography on silica gel (eluting with 90:10 dichloromethane:methanol to provide 1.5 g of 8-benzyloxy-2-[2-methoxy(ethoxymethyl)]-1-methyl-5-oxido-1H-imidazo[4,5-c]quinoline as an oil.

Part D

The modification of Part C of Example 3 described in Part E of Example 48 was used to convert 8-benzyloxy-2-[2-methoxy(ethoxymethyl)]-1-methyl-5-oxido-1H-imidazo[4,5-c]quinoline (1.4 g, 3.6 mmol) to 0.6 g of 8-benzyloxy-2-[2-methoxy(ethoxymethyl)]-1-methyl-1H-imidazo[4,5-c]quinolin-4-amine, which was obtained as off-white needles, mp 159-162° C.;

$^1$H NMR (300 MHz, DMSO) δ 7.67 (d, J=7.7 Hz, 1H), 7.53 (m, 3H), 7.37 (m, 3H), 7.20 (dd, J=9.1, 2.8 Hz, 1H), 6.36 (s, 2H), 5.25 (s, 2H), 4.80 (s, 2H), 4.14 (s, 3H), 3.63 (m, 2H), 3.48 (m, 2H), 3.23 (s, 3H);

MS (APCI) m/z 393 (M+H)$^+$;

Anal. Calcd. for $C_{22}H_{24}N_4O_3 \cdot 0.5 H_2O$: % C, 65.82; % H, 6.27; % N, 13.95. Found: % C, 65.97; % H, 5.97; % N, 13.70.

Examples 61-66

Part A

A solution of 8-benzyloxy-2-butyl-1-methyl-1H-imidazo[4,5-c]quinolin-4-amine (14.65 g, 42.4 mmol), prepared as described in Parts A-C of Example 59, in ethanol (1.2 L) was added to 10% palladium on carbon (6.77 g, 63.6 mmol) and a small amount of ethanol in a Parr vessel. The reaction was placed under hydrogen pressure (50 psi, 3.4×10$^5$ Pa) for 3.5 hours. The catalyst was removed by filtration and washed with ethyl acetate. The filtrate was concentrated under reduced pressure to a small volume. Hexanes were added, and the resulting mixture was allowed to stand overnight in a refrigerator. Crystals formed and were isolated by filtration, washed with hexanes (500 mL), and dried for three days under high vacuum to provide 9.40 g of 2-butyl-1-methyl-1H-imidazo[4,5-c]quinolin-8-ol as a white solid, mp 219-220.2° C.

$^1$H NMR (300 MHz, DMSO-d$_6$): δ 9.99 (s, 1H), 8.89 (s, 1H), 7.97 (d, J=9.0 Hz, 1H), 7.73 (d, J=2.5 Hz, 1H), 7.21 (dd, J=9.0, 2.7 Hz, 1H), 4.13 (s, 3H), 2.94 (t, J=7.6 Hz, 2H), 1.79 (quintet, J=7.6 Hz, 2H), 1.44 (sextet, J=7.4 Hz, 2H), 0.95 (t, J=7.3 Hz, 3H).

MS (APCI) m/z 256 (M+H)$^+$;

Anal. Calcd. for C$_{15}$H$_{12}$N$_3$O: % C, 70.56; % H, 6.71; % N, 16.46. Found: % C, 70.60; % H, 6.65; % N, 16.38.

Part B

Under a nitrogen atmosphere, a 0.08 M solution of 2-butyl-1-methyl-1H-imidazo[4,5-c]quinolin-8-ol (1 equivalent, ~1 g) in DMF was heated at 85° C. until it was homogeneous. Solid cesium carbonate (2 equivalents) was heated, and the reaction was stirred at 85° C. for 20-40 minutes. The heat was removed, and a solution of the alkyl bromide indicated in the table below (1.2 equivalents) in DMF (5-10 mL) was added. The reaction was stirred at 85° C. for between two and 45 hours or until an analysis by TLC indicated the starting material was consumed. Optionally, methanol (1-2 mL) was added, and the reaction mixture was filtered to remove solids. The volatiles were removed under reduced pressure, and the residue was dissolved in ethyl acetate. The resulting solution was washed with water and concentrated under reduced pressure to provide a solid.

Part C

Over a period of 20 minutes, mCPBA (1 equivalent, 65% pure) was added in four portions to a 0.05-0.1 M solution of the material from Part B (1 equivalent) in chloroform. For Example 61, a 1.5:1 mixture of chloroform and DMF was used as the solvent. The reaction was stirred at ambient temperature for between four and 28 hours, and optionally additional mCPBA was added in small portions until an analysis by TLC indicated that the starting material was consumed. The solution was then washed with saturated aqueous sodium bicarbonate and concentrated under reduced pressure. For Example 66, the reaction product was purified by column chromatography on silica gel (eluting with 90:10 dichloromethane:methanol). A description of the last step in the synthesis, the purification, and the characterization for each Example follows the table.

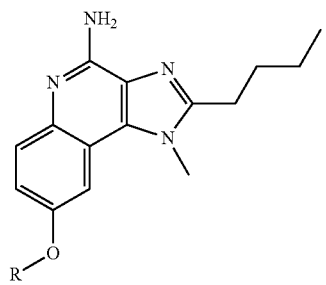

| Example | Alkyl bromide | R |
|---|---|---|
| 61 | {4-[(6-Bromohexyl)oxy]butyl}benzene | 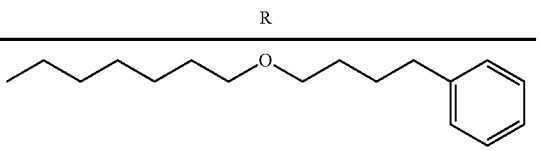 |
| 62 | 1-Bromo-3-phenylpropane | 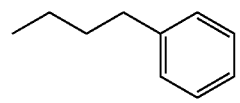 |
| 63 | 4-(Trifluoromethoxy)benzyl bromide | 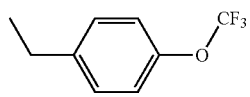 |
| 64 | α-Bromo-m-tolunitrile | 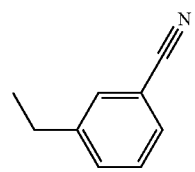 |
| 65 | 3-Methoxybenzyl bromide | 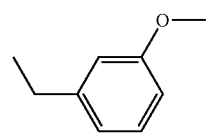 |

-continued

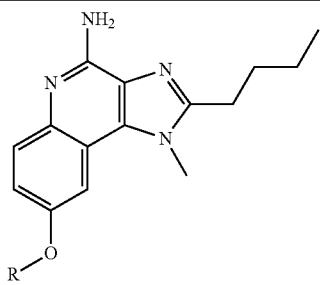

| Example | Alkyl bromide | R |
|---|---|---|
| 66 | (1-Bromoethyl)benzene | 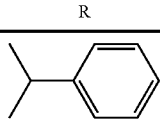 |

For examples 61, 64, and 66, the product was purified by preparative high-performance liquid chromatography (prep HPLC) with fraction collection by UV triggering. The prep HPLC fractions were analyzed using a Micromass Platform LC/MS, and the appropriate fractions were centrifuge evaporated to provide the trifluoroacetate salt of the desired compound. Prep HPLC separations were done by reversed phase chromatography with Phenomenex LUNA C18(2) columns. The mobile phase was a gradient mixture of water and acetonitrile (0.05% trifluoroacetic acid in each). Separation conditions are shown in the table below.

| Example | Column Dimensions | Particle Size | Flow | Gradient |
|---|---|---|---|---|
| 61 | 21.2 × 60 mm | 10 μm | 30 mL/min | 5 to 95% acetonitrile in 20 min |
| 64 | 10 × 50 mm | 5 μm | 16 mL/min | 5 to 95% acetonitrile in 6.5 min |
| 66 | 10 × 50 mm | 5 μm | 16 mL/min | Various acetonitrile gradients |

Example 61

2-Butyl-1-methyl-8-{[6-(4-phenylbutoxy)hexyl]oxy}-1H-imidazo[4,5-c]quinolin-4-amine trifluoroacetate Under a nitrogen atmosphere, trichloroacetyl isocyanate (0.9 mL, 7 mmol) was added dropwise to a solution of 2-butyl-1-methyl-5-oxido-8-{[6-(4-phenylbutoxy)hexyl]oxy}-1H-imidazo[4,5-c]quinoline (2.5 g, 5.0 mmol) in anhydrous dichloromethane (45 mL). The reaction was stirred for five hours, and then four drops of ammonium hydroxide (7% by weight in methanol) were added. The reaction was stirred overnight, and most of the volatiles were removed under reduced pressure. Diethyl ether was added to the remaining solution, and a solid precipitated. The solid was purified by prep HPLC as described above to provide an oil, which was dissolved in methanol. The resulting solution was filtered and concentrated under reduced pressure to provide 43.8 mg of 2-butyl-1-methyl-8-{[6-(4-phenylbutoxy)hexyl]oxy}-1H-imidazo[4,5-c]quinolin-4-amine trifluoroacetate as a white wax.

$^1$H NMR (500 MHz, DMSO-$d_6$) δ 13.56 (s, 1H), 8.71 (s, 2H), 7.74 (d, J=9.0 Hz, 1H), 7.69 (d, J=3.0 Hz, 1H), 7.36 (dd, J=9.0, 3.0 Hz, 1H), 7.25-7.22 (m, 2H), 7.15-7.11 (m, 3H), 4.18 (s, 3H), 4.14 (t, J=6 Hz, 2H), 3.35 (t, J=6.5 Hz, 2H), 3.34 (t, J=6.5 Hz, 2H), 2.99 (t, J=7.5 Hz, 2H), 2.57 (m, 2H), 1.79-1.73 (m, 4H), 1.59-1.33 (m, 12H), 0.96 (t, J=7.5 Hz, 3H);

MS (EI) m/z 503.3404 (503.3386 calcd for $C_{31}H_{42}N_4O_2$).

Example 62

2-Butyl-1-methyl-8-(3-phenylpropoxy)-1H-imidazo[4,5-c]quinolin-4-amine

A modification of the general method described in Part C of Example 3 was followed using 2-butyl-1-methyl-5-oxido-8-(3-phenylpropoxy)-1H-imidazo[4,5-c]quinoline (0.360 g, 0.924 mmol) as the starting material. Following the reaction with sodium methoxide, the reaction product was collected in two crops. The first crop was purified by column chromatography on silica gel (eluting with 90:10 dichloromethane:methanol) to provide 17.6 mg of 2-butyl-1-methyl-8-(3-phenylpropoxy)-1H-imidazo[4,5-c]quinolin-4-amine as a light-yellow solid.

$^1$H NMR (300 MHz, DMSO-$d_6$) δ7.59 (d, J=2.4 Hz, 1H), 7.55 (d, J=9.3 Hz, 1H), 7.27 (m, 5H), 7.14 (dd, J=9.0, 2.7 Hz, 1H), 6.36 (br s, 2H), 4.11 (t, J=6.6 Hz, 2H), 4.09 (s, 3H), 2.92 (t, J=7.8 Hz, 2H), 2.79 (t, J=7.5 Hz, 2H), 2.05 (pentet, J=8.1, 2H), 1.73 (pentet, J=8.1, 2H), 1.43 (sextet, J=7.2 Hz, 2H), 0.94 (t, J=7.2 Hz, 3H);

$^{13}$C NMR (75 MHz, DMSO-$d_6$) δ53.4, 153.3, 150.5, 141.8, 139.8, 133.3, 128.7, 128.6, 127.7, 126.8, 126.1, 116.6, 115.7, 103.0, 67.4, 33.3, 32.0, 30.9, 29.8, 26.6, 22.2, 14.1;

MS (APCI) m/z 389 (M+H)$^+$.

Example 63

2-Butyl-1-methyl-8-{[4-(trifluoromethoxy)benzyl]oxy}-1H-imidazo[4,5-c]quinolin-4-amine The general method described in Example 61 was followed using 2-butyl-1-methyl-8-{[4-(trifluoromethoxy)benzyl]oxy}-5-oxido-1H-imidazo[4,5-c]quinoline (0.380 g, 0.853 mmol) in lieu of 2-butyl-1-methyl-5-oxido-8-{[6-(4-phenylbutoxy)hexyl]oxy}-1H-imidazo[4,5-c]quinoline. The crude product was purified by column chromatography on silica gel (eluting with 90:10 dichloromethane:methanol) to provide 93.9 mg of 2-butyl-1-methyl-8-{[4-(trifluoromethoxy)benzyl]oxy}-1H-imidazo[4,5-c]quinolin-4-amine as a white powder, mp 219.4-220.2° C.

$^1$H NMR (300 MHz, DMSO-d$_6$) δ 7.65 (d, J=2.2 Hz, 2H), 7.64-7.62 (m, 1H), 7.54 (d, J=9.3 Hz, 1H), 7.42 (d, J=0.8 Hz, 1H), 7.40 (d, J=0.8 Hz, 1H), 7.19 (dd, J=9.6, 3 Hz, 1H), 6.22 (s, 2H), 5.28 (s, 2H), 4.07 (s, 3H), 2.91 (t, J=7.5 Hz, 2H), 1.75 (pentet, J=7.2 Hz, 2H), 1.42 (sextet, J=7.5, 2H), 0.94 (t, J=7.2 Hz, 3H), MS (EI) m/z 445.1841 (445.1851 calcd. for C$_{23}$H$_{23}$F$_3$N$_4$O$_2$).

Example 64

3-{[(4-Amino-2-butyl-1-methyl-1H-imidazo[4,5-c]quinolin-8-yl)oxy]methyl}benzonitrile trifluoroacetate Under a nitrogen atmosphere, ammonium hydroxide (10 mL) was added to a solution of 3-{[(4-amino-2-butyl-1-methyl-5-oxido-1H-imidazo[4,5-c]quinolin-8-yl)oxy]methyl}benzonitrile (0.490 g, 1.26 mmol) in anhydrous dichloromethane (46 mL), and the reaction was cooled to 0° C. and stirred rapidly. p-Toluenesulfonyl chloride (0.241 g, 1.26 mmol) was added, and the reaction was allowed to warm slowly and stirred for three days. A precipitate was present in the reaction. Water was added, and the mixture was stirred for four hours. The precipitate was isolated by filtration, washed with water, recrystallized from methanol, and dried in a vacuum oven overnight. The solid was further purified by prep HPLC as described above to provide 41.8 mg of 3-{[(4-amino-2-butyl-1-methyl-1H-imidazo[4,5-c]quinolin-8-yl)oxy]methyl}benzonitrile trifluoroacetate as a white powder.

$^1$H NMR (300 MHz, DMSO-d$_6$) δ 8.72 (br s, 1H), 7.99 (br s, 1H), 7.86 (m, 2H), 7.81 (d, J=2.7 Hz, 1H), 7.77 (d, J=9.3 Hz, 1H), 7.65 (t, J=7.5 Hz, 1H), 7.48 (dd, J=9.0, 2.7 Hz, 1H), 5.37 (br s, 2H), 4.16 (s, 3H), 2.99 (t, J=7.5 Hz, 2H), 1.76 (pentet, J=7.8 Hz, 2H), 1.44 (sextet, J=7.5 Hz, 2H), 0.95 (t, J=7.5 Hz, 3H);

$^{13}$C NMR (125 MHz, DMSO-d$_6$) δ157.0, 155.0, 148.2, 138.8, 135.6, 132.8, 132.2, 131.4, 130.2, 124.7, 120.4, 119.0, 118.8, 114.2, 111.9, 105.7, 69.0, 33.8, 29.5, 26.6, 22.1, 14.1;

MS (EI) m/z 385.1910 (385.1903 calcd for C$_{23}$H$_{23}$N$_5$O).

Example 65

2-Butyl-8-[(3-methoxybenzyl)oxy]-1-methyl-1H-imidazo[4,5-c]quinolin-4-amine

The general method described in Example 61 was followed using 2-butyl-1-methyl-8-[3-(methoxybenzyl)oxy]-5-oxido-1H-imidazo[4,5-c]quinoline (0.420 g, 1.07 mmol) in lieu of 2-butyl-1-methyl-5-oxido-8-{[6-(4-phenylbutoxy)hexyl]oxy}-1H-imidazo[4,5-c]quinoline. The crude product was purified by column chromatography on silica gel (eluting with 90:10 dichloromethane:methanol) to provide 34 mg of 2-butyl-8-[3-(methoxybenzyl)oxy]-1-methyl-1H-imidazo[4,5-c]quinolin-4-amine as a white solid, mp 191.6-192.5° C.

$^1$H NMR (300 MHz, DMSO-d$_6$) δ 7.65 (d, J=3.3 Hz, 1H), 7.53 (d, J=8.7 Hz, 1H), 7.32 (t, J=8.7 Hz, 1H), 7.16 (dd, J=9.3, 3.0 Hz, 1H), 7.09 (s, 1H), 7.07 (s, 1H), 6.90 (dd, J=7.2, 1.8 Hz, 1H), 6.21 (s, 2H), 5.21 (s, 2H), 4.06 (s, 3H), 3.76 (s, 3H), 2.91 (t, J=7.2 Hz, 2H), 1.75 (pentet, J=6.9 Hz, 2H), 1.45 (sextet, J=6.9 Hz, 2H), 0.94 (t, J=7.5 Hz, 3H);

$^{13}$C NMR (75 MHz, DMSO-d$_6$) δ 160.7, 154.6, 154.0, 151.4, 140.3, 134.3, 130.7, 128.2, 120.8, 117.7, 116.2, 114.3, 114.2, 104.2, 70.3, 55.8, 33.5, 30.0, 26.8, 22.4, 14.2;

MS (EI) m/z 391.2131 (391.2134 calcd for C$_{23}$H$_{26}$N$_4$O$_2$);

Anal. Calcd. for C$_{23}$H$_{26}$N$_4$O$_2$·0.8 H$_2$0: % C, 68.23; % H, 6.87; % N, 13.84. Found: % C, 68.40; % H, 6.63; % N, 13.75.

Example 66

2-Butyl-1-methyl-8-(1-phenylethoxy)-1H-imidazo[4,5-c]quinolin-4-amine trifluoroacetate The general method described in Example 61 was followed using 2-butyl-1-methyl-5-oxido-8-(2-phenylethoxy)-1H-imidazo[4,5-c]quinoline (0.150 g, 0.399 mmol) in lieu of 2-butyl-1-methyl-5-oxido-8-{[6-(4-phenylbutoxy)hexyl]oxy}-1H-imidazo[4,5-c]quinoline. The crude product was purified by prep HPLC as described above to provide 100 mg of 2-butyl-1-methyl-8-(1-phenylethoxy)-1H-imidazo[4,5-c]quinolin-4-amine trifluoroacetate as a white powder, mp 183.4-184.20° C.

$^1$H NMR (500 MHz, DMSO-d$_6$) δ 8.60 (br s, 2H), 7.68 (d, J=9.0 Hz, 1H), 7.63 (d, J=2.7 Hz, 1H), 7.49 (d, J=6.9 Hz, 2H), 7.4-7.24 (m, 4H), 5.72 (q, J=6.0 Hz, 1H), 4.02 (s, 3H), 2.96 (t, J=7.8 Hz, 2H), 1.75 (pentet, J=7.2 Hz, 2H), 1.64 (d, J=6.0 Hz, 3H), 1.42 (sextet, J=7.2 Hz, 2H), 0.95 (t, J=7.2 Hz, 3H);

$^{13}$C NMR (125 MHz, DMSO-d$_6$) δ 156.5, 154.0, 147.6, 142.5, 135.1, 128.6, 127.9, 127.6, 125.7, 124.1, 119.7, 119.3, 113.6, 106.0, 75.6, 33.3, 28.9, 26.1, 24.1, 21.7, 13.6;

MS (ESI) m/z 375.2205 (375.2185 calcd for C$_{23}$H$_{26}$N$_4$O, M+H).

Example 67

8-Benzyloxy-1-(2-methylpropyl)-1H-imidazo[4,5-c]quinolin-4-amine

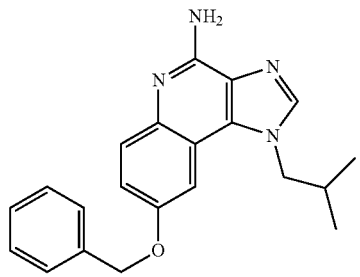

Part A

The general method described in Part E of Example 1 was used to convert 6-benzyloxy-4-chloro-3-nitroquinoline (16.0 g, 50.8 mmol), prepared as described in Parts A-D of Example 57, to 16.7 g of (6-benzyloxy-3-nitroquinolin-4-yl)-(2-methylpropyl)amine. The reaction was complete in 30 minutes, and the product was obtained as an orange solid.

Part B

A modification of the general procedure described in Part B of Example 46 was followed using (6-benzyloxy-3-nitroquinolin-4-yl)-(2-methylpropyl)amine (4.6 g, 14 mmol) in lieu of (7-benzyloxy-3-nitroquinolin-4-yl)-(2-phenoxyethyl)amine. The reaction was maintained under hydrogen pressure for four hours, and the reaction mixture was filtered through a layer of CELITE filter aid. After the filter cake was washed with toluene, the filtrate was concentrated to a volume of 100 mL.

Part C

Triethyl orthoformate (2.55 g, 17.2 mmol) and a catalytic amount of pyridine hydrochloride were added to the solution from Part B. The reaction was heated at reflux for five hours, allowed to cool to room temperature, and stirred overnight. The reaction mixture was then cooled, and a precipitate formed. The precipitate was isolated by filtration and washed with hexanes to provide 3.74 g of 8-benzyloxy-1-(2-methylpropyl)-1H-imidazo[4,5-c]quinoline as a pale yellow solid, mp 129-133° C.

Part D

The general method described in Part B of Example 3 was followed using 8-benzyloxy-1-(2-methylpropyl)-1H-imidazo[4,5-c]quinoline (2.1 g, 6.3 mmol) in lieu of 7-benzyloxy-2-methyl-1-(2-methylpropyl)-1H-imidazo[4,5-c]quinoline. After the work-up, 2.16 g of 8-benzyloxy-1-(2-methylpropyl)-5-oxido-1H-imidazo[4,5-c]quinoline were obtained as a white solid and used without purification.

Part E

A modification of the general method described in Part C of Example 3 was followed using 8-benzyloxy-1-(2-methylpropyl)-5-oxido-1H-imidazo[4,5-c]quinoline (2.0 g, 5.8 mmol) as the starting material. The reaction with trichloroacetyl isocyanate was not complete after one hour as evidenced by a TLC analysis. Additional trichloroacetyl isocyanate (0.1 equivalent) was added, and the reaction was stirred for an additional hour. Following the reaction with sodium methoxide, the solid product was isolated by filtration and recrystallized from ethanol. The crystals were dried overnight in a vacuum oven at 45° C. to provide 1.6 g of 8-benzyloxy-1-(2-methylpropyl)-1H-imidazo[4,5-c]quinolin-4-amine as a white solid, mp 214-216° C.

$^1$H NMR (300 MHz, DMSO) δ 8.15 (s, 1H), 7.56 (d, 1H), 7.40 (m, 6H), 7.20 (dd, J=9.0, 2.6 Hz, 1H), 6.37 (s, 2H), 5.24 (s, 2H), 4.37 (d, J=7.3 Hz, 2H), 2.15 (m, 1H), 0.88 (d, J=6.6 Hz, 6H);

MS (APCI) m/z 347 (M+H)$^+$;

Anal. Calcd. for $C_{21}H_{22}N_4O$: % C, 72.81; % H, 6.40; % N, 16.17. Found: % C, 72.74; % H, 6.32; % N, 16.11.

Example 68

8-Benzyloxy-2-ethoxymethyl-1-(2-methylpropyl)-1H-imidazo[4,5-c]quinolin-4-amine

Part A

A modification of the general method described in Part B of Example 67 was used to reduce (6-benzyloxy-3-nitroquinolin-4-yl)-(2-methylpropyl)amine (10.6 g, 30.2 mmol), which was prepared as described in Part A of Example 67. The hydrogenation was allowed to proceed for five hours. After the reaction, the toluene was removed under reduced pressure to provide 9.1 g of 6-benzyloxy-N$^4$-(2-methylpropyl)quinoline-3,4-diamine as a brown oil.

Part B

Ethoxyacetyl chloride (3.81 g, 31.1 mmol) was slowly added to a chilled solution of 6-benzyloxy-N$^4$-(2-methylpropyl)quinoline-3,4-diamine (9.1 g, 28.3 mmol) in pyridine (60 mL). The reaction was allowed to warm to ambient temperature and then heated at reflux for three hours. The solvent was removed under reduced pressure, and the residue was dissolved in dichloromethane (200 mL). The resulting solution was washed with water (3×100 mL) and concentrated under reduced pressure. The concentrated solution was passed through a layer of silica gel (eluting with dichloromethane:methanol 95:5) and concentrated under reduced pressure to provide 3.6 g of 8-benzyloxy-2-ethoxymethyl-1-(2-methylpropyl)-1H-imidazo[4,5-c]quinoline as an oil.

Part C

A modification of the general method described in Part C of Example 60 was used to convert 8-benzyloxy-2-ethoxymethyl-1-(2-methylpropyl)-1H-imidazo[4,5-c]quinoline (3.7 g, 9.4 mmol) to 2.6 g of 8-benzyloxy-2-ethoxymethyl-1-(2-methylpropyl)-5-oxido-1H-imidazo[4,5-c]quinoline. The reaction was complete in three hours, and the product was used without purification.

Part D

A modification of the general method described in Part C of Example 3 was followed using 8-benzyloxy-2-ethoxymethyl-1-(2-methylpropyl)-5-oxido-1H-imidazo[4,5-c]quinoline (2.6 g, 6.4 mmol) as the starting material and chloroform as the solvent. The reaction with trichloroacetyl isocyanate was not complete after one hour as evidenced by a TLC analysis. Additional trichloroacetyl isocyanate was added, and the reaction was stirred overnight. Following the reaction with sodium methoxide, the solid product was isolated by filtration and washed with methanol and a mixture of dichloromethane and water. The solid was isolated by filtration and recrystallized from 2-methoxyethyl ether. The crystals were dried under high vacuum to provide 8-benzyloxy-2-ethoxymethyl-1-(2-methylpropyl)-1H-imidazo[4,5-c]quinolin-4-amine as a white solid, mp 183-184° C.

$^1$H NMR (300 MHz, DMSO) δ 7.52 (d, J=7.0 Hz, 1H), 7.40 (m, 6H), 7.20 (dd, J=9.1, 2.6 Hz, 1H), 6.40 (s, 2H), 5.24 (s, 2H), 4.75 (s, 2H), 4.43 (d, J=7.3 Hz, 2H), 3.56 (q, J=7.0, 2H), 2.24 (septet, J=6.6 Hz, 1H), 1.15 (t, J=7.0 Hz, 3H), 0.89 (d, J=6.6 Hz, 6H);

MS (APCI) m/z 405 (M+H)$^+$;

Anal. Calcd. for $C_{24}H_{28}N_4O$: % C, 71.26; % H, 6.98; % N, 13.85. Found: % C, 70.96; % H, 6.79; % N, 13.54.

Example 69

8-Benzyloxy-2-methyl-1-[5-(methylsulfonyl)pentyl]-1H-imidazo[4,5-c]quinolin-4-amine

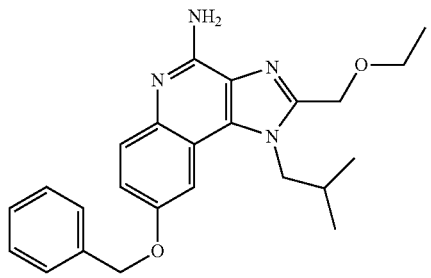

Part A

A modification of the general method described in Part A of Example 46 was followed using 6-benzyloxy-4-chloro-3-nitroquinoline (10.5 g, 34 mmol), prepared as described in Parts A-D of Example 57, in lieu of 7-benzyloxy-4-chloro-3-nitroquinoline and 5-amino-1-pentanol (3.5 g, 34 mmol) in lieu of 2-phenoxyethylamine. The reaction was heated at reflux for two hours and then allowed to cool to ambient temperature slowly and stirred overnight. An analysis by TLC indicated the presence of starting material, and additional 5-amino-1-pentanol (0.2 equivalent) was added. The reaction was heated at reflux until the reaction was complete as indicated by TLC. Following the work-up, the crude product was purified by column chromatography on silica gel (eluting with 95:5 dichloromethane:methanol) to provide 5.95 g of 5-{[6-(benzyloxy)-3-nitroquinolin-4-yl]amino}pentan-1-ol as a yellow solid.

Part B

Under a nitrogen atmosphere, thionyl chloride (1.7 mL, 23 mmol) was added to a mixture of 5-{[6-(benzyloxy)-3-nitroquinolin-4-yl]amino}pentan-1-ol (5.95 g, 15.6 mmol) and anhydrous dichloromethane (78 mL). The reaction became homogeneous and was heated at reflux for 1.5 hours, at which time a yellow precipitate formed. The volatiles were removed under reduced pressure, and the residue was partitioned between dilute aqueous sodium carbonate (100 mL) and dichloromethane (150 mL). The aqueous layer was washed with dichloromethane (50 mL), and the combined organic solutions were washed with brine (50 mL), dried over sodium sulfate, filtered, and concentrated under reduced pressure to provide 6.24 g of 6-benzyloxy-N-(5-chloropentyl)-3-nitroquinolin-4-amine as a yellow oil.

Part C

Under a nitrogen atmosphere, solid sodium thiomethoxide (1.38 g, 18.7 mmol, 95% pure) was added to a solution of 6-benzyloxy-N-(5-chloropentyl)-3-nitroquinolin-4-amine (6.24 g, 15.6 mmol) in DMF. The reaction was stirred at ambient temperature for 30 minutes and then heated at 80° C. for one hour, at which time a yellow precipitate formed. The reaction mixture was partitioned between water (390 mL) and dichloromethane (150 mL). The aqueous layer was washed with dichloromethane (100 mL), and the combined organic fractions were washed with saturated aqueous sodium bicarbonate (100 mL) and brine (100 mL), dried over sodium sulfate, filtered, and concentrated under reduced pressure to provide a red oil. An analysis by nuclear magnetic resonance spectroscopy indicated the presence of a large amount of starting material. The reaction product was dissolved in DMF (78 mL), treated with sodium thiomethoxide, and heated at reflux for two hours. The work-up described above was repeated, and the crude product was purified by column chromatography on silica gel (eluting with 70:30 ethyl acetate:hexane) to provide 5.1 g of 6-benzyloxy-N-[5-(methylthio)pentyl]-3-nitroquinolin-4-amine as a yellow oil.

Part D

A modification of the general method described in Part B of Example 46 was followed using 6-benzyloxy-N-[5-(methylthio)pentyl]-3-nitroquinolin-4-amine (5.1 g, 12 mmol) in lieu of (7-benzyloxy-3-nitro-quinolin-4-yl)-(2-phenoxyethyl)amine. The reaction was maintained under hydrogen pressure (49 psi, 3.4×10$^5$ Pa) for three hours. The reaction mixture was filtered through a layer of CELITE filter aid, and the filter cake was washed with methanol (100 mL) and chloroform (50 mL). The filtrate was concentrated under reduced pressure to provide 6-benzyloxy-N$^4$-[5-(methylthio)pentyl]quinoline-3,4-diamine as a yellow oil, which was used without purification.

Part E

Trimethyl orthoacetate (1.7 mL, 14 mmol) was added to a solution of the material from Part D in toluene (41 mL). Pyridine hydrochloride (0.1 g) was then added, and the reaction was heated at reflux for one hour. A Dean-Stark trap was used to collect the volatiles. The reaction was allowed to cool to ambient temperature, and the solvent was removed under reduced pressure. The crude product was purified by column chromatography on silica gel (eluting with 95:5 dichloromethane:methanol) to provide 5.03 g of 8-benzyloxy-2-methyl-1-[5-(methylthio)pentyl]-1H-imidazo[4,5-c]quinoline as a white solid.

Part F

Over a period of 13 minutes, mCPBA (6.2 g, 27 mmol, 75% pure) was added in portions to a solution of 8-benzyloxy-2-methyl-1-[5-(methylthio)pentyl]-1H-imidazo[4,5-c]quinoline (3.3 g, 8.1 mmol) in chloroform (41 mL). The reaction was stirred for 15 minutes, and then a precipitate formed. Additional chloroform (41 mL) was added, but the precipitate did not dissolve Ammonium hydroxide (40 mL) and p-toluenesulfonyl chloride were then added to the mixture, and the reaction was stirred for ten minutes. The aqueous layer was washed with dichloromethane (2×50 mL), and the combined organic solutions were concentrated under reduced pressure to yield a red, semi-solid. The solid was purified by column chromatography on silica gel (eluting with 90:10 dichloromethane:methanol) and recrystallized from methanol (80 mL/g) to provide 1.4 g of 8-benzyloxy-2-methyl-1-[5-(methylsulfonyl)pentyl]-1H-imidazo[4,5-c]quinolin-4-amine as colorless needles, mp 215-217° C.

$^1$H NMR (300 MHz, DMSO-d$_6$) δ 7.55 (d, J=8.4 Hz, 1H), 7.51-7.33 (m, 6H), 7.17 (dd, J=8.7, 2.5 Hz, 1H), 6.23 (bs, 2H), 5.26 (bs, 2H), 4.45 (t, J=7.2 Hz, 2H), 3.07 (t, J=7.5 Hz, 2H), 2.89 (s, 3H), 2.59 (s, 3H), 1.81-1.65 (m, 4H), 1.50-1.40 (m, 2H);

MS (APCI) m/z 453 (M+H)$^+$;

Anal. Calcd. for C$_{24}$H$_{28}$N$_4$O$_3$S: % C, 63.69; % H, 6.24; % N, 12.38. Found: % C, 63.76; % H, 6.39; % N, 12.45.

Examples 70-73

Part A

A solution of 6-benzyloxy-4-chloro-3-nitroquinoline (14.47 g, 46.29 mmol), prepared in Parts A-D of Example 57, and triethylamine (8.4 mL, 60.2 mmol) in dichloromethane (200 mL) was cooled to 0° C. tert-Butyl N-(4-aminobutyl)carbamate (8.71 g, 46.3 mmol) was added; the reaction was stirred for 15 minutes at 0° C. and then allowed to warm to ambient temperature and stirred for five hours. An analysis by TLC indicated the presence of starting material; therefore, additional tert-butyl N-(4-aminobutyl)carbamate (0.5 mL, 2.6 mmol) was added. The reaction was stirred overnight and then washed with water (2×200 mL). The combined washings were extracted with chloroform after the addition of sodium chloride. The combined organic solutions were dried over sodium sulfate, filtered, and concentrated under reduced pressure. The crude product was recrystallized from ethyl acetate (100 mL). The crystals were isolated by filtration and washed with cold hexanes to provide 17.62 g of tert-butyl[4-(6-benzyloxy-3-nitroquinolin-4-ylamino)butyl]carbamate as an orange powder.

Part B tert-Butyl[4-(6-benzyloxy-3-nitroquinolin-4-ylamino)butyl]carbamate (17.62 g, 37.77 mmol) was dissolved in toluene (600 mL) with heating and added to a Parr vessel charged with 5% platinum on carbon (2.20 g). The vessel was placed under hydrogen pressure (30 psi, 2.1×10$^5$ Pa) for three hours. The reaction mixture was filtered through a layer of CELITE filter aid, and the filtrate was concentrated under reduced pressure to provide 15.5 g of tert-butyl{4-[3-amino-6-(benzyloxy)quinolin-4-ylamino]butyl}carbamate as a brown solid.

Part C

For Examples 70-72, the following procedure was used. Under a nitrogen atmosphere, the reagent from the table below (1.5 equivalents) and pyridine hydrochloride (0.01-0.02 equivalents) were added to a solution of tert-butyl{4-[3-amino-6-(benzyloxy)quinolin-4-ylamino]butyl}carbamate (29-36 mmol, 1 equivalent) in toluene (200 mL), and the reaction was heated at reflux for three to five hours. The toluene was removed under reduced pressure. The residue was dissolved in a small amount of toluene, which was removed under reduced pressure. This was repeated three times. The resulting solid was dried under high vacuum at 100° C. to provide the tert-butyl{4-(8-benzyloxy-1H-imidazo[4,5-c]quinolin-1-yl]butyl}carbamate with the substituent indicated in the table below.

For Example 73, a modification of the general method described for Part C of Example 50 was followed using tert-butyl{4-[3-amino-6-(benzyloxy)quinolin-4-ylamino]butyl}carbamate (9.25 g, 21.2 mmol) in lieu of tert-butyl{4-[3-amino-7-(benzyloxy)quinolin-4-ylamino]butyl}carbamate and ethoxyacetyl chloride (2.86 g, 23.3 mmol) in lieu of methoxypropionyl chloride. After the cyclization reaction, the solvent was removed under reduced pressure, and the residue was dissolved in chloroform (400 mL). The resulting solution was washed with water (2×200 mL) and brine (1×200 mL), concentrated under reduced pressure, and dried under high vacuum to provide a brown oil. The crude product was purified by column chromatography on silica gel (400 g, eluting with 95:5 dichloromethane:methanol). The resulting solid was triturated with diethyl ether and isolated by filtration to provide 5.37 g of tert-butyl{4-(8-benzyloxy-2-ethoxymethyl-1H-imidazo[4,5-c]quinolin-1-yl]butyl}carbamate as an off-white powder.

Part D mCPBA (1 equivalent, 60% pure) was added to a 0.1 M solution of the material from Part C (1 equivalent) in chloroform. The reaction was stirred under a nitrogen atmosphere overnight. During the reaction additional mCPBA was added if the reaction had appeared to stall. The reaction was then washed with 1% aqueous sodium carbonate (2-3×) and brine (1×), dried over sodium sulfate, filtered, and concentrated under reduced pressure.

Part E

Excess ammonium hydroxide and p-toluenesulfonyl chloride (1 equivalent) were added to a 0.5-2 M solution of the material from Part D (1 equivalent) in dichloroethane. The reaction was heated at 70° C. for one to two hours and then allowed to cool to room temperature. The organic solution was washed with 1% aqueous sodium carbonate (3×), dried over sodium sulfate, filtered, and concentrated under reduced pressure. For Examples 70, 71, and 73, the material was used without purification. For Example 72, the crude product was purified by column chromatography on silica gel (eluting sequentially with 92.5:7.5 dichloromethane:methanol and 90:10 dichloromethane:methanol).

Part F

A modification of the general method described in Part F of Example 50 was followed. A solution of the material from Part E and hydrochloric acid in ethanol was heated at reflux for 30 minutes to two hours. The salt obtained from the reaction was dissolved in water, and the aqueous solution was washed with chloroform. Concentrated ammonium hydroxide was added to the aqueous solution until the pH was basic. The desired product was either isolated by filtration (Example 70) or extracted with chloroform (Examples 71-73). The combined organic extracts were washed with brine or 1% aqueous sodium carbonate, dried over sodium sulfate, filtered, and concentrated under reduced pressure to provide the compound shown in the table below. For each example, the purification and characterization of the product is shown below the table.

| Example | Reagent for Part C | R |
|---|---|---|
| 70 | Trimethyl orthovalerate | —CH$_2$CH$_2$CH$_2$CH$_3$ |
| 71 | Triethyl orthopropionate | —CH$_2$CH$_3$ |
| 72 | Triethyl orthoacetate | —CH$_3$ |
| 73 | Ethoxyacetyl chloride | —CH$_2$OCH$_2$CH$_3$ |

Example 70

1-(4-Aminobutyl)-8-benzyloxy-2-butyl-1H-imidazo[4,5-c]quinolin-4-amine

The isolated solid was dried overnight in a vacuum oven at 60° C. to provide 1-(4-aminobutyl)-8-benzyloxy-2-butyl-1H-imidazo[4,5-c]quinolin-4-amine as a white powder, m.p. 161.2-163.6° C.
$^1$H NMR (300 MHz, DMSO-d$_6$) δ 7.58-7.33 (m, 7H), 7.19 (dd, J=9.4, 2.5 Hz, 1H), 6.23 (s, 2H), 5.25 (s, 2H), 4.45 (t, J=7.5 Hz, 2H), 3.32 (br s, 2H), 2.90 (m, 2H), 2.55 (m, 2H), 1.80 (m, 4H), 1.43 (m, 4H), 0.95 (t, J=7.5 Hz, 3H);
$^{13}$C NMR (75 MHz, DMSO-d$_6$) δ 153.4, 153.2, 150.7, 140.1, 137.7, 132.3, 128.8, 128.1, 128.0, 127.8, 127.2, 117.2, 115.1, 103.0, 69.9, 45.1, 41.6, 30.4, 30.0, 27.9, 26.6, 22.3, 14.2; MS (APCI) m/z 418 (M+H)$^+$;
Anal. Calcd. for C$_{25}$H$_{31}$N$_5$O 0.15 H$_2$O: % C, 71.45; % H, 7.51; % N, 16.67. Found: % C, 71.22; % H, 7.59; % N, 16.52.

Example 71

1-(4-Aminobutyl)-8-benzyloxy-2-ethyl-1H-imidazo[4,5-c]quinolin-4-amine

The product was isolated as a tan solid.
$^1$H NMR (300 MHz, DMSO-d$_6$) δ 7.58-7.33 (m, 7H), 7.18 (dd, J=9.0, 2.6 Hz, 1H), 6.25 (s, 2H), 5.25 (s, 2H), 4.43 (m, 2H), 3.25 (br s, 2H), 2.93 (q, J=7.5 Hz, 2H), 1.77 (m, 2H), 1.41 (m, 4H), 1.36 (m, 3H).

Example 72

1-(4-Aminobutyl)-8-benzyloxy-2-methyl-1H-imidazo[4,5-c]quinolin-4-amine

The product was isolated as an off-white powder.
$^1$H NMR (300 MHz, DMSO-d$_6$) δ 7.57-7.31 (m, 7H), 7.17 (dd, J=9.0, 2.7 Hz, 1H), 6.27 (s, 2H), 5.25 (s, 2H), 4.43 (m, 2H), 3.34 (br s, 2H), 2.58 (s, 3H), 2.55 (m, 2H), 1.76 (m, 2H), 1.40 (m, 2H).

Example 73

1-(4-Aminobutyl)-8-benzyloxy-2-ethoxymethyl-1H-imidazo[4,5-c]quinolin-4-amine

The product was isolated as an orange solid.
$^1$H NMR (300 MHz, DMSO-$d_6$) δ 7.59-7.32 (m, 7H), 7.22 (dd, J=9.0, 2.7 Hz, 1H), 6.36 (s, 2H), 5.27 (s, 2H), 4.77 (s, 2H), 4.54 (m, 2H), 3.56 (m, 2H), 2.58 (t, J=6.8 Hz, 2H), 1.85 (m, 2H), 1.47 (m, 2H), 1.17 (t, J=7.0 Hz, 3H);
MS (APCI) m/z 420 (M+H)$^+$.

Examples 74-77

Under a nitrogen atmosphere, a 0.50-0.1 M solution of the starting material indicated in the table below (1-2 g) in the solvent indicated in the table below was cooled to 0° C. Phenyl isocyanate (1 equivalent) was added dropwise. The reaction was stirred for 15 minutes at 0° C. and then allowed to warm to ambient temperature and stirred for two hours or overnight, at which time a precipitate had formed. The purification and characterization of each compound is given below the table.

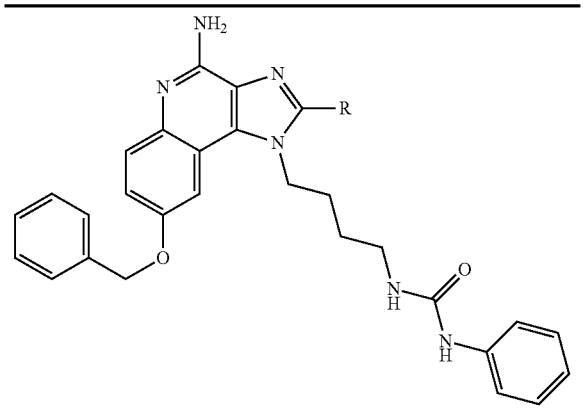

| Example | Starting Material | Solvent | R |
|---|---|---|---|
| 74 | Example 70 | dichloromethane | —CH$_2$CH$_2$CH$_2$CH$_3$ |
| 75 | Example 71 | dichloromethane | —CH$_2$CH$_3$ |
| 76 | Example 72 | chloroform | —CH$_3$ |
| 77 | Example 73 | chloroform | —CH$_2$OCH$_2$CH$_3$ |

Example 74

N-{4-[4-Amino-8-(benzyloxy)-2-butyl-1H-imidazo[4,5-c]quinolin-1-yl]butyl}-N'-phenylurea The volatiles were removed under reduced pressure. The residue was dissolved in dichloromethane and diluted with hexanes. The resulting precipitate was isolated by filtration and subsequently dried overnight in a vacuum oven at 60° C. The product was purified by column chromatography on silica gel (200 g, eluting with 85:15 dichloromethane:methanol). The purified product was dried in a vacuum oven at 60° C. to provide 0.83 g of N-{4-[4-amino-8-(benzyloxy)-2-butyl-1H-imidazo[4,5-c]quinolin-1-yl]butyl}-N'-phenylurea as yellow microcrystals, m.p. 190-194° C.
$^1$H NMR (300 MHz, DMSO-$d_6$) δ 8.42 (s, 1H), 7.57 (d, J=9.3 Hz, 1H), 7.47 (m, 3H), 7.36 (m, 5H), 7.19 (m, 3H), 6.87 (t, J=7.3 Hz, 1H), 6.41 (s, 2H), 6.17 (m, 1H), 5.24 (s, 2H), 4.50 (m, 2H), 3.12 (m, 2H), 2.92 (m, 2H), 1.78 (m, 4H), 1.55 (m, 2H), 1.43 (m, 2H), 0.93 (t, J=7.3 Hz, 3H);
$^{13}$C NMR (125 MHz, DMSO-$d_6$) 155.6, 153.8, 153.5, 150.4, 140.9, 139.2, 137.6, 132.5, 128.9, 128.8, 128.1, 127.9, 127.4, 127.1, 121.3, 118.0, 117.5, 115.0, 102.9, 70.0, 44.9, 39.0, 30.0, 27.9, 27.4, 26.5, 22.3, 14.1;
MS (APCI) m/z 537 (M+H)$^+$;
Anal. Calcd. for C$_{32}$H$_{36}$N$_6$O$_2$.0.50 H$_2$O: % C, 70.44; % H, 6.84; % N, 15.40. Found: % C, 70.17; % H, 6.66; % N, 15.32.

Example 75

N-{4-[4-Amino-8-(benzyloxy)-2-ethyl-1H-imidazo[4,5-c]quinolin-1-yl]butyl}-N'-phenylurea hydrochloride The volatiles were removed under reduced pressure, and 1M aqueous hydrochloric acid was added to the residue. The reaction was heated at reflux for two days. A precipitate formed and was isolated by filtration. The product was recrystallized from methanol and a small amount of dichloromethane. The crystals were isolated by filtration, washed with cold methanol, and dried in a vacuum oven at 60° C. to provide 0.59 g of N-{4-[4-amino-8-(benzyloxy)-2-ethyl-1H-imidazo[4,5-c]quinolin-1-yl]butyl}-N'-phenylurea hydrochloride as a yellow, crystalline solid, mp>250° C. An additional 0.66 g was obtained after concentrating the mother liquor under reduced pressure.
$^1$H NMR (300 MHz, DMSO-$d_6$) δ 13.62 (s, 1H), 8.64 (s, 1H), 8.58 (br s, 2H), 7.79 (d, J=9.4 Hz, 1H), 7.58 (d, J=2.5 Hz, 1H), 7.48 (m, 2H), 7.42-7.34 (m, 5H), 7.18 (m, 2H), 6.87 (m, 1H), 6.36 (t, J=5.6 Hz, 1H), 5.32 (s, 2H), 4.60 (m, 2H), 3.12 (m, 2H), 3.02 (q, J=7.5 Hz, 2H), 1.80 (m, 2H), 1.57 (m, 2H), 1.38 (t, J=7.5 Hz, 3H);
$^{13}$C NMR (125 MHz, DMSO-$d_6$) δ 157.9, 155.8, 155.6, 148.1, 141.0, 136.9, 134.8, 128.9, 128.9, 128.4, 128.3, 128.0, 125.1, 121.2, 120.4, 119.6, 117.8, 113.6, 104.5, 70.2, 45.3, 38.8, 27.5, 27.3, 20.4, 12.0;
MS (APCI) m/z 509 (M+H)$^+$;
Anal. Calcd. for C$_{30}$H$_{32}$N$_6$O$_2$.1.0 HCl.0.20 H$_2$O: % C, 65.67; % H, 6.14; % N, 15.32; % Cl, 6.46. Found: % C, 65.38; % H, 6.17; % N, 15.22; % Cl, 6.45.

Example 76

N-{4-[4-Amino-8-(benzyloxy)-2-methyl-1H-imidazo[4,5-c]quinolin-1-yl]butyl}-N'-phenylurea The reaction precipitate was isolated by filtration and dried overnight in a vacuum oven at 60° C. The solid was triturated with chloroform (250 mL) containing small amounts of methanol and dichloromethane, isolated by filtration, and mixed with dilute ammonium hydroxide and chloroform. The aqueous solution was extracted with chloroform (4×200 mL), and the combined organic fractions were concentrated under reduced pressure. The residue was recrystallized from methanol and then purified by column chromatography on silica gel (200 mL, eluting sequentially with 90:10 and 87:13 chloroform:methanol to provide 0.74 g of N-{4-[4-amino-8-(benzyloxy)-2-methyl-1H-imidazo[4,5-c]quinolin-1-yl]butyl}-N'-phenylurea as a white powder, m.p. 202.1-204.5° C.
$^1$H NMR (300 MHz, DMSO-$d_6$) δ 8.38 (s, 1H), 7.55 (d, J=8.7 Hz, 1H), 7.49-7.44 (m, 3H), 7.40-7.31 (m, 5H), 7.21-7.16 (m, 3H), 6.88 (m, 1H), 6.27 (s, 2H), 6.14 (m, 1H), 5.23 (s, 2H), 4.48 (m, 2H), 3.11 (m, 2H), 2.60 (s, 3H), 1.80 (m, 2H), 1.53 (m, 2H);

$^{13}$C NMR (125 MHz, DMSO-$d_6$) δ 155.6, 153.3, 150.6, 150.2, 140.9, 139.6, 137.6, 132.4, 128.9, 128.8, 128.1, 127.9, 127.9, 127.1, 121.3, 118.0, 117.4, 115.0, 102.7, 69.9, 45.2, 39.1, 27.7, 27.5, 13.9;

MS (APCI) m/z 495 (M+H)$^+$;

Anal. Calcd. for $C_{29}H_{30}N_6O_2 \cdot 0.50\,H_2O$: % C, 69.17; % H, 6.21; % N, 16.69. Found: % C, 69.27; % H, 6.16; % N, 16.81.

Example 77

N-{4-[4-Amino-8-(benzyloxy)-2-ethoxymethyl-1H-imidazo[4,5-c]quinolin-1-yl]butyl}-N'-phenylurea The reaction precipitate was isolated by filtration and dried overnight in a vacuum oven at 60° C. to provide N-{4-[4-amino-8-(benzyloxy)-2-ethoxymethyl-1H-imidazo[4,5-c]quinolin-1-yl]butyl}-N-phenylurea as an off-white powder, m.p. 186.1-188.5° C.

$^1$H NMR (300 MHz, DMSO-$d_6$) δ 8.39 (s, 1H), 7.58 (d, J=9.4 Hz, 1H), 7.47 (m, 3H), 7.35 (m, 5H), 7.18 (m, 3H), 6.87 (m, 1H), 6.38 (s, 2H), 6.16 (m, 1H), 5.24 (s, 2H), 4.77 (s, 2H), 4.55 (t, J=7.5 Hz, 2H), 3.55 (q, J=6.9 Hz, 2H), 3.13 (m, 2H), 1.86 (m, 2H), 1.58 (m, 2H), 1.15 (t, J=6.9 Hz, 3H);

$^{13}$C NMR (75 MHz, DMSO-$d_6$) δ 155.5, 153.3, 151.0, 149.3, 140.9, 140.5, 137.6, 133.0, 128.9, 128.8, 128.1, 128.0, 127.9, 127.0, 121.2, 117.9, 114.9, 102.9, 69.9, 65.7, 64.6, 45.5, 39.2, 28.1, 27.6, 15.3;

MS (APCI) m/z 539 (M+H)$^+$;

Anal. Calcd. for $C_{31}H_{34}N_6O_3 \cdot 0.20\,H_2O$: % C, 68.67; % H, 6.40; % N, 15.50. Found: % C, 68.53; % H, 6.25; % N, 15.30.

Examples 78-89

Under a nitrogen atmosphere, a 0.50-0.1 M solution of the starting material indicated in the table below (1-2 g, 1 equivalent) and triethylamine (1.1 equivalents) in anhydrous dichloromethane was cooled to 0° C. The reagent indicated in the table below (1 equivalent) was added dropwise over a period of five to ten minutes. The reaction was stirred for 15 minutes at 0° C. and then allowed to warm to ambient temperature and stirred for two hours or overnight. The reaction was washed with water (100 mL) and brine (2×100 mL), dried over sodium sulfate, filtered, and concentrated under reduced pressure. The purification and characterization of each compound is given below the table.

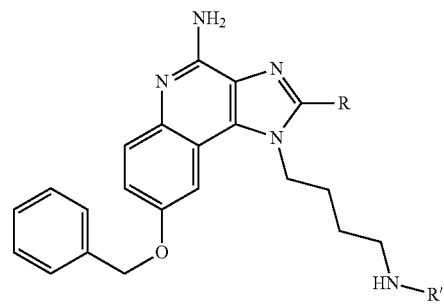

| Example | Starting Material | R | Reagent | R' |
|---|---|---|---|---|
| 78 | Example 70 | —CH$_2$CH$_2$CH$_2$CH$_3$ | Methanesulfonyl chloride | —S(=O)(=O)—CH$_3$ |
| 79 | Example 70 | —CH$_2$CH$_2$CH$_2$CH$_3$ | Benzoyl chloride | —C(=O)—C$_6$H$_5$ |
| 80 | Example 70 | —CH$_2$CH$_2$CH$_2$CH$_3$ | Benzenesulfonyl chloride | —S(=O)(=O)—C$_6$H$_5$ |
| 81 | Example 70 | —CH$_2$CH$_2$CH$_2$CH$_3$ | 4-Morpholinecarbonyl chloride | —C(=O)—N(morpholine) |

-continued

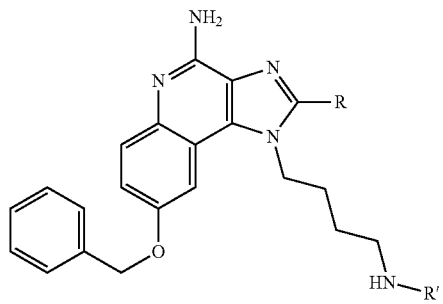

| Example | Starting Material | R | Reagent | R' |
|---|---|---|---|---|
| 82 | Example 71 | —CH₂CH₃ | Benzoyl chloride | phenyl ketone |
| 83 | Example 72 | —CH₃ | 4-Morpholinecarbonyl chloride | morpholine carbonyl |
| 84 | Example 73 | —CH₂OCH₂CH₃ | 4-Morpholinecarbonyl chloride | morpholine carbonyl |
| 85 | Example 72 | —CH₃ | Benzoyl chloride | phenyl ketone |
| 86 | Example 73 | —CH₂OCH₂CH₃ | Methanesulfonyl chloride | —S(O)₂CH₃ |
| 87 | Example 71 | —CH₂CH₃ | 4-Morpholinecarbonyl chloride | morpholine carbonyl |
| 88 | Example 72 | —CH₃ | Methanesulfonyl chloride | —S(O)₂CH₃ |
| 89 | Example 71 | —CH₂CH₃ | Methanesulfonic anhydride | —S(O)₂CH₃ |

Example 78

N-{4-[4-Amino-8-(benzyloxy)-2-butyl-1H-imidazo[4,5-c]quinolin-1-yl]butyl}methanesulfonamide The crude product was recrystallized from ethyl acetate. The crystals were dried overnight in a vacuum oven at 60° C. to provide 1.74 g of N-{4-[4-amino-8-(benzyloxy)-2-butyl-1H-imidazo[4,5-c]quinolin-1-yl]butyl}methanesulfonamide as orange microcrystals, mp 178.5-181.6° C.

$^1$H NMR (300 MHz, DMSO-$d_6$) δ 7.57-7.49 (m, 3H), 7.44-7.34 (m, 4H), 7.17 (dd, J=8.8, 2.4 Hz, 1H), 7.02 (t, J=5.9 Hz, 1H), 6.23 (s, 2H), 5.24 (s, 2H), 4.48 (m, 2H), 2.93 (m, 4H), 2.83 (s, 3H), 1.80 (m, 4H), 1.56 (m, 2H), 1.45 (m, 2H), 0.96 (t, J=7.3, 3H);

$^{13}$C NMR (75 MHz, DMSO-$d_6$) 153.5, 153.2, 150.6, 140.1, 137.7, 132.3, 128.8, 128.1, 127.9, 127.2, 117.2, 115.1, 102.9, 69.9, 44.7, 42.5, 39.3, 30.1, 27.7, 26.9, 26.5, 22.3, 14.2;

MS (APCI) m/z 496 (M+H)$^+$;

Anal. Calcd. for $C_{26}H_{33}N_5O_3S$: % C, 63.01; % H, 6.71; % N, 14.13; % S, 6.47. Found: % C, 62.77; % H, 6.52; % N, 14.07; % S, 6.31.

Example 79

N-{4-[4-Amino-8-(benzyloxy)-2-butyl-1H-imidazo[4,5-c]quinolin-1-yl]butyl}benzamide The crude product was dissolved in a small volume of dichloromethane:methanol, and hexanes were added. The resulting precipitate was isolated by filtration, washed with hexanes, and dried under high vacuum at 70° C. The solid was recrystallized from dichloroethane, isolated by filtration, washed with cold dichloroethane, and dried in a vacuum oven. The crystals were dissolved in a small amount of dichloromethane and methanol and concentrated under reduced pressure to provide 1.56 g of N-{4-[4-amino-8-(benzyloxy)-2-butyl-1H-imidazo[4,5-c]quinolin-1-yl]butyl}benzamide as a tan powder, mp 173.3-174.5° C. $^1$H NMR (300 MHz, DMSO-$d_6$) δ 8.48 (m, 1H), 7.76 (m, 2H), 7.57-7.32 (m, 10H), 7.17 (m, 1H), 6.24 (s, 2H), 5.22 (s, 2H), 4.50 (m, 2H), 3.29 (m, 2H), 2.90 (t, J=7.8 Hz, 2H), 1.77 (m, 4H), 1.62 (m, 2H), 1.39 (m, 2H), 0.90 (t, J=7.3 Hz, 3H);

$^{13}$C NMR (75 MHz, DMSO-$d_6$) δ 166.6, 153.5, 153.2, 150.6, 140.0, 137.6, 134.9, 132.3, 131.3, 128.8, 128.5, 128.1, 128.0, 127.9, 127.4, 127.2, 117.3, 115.1, 102.8, 69.9, 44.8, 30.1, 28.0, 26.7, 26.5, 22.3, 14.1;

MS (APCI) m/z 522 (M+H)$^+$;

Anal. Calcd. for $C_{32}H_{35}N_5O_2$: % C, 73.68; % H, 6.76; % N, 13.42. Found: % C, 73.39; % H, 6.68; % N, 13.41.

Example 80

N-{4-[4-Amino-8-(benzyloxy)-2-butyl-1H-imidazo[4,5-c]quinolin-1-yl]butyl}benzenesulfonamide At the completion of the reaction, a precipitate was present, and was isolated by filtration. No aqueous work-up was carried out. The solid was recrystallized from dichloroethane, isolated by filtration, washed with cold dichloroethane, and dried in a vacuum oven at 80° C. to provide 1.88 g of N-{4-[4-amino-8-(benzyloxy)-2-butyl-1H-imidazo[4,5-c]quinolin-1-yl]butyl}benzenesulfonamide as tan powder, m.p. 203.9-205.1° C.

$^1$H NMR (300 MHz, DMSO-$d_6$) δ 7.73 (m, 2H), 7.56-7.46 (m, 7H), 7.34 (m, 3H), 7.30 (m, 1H), 7.16 (dd, J=9.3, 2.4 Hz, 1H), 6.21 (s, 2H), 5.23 (s, 2H), 4.41 (m, 2H), 2.85 (m, 2H), 2.73 (m, 2H), 1.76 (m, 4H), 1.45 (m, 4H), 0.95 (t, J=7.3 Hz, 3H);

$^{13}$C NMR (125 MHz, DMSO-$d_6$) δ 153.5, 153.2, 150.6, 140.9, 140.1, 137.7, 132.6, 132.3, 129.5, 128.8, 128.1, 128.0, 127.8, 127.2, 126.7, 117.3, 115.1, 102.9, 69.9, 44.6, 42.6, 30.0, 27.4, 26.6, 26.5, 22.3, 14.2;

MS (APCI) m/z 558 (M+H)$^+$;

Anal. Calcd. for $C_{31}H_{35}N_5O_3S$: % C, 66.76; % H, 6.33; % N, 12.56; % S, 5.75. Found: % C, 66.47; % H, 5.92; % N, 12.37; % S, 5.53.

Example 81

N-{4-[4-Amino-8-(benzyloxy)-2-butyl-1H-imidazo[4,5-c]quinolin-1-yl]butyl}morpholine-4-carboxamide At the completion of the reaction, a precipitate was present and was isolated by filtration. The filtrate was subjected to the aqueous work-up conditions, and the resulting solid was recrystallized from dichloroethane, isolated by filtration, and dried under high vacuum. The reaction precipitate was triturated with water overnight, isolated by filtration, washed with water, and dried for two days in a vacuum oven at 80° C. to provide N-{4-[4-amino-8-(benzyloxy)-2-butyl-1H-imidazo[4,5-c]quinolin-1-yl]butyl}morpholine-4-carboxamide as a white powder, mp 177.2-178.6° C.

$^1$H NMR (300 MHz, DMSO-$d_6$) δ 7.58-7.50 (m, 3H), 7.43-7.31 (m, 4H), 7.18 (dd, J=8.8, 2.4 Hz, 1H), 6.51 (m, 1H), 6.25 (s, 2H), 5.23 (s, 2H), 4.47 (m, 2H), 3.44 (m, 4H), 3.15 (m, 4H), 3.05 (m, 2H), 2.90 (m, 2H), 1.77 (m, 4H), 1.45 (m, 4H), 0.95 (t, J=7.3 Hz, 3H);

$^{13}$C NMR (125 MHz, DMSO-$d_6$) δ 158.0, 153.3, 153.3, 150.6, 139.9, 137.7, 132.3, 128.8, 128.1, 127.9, 127.2, 117.3, 115.1, 102.9, 69.9, 66.2, 44.9, 44.1, 30.1, 27.9, 27.3, 26.5, 22.3, 14.2;

MS (APCI) m/z 531 (M+H)$^+$;

Anal. Calcd. for $C_{30}H_{38}N_6O_3 \cdot 0.65 H_2O$: % C, 66.44; % H, 7.30; % N, 15.50. Found: % C, 66.37; % H, 7.04; % N, 15.60.

Example 82

N-{4-[4-Amino-8-(benzyloxy)-2-ethyl-1H-imidazo[4,5-c]quinolin-1-yl]butyl}benzamide At the completion of the reaction, a precipitate was present and was isolated by filtration. The precipitate was triturated with water, isolated by filtration, and dried under high vacuum oven to provide 1.55 g of N-{4-[4-amino-8-(benzyloxy)-2-ethyl-1H-imidazo[4,5-c]quinolin-1-yl]butyl}benzamide as a white powder, mp 226-230° C.

$^1$H NMR (300 MHz, DMSO-$d_6$) δ 8.49 (t, J=5.4 Hz, 1H), 7.78 (d, J=6.8 Hz, 2H), 7.57 (d, J=838 Hz, 1H), 7.50-7.32 (m, 9H), 7.17 (m, 1H), 6.28 (s, 2H), 5.22 (s, 2H), 4.49 (t, J=6.8 Hz, 2H), 3.30 (m, 2H), 2.93 (m, 2H), 1.84 (m, 2H), 1.63 (m, 2H), 1.35 (t, J=7.3 Hz, 3H);

$^{13}$C NMR (125 MHz, DMSO-$d_6$) δ 166.2, 154.0, 152.8, 150.2, 139.6, 137.2, 134.5, 132.0, 130.7, 128.3, 128.1, 127.6, 127.5, 127.4, 127.0, 126.7, 116.8, 114.6, 102.4, 69.5, 44.3, 38.6, 27.5, 26.2, 20.0, 12.0;

MS (APCI) m/z 494 (M+H)$^+$;

Anal. Calcd. for $C_{30}H_{31}N_5O_2$: % C, 73.00; % H, 6.33; % N, 14.19. Found: % C, 72.61; % H, 6.40; % N, 14.10.

Example 83

N-{4-[4-Amino-8-(benzyloxy)-2-methyl-1H-imidazo[4,5-c]quinolin-1-yl]butyl}morpholine-4-carboxamide The crude product was recrystallized from dichloroethane, and the crystals were isolated by filtration, washed with cold dichloroethane, and dried in a vacuum oven at 70° C. The mother liquor was concentrated under reduced pressure, and the residue was purified by column chromatography on silica gel (200 mL, eluting with 90:10 dichloromethane:methanol). The solid recovered from the column chromatography was dried for two days in a vacuum oven at 60° C. to provide N-{4-[4-amino-8-(benzyloxy)-2-methyl-1H-imidazo[4,5-c]quinolin-1-yl]butyl}morpholine-4-carboxamide as a white powder, mp 177.8-179.5° C.
$^1$H NMR (300 MHz, DMSO-$d_6$) δ 7.58-7.50 (m, 3H), 7.44-7.34 (m, 4H), 7.18 (dd, J=8.7-2.5, 1H), 6.52 (m, 1H), 6.35 (s, 2H), 5.24 (s, 2H), 4.45 (m, 2H), 3.44 (m, 4H), 3.15 (m, 4H), 3.05 (m, 2H), 2.59 (s, 3H), 1.77 (m, 2H), 1.48 (m, 2H);
$^{13}$C NMR (125 MHz, DMSO-$d_6$) δ 157.9, 153.3, 150.5, 150.2, 139.7, 137.7, 132.5, 128.8, 128.1, 127.9, 127.7, 127.0, 117.3, 115.0, 102.8, 69.9, 66.2, 45.2, 44.1, 27.6, 27.3, 13.9;
MS (APCI) m/z 489 (M+H)$^+$;
Anal. Calcd. for $C_{22}H_{32}N_6O_3 \cdot 0.15 H_2O$: % C, 66.01; % H, 6.63; % N, 17.11. Found: % C, 65.88; % H, 6.80; % N, 17.26.

Example 84

N-{4-[4-Amino-8-(benzyloxy)-2-ethoxymethyl-1H-imidazo[4,5-c]quinolin-1-yl]butyl}morpholine-4-carboxamide The crude product was purified by column chromatography on silica gel, and the resulting solid was dried in a vacuum oven at 60° C. to provide 1.21 g of N-{4-[4-amino-8-(benzyloxy)-2-ethoxymethyl-1H-imidazo[4,5-c]quinolin-1-yl]butyl}morpholine-4-carboxamide as a yellow powder, mp 150.4-152.8° C.
$^1$H NMR (300 MHz, DMSO-$d_6$) δ 7.59-7.50 (m, 3H), 7.45-7.34 (m, 4H), 7.21 (dd, J=9.4, 2.5 Hz, 1H), 6.52 (m, 1H), 6.42 (s, 2H), 5.24 (s, 2H), 4.77 (s, 2H), 4.53 (m, 2H), 3.55 (q, J=6.9 Hz, 2H), 3.44 (m, 4H), 3.15 (m, 4H), 3.07 (m, 2H), 1.82 (m, 2H), 1.54 (m, 2H), 1.16 (t, J=6.9 Hz, 3H);
$^{13}$C NMR (75 MHz, DMSO-$d_6$) δ 157.9, 153.4, 150.9, 149.4, 140.2, 137.6, 133.1, 128.8, 128.1, 127.9, 127.0, 117.9, 114.9, 103.1, 69.9, 66.2, 65.7, 64.6, 45.6, 44.1, 28.1, 27.5, 15.3; MS (APCI) m/z 533 (M+H)$^+$;
Anal. Calcd. for $C_{29}H_{36}N_6O_4$: % C, 65.39; % H, 6.81; % N, 15.78. Found: % C, 65.21; % H, 6.52; % N, 15.49.

Example 85

N-{4-[4-Amino-8-(benzyloxy)-2-methyl-1H-imidazo[4,5-c]quinolin-1-yl]butyl}benzamide The general method described for Examples 78-89 was followed with the exception that chloroform was used as the solvent. The crude product was recrystallized from dichloroethane, isolated by filtration, washed with cold methanol, and dried in a vacuum oven at 60° C. The resulting solid was purified by column chromatography on silica gel (200 mL, eluting sequentially with 93:7 and 90:10 chloroform:methanol) and a second recrystallization from dichloroethane to provide 0.50 g of N-{4-[4-amino-8-(benzyloxy)-2-methyl-1H-imidazo[4,5-c]quinolin-1-yl]butyl}benzamide as a white powder, mp 244.2-245.2° C.
$^1$H NMR (300 MHz, DMSO-$d_6$) δ 8.47 (t, J=5.6 Hz, 1H), 7.76 (m, 2H), 7.56-7.32 (m, 10H), 7.16 (m, 1H), 6.27 (s, 2H), 5.21 (s, 2H), 4.49 (m, 2H), 3.28 (m, 2H), 2.59 (s, 3H), 1.84 (m, 2H), 1.61 (m, 2H);
$^{13}$C NMR (125 MHz, DMSO-$d_6$) δ 166.6, 153.2, 150.6, 150.1, 140.1, 137.7, 135.4, 132.4, 131.3, 128.8, 128.5, 128.1, 128.0, 127.9, 127.4, 127.1, 117.3, 115.0, 102.8, 69.9, 45.1, 39.1, 27.8, 26.7, 13.9;
MS (APCI) m/z 480 (M+H)$^+$;
Anal. Calcd. for $C_{29}H_{29}N_5O_2$: % C, 72.63; % H, 6.10; % N, 14.60. Found: % C, 72.28; % H, 6.15; % N, 14.59.

Example 86

N-{4-[4-Amino-8-(benzyloxy)-2-ethoxymethyl-1H-imidazo[4,5-c]quinolin-1-yl]butyl}methanesulfonamide The general method described for Examples 78-89 was followed with the exception that chloroform was used as the solvent. The crude product was purified by column chromatography on silica gel (120 g, eluting with 92.5:7.5 dichloromethane:methanol) and dried in a vacuum oven at 60° C. to provide N-{4-[4-amino-8-(benzyloxy)-2-ethoxymethyl-1H-imidazo[4,5-c]quinolin-1-yl]butyl}methanesulfonamide as an off-white powder, mp 182.3-184.6° C.
$^1$H NMR (300 MHz, DMSO-$d_6$) δ 7.58-7.34 (m, 7H), 7.21 (dd, J=9.4, 2.5 Hz, 1H), 7.01 (m, 1H), 6.37 (s, 2H), 5.25 (s, 2H), 4.77 (s, 2H), 4.55 (m, 2H), 3.56 (m, 2H), 2.96 (m, 2H), 2.83 (s, 3H), 1.87 (m, 2H), 1.60 (m, 2H), 1.17 (t, J=6.9 Hz, 3H);
$^{13}$C NMR (75 MHz, DMSO-$d_6$) δ 153.3, 15.9, 149.3, 140.4, 137.6, 133.0, 128.8, 128.1, 127.9, 127.1, 117.8, 114.9, 103.2, 69.9, 65.8, 64.6, 45.4, 42.6, 27.9, 27.2, 15.3;
MS (APCI) m/z 498 (M+H)$^+$;
Anal. Calcd. for $C_{25}H_{31}N_5O_4S$: % C, 60.34; % H, 6.28; % N, 14.07. Found: % C, 59.99; % H, 6.19; % N, 13.87.

Example 87

N-{4-[4-Amino-8-(benzyloxy)-2-ethyl-1H-imidazo[4,5-c]quinolin-1-yl]butyl}morpholine-4-carboxamide The crude product was recrystallized from dichloroethane (100 mL), isolated by filtration, washed with cold dichloroethane, and dried in a vacuum oven at 60° C. to provide 1.40 g of N-{4-[4-amino-8-(benzyloxy)-2-ethyl-1H-imidazo[4,5-c]quinolin-1-yl]butyl}morpholine-4-carboxamide as a white powder, mp 190.1-191.3° C.
$^1$H NMR (300 MHz, DMSO-$d_6$) δ 7.57-7.50 (m, 3H), 7.43-7.33 (m, 4H), 7.18 (dd, J=8.8, 2.4 Hz, 1H), 6.51 (t, J=5.4 Hz, 1H), 6.22 (s, 2H), 5.23 (s, 2H), 4.45 (t, J=7.3 Hz, 2H), 3.44 (m, 4H), 3.15 (m, 4H), 3.05 (m, 2H), 2.93 (m, 2H), 1.76 (m, 2H), 1.50 (m, 2H), 1.36 (m, 3H);
$^{13}$C NMR (125 MHz, DMSO-$d_6$) δ 157.5, 154.0, 152.8, 150.2, 139.6, 137.2, 131.2, 128.3, 127.6, 127.5, 127.4, 126.8, 116.8, 114.6, 102.4, 69.5, 65.8, 44.4, 43.7, 27.4, 26.9, 19.9, 12.1;
MS (APCI) m/z 503 (M+H)$^+$;
Anal. Calcd. for $C_{28}H_{34}N_6O_3$: % C, 66.91; % H, 6.82; % N, 16.72. Found: % C, 66.64; % H, 6.70; % N, 16.60.

Example 88

N-{4-[4-Amino-8-(benzyloxy)-2-methyl-1H-imidazo[4,5-c]quinolin-1-yl]butyl}methanesulfonamide The general method described for Examples 78-89 was followed with the exception that chloroform was used as the solvent. At the completion of the reaction, a precipitate was present and was isolated by filtration. The resulting solid was triturated with water and isolated by filtration to provide a hydrochloride salt. The salt was mixed with ammonium hydroxide, and the resulting mixture was extracted with chloroform (5×). The combined extracts were dried over sodium sulfate, filtered, and concentrated to provide 0.57 g of an off-white solid. The solid was recrystallized from methanol, isolated by filtration, washed with diethyl ether, and dried for two days in a vacuum oven at 60° C. to provide N-{4-[4-amino-8-(benzyloxy)-2-methyl-1H-imidazo[4,5-c]quinolin-1-yl]butyl}methanesulfonamide as an off-white powder.

$^1$H NMR (300 MHz, DMSO-$d_6$) δ 7.56-7.49 (m, 3H), 7.44-7.34 (m, 4H), 7.17 (m, 1H), 7.01 (t, J=5.6 Hz, 1H), 6.25 (s, 2H), 5.25 (s, 2H), 4.46 (m, 2H), 2.95 (m, 2H), 2.83 (s, 3H), 2.59 (s, 3H), 1.80 (m, 2H), 1.55 (m, 2H);

$^{13}$C NMR (125 MHz, DMSO-$d_6$) δ153.2, 150.6, 150.1, 140.1, 137.7, 132.4, 128.8, 128.1, 128.0, 127.9, 127.1, 117.2, 115.9, 102.9, 70.0, 45.0, 42.5, 39.5, 27.5, 27.0, 13.9;

MS (APCI) m/z 454 (M+H)$^+$;

Anal. Calcd for $C_{23}H_{22}N_5O_3S \cdot 0.70$ H$_2$O: C, 59.26; H, 6.14; N, 15.02; S, 6.88. Found: C, 59.25; H, 6.19; N, 15.08; S, 7.00.

Example 89

N-{4-[4-Amino-8-(benzyloxy)-2-ethyl-1H-imidazo[4,5-c]quinolin-1-yl]butyl} methanesulfonamide The general method described for Examples 78-89 was followed with the exception that acetonitrile was used as the solvent. Heating was required to dissolve the starting material, and the triethylamine and methanesulfonic anhydride were added when the solution was warm. The crude product was purified by column chromatography on silica gel (130 g, eluting with 92.5:7.5 dichloromethane:methanol) to provide 1.4 g of a white powder. The powder was recrystallized from dichloroethane, isolated by filtration, washed with hexanes, and dried in a vacuum oven to provide 1.05 g of N-{4-[4-amino-8-(benzyloxy)-2-ethyl-1H-imidazo[4,5-c]quinolin-1-yl]butyl}methanesulfonamide as a yellow powder, mp 186-191° C. $^1$H NMR (300 MHz, DMSO-$d_6$) δ 7.58-7.50 (m, 3H), 7.44-7.34 (m, 4H), 7.18 (m, 1H), 7.02 (m, 1H), 6.29 (s, 2H), 5.25 (s, 2H), 4.47 (m, 2H), 2.94 (m, 4H), 2.83 (s, 3H), 1.81 (m, 2H), 1.56 (m, 2H), 1.37 (t, J=7.3 Hz, 3H);

$^{13}$C NMR (75 MHz, DMSO-$d_6$) δ 154.4, 153.2, 150.6, 140.0, 137.7, 132.4, 128.8, 128.1, 127.9, 127.2, 117.2, 115.1, 102.9, 69.9, 44.6, 42.5, 39.5, 27.7, 27.0, 20.3, 12.4;

MS (APCI) m/z 468 (M+H)$^+$;

Anal. Calcd. for $C_{24}H_{29}N_5O_3S \cdot 0.50$ H$_2$O: % C, 60.48; % H, 6.35; % N, 14.70; % S, 6.73. Found: % C, 60.37; % H, 6.41; % N, 14.63; % S, 6.51.

Example 90

4-Amino-2-ethyl-1-methyl-1H-imidazo[4,5-c]quinolin-8-ol

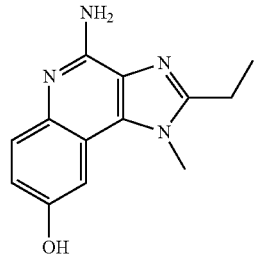

The general method described in Example 5 was followed using 8-benzyloxy-2-ethyl-1-methyl-1H-imidazo[4,5-c]quinolin-4-amine (0.47 g, 1.4 mmol), prepared as described in Example 57, in lieu of 7-benzyloxy-2-propyl-1-(2-methylpropyl)-1H-imidazo[4,5-c]quinolin-4-amine. The hydrogenation was complete in four hours, and after the catalyst was removed by filtration, the filtrate was concentrated under reduced pressure to a small volume. Hexanes were added, and a precipitate formed, which was isolated by filtration and washed with hexanes. The solid was recrystallized from methanol to provide 70 mg of 4-amino-2-ethyl-1-methyl-1H-imidazo[4,5-c]quinolin-8-ol as a white, crystalline solid, mp>240° C.

$^1$H NMR (300 MHz, DMSO-$d_6$) δ 9.23 (s, 1H), 7.52 (d, J=2.6 Hz, 1H), 7.47 (d, J=8.9 Hz, 1H), 6.96 (dd, J=8.9, 2.6 Hz, 1H), 6.03 (s, 2H), 4.06 (s, 3H), 2.92 (q, J=7.5 Hz, 2H), 1.33 (t, J=7.5 Hz, 3H);

MS (EI) m/z 242.1172 (242.1168 calcd for $C_{13}H_{14}N_4O$);

Anal. Calcd. for $C_{13}H_{14}N_4O$: % C, 64.45; % H, 5.82; % N, 23.12. Found: % C, 63.97; % H, 5.81; % N, 23.14.

Examples 91-103

A 0.01-0.03 M solution of the starting material indicated in the table below (~1 g) in ethanol was added to a Parr vessel charged with 10% palladium on carbon (0.3-0.7 g), and the reaction was placed under hydrogen pressure (50 psi, 3.4×10$^5$ Pa) for between four and 24 hours. The reaction mixture was filtered through a layer of CELITE filter aid, and the filter cake was washed with ethanol. The filtrate was concentrated under reduced pressure. The purification and characterization for each compound is given below the table.

| Example | Starting Material | R | R' |
|---|---|---|---|
| 91 | Example 75 | —CH$_2$CH$_3$ | phenyl-NH-C(=O)-CH$_2$- |
| 92 | Example 76 | —CH$_3$ | phenyl-NH-C(=O)-CH$_2$- |
| 93 | Example 77 | —CH$_2$OCH$_2$CH$_3$ | phenyl-NH-C(=O)-CH$_2$- |
| 94 | Example 78 | —CH$_2$CH$_2$CH$_2$CH$_3$ | —S(=O)$_2$—CH$_3$ |

-continued

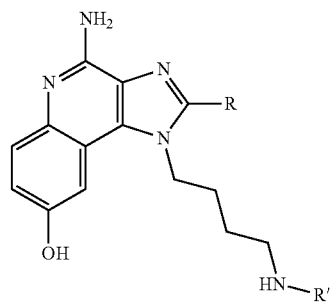

| Example | Starting Material | R | R' |
|---|---|---|---|
| 95 | Example 79 | —CH$_2$CH$_2$CH$_2$CH$_3$ | 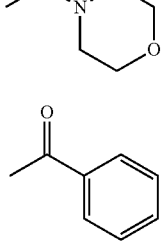 |
| 96 | Example 80 | —CH$_2$CH$_2$CH$_2$CH$_3$ | |
| 97 | Example 81 | —CH$_2$CH$_2$CH$_2$CH$_3$ | 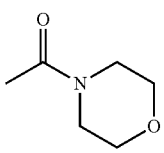 |
| 98 | Example 82 | —CH$_2$CH$_3$ | |
| 99 | Example 83 | —CH$_3$ | 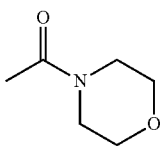 |
| 100 | Example 84 | —CH$_2$OCH$_2$CH$_3$ | 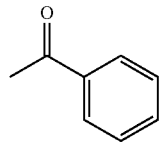 |
| 101 | Example 85 | —CH$_3$ | |
| 102 | Example 87 | —CH$_2$CH$_3$ | 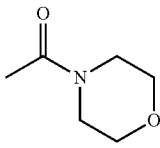 |

-continued

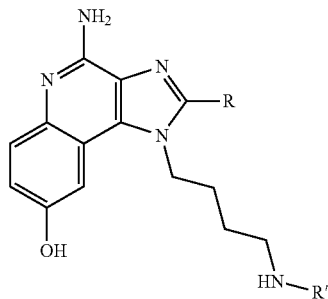

| Example | Starting Material | R | R' |
|---|---|---|---|
| 103 | Example 89 | —CH$_2$CH$_3$ | |

Example 91

N-[4-(4-Amino-2-ethyl-8-hydroxy-1H-imidazo[4,5-c]quinolin-1-yl)butyl]-N'-phenylurea

The crude product, obtained as the hydrochloride salt, was stirred with aqueous ammonium hydroxide (pH 11) for two hours, isolated by filtration, and washed with water. The solid was then recrystallized from methanol, and the crystals were isolated by filtration, washed with cold methanol, and dried in a vacuum oven at 60° C. to provide 0.44 g of N-[4-(4-amino-2-ethyl-8-hydroxy-1H-imidazo[4,5-c]quinolin-1-yl)butyl]-N'-phenylurea as a brown solid.

$^1$H NMR (300 MHz, DMSO-d$_6$) δ 9.35 (s, 1H), 8.40 (s, 1H), 7.47 (d, J=8.7 Hz, 1H), 7.37 (m, 3H), 7.20 (m, 2H), 6.96 (dd, J=8.7, 2.5 Hz, 1H), 6.87 (t, J=7.5 Hz, 1H), 6.16 (t, 5.6 Hz, 1H), 6.08 (s, 2H), 4.45 (m, 2H), 3.16 (m, 2H), 2.93 (q, J=7.5 Hz, 2H), 1.83 (m, 2H), 1.61 (m, 2H), 1.35 (m, 3H);

$^{13}$C NMR (125 MHz, DMSO-d$_6$) δ 157.5, 156.0, 154.1, 151.9, 142.8, 140.9, 134.2, 130.9, 129.8, 129.0, 123.2, 119.9, 119.0, 117.5, 105.5, 46.7, 40.8, 29.8, 29.2, 22.2, 14.3;

MS (APCI) m/z 419 (M+H)$^+$;

Anal. Calcd. for C$_{23}$H$_{26}$N$_6$O$_2$·0.25 H$_2$O: % C, 65.31; % H, 6.32; % N, 19.87. Found: % C, 65.35; % H, 6.21; % N, 19.74.

Example 92

N-[4-(4-Amino-8-hydroxy-2-methyl-1H-imidazo[4,5-c]quinolin-1-yl)butyl]-N'-phenylurea

The crude product was purified by column chromatography on silica gel (eluting with 89:10:1 dichloromethane:methanol:ammonium hydroxide) to provide 0.270 g of N-[4-(4-amino-8-hydroxy-2-methyl-1H-imidazo[4,5-c]quinolin-1-yl)butyl]-N'-phenylurea as a peach-colored solid.

$^1$H NMR (300 MHz, DMSO-d$_6$) δ 9.32 (s, 1H), 8.38 (s, 1H), 7.46 (d, J=8.7 Hz, 1H), 7.35 (m, 3H), 7.20 (m, 2H), 6.96 (dd, J=8.7, 2.5 Hz, 1H), 6.87 (m, 1H), 6.16 (t, J=5.6 Hz, 1H), 6.10 (s, 2H), 4.45 (m, 2H), 3.15 (m, 2H), 2.59 (s, 3H), 1.85 (m, 2H), 1.59 (m, 2H);

$^{13}$C NMR (125 MHz, DMSO-d$_6$) δ 155.1, 151.8, 149.5, 149.3, 140.4, 138.4, 131.8, 128.5, 127.3, 126.5, 120.9, 117.5, 116.6, 115.0, 103.0, 44.7, 38.6, 27.3, 26.9, 13.4;

MS (APCI) m/z 405 (M+H)$^+$;

Anal. Calcd. for $C_{22}H_{24}N_6O_2 \cdot 0.25\,H_2O$: % C, 64.61; % H, 6.04; % N, 20.55. Found: % C, 64.27; % H, 6.07; % N, 20.21.

Example 93

N-[4-(4-Amino-2-ethoxymethyl-8-hydroxy-1H-imidazo[4,5-c]quinolin-1-yl)butyl]-N'-phenylurea

The crude product was recrystallized from methanol; the crystals were isolated by filtration and dried for two days in a vacuum oven at 60° C. to provide 0.72 g of N-[4-(4-amino-2-ethoxymethyl-8-hydroxy-1H-imidazo[4,5-c]quinolin-1-yl)butyl]-N'-phenylurea as a fine, pinkish-white powder, mp 218.4-220.8° C.

$^1$H NMR (300 MHz, DMSO-$d_6$) δ 9.38 (s, 1H), 8.38 (s, 1H), 7.48 (d, J=8.7 Hz, 1H), 7.36 (m, 3H), 7.20 (m, 2H), 6.99 (dd, J=8.7, 2.5 Hz, 1H), 6.87 (m, 1H), 6.21 (s, 2H), 6.16 (t, J=5.6 Hz, 1H), 4.76 (s, 2H), 4.51 (m, 2H), 3.54 (q, J=6.9 Hz, 2H), 3.16 (m, 2H), 1.89 (m, 2H), 1.64 (m, 2H), 1.14 (t, J=6.9 Hz, 3H);

$^{13}$C NMR (75 MHz, DMSO-$d_6$) δ 155.6, 152.3, 150.3, 149.0, 140.9, 139.4, 132.9, 128.9, 127.9, 127.0, 121.3, 118.0, 117.6, 115.4, 103.9, 65.8, 64.6, 45.6, 39.1, 28.1, 27.4, 15.3;

MS (APCI) m/z 449 (M+H)$^+$;

Anal. Calcd. for $C_{24}H_{28}N_6O_3 \cdot 0.25\,H_2O$: % C, 63.63; % H, 6.34; % N, 18.55. Found: % C, 63.57; % H, 6.42; % N, 18.63.

Example 94

N-[4-(4-Amino-2-butyl-8-hydroxy-1H-imidazo[4,5-c]quinolin-1-yl)butyl]methanesulfonamide

The crude product was recrystallized from ethanol; the crystals were isolated by filtration, washed with cold ethanol, and dried under high vacuum to provide 0.74 g of N-[4-(4-amino-2-butyl-8-hydroxy-1H-imidazo[4,5-c]quinolin-1-yl)butyl]methanesulfonamide as a tan powder, mp 223-227° C.

$^1$H NMR (300 MHz, DMSO-$d_6$) δ 9.33 (s, 1H), 7.46 (d, J=8.8 Hz, 1H), 7.33 (d, J=2.9 Hz, 1H), 7.01 (t, J=5.9 Hz, 1H), 6.96 (dd, J=8.8, 2.4 Hz, 1H), 6.08 (s, 2H), 4.43 (t, J=7.3 Hz, 2H), 2.99 (m, 2H), 2.90 (m, 2H), 2.87 (s, 3H), 1.81 (m, 4H), 1.62 (m, 2H), 1.44 (m, 2H), 0.96 (t, J=7.3 Hz, 3H);

$^{13}$C NMR (75 MHz, DMSO-$d_6$) δ 153.2, 152.2, 150.0, 138.9, 132.1, 127.8, 127.2, 117.0, 115.5, 103.5, 44.7, 42.5, 30.1, 27.8, 26.7, 26.5, 22.3, 14.2;

MS (APCI) m/z 406 (M+H)$^+$;

Anal. Calcd. for $C_{19}H_{27}N_5O_3S$: % C, 56.28; % H, 6.71; % N, 17.27; % S, 7.91. Found: % C, 56.00; % H, 6.61; % N, 17.18; % S, 7.73.

Example 95

N-[4-(4-Amino-2-butyl-8-hydroxy-1H-imidazo[4,5-c]quinolin-1-yl)butyl]benzamide

The crude product was recrystallized from ethanol; the crystals were isolated by filtration, washed with cold ethanol, and dried in a vacuum oven at 60° C. to provide 0.54 g of N-[4-(4-amino-2-butyl-8-hydroxy-1H-imidazo[4,5-c]quinolin-1-yl)butyl]benzamide as a white powder, mp 188.2-189.5° C.

$^1$H NMR (300 MHz, DMSO-$d_6$) δ 9.36 (s, 1H), 8.49 (m, 1H), 7.80 (m, 2H), 7.51-7.41 (m, 4H), 7.36 (d, J=2.4 Hz, 1H), 6.97 (dd, J=8.8, 2.4, 1H), 6.11 (s, 2H), 4.46 (t, J=7.3 Hz, 2H), 3.33 (m, 2H), 2.89 (m, 2H), 1.87 (m, 2H), 1.73 (m, 4H), 1.39 (m, 2H), 0.90 (t, J=7.3 Hz, 3H);

$^{13}$C NMR (75 MHz, DMSO-$d_6$) δ 166.7, 153.2, 152.2, 149.9, 138.9, 134.9, 132.1, 131.4, 128.6, 127.8, 127.4, 127.2, 117.0, 115.5, 103.5, 44.9, 39.0, 30.1, 28.0, 26.5, 22.3, 14.1;

MS (APCI) m/z 432 (M+H)$^+$;

Anal. Calcd. for $C_{25}H_{29}N_5O_2 \cdot 1.15\,H_2O$: % C, 66.40; % H, 6.98; % N, 15.49. Found: % C, 66.16; % H, 6.72; % N, 15.54.

Example 96

N-[4-(4-Amino-2-butyl-8-hydroxy-1H-imidazo[4,5-c]quinolin-1-yl)butyl]benzenesulfonamide

The crude product was recrystallized from methanol (31 mL/g); the crystals were isolated by filtration, washed with cold methanol, and dried for two days in a vacuum oven at 80° C. to provide 0.25 g of N-[4-(4-amino-2-butyl-8-hydroxy-1H-imidazo[4,5-c]quinolin-1-yl)butyl]benzenesulfonamide as a fine white powder, mp 219-223° C.

$^1$H NMR (300 MHz, DMSO-$d_6$) δ 9.33 (s, 1H), 7.76 (m, 2H), 7.66-7.52 (m, 4H), 7.47 (d, J=9.3 Hz, 1H), 7.29 (d, J=2.4 Hz, 1H), 6.96 (dd, J=8.8, 2.4 Hz, 1H), 6.10 (s, 2H), 4.37 (m, 2H), 2.87-2.78 (m, 4H), 1.77 (m, 4H), 1.55-1.40 (m, 4H), 0.95 (t, J=7.3 Hz, 3H);

$^{13}$C NMR (125 MHz, DMSO-$d_6$) δ 153.2, 152.2, 149.9, 140.8, 138.8, 132.7, 132.1, 129.5, 127.7, 127.1, 126.7, 117.1, 115.5, 103.6, 44.7, 42.6, 30.0, 27.7, 26.5, 26.4, 22.3, 14.2;

MS (APCI) m/z 468 (M+H)$^+$;

Anal. Calcd. for $C_{24}H_{29}N_5O_3S \cdot 0.23\,H_2O$: % C, 61.11; % H, 6.30; % N, 14.85; % S, 6.80. Found: % C, 61.16; % H, 6.32; % N, 14.89; % S, 6.85.

Example 97

N-[4-(4-Amino-2-butyl-8-hydroxy-1H-imidazo[4,5-c]quinolin-1-yl)butyl]morpholine-4-carboxamide

The crude product was recrystallized from methanol (29 mL/g); the crystals were isolated by filtration, washed with cold methanol, and dried for several days in a vacuum oven to provide 0.21 g of N-[4-(4-amino-2-butyl-8-hydroxy-1H-imidazo[4,5-c]quinolin-1-yl)butyl]morpholine-4-carboxamide as a white solid, mp 177-182° C.

$^1$H NMR (300 MHz, DMSO-$d_6$) δ 9.33 (s, 1H), 7.46 (d, J=8.8 Hz, 1H), 7.32 (d, J=2.4 Hz, 1H), 6.96 (dd, J=9.3, 2.9 Hz, 1H), 6.53 (t, J=5.4 Hz, 1H), 6.08 (s, 2H), 4.42 (t, J=7.3 Hz, 2H), 3.49 (m, 4H), 3.20 (m, 4H), 3.10 (m, 2H), 2.89 (m, 2H), 1.78 (m, 4H), 1.58 (m, 2H), 1.44 (m, 2H), 0.95 (m, 3H);

$^{13}$C NMR (75 MHz, DMSO-$d_6$) δ 158.0, 153.1, 152.2, 150.0, 138.9, 132.1, 127.8, 127.2, 117.0, 115.6, 103.5, 66.3, 44.9, 44.1, 30.1, 27.9, 27.2, 26.5, 22.3, 14.2;

MS (APCI) m/z 441 (M+H)$^+$;

Anal. Calcd. for $C_{23}H_{32}N_6O_3$: % C, 62.71; % H, 7.32; % N, 19.08. Found: % C, 62.36; % H, 7.40; % N, 18.96.

Example 98

N-[4-(4-Amino-2-ethyl-8-hydroxy-1H-imidazo[4,5-c]quinolin-1-yl)butyl]benzamide

The crude product was recrystallized from chloroform and dried for several days in a vacuum oven at 70° C. The solid was triturated with diethyl ether and then dissolved in a mixture of dichloromethane and methanol. The solvents were removed under reduced pressure, and the resulting powder was dried for several days in a vacuum oven at 70° C. to provide N-[4-(4-amino-2-ethyl-8-hydroxy-1H-imidazo[4,5-c]quinolin-1-yl)butyl]benzamide as an off-white powder.

¹H NMR (300 MHz, DMSO-d₆) δ 9.39 (m, 1H), 8.50 (m, 1H), 7.81 (m, 2H), 7.50-7.44 (m, 4H), 7.37 (d, J=2.5 Hz, 1H), 6.98 (dd, J=8.7, 2.5 Hz, 1H), 6.16 (s, 2H), 4.46 (m, 2H), 3.34 (q, J=6.2 Hz, 2H), 2.92 (m, 2H), 1.88 (m, 2H), 1.71 (m, 2H), 1.34 (t, J=7.5 Hz, 3H);

¹³C NMR (75 MHz, DMSO-d₆) δ 166.7, 154.2, 152.3, 150.0, 138.8, 135.0, 132.3, 131.4, 128.6, 127.7, 127.5, 127.1, 117.1, 115.5, 103.6, 44.8, 27.9, 26.6, 20.3, 12.4;

MS (APCI) m/z 404 (M+H)⁺;

Anal. Calcd. for $C_{23}H_{25}N_5O_2 \cdot 0.50 H_2O$: % C, 66.97; % H, 6.35; % N, 16.98. Found: % C, 66.80; % H, 6.16; % N, 16.79.

Example 99

N-[4-(4-Amino-8-hydroxy-2-methyl-1H-imidazo[4,5-c]quinolin-1-yl)butyl]morpholine-4-carboxamide The crude product was purified by column chromatography on silica gel (100 mL, eluting with 84:15:1 dichloromethane:methanol:ammonium hydroxide) to provide 0.280 g of N-[4-(4-amino-8-hydroxy-2-methyl-1H-imidazo[4,5-c]quinolin-1-yl)butyl]morpholine-4-carboxamide as an off-white powder.

¹H NMR (300 MHz, DMSO-d₆) δ 9.31 (s, 1H), 7.46 (d, J=8.7 Hz, 1H), 7.32 (d, J=2.5 Hz, 1H), 6.95 (m, 1H), 6.51 (m, 1H), 6.10 (s, 2H), 4.41 (t, J=7.5 Hz, 2H), 3.49 (m, 4H), 3.20 (m, 4H), 3.10 (m, 2H), 2.58 (s, 3H), 1.81 (m, 2H), 1.54 (m, 2H);

¹³C NMR (125 MHz, DMSO-d₆) δ 157.1, 151.3, 149.0, 148.9, 138.0, 131.3, 126.9, 126.1, 116.1, 114.6. 102.5, 65.3, 44.3, 43.3, 26.7, 26.3, 13.0;

MS (APCI) m/z 399 (M+H)⁺;

Anal. Calcd. for $C_{20}H_{26}N_6O_3 \cdot 0.25 H_2O$: % C, 59.61; % H, 6.63; % N, 20.86. Found: % C, 59.54; % H, 6.59; % N, 20.71.

Example 100

N-[4-(4-Amino-2-ethoxymethyl-8-hydroxy-1H-imidazo[4,5-c]quinolin-1-yl)butyl]morpholine-4-carboxamide The crude product was triturated with diethyl ether and dried overnight in a vacuum oven at 60° C. The solid was then mixed with methanol, and the mixture was concentrated under reduced pressure. The solid was then dried for two days in a vacuum oven at 60° C. to provide N-[4-(4-amino-2-ethoxymethyl-8-hydroxy-1H-imidazo[4,5-c]quinolin-1-yl)butyl]morpholine-4-carboxamide as a fine, pinkish-white powder.

¹H NMR (300 MHz, DMSO-d₆) δ 6.40 (s, 1H), 7.48 (d, J=9.4 Hz, 1H), 7.34 (d, J=2.5 Hz, 1H), 6.99 (dd, J=8.7, 2.5 Hz, 1H), 6.53 (m, 1H), 6.26 (s, 2H), 4.76 (s, 2H), 4.48 (m, 2H), 3.56-3.47 (m, 6H), 3.20 (m, 4H), 3.11 (m, 2H), 1.85 (m, 2H), 1.60 (m, 2H), 1.16 (m, 3H);

¹³C NMR (75 MHz, DMSO-d₆) δ 158.0, 152.4, 150.2, 149.1, 139.1, 123.9, 127.7, 126.9, 117.6, 115.4, 103.9, 66.3, 65.7, 64.6, 45.7, 44.1, 28.0, 27.3, 15.3;

MS (APCI) m/z 443 (M+H)⁺;

Anal. Calcd. for $C_{22}H_{30}N_6O_4 \cdot 0.77 H_2O$: % C, 57.90; % H, 6.97; % N, 18.41. Found: % C, 58.29; % H, 6.95; % N, 18.45.

Example 101

N-[4-(4-Amino-8-hydroxy-2-methyl-1H-imidazo[4,5-c]quinolin-1-yl)butyl]benzamide The crude product was recrystallized from methanol (10 mL); the crystals were isolated by filtration and dried in a vacuum oven at 60° C. to provide 0.106 g of N-[4-(4-amino-8-hydroxy-2-methyl-1H-imidazo[4,5-c]quinolin-1-yl)butyl]benzamide as a pink, crystalline solid.

¹H NMR (300 MHz, DMSO-d₆) δ 9.33 (s, 1H), 8.48 (t, J=5.6 Hz, 1H), 7.79 (m, 2H), 7.51-7.41 (m, 4H), 7.35 (d, J=2.5 Hz, 1H), 6.96 (dd, J=9.3, 2.5 Hz, 1H), 6.11 (s, 2H), 4.46 (m, 2H), 2.58 (s, 3H), 1.88 (m, 2H), 1.68 (m, 2H);

¹³C NMR (75 MHz, DMSO-d₆) δ 166.7, 152.2, 149.9, 149.8, 138.9, 135.0, 132.2, 131.4, 128.6, 127.8, 127.5, 127.0, 117.0, 115.5, 103.4, 45.2, 27.7, 26.6, 13.9;

MS (APCI) m/z 390 (M+H)⁺;

Anal. Calcd. for $C_{22}H_{23}N_5O_2 \cdot 0.50 H_2O$: % C, 66.32; % H, 6.07; % N, 17.58. Found: % C, 66.26; % H, 5.88; % N, 17.55.

Example 102

N-[4-(4-Amino-2-ethyl-8-hydroxy-1H-imidazo[4,5-c]quinolin-1-yl)butyl]morpholine-4-carboxamide The crude product was recrystallized from 2-propanol; the crystals were dried for two days in a vacuum oven and then dissolved in a mixture of ethanol, methanol, and dichloromethane. The solvents were removed under reduced pressure, and the resulting solid was triturated with diethyl ether and dried in a vacuum oven to provide N-[4-(4-amino-2-ethyl-8-hydroxy-1H-imidazo[4,5-c]quinolin-1-yl)butyl]morpholine-4-carboxamide as an off-white powder.

¹H NMR (300 MHz, DMSO-d₆) δ 9.34 (s, 1H), 7.47 (d, J=8.7 Hz, 1H), 7.32 (d, J=1.9 Hz, 1H), 6.97 (dd, J=8.7, 2.5 Hz, 1H), 6.53 (m, 1H), 6.10 (s, 2H), 4.42 (t, J=7.5 Hz, 2H), 3.49 (m, 4H), 3.20 (m, 4H), 3.10 (m, 2H), 2.92 (q, J=7.5 Hz, 2H), 1.80 (m, 2H), 1.56 (m, 2H), 1.36 (t, J=7.5 Hz, 3H);

¹³C NMR (75 MHz, DMSO-d₆) δ 158.0, 154.2, 152.3, 149.9, 138.7, 132.3, 127.7, 127.0, 117.1, 115.5, 103.6, 66.2, 44.9, 44.1, 27.8, 27.2, 20.3, 12.5;

MS (APCI) m/z 413 (M+H)⁺;

Anal. Calcd. for $C_{21}H_{28}N_6O_3 \cdot 0.75 H_2O$: % C, 59.21; % H, 6.68; % N, 19.73. Found: % C, 59.09; % H, 6.78; % N, 19.42.

Example 103

N-[4-(4-Amino-2-ethyl-8-hydroxy-1H-imidazo[4,5-c]quinolin-1-yl)butyl]methanesulfonamide The crude product was recrystallized from ethanol in the presence of activated carbon (0.1 g). The crystals were isolated by filtration, washed with cold ethanol, and then dissolved in a mixture of methanol, dichloromethane, and methanol. The solvent was filtered, concentrated under reduced pressure, and dried under high vacuum at 70° C. to provide 0.36 g of N-[4-(4-amino-2-ethyl-8-hydroxy-1H-imidazo[4,5-c]quinolin-1-yl)butyl]methanesulfonamide as a white solid, mp 127.8-130.2° C.

¹H NMR (300 MHz, DMSO-d₆) δ 9.34 (s, 1H), 7.47 (d, J=8.8 Hz, 1H), 7.34 (d, J=2.9 Hz, 1H), 7.03-6.94 (m, 2H), 6.14 (s, 2H), 4.43 (m, 2H), 3.02-2.90 (m, 4H), 2.86 (s, 3H), 1.85 (m, 2H), 1.62 (m, 2H), 1.37 (t, J=7.3 Hz, 3H);

¹³C NMR (75 MHz, DMSO-d₆) δ 154.2, 152.3, 149.9, 138.6, 132.3, 127.6, 127.0, 117.1, 115.5, 103.6, 44.7, 42.5, 27.7, 26.7, 20.3, 12.4;

MS (APCI) m/z 378 (M+H)⁺;

Anal. Calcd. for $C_{17}H_{23}N_5O_3S \cdot 0.50 H_2O$: % C, 52.83; % H, 6.26; % N, 18.12; % S, 8.30. Found: % C, 52.86; % H, 6.30; % N, 18.25; % S, 8.29.

Example 104

2-(Ethoxymethyl)-7-[(2-methylbenzyl)oxy]-1-(2-methylpropyl)-1H-imidazo[4,5-c]quinolin-4-amine

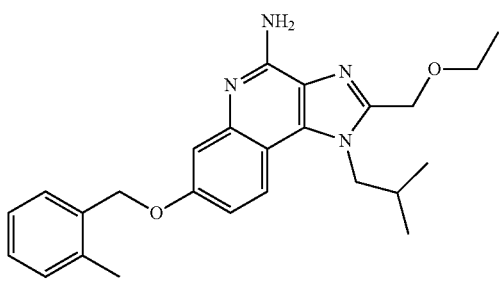

4-Amino-2-ethoxymethyl-1-(2-methylpropyl)-1H-imidazo[4,5-c]quinolin-7-ol (750 mg, 2.39 mmol) was dissolved with heating in DMF (50 mL). Solid cesium carbonate (1.55 g, 4.77 mmol) was added. After 15 minutes, 2-methylbenzyl chloride (487 mg, 2.63 mmol) was added to the mixture. The reaction was stirred overnight at ambient temperature, then was poured onto water (500-750 mL) and a milky white precipitate formed immediately. The mixture was stirred for 1 hour, and then the precipitate was isolated by filtration. The solid was purified by flash chromatography (silica gel, gradient elution with 0.5-2% methanol in chloroform) followed by recrystallization from 2-propanol. The final product was isolated by filtration and dried overnight under vacuum at 60° C. to provide 780 mg of 2-(ethoxymethyl)-7-[(2-methylbenzyl)oxy]-1-(2-methylpropyl)-1H-imidazo[4,5-c]quinolin-4-amine as an off white solid, mp 216.0-218.0° C.

Anal. calcd for $C_{25}H_{30}N_4O_2$: C, 71.74; H, 7.22; N, 13.39. Found: C, 71.70; H, 7.57; N, 13.30.

Example 105

(4-Amino-8-benzyloxy-2-ethoxymethyl-1H-imidazo[4,5-c]quinolin-1-yl)-2-methylpropan-2-ol

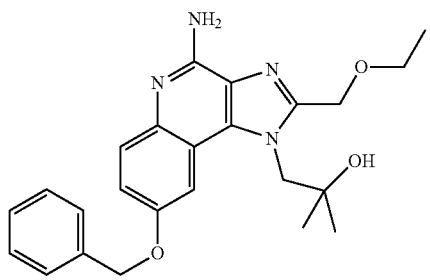

Part A

1-{[3-Amino-6-(benzyloxy)quinolin-4-yl]amino}-2-methylpropan-2-ol was prepared according to the general methods described in Parts A and B of Example 54 using 6-benzyloxy-4-chloro-3-nitroquinoline in lieu of 7-benzyloxy-4-chloro-3-nitroquinoline in Part A. Ethoxyacetyl chloride (5.37 g, 43.8 mmol) was added to a solution of 1-{[3-amino-6-(benzyloxy)quinoline-4-yl]amino}-2-methylpropan-2-ol (7.45 g, 22.1 mmol) in acetonitrile (230 mL), and the reaction was stirred overnight. The solvent was removed under reduced pressure, and the residue was dissolved in dichloromethane. The resulting solution was washed with aqueous sodium bicarbonate, dried over magnesium sulfate, filtered, and concentrated under reduced pressure. The residue was purified by column chromatography on a HORIZON HPFC system (an automated, modular high-performance flash purification product available from Biotage, Inc, Charlottesville, Va., USA) (silica gel cartridge, eluting with dichloromethane:methanol ranging in ratios from 98:2 to 95:5) to provide N-{6-benzyloxy-4-[(2-hydroxy-2-methylpropyl)amino]quinolin-3-yl}-2-ethoxyacetamide hydrochloride.

Part B

The material from Part A was treated with a solution of ammonia in methanol (2 M) in a pressure vessel. The reaction was heated at 160° C. for six hours and then concentrated under reduced pressure to provide (8-benzyloxy-2-ethoxymethyl-1H-imidazo[4,5-c]quinolin-1-yl)-2-methylpropan-2-ol as a white solid, mp 138-140° C.

Part C

Peracetic acid (2.0 mL of 32% by weight in dilute acetic acid, 9.5 mmol) was added to a solution of (8-benzyloxy-2-ethoxymethyl-1H-imidazo[4,5-c]quinolin-1-yl)-2-methylpropan-2-ol (2.5 g, 6.2 mmol) in ethyl acetate (400 mL), and the reaction was stirred for two days at ambient temperature. The volatiles were removed under reduced pressure, and the residue was dissolved in dichloromethane. The resulting solution was washed with aqueous sodium bicarbonate and water, dried over magnesium sulfate, filtered, and concentrated under reduced pressure. The crude product was recrystallized from a mixture of ethyl acetate, hexanes, and 2-propanol and then purified by column chromatography on a HORIZON HPFC system (silica gel cartridge, eluting with dichloromethane:methanol ranging in ratios from 98:2 to 90:10) to provide 1.9 g of (8-benzyloxy-2-ethoxymethyl-5-oxido-1H-imidazo[4,5-c]quinolin-1-yl)-2-methylpropan-2-ol as a solid, mp 228-230° C.

Part D

A modification of the general method described in Part G of Example 54 was used to aminate (8-benzyloxy-2-ethoxymethyl-5-oxido-1H-imidazo[4,5-c]quinolin-1-yl)-2-methylpropan-2-ol (1.45 g, 3.44 mmol). The reaction was stirred for three hours, and after the aqueous work-up the product was recrystallized from 2-propanol to provide (4-amino-8-benzyloxy-2-ethoxymethyl-1H-imidazo[4,5-c]quinolin-1-yl)-2-methylpropan-2-ol as a white, crystalline solid, mp 181-182° C.

Anal. Calcd. for $C_{24}H_{28}N_4O_3$: % C, 68.55; % H, 6.71: % N, 13.32. Found: % C, 68.45; % H, 6.62; % N, 13.46.

Example 106

N-[4-(4-Amino-7-benzyloxy-2-ethyl-1H-imidazo[4,5-c]quinolin-1-yl)butyl]methanesulfonamide

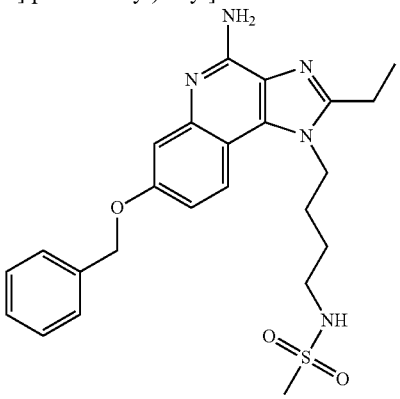

Part A tert-Butyl N-(4-aminobutyl)carbamate (28.6 g, 152.0 mmol) was added dropwise to a solution of 7-benzyloxy-4- chloro-3-nitroquinoline (40.7 g, 138 mmol), prepared in Parts A-D of Example 1, and triethylamine (38.5 mL, 276 mmol) in dichloromethane over a period of 1.5 hours. After the reaction was stirred for 18 hours, the reaction mixture was washed twice with water and once with saturated aqueous sodium chloride. The organic was dried over anhydrous magnesium sulfate, filtered and concentrated under reduced pressure. The crude product was recrystallized from 2-propanol to afford 51.4 g of tert-butyl[4-(7-benzyloxy-3-nitroquinolin-4-ylamino)butyl]carbamate as a golden brown powder.

Part B tert-Butyl[4-(7-benzyloxy-3-nitroquinolin-4-ylamino)butyl]carbamate (20.36 g, 43.6 mmol) was slurried in toluene (450 mL) and added to a Parr vessel charged with 5% platinum on carbon (4.3 g) and a small amount of toluene. 2-Propanol (50 mL) was added, and the vessel was charged with hydrogen (30 psi, $2.1 \times 10^5$ Pa). The hydrogen was replaced three times. After 4 hours, the catalyst was removed by filtration through a layer of CELITE filter aid, and the filter cake was rinsed with toluene (0.5 L), 50% toluene/2-propanol (0.5 L), and 2-propanol (0.25 L). The filtrate was concentrated under reduced pressure, and the residue was mixed with toluene and concentrated under reduced pressure to provide 20.7 g of tert-butyl[4-(3-amino-7-benzyloxyquinolin-4-ylamino)butyl]carbamate as a viscous, black oil.

Part C tert-Butyl[4-(3-amino-7-benzyloxyquinolin-4-ylamino)butyl]carbamate (20.7 g, 43.6 mmol) was dissolved in toluene (225 mL). Pyridine hydrochloride (2.03 g) and trimethyl orthopropionate (6.2 mL, 43.6 mmol) were added, and the mixture was heated at reflux for 3.25 hours. The reaction was allowed to cool to room temperature; a fine precipitate formed. The precipitate was isolated by filtration and washed with toluene. The off-white solid was allowed to dry for 2 hours under vacuum. The filtrate was evaporated, and the residue was dissolved in dichloromethane. The resulting solution was washed with water and brine, dried over magnesium sulfate, filtered and concentrated under reduced pressure to afford a brown amorphous solid. The solids were combined to provide 17.2 g of tert-butyl[4-(7-benzyloxy-2-ethyl-1H-imidazo[4,5-c]quinolin-1-yl)butyl]carbamate.

Part D mCPBA (10.6 g, 33.7 mmol) was added in one portion to a solution of tert-butyl[4-(7-benzyloxy-2-ethyl-1H-imidazo[4,5-c]quinolin-1-yl)butyl]carbamate (16.0 g, 33.7 mmol) in chloroform (270 mL). After the reaction was stirred for 1.5 hours, ammonium hydroxide (270 mL) was added. The mixture was stirred for 15 minutes, and p-toluenesulfonyl chloride (6.42 g, 33.7 mmol) was added in three portions. The reaction was stirred for 18 hours. The layers were separated, and the aqueous layer was extracted with dichloromethane. The combined organic fractions were washed with water and brine, dried over sodium sulfate, filtered, and concentrated under reduced pressure. The residue was recrystallized from acetonitrile to afford 9.73 g of tert-butyl[4-(4-amino-7-benzyloxy-2-ethyl-1H-imidazo[4,5-c]quinolin-1-yl)butyl]carbamate as a gray powder.

Part E

Concentrated hydrochloric acid (18 mL) was added to a solution of tert-butyl[4-(4-amino-7-benzyloxy-2-ethyl-1H-imidazo[4,5-c]quinolin-1-yl)butyl]carbamate (9.0 g, 18 mmol) in ethanol (100 mL), and the reaction was stirred for 15 minutes. The ethanol was removed under reduced pressure, and the residue was twice dissolved in ethanol and concentrated under reduced pressure. The solid residue was stirred with brine (25 mL) and water (100 mL), and the pH of the mixture was adjusted to 14 with the addition of 50% aqueous sodium hydroxide. Dichloromethane was added, and the layers were separated. The aqueous layer was extracted twice with dichloromethane (100 mL) and twice with chloroform (100 mL). The combined organic fractions were dried over sodium sulfate, filtered, and concentrated under reduced pressure to provide 7.00 g of 1-(4-aminobutyl)-7-benzyloxy-2-ethyl-1H-imidazo[4,5-c]quinolin-4-amine as an off-white powder.

Part F 1-(4-Aminobutyl)-7-benzyloxy-2-ethyl-1H-imidazo[4,5-c]quinolin-4-amine (7.0 g, 18 mmol) was mixed with chloroform (180 mL), and the suspension was cooled with an ice/water bath. Methanesulfonyl chloride (1.59 mL, 20.5 mmol) was added dropwise, and the reaction was stirred for 18 hours. Saturated aqueous sodium carbonate was added to the solution, and the layers were separated. The precipitate in the aqueous layer was isolated by filtration, washed with ethanol and diethyl ether, and recrystallized from a mixture of methanol and chloroform. During the recrystallization, the hot solution was filtered through a glass fiber filter. N-[4-(4-Amino-7-benzyloxy-2-ethyl-1H-imidazo[4,5-c]quinolin-1-yl)butyl]methanesulfonamide (2.96 g) was isolated as an off-white solid. The organic layer was concentrated under reduced pressure, and the residue was stirred with boiling methanol and isolated by filtration to afford 1.90 g of N-[4-(4-amino-7-benzyloxy-2-ethyl-1H-imidazo[4,5-c]quinolin-1-yl)butyl]methanesulfonamide as a white solid, mp 213.5-215° C.

$^1$H NMR (300 MHz, DMSO-$d_6$) δ 7.93 (d, J=9.0 Hz, 1H), 7.49-7.29 (m, 5H), 7.11 (d, J=2.6 Hz, 1H), 6.98-6.95 (m, 1H), 6.96 (dd, J=8.8, 2.7 Hz, 1H), 6.36 (s, 2H), 5.19 (s, 2H), 4.47-4.42 (m, 2H), 2.96 (q, J=6.6 Hz, 2H), 2.88 (q, J=7.5 Hz, 2H), 2.84 (s, 3H), 1.86-1.76 (m, 2H), 1.64-1.54 (m, 2H), 1.35 (t, J=7.4 Hz, 3H);

MS (ESI) m/z 468.2077 (Calcd. For $C_{24}H_{29}N_5O_3S$ 468.2069, M+H);

Anal. Calcd. for $C_{24}H_{29}N_5O_3S$: % C, 61.65; % H, 6.25; % N, 14.98. Found: % C, 61.51; % H, 6.30; % N, 14.98.

Example 107

N-[4-(4-Amino-2-ethyl-7-hydroxy-1H-imidazo[4,5-c]quinolin-1-yl)butyl]methanesulfonamide

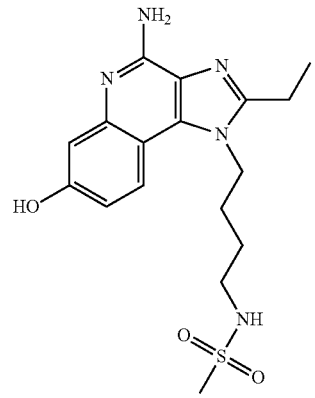

A warm solution of N-[4-(4-amino-7-benzyloxy-2-ethyl-1H-imidazo[4,5-c]quinolin-1-yl)butyl]methanesulfonamide (2.00 g, 4.28 mmol), prepared in Example 106, in acetonitrile (250 mL) and methanol (50 mL) was added to a Parr vessel containing 10% palladium on carbon (1.00 g) and a small amount of acetonitrile. The vessel was placed under hydrogen pressure (25 psi, $1.7 \times 10^5$ Pa) and recharged three times with hydrogen over a period of 21 hours. Concentrated hydrochloric acid (30 mL) was then added to the reaction mixture, which was filtered through a layer of CELITE filter aid. The filter cake was washed with water (200 mL), and the filtrate was concentrated under reduced pressure. Ethanol (2×100 mL) was added to the residue and concentrated under reduced pressure to afford a white solid. The solid was mixed with water (30 mL), and the pH was adjusted to 8 with the addition of 1M aqueous sodium hydroxide. The resulting white, granular precipitate was isolated by filtration, washed with water and ethanol, stirred with hot ethanol, and isolated by filtration to provide 0.860 g of N-[4-(4-amino-2-ethyl-7-hydroxy-1H-imidazo[4,5-c]quinolin-1-yl)butyl]methanesulfonamide as a white powder, mp 220° C. (decomposition).

$^1$H NMR (300 MHz, DMSO-$d_6$) δ 9.42 (s, 1H), 7.83 (d, J=8.9 Hz, 1H), 6.97 (t, J=5.8 Hz, 1H), 6.93 (d, J=2.4 Hz, 1H), 6.78 (dd, J=8.8, 2.4 Hz, 1H), 6.29 (s, 2H), 4.44-4.39 (m, 2H), 2.99-2.84 (m, 4H), 2.84 (s, 3H), 1.86-1.76 (m, 2H), 1.64-1.55 (m, 2H), 1.34 (t, J=7.4 Hz, 3H);

$^{13}$C NMR (75 MHz, DMSO-$d_6$) δ 156.0, 152.6, 151.6, 146.5, 132.9, 124.4, 120.9, 111.9, 109.6, 108.0, 44.1, 41.9, 39.1, 26.9, 26.3, 19.8, 12.0;

MS (ESI) m/z 378.1597 (Calcd. for $C_{17}H_{23}N_5O_3S$ 378.1600, M+H).

Anal. Calcd. for $C_{17}H_{23}N_5O_3S$: % C, 54.09; % H, 6.14; % N, 18.55. Found: % C, 53.83; % H, 6.35; % N, 18.21.

Example 108

2-Ethoxymethyl-1-(2-methylpropyl)-8-(pyridin-3-ylmethoxy)-1H-imidazo[4,5-c]quinolin-4-amine

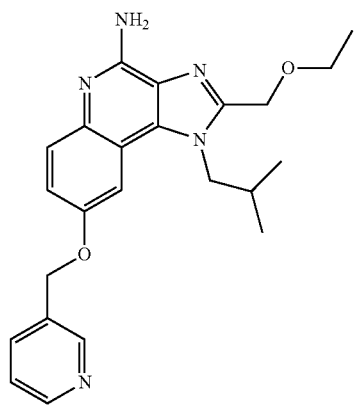

Part A

A mixture of 5-hydroxyanthranilic acid (100 g, 0.653 mol) and acetic anhydride (500 mL, 5.29 mol) was stirred at reflux for 2 hours. The solution was concentrated under reduced pressure and the residue was dried overnight under reduced pressure to provide 143 g of 6-acetoxy-2-methylbenzo[d][1,3]oxazin-4-one as an off white solid.

Part B

A solution of 6-acetoxy-2-methylbenzo[d][1,3]oxazin-4-one (143 g, 0.653 mol) in 1.44 L of glacial acetic acid was stirred overnight with sodium azide (44.66 g, 0.687 mol). The solution was concentrated under reduced pressure and toluene (1.2 L) was then added. After stirring for one hour, a solid formed. The solid was recovered by filtration and then dried overnight under reduced pressure. The solid was dissolved in 2 L of water and the pH was adjusted to 1 with concentrated hydrochloric acid. After stirring for 3 hours, the resulting solid was filtered and dried overnight under a flow of air to give 164.1 g of 5-acetoxy-2-(5-methyltetrazol-1-yl)benzoic acid as an off white solid.

Part C

Cesium carbonate (176 g, 1.13 mol) was added to a solution of 5-acetoxy-2-(5-methyltetrazol-1-yl)benzoic acid (164 g, 0.620 mol) in 1.8 L of acetone. The mixture was stirred vigorously and iodoethane (116 g, 0.682 mol) diluted with 100 mL of acetone was added dropwise over a one-hour period. The reaction was stirred overnight at ambient temperature and was then concentrated under reduced pressure. The resulting solid was partitioned between dichloromethane and water. The aqueous fraction was extracted with dichloromethane and the combined organic fractions were dried over sodium sulfate, filtered, and concentrated to give 166 g of ethyl 5-acetoxy-2-(5-methyltetrazol-1-yl)benzoate as a brown oil.

Part D

Ethyl 5-acetoxy-2-(5-methyltetrazol-1-yl)benzoate (164 g, 0.565 mol) was dissolved in 500 mL of DMF and immersed in a water bath. Potassium ethoxide (52.3 g, 0.621 mol) was added to this solution portionwise, keeping the reaction temperature below 40° C. After 30 minutes, the reaction was poured into 4 L of water and ammonium chloride was added to the solution until the product precipitated. After one hour of stirring, the precipitate was filtered and dried under a flow of air to give 98.5 g of ethyl 5-hydroxy-2-(5-methyltetrazol-1-yl)benzoate as a white solid.

Part E

Potassium carbonate (110 g, 0.793 mol) was added to a solution of ethyl 5-hydroxy-2-(5-methyltetrazol-1-yl)benzoate (98.5 g, 0.397 mol) in 500 mL of DMF. After vigorous stirring for 30 minutes, benzyl bromide (75 g, 0.438) was added and the reaction was stirred overnight. The solution was filtered and then concentrated under reduced pressure (at 50° C.). The resulting solid was slurried in 400 mL of dichloromethane and filtered. The filtrate was concentrated under reduced pressure to give 115 g of ethyl 5-benzyloxy-2-(5-methyltetrazol-1-yl)benzoate as a brown oil.

Part F

Potassium ethoxide (57.5 g, 0.682 mol) was added portionwise to a solution of ethyl 5-benzyloxy-2-(5-methyltetrazol-1-yl)benzoate (115.6 g, 0.341 mol) in 550 mL of DMF. The reaction exothermed and the temperature increased by 35 degrees. The reaction mixture was cooled in an ice bath and stirred for 1 hour. The solution was then poured into 6 L of water containing 500 g of ammonium chloride. A yellow-orange precipitate formed. After stirring overnight, the reaction was filtered. The recovered solid was dried at 50° C. in a vacuum oven to provide 100 g of 7-(benzyloxy)tetraazolo[1,5-a]quinolin-5-ol.

Part G

A slurry of 7-(benzyloxy)tetraazolo[1,5-a]quinolin-5-ol (99.7 g, 0.341 mol) in 500 mL of acetic acid was prepared and, to this, nitric acid was added (70%, 28.2 mL, 0.443 mol). The mixture was heated at 100° C. for 30 minutes. The reaction was then cooled to 15° C. and filtered. The solid was dried for 2 days under a flow of air to provide 81 g of 7-benzyloxy-4-nitrotetraazolo[1,5-a]quinolin-5-ol as a light tan solid.

Part H

DMF (50 mL) was cooled to 0° C., and phosphorous oxychloride (10.92 g, 71.2 mmol) was added dropwise. The cooling bath was removed and after stirring for 30 minutes, the resulting peach colored solution was added dropwise to a slurry of 7-benzyloxy-4-nitrotetraazolo[1,5-a]quinolin-5-ol (20 g, 59.3 mmol) in DMF (15 mL). The reaction was stirred until the starting material had been consumed and was then poured over 2 L of ice. The resulting yellow-brown precipitate was filtered, rinsed with water, and then slurried in dichloromethane. To this slurry was added isobutylamine (21.6 g, 297 mmol) and the mixture was stirred overnight at ambient temperature. The mixture was then filtered, the filtrate dried over sodium sulfate, and concentrated under reduced pressure to provide 23 g of a dark green solid. The material was purified using chromatography on silica, eluting with a gradient of 0-4% methanol in chloroform. A final recrystallization from acetonitrile yielded 10 g of 7-(benzyloxy)-N-(2-methylpropyl)-4-nitrotetraazolo[1,5-a]quinolin-5-amine as a yellow-brown solid.

Part I 7-(Benzyloxy)-N-(2-methylpropyl)-4-nitrotetraazolo[1,5-a]quinolin-5-amine (10 g, 25.4 mmol) was shaken in 200 mL of acetonitrile with 5% platinum on carbon (1 g) under 50 psi ($3.45 \times 10^5$ Pa) of hydrogen. After 5 hours, the mixture was filtered through CELITE filter agent. Some product was isolated as a solid on the top of the filter cake. This solid was collected, dissolved in warm DMF, and filtered again through fresh CELITE filter agent. The combined filtrates were cooled and allowed to sit overnight. The resulting precipitate was collected in 2 crops to yield 7.6 g of 7-(benzyloxy)-$N^5$-(2-methylpropyl)tetraazolo[1,5-a]quinoline-4,5-diamine as a brown solid.

Part J

Ethoxyacetyl chloride (2.7 g, 22 mmol) was added dropwise to a solution of 7-(benzyloxy)-$N^5$-(2-methylpropyl)tetraazolo[1,5-a]quinoline-4,5-diamine (7.6 g, 21 mmol) in 200 mL of pyridine. The solution was stirred for 1 hour and additional ethoxyacetyl chloride was added. The solution was refluxed overnight, after which the solvent was removed. The solid material was dissolved in 300 mL of chloroform and stirred with 150 mL of 1% aqueous sodium carbonate. The pH was adjusted to 10 with 10% sodium hydroxide. The organic fraction was washed with 2 portions of 1% sodium carbonate and once with brine solution. The organic fraction was then dried over sodium sulfate and concentrated to give 8.8 g of 8-(benzyloxy)-5-(ethoxymethyl)-6-(2-methylpropyl)-6H-imidazo[4,5-c]tetraazolo[1,5-a]quinoline as a tan solid. A small portion was recrystallized from ethanol to provide an analytical sample, mp 183.5-184.5° C.

Anal. Calcd. For $C_{24}H_{26}N_6O_2$: % C, 66.96; % H, 6.09; % N, 19.52. Found: % C, 66.62; % H, 5.81; % N, 19.48.

Part K 8-(Benzyloxy)-5-(ethoxymethyl)-6-(2-methylpropyl)-6H-imidazo[4,5-c]tetraazolo[1,5-a]quinoline (8 g, 18.6 mmol) was shaken overnight in 100 mL of ethanol and 300 mL of acetonitrile with 10% palladium on carbon (1 g) under 50 psi ($3.45 \times 10^5$ Pa) of hydrogen. The mixture was shaken with additional catalyst for another day. The mixture was diluted with 500 mL of methanol; heated to near reflux; and filtered through CELITE filter agent. Upon cooling, a precipitate formed. The solid (4.2 g) was recovered by filtration. The filtrate was concentrated to dryness, slurried again in methanol, and filtered to provide a second crop of solid (1 g). The second crop was recrystallized from methanol: acetonitrile to yield 650 mg of 5-(ethoxymethyl)-6-(2-methylpropyl)-6H-imidazo[4,5-c]tetraazolo[1,5-a]quinolin-8-ol as a white solid.

Anal. Calcd. for $C_{17}H_{20}N_6O_2$: % C, 59.99; % H, 5.92; % N, 24.69. Found: % C, 59.82; % H, 5.89; % N, 24.89.

Part L 5-(Ethoxymethyl)-6-(2-methylpropyl)-6H-imidazo[4,5-c]tetraazolo[1,5-c]quinolin-8-ol (260 mg, 0.76 mmol), was stirred in 10 mL of tetrahydrofuran (THF), 3-pyridylcarbinol (87 mg, 0.80 mmol), and triphenylphosphine (299 mg, 1.14 mmol). Diisopropyl azodicarboxylate (231 mg, 1.14 mmol) was added dropwise to the mixture. After 30 minutes, 2 additional drops of 3-pyridylcarbinol were added and the reaction was stirred overnight at ambient temperature. Analysis by thin layer chromatography indicated that a small amount of starting material still remained. Additional amounts of the reagents were added until all of the starting material was consumed. The reaction was filtered through an acidic ion exchange resin and the resin was washed with methanol, followed by 1M ammonia in methanol. The filtrate was concentrated under reduced pressure to provide 280 mg of 5-(ethoxymethyl)-6-(2-methylpropyl)-8-(pyridin-3-ylmethoxy)-6H-imidazo[4,5-c]tetraazolo[1,5-a]quinoline as an off white solid.

Part M 5-(Ethoxymethyl)-6-(2-methylpropyl)-8-(pyridin-3-ylmethoxy)-6H-imidazo[4,5-c]tetraazolo[1,5-a]quinoline (300 mg, 0.69 mmol) and triphenyphosphine (1 g, 4.17 mmol) were combined in a sealed vial and heated at 150° C. with stirring for 4 hours. The reaction was cooled to ambient temperature; diluted with chloroform; and purified by flash column chromatography on silica eluting with 5-10% gradient of methanol in chloroform. The clean fractions were concentrated under vacuum to provide a brown solid. This solid was refluxed for 1 hour in 4 mL of 3M aqueous HCl. The pH was adjusted to 14 by adding solid potassium hydroxide, and the resulting precipitate was filtered. The solid was dried under reduced pressure to provide 2-ethoxymethyl-1-(2-methylpropyl)-8-(pyridin-3-ylmethoxy)-1H-imidazo[4,5-c]quinolin-4-amine as an off-white solid, mp 204.0-206.0° C.

MS (APCI) m/z 406 (M+H)$^+$;

Anal. Calcd. For $C_{23}H_{27}N_5O_2$: % C, 68.12; % H, 6.71; % N, 17.27. Found: % C, 67.47; % H, 7.13; % N, 17.09.

Example 109

3-{[(4-Amino-2-ethoxymethyl-1-(2-methylpropyl)-1H-imidazo[4,5-c]quinolin-8-yl)oxy]methyl}benzoic acid

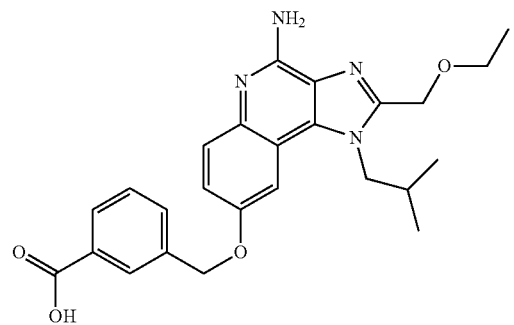

Part A 5-(Ethoxymethyl)-6-(2-methylpropyl)-6H-imidazo[4,5-c]tetraazolo[1,5-c]quinolin-8-ol, 4.0 g, 11.75 mmol was dissolved in 100 mL of DMF and stirred with potassium carbonate (3.3 g, 23.5 mmol) for 30 minutes. To this mixture was added methyl 3-(bromomethyl)benzoate (2.8 g, 12.33 mmol) and the reaction was stirred overnight. The reaction was poured into 10 volumes of water and the precipitate was sequentially filtered, dissolved in dichloromethane, dried over magnesium sulfate, filtered, and concentrated to give 6.1 g of methyl 3-{[(5-ethoxymethyl-6-(2-methylpropyl)-6H-imidazo[4,5-c]tetraazolo[1,5-c]quinolin-8-yl)oxy]methyl}benzoate as a white solid.

Part B

Methyl 3-{[(5-ethoxymethyl-6-(2-methylpropyl)-6H-imidazo[4,5-c]tetraazolo[1,5-a]quinolin-8-yl)oxy]methyl}benzoate (2.6 g, 5.32 mmol) was reduced to 3-{[(4-amino-2-ethoxymethyl-1-(2-methylpropyl)-1H-imidazo[4,5-c]quinolin-8-yl)oxy]methyl}benzoic acid using the general method described in Example 108, part M, to give the sodium salt as a white solid. The solid was dissolved in methanol and the pH was adjusted to 8. The resulting precipitate was filtered and dried to give 800 mg of 3-{[(4-amino-2-ethoxymethyl-1-(2-methylpropyl)-1H-imidazo[4,5-c]quinolin-8-yl)oxy]methyl}benzoic acid as an off white powder.

MS (APCI) m/z 449 (M+H)$^+$;

Anal. Calcd. For $C_{25}H_{28}N_4O_4 \cdot 0.1\ H_2O$: % C, 66.68; % H, 6.31; % N, 12.44. Found: % C, 66.50; % H, 6.13; % N, 12.26.

Example 110

3-{(4-Amino-2-ethoxymethyl-1-(2-methylpropyl)-1H-imidazo[4,5-c]quinolin-8-yl)oxy]methyl)}benzyl alcohol

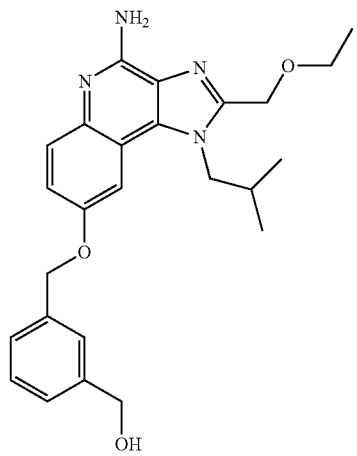

3-{[(4-Amino-2-ethoxymethyl-1-(2-methylpropyl)-1H-imidazo[4,5-c]quinolin-8-yl)oxy]methyl}benzoic acid (800 mg, 1.78 mmol) was stirred in anhydrous THF under inert conditions and lithium aluminum hydride (250 mg, 6.58 mmol) was added portionwise. After 15 minutes, 0.25 mL of water was added, followed by 0.25 mL of 15% aqueous sodium hydroxide, followed by 0.75 ml of water. The resulting mixture was concentrated and purified using flash column chromatography on silica gel, eluting with a gradient of 0-10% methanol in chloroform. Clean fractions were concentrated and recrystallized from acetonitrile to give 360 mg of 3-{(4-amino-2-ethoxymethyl-1-(2-methylpropyl)-1H-imidazo[4,5-c]quinolin-8-yl)oxy]methyl)}benzyl alcohol as pink crystals, mp 164.2-167.2° C.

MS (APCI) m/z 435 (M+H)$^+$;

Anal. Calcd. For $C_{25}H_{30}N_4O_3$: % C, 69.10; % H, 6.96; % N, 12.89. Found: % C, 68.89; % H, 6.86; % N, 12.97.

Example 111

1-[4-Amino-7-benzyloxy-2-(2-methoxyethyl)-1H-imidazo[4,5-c]quinolin-1-yl]-2-methylpropan-2-ol

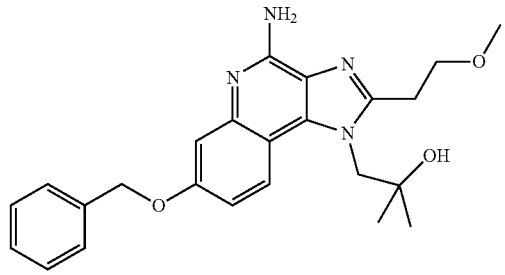

Part A

7-Benzyloxy-4-chloro-3-nitroquinoline (66.4 g, 0.21 mol) was dissolved in a mixture of dichloromethane (1.5 L) and triethylamine (59 mL, 0.422 mol). A solution of 1-amino-2-methyl-2-propanol (22.5 g, 0.25 mol) in dichloromethane (100 mL) was added dropwise. The reaction was stirred at ambient temperature for 3 hours and then quenched with 1% aqueous sodium carbonate solution. A precipitate formed which was filtered to provide 60 g of crude 1-(7-benzyloxy-3-nitroquinolin-4-ylamino)-2-methylpropan-2-ol as a yellow-brown solid.

MS (APCI) m/z 368 (M+H)$^+$.

Part B

To 1.6 L of acetonitrile was added the 60 g of product from part A. To this slurry was then added 11 g of 5% platinum on carbon catalyst and the mixture was shaken for 14 hours under 50 psi (3.4×10$^5$ Pa) of hydrogen. The reaction mixture was then taken up in 2.5 L of methanol and filtered through CELITE filter agent, which was washed with 1 L of hot methanol. The combined filtrates were concentrated under reduced pressure to yield 53.6 g of 1-(3-amino-7-benzyloxyquinolin-4-ylamino)-2-methylpropan-2-ol as a brown solid.

Part C 1-(3-Amino-7-benzyloxyquinolin-4-ylamino)-2-methylpropan-2-ol (25 g, 74.09 mmol) was added to 500 mL of pyridine. To this mixture was added in a dropwise manner a solution of methoxypropionyl chloride (10 g, 81.5 mmol) dissolved in 20 mL of toluene. After approximately half of the acid chloride had been added, the reaction mixture became completely homogenous. Two hours after the addition of the acid chloride, the reaction mixture was heated to reflux and maintained overnight. The solvent was concentrated through the use of a Dean-Stark trap. Cooling to ambient temperature provided a white precipitate, which was collected by filtration. The solid was slurried in 1 L of 1% hot aqueous sodium carbonate (75-80° C.) for 1 hour. The mixture was then cooled in an ice bath and the solid material was filtered, rinsed with water, and dried to yield 22.7 g of 1-[7-benzyloxy-2-(2-methoxyethyl)-1H-imidazo[4,5-c]quinolin-1-yl]-2-methylpropan-2-ol as a white solid, mp 170-171.5° C.

Anal. Calcd. For $C_{24}H_{27}N_3O_3$: % C, 71.09; % H, 6.71; % N, 10.36. Found: % C, 70.99; % H, 6.70; % N, 10.39.

Part D

3-Chloroperoxybenzoic acid (mCPBA, 60% pure, 11.7 g, 40.7 mmol) was added portionwise to a solution of 1-[7-benzyloxy-2-(2-methoxyethyl)-1H-imidazo[4,5-c]quinolin-1-yl]-2-methylpropan-2-ol (15 g, 37.0 mmol) in dichloromethane (300 mL). The mixture was stirred overnight at ambient temperature. A small amount of the starting material remained and 2 g of mCPBA was added. The reaction was stirred for 45 minutes followed by the addition of 150 mL of aqueous ammonium hydroxide. p-Toluenesulfonic acid (8.5 g, 44.4 mmol) was added portionwise over 15 minutes and the reaction was stirred for 1 hour. The layers were separated and the organic fraction was washed with two 100 mL portions of 1% aqueous sodium carbonate solution. The organic fraction was dried over anhydrous sodium sulfate, filtered, and concentrated under reduced pressure to yield 18 g of a brown solid. A small portion of the solid (1 g) was recrystallized from acetonitrile to provide 0.6 g of 1-[4-amino-7-benzyloxy-2-(2-methoxyethyl)-1H-imidazo[4,5-c]quinolin-1-yl]-2-methylpropan-2-ol as an off white solid, mp 185-186.5° C.

Anal. Calcd. for $C_{24}H_{28}N_4O_3$: % C, 68.55; % H, 6.71; % N, 13.32. Found: % C, 68.49; % H, 6.82; % N, 13.35.

Example 112

4-Amino-1-(2-hydroxy-2-methylpropyl)-2-(2-methoxyethyl)-1H-imidazo[4,5-c]quinolin-7-ol

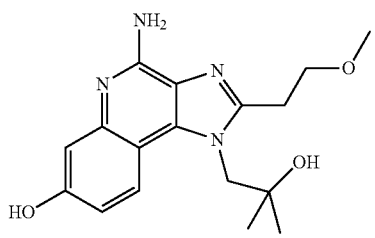

The general method described in Example 5 was used to convert 1-[4-amino-7-benzyloxy-2-(2-methoxyethyl)-1H-imidazo[4,5-c]quinolin-1-yl]-2-methylpropan-2-ol (14.0 g) to 7 g of 4-amino-1-(2-hydroxy-2-methylpropyl)-2-(2-methoxyethyl)-1H-imidazo[4,5-c]quinolin-7-ol as an off-white solid. A small portion of the solid was recrystallized from methanol to provide an analytical sample, mp 258.0-260.0° C.

Anal. Calcd. for $C_{17}H_{22}N_4O_3 \cdot CH_3OH$: % C, 59.65; % H, 7.23; % N, 15.46. Found: % C, 59.39; % H, 7.37; % N, 15.67.

Example 113

1-[4-Amino-2-(2-methoxyethyl)-7-(3-nitrobenzyloxy)-1H-imidazo[4,5-c]quinolin-1-yl]-2-methylpropan-2-ol

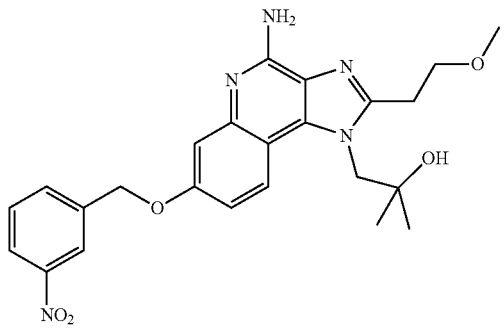

Potassium carbonate (2.1 g, 15.0 mmol) was added to a solution of 4-amino-1-(2-hydroxy-2-methylpropyl)-2-(2-methoxyethyl)-1H-imidazo[4,5-c]quinolin-7-ol (2.5 g, 7.5 mmol) in DMF (50 mL). After stirring for 15 minutes, 3-nitrobenzyl bromide (1.7 g, 8.3 mmol) was added. The reaction was stirred at ambient temperature overnight and then poured into 600 mL of water. A light yellow precipitate formed. An additional 20 g of potassium carbonate was added and the mixture was stirred for 30 minutes. The precipitate was filtered, taken up in 700 mL of methanol, and concentrated under reduced pressure to yield 3.3 g of a yellow solid. The solid was recrystallized from methanol to give 175 mg of 1-[4-amino-2-(2-methoxyethyl)-7-(3-nitrobenzyloxy)-1H-imidazo[4,5-c]quinolin-1-yl]-2-methylpropan-2-ol as yellow needles, mp 125.0-127.0° C.

MS (APCI) m/z 466 (M+H)⁺;

Anal. Calcd. for $C_{24}H_{27}N_5O_5 \cdot CH_3OH$: % C, 60.35; % H, 6.28; % N, 14.08. Found: % C, 60.08; % H, 6.17; % N, 14.10.

Example 114

1-[4-Amino-7-(3-aminobenzyloxy)-2-(2-methoxyethyl)-1H-imidazo[4,5-c]quinolin-1-yl]-2-methylpropan-2-ol

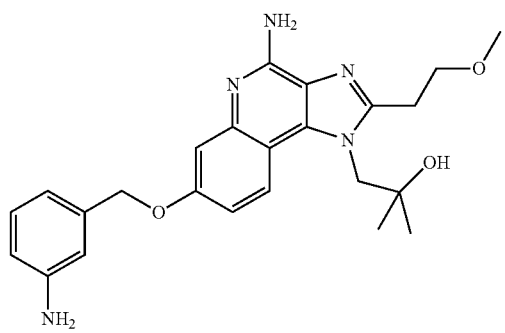

1-[4-Amino-2-(2-methoxyethyl)-7-(3-nitrobenzyloxy)-1H-imidazo[4,5-c]quinolin-1-yl]-2-methylpropan-2-ol (3.1 g, 6.66 mmol) was mixed with 100 mL of warm ethanol and 1 g of 5% platinum on carbon. The mixture was shaken under hydrogen pressure (50 psi, $3.4 \times 10^5$ pa) for 5 hours. The material had come out of solution so an additional 100 mL of methanol and 0.5 g platinum catalyst were added. After shaking under hydrogen pressure overnight, the mixture was filtered through CELITE filter agent. The filter cake was washed with 3×75 mL portions of hot methanol and the filtrates were combined and concentrated under reduced pressure. An orange foam resulted which was purified by column chromatography using silica gel. The polar component of the eluent was chloroform:methanol:2% aqueous ammonium hydroxide 80:18:2 (CMA), and elution was carried out with CMA:chloroform in a gradient from 0:100 to 40:60. Fractions containing product were combined and concentrated to yield 1.55 g of 1-[4-amino-7-(3-aminobenzyloxy)-2-(2-methoxyethyl)-1H-imidazo[4,5-c]quinolin-1-yl]-2-methylpropan-2-ol as an off-white solid. A small portion was recrystallized from acetonitrile to provide an analytical sample, mp 203.0-206.0° C.

MS (APCI) m/z 436 (M+H)⁺;

Anal. Calcd. for $C_{24}H_{29}N_5O_3$: % C, 66.19; % H, 6.71; % N, 16.08. Found: % C, 65.84; % H, 6.94; % N, 16.00.

Example 115

1-[4-Amino-2-(2-methoxyethyl)-7-(pyridin-3-yl-methoxy)-1H-imidazo[4,5-c]quinolin-1-yl]-2-methylpropan-2-ol

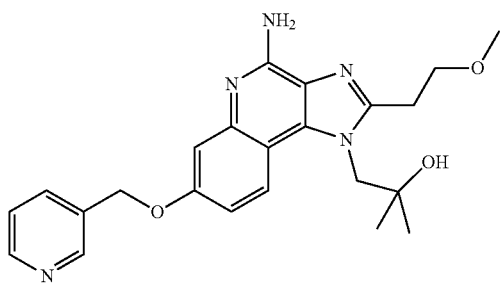

4-Amino-1-(2-hydroxy-2-methylpropyl)-2-(2-methoxyethyl)-1H-imidazo[4,5-c]quinolin-7-ol, (2.5 g, 7.5 mmol) was slurried in 75 mL of THF to which 3-pyridylcarbinol (350 mg, 3.18 mmol) and triphenylphosphine (1.59 g, 6.06 mmol) were added. To this was added 1.2 g (5.93 mmol) of diisopropyl azodicarboxylate (DIAD) and the reaction mixture was stirred for 45 minutes. Approximately 3 additional equivalents of each reagent were added to complete the reaction. The reaction mixture was then concentrated and partitioned between chloroform and aqueous sodium carbonate. The organic fraction was dried and passed through an ion exchange resin with methanol, followed by 1M ammonia in methanol as the eluents. The solvent was concentrated and the residue was purified by flash column chromatography on silica gel using a gradient of 0-40% CMA in chloroform. The desired fractions were concentrated to produce an oil which was taken up in 20 mL of refluxing acetonitrile. Upon cooling, white crystals formed which were filtered and dried to provide 0.55 g of 1-[4-amino-2-(2-methoxyethyl)-7-(pyridin-3-ylmethoxy)-1H-imidazo[4,5-c]quinolin-1-yl]-2-methylpropan-2-ol, mp 200.0-202.0° C.

MS (APCI) m/z 422 (M+H)$^+$;

Anal. Calcd. for $C_{23}H_{27}N_5O_3$.1.33 $H_2O$: % C, 62.02; % H, 6.71; % N, 15.72. Found: % C, 61.84; % H, 6.25; % N, 15.72.

Example 116

7-(Furan-3-ylmethoxy)-2-methyl-1-(2-methylpropyl)-1H-imidazo[4,5-c]quinolin-4-amine

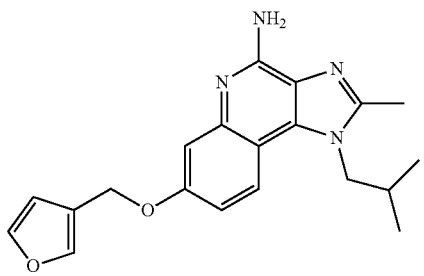

Part A

7-Benzyloxy-2-methyl-1-(2-methylpropyl)-1H-imidazo[4,5-c]quinoline (16.11 g, 46.6 mmol), 10% palladium on carbon (4.96 g), and ethanol (380 mL) were combined. The mixture was shaken overnight under 50 psi (3.4×10$^5$ Pa) of hydrogen and then filtered. The solids were washed with ethyl acetate, and the filtrate was concentrated. Diethyl ether was added to the residue and a green solid formed. The solid was recrystallized from acetonitrile to give 6.63 g of 2-methyl-1-(2-methylpropyl)-1H-imidazo[4,5-c]quinolin-7-ol as a beige solid.

Anal. Calcd. for $C_{15}H_{17}N_3O$: % C, 70.56; % H, 6.71; % N, 16.46. Found: % C, 70.33; % H, 6.66; % N, 16.35.

Part B

2-Methyl-1-(2-methylpropyl)-1H-imidazo[4,5-c]quinolin-7-ol (300 mg, 1.17 mmol), triphenylphosphine (921 mg, 3.51 mmol), and 3-furanmethanol (173 mg, 1.76 mmol) were slurried in 20 mL of anhydrous THF. After 5 minutes diisopropyl azodicarboxylate (710 mg, 3.51 mmol) was added dropwise to the mixture. The resulting homogeneous solution was stirred six days. Analysis of the reaction by HPLC indicated that mostly starting material was present. Additional portions of triphenylphosphine (150 mg), 3-furanmethanol (0.5 mL) were added followed by diisopropyl azodicarboxylate (1 mL). Analysis of the reaction after 1 hour indicated that all of the 2-methyl-1-(2-methylpropyl)-1H-imidazo-[4,5-c]quinolin-7-ol was consumed. The reaction was filtered through an acidic ion-exchange resin with methanol followed by 1M ammonia in methanol. The filtrate was concentrated to give 500 mg of 7-(furan-3-ylmethoxy)-2-methyl-1-(2-methylpropyl)-1H-imidazo[4,5-c]quinoline as a dark orange oil.

Part C 7-(Furan-3-ylmethoxy)-2-methyl-1-(2-methylpropyl)-1H-imidazo[4,5-c]quinoline (500 mg) was dissolved in 30 mL of dichloromethane and 3-chloroperoxybenzoic acid (60% pure, 403 mg) was added. The reaction was stirred for 30 minutes at ambient temperature and then 30 mL of aqueous ammonium hydroxide was added. After 10 minutes, p-toluenesulfonyl chloride (268 mg, 1.40 mmol) was added and the reaction was stirred for an additional 15 minutes. The layers were separated and the aqueous fraction was washed with two portions of dichloromethane (20 mL). The organic fractions were combined and washed three times with 20 mL portions of aqueous sodium carbonate. The combined sodium carbonate fractions were extracted with four portions of chloroform (20 mL). All of the organic fractions were combined, dried over magnesium sulfate, and concentrated to yield an orange foam. The crude product was purified using flash column chromatography on silica gel, eluting with a gradient of methanol in chloroform. The clean fractions were combined, concentrated, and the resulting solid was recrystallized from acetonitrile to give 102 mg of 7-(furan-3-ylmethoxy)-2-methyl-1-(2-methylpropyl)-1H-imidazo[4,5-c]quinolin-4-amine as a white powder, mp 181.0-183.0.

MS (APCI) m/z 351 (M+H)$^+$;

Anal. Calcd. for $C_{20}H_{22}N_4O_2$.0.6 $CH_3CN$: % C, 67.89; % H, 6.40; % N, 17.18. Found: % C, 67.72; % H, 6.67; % N, 16.95.

Example 117

3-{[(4-Amino-1-(2-hydroxy-2-methylpropyl)-2-(2-methoxyethyl)-1H-imidazo[4,5-c]quinolin-7-yl)oxy]methyl}benzonitrile

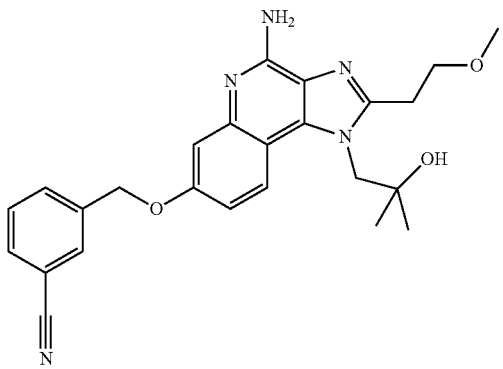

4-Amino-1-(2-hydroxy-2-methylpropyl)-2-(2-methoxyethyl)-1H-imidazo[4,5-c]quinolin-7-ol, (3.5 g, 10.6 mmol); potassium carbonate (2.9 g, 21.2 mmol) and DMF (100 mL) were combined. After 10 minutes, α-bromo-m-tolunitrile (2.25 g, 11.6 mmol) was added and the reaction was stirred overnight. The mixture was poured into 1.5 L of water and a white precipitate formed. The water was decanted and the residue was dissolved in 350 mL of chloroform. The solution was washed with two portions of water (100 mL). The organic fraction was dried and concentrated to give 4.8 g of a pale yellow foam. Purification by flash column chromatography on silica gel (eluting with a gradient of 0-20% CMA in chloroform) followed by recrystallization from acetonitrile provided 550 mg of 3-{[(4-amino-1-(2-hydroxy-2-methylpropyl)-2-(2-methoxyethyl)-1H-imidazo[4,5-c]quinolin-7-yl)oxy]methyl}benzonitrile as pale yellow crystals, mp 195.7-197.2° C.

MS (APCI) m/z 446 (M+H)$^+$;

Anal. Calcd. for $C_{25}H_{27}N_5O_3$: % C, 67.40; % H, 6.11; % N, 15.72. Found: % C, 67.26; % H, 6.36; % N, 15.86.

Example 118

N-{3-[(4-Amino-1-(2-hydroxy-2-methylpropyl)-2-(2-methoxyethyl)-1H-imidazo[4,5-c]quinoline-7-yloxy)methyl]phenyl}methanesulfonamide

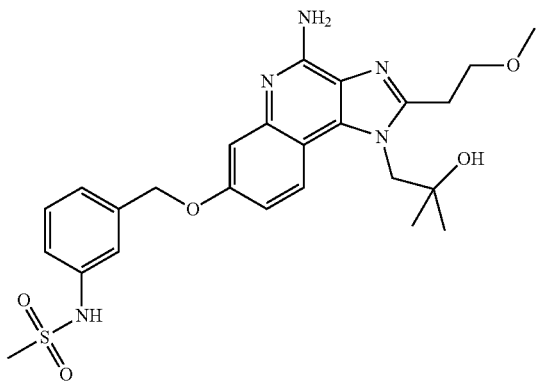

1-[4-Amino-7-(3-aminobenzyloxy)-2-(2-methoxyethyl)-1H-imidazo[4,5-c]quinolin-1-yl]-2-methylpropan-2-ol, (850 mg, 1.95 mmol) and triethyl amine (600 mg, 5.85 mmol) were dissolved in 100 mL of 1:1 acetonitrile:dichloromethane. The solution was cooled in an ice bath and methanesulfonic anhydride (375 mg, 2.15 mmol) was added in small portions. After 4 hours, a second molar equivalent of methanesulfonic anhydride was added and the reaction was stirred overnight. The solvent was removed under reduced pressure. The resulting brown oil was taken up in dichloromethane and washed with 1% aqueous sodium carbonate, dried, and concentrated under reduced pressure. The resulting solid was purified by flash column chromatography on silica gel (eluting with a gradient of 0-20% CMA in chloroform) followed by recrystallization from acetonitrile to provide 439 mg of N-{3-[(4-amino-1-(2-hydroxy-2-methylpropyl)-2-(2-methoxyethyl)-1H-imidazo[4,5-c]quinoline-7-yloxy)methyl]phenyl}methanesulfonamide as white crystals.

MS (APCI) m/z 514 (M+H)$^+$;

Anal. Calcd. for $C_{25}H_{31}N_5O_5S \cdot 0.55 H_2O$: % C, 56.67; % H, 6.24; % N, 13.22. Found: % C, 56.93; % H, 6.35; % N, 13.23.

Examples 119-121

Part A (4-Amino-7-benzyloxy-2-ethoxymethyl-1H-imidazo[4,5-c]quinolin-1-yl)-2-methylpropan-2-ol was debenzylated using the general method of Example 5. Upon completion of the reaction, the catalyst was removed by filtration through a polytetrafluoroethylene (PTFE) membrane and the filtrate was concentrated under reduced pressure to give a tan solid. The solid was slurried in 1% aqueous sodium carbonate. This formed a gooey slurry. The pH was lowered to 1 with the addition of concentrated hydrochloric acid. When a homogenous solution was formed, the pH was adjusted back to 5 with the addition of 1% aqueous sodium carbonate. A solid precipitated and was collected by filtration. The solid was dried under a stream of air to give 4-amino-2-ethoxymethyl-1-(2-hydroxy-2-methylpropyl)-1H-imidazo[4,5-c]quinolin-7-ol as an off-white solid.

MS (APCI) m/z 331 (M+H)$^+$.

Part B

The general method described for Examples 7-20 was followed, substituting the benzylhalides in the general procedure with those from the table below. For each example, the purification and characterization of the product is described below the table.

| Example | Halide | R |
|---|---|---|
| 119 | benzyl 2-bromoethyl ether | |
| 120 | 1-(3-bromopropyl) pyrrole | |

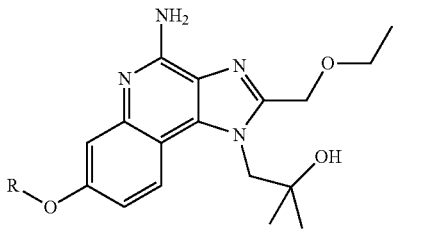

| Example | Halide | R |
|---|---|---|
| 121 | 1-bromomethyl-2-[phenyl-sulfonyl)methyl]benzene | PhSO₂ group on ethylbenzene |

Example 119

1-[4-Amino-7-(2-benzyloxyethoxy)-2-ethoxymethyl-1H-imidazo[4,5-c]quinolin-1-yl]-2-methylpropan-2-ol Upon precipitating the product from water, the water/DMF solution was decanted and the residue was dissolved in chloroform and dried over magnesium sulfate. The solution was filtered and eluted through a silica gel chromatography column using a gradient of 0-10% methanol in chloroform. Clean fractions were concentrated and the solid material was slurried in ice-cold acetonitrile. The precipitate was recovered by filtration to give 1-[4-amino-7-(2-benzyloxyethoxy)-2-ethoxymethyl-1H-imidazo[4,5-c]quinolin-1-yl]-2-methylpropan-2-ol as a white solid, mp 131.0-132.0° C.

MS (APCI) m/z 465 (M+H)⁺;

Anal. Calcd. for $C_{26}H_{32}N_4O_4$: % C, 67.22; % H, 6.94; % N, 12.06. Found: % C, 67.13; % H, 7.03; % N, 12.07.

Example 120

1-{4-Amino-2-ethoxymethyl-7-[3-(pyrrol-1-yl)propoxy]-1H-imidazo[4,5-c]quinolin-1-yl}-2-methyl-propan-2-ol Upon precipitating the product from water, the water/DMF solution was decanted and the residue was dissolved in chloroform and dried over sodium sulfate. The solution was filtered and eluted through a silica gel chromatography column using a 0-10% chloroform:methanol gradient. Clean fractions were concentrated and the solid material was recrystallized from acetonitrile to provide 1-{4-[amino-2-ethoxymethyl-7-[3-(pyrrol-1-yl)propoxy]-1H-imidazo[4,5-c]quinolin-1-yl}-2-methylpropan-2-ol as pale yellow crystals, mp 182.5-183.5° C.

MS (APCI) m/z 438 (M+H)⁺;

Anal. Calcd. for $C_{24}H_{31}N_5O_3$: % C, 65.88; % H, 7.14; % N, 16.01. Found: % C, 65.68; % H, 7.39; % N, 16.07.

Example 121

1-{4-Amino-7-[2-(benzenesulfonylmethyl)benzyloxy]-2-ethoxymethyl-1H-imidazo[4,5-c]quinolin-1-yl}-2-methylpropan-2-ol Upon precipitating the product from water, the water/DMF solution was filtered and the residue was dissolved in chloroform and dried over sodium sulfate. The solution was filtered and eluted through a silica gel chromatography column using a chloroform:methanol gradient. Clean fractions were concentrated and the yellow oil was dissolved in isopropanol and concentrated to give 1-{4-amino-7-[2-(benzenesulfonylmethyl)benzyloxy]-2-ethoxymethyl-1H-imidazo[4,5-c]quinolin-1-yl}-2-methylpropan-2-ol as a yellow foam.

MS (APCI) m/z 575 (M+H)⁺;

Anal. Calcd. for $C_{31}H_{34}N_4O_5S \cdot 0.75\ C_3H_7OH \cdot 0.33\ H_2O$: % C, 63.83; % H, 6.55; % N, 8.95. Found: % C, 63.45; % H, 6.49; % N, 8.80.

Example 122

1-{4-Amino-2-ethoxymethyl-7-[3-(pyridin-3-yl)propoxy]-1H-imidazo[4,5-c]quinolin-1-yl}-2-methylpropan-2-ol

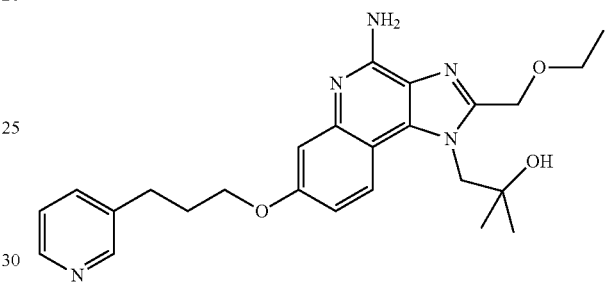

Part A

4-Amino-2-ethoxymethyl-1-(2-hydroxy-2-methylpropyl)-1H-imidazo[4,5-c]quinolin-7-ol (2.35 g, 7.1 mmol), cesium carbonate (4.6 g, 14.2 mmol), and DMF (50 mL) were combined. Propargyl bromide (80% in toluene, 3.2 g, 21.3 mmol) was added and the reaction was stirred overnight. The reaction was poured into 500 mL of water and solid potassium carbonate was added to keep the mixture basic. A precipitate formed. Filtration of the reaction followed by air drying of the recovered solid provided 1.8 g of 1-[4-amino-2-ethoxymethyl-7-(prop-2-ynyloxy)-1H-imidazo[4,5-c]quinolin-1-yl]-2-methylpropan-2-ol as an off white powder.

Part B

1-[4-Amino-2-ethoxymethyl-7-(prop-2-ynyloxy)-1H-imidazo[4,5-c]quinolin-1-yl]-2-methylpropan-2-ol (1.50 g, 4.07 mmol), 3-iodopyridine (920 mg, 4.48 mmol), 1.5 mL of anhydrous triethylamine, $PdCl_2(PPh_3)_2$ (57 mg, 0.08 mmol), copper (I) iodide (30 mg, 0.16 mmol), and DMF (50 mL) were combined. The reaction mixture was heated to 60° C. for 5 days. Additional amounts of catalyst, copper iodide, and iodopyridine were added during the course of the reaction. The reaction was poured into a solution of water (500 mL) and saturated aqueous potassium carbonate (50 mL). The reaction was stirred overnight and the resulting precipitate was recovered by filtration. The solid was dissolved in dichloromethane, dried over magnesium sulfate, filtered and purified using flash column chromatography on silica gel (eluting with a gradient of 0-7% methanol in dichloromethane) to yield 800 mg of 1-{4-amino-2-ethoxymethyl-7-[3-(pyridin-3-yl)prop-2-ynyloxy]-1H-imidazo[4,5-c]quinolin-1-yl}-2-methylpropan-2-ol as an orange-brown semi-solid.

MS (APCI) m/z 446 (M+H)⁺.

Part C

1-{4-Amino-2-ethoxymethyl-7-[3-(pyridin-3-yl)prop-2-ynyloxy]-1H-imidazo[4,5-c]quinolin-1-yl}-2-methylpropan- 2-ol (800 mg, 1.79 mmol) was dissolved in warm ethanol. To this was added 200 mg of 10% palladium on carbon and the mixture was shaken under 50 psi (3.4×10$^5$ Pa) of hydrogen. After 24 hours, an additional 200 mg of palladium catalyst was added and the reaction was shaken for a further 24 hours under 50 psi of hydrogen. The catalyst was removed by filtration and the filtrate was concentrated under reduced pressure to give a solid. This material was purified using flash column chromatography on silica, eluting with a gradient of 0-10% methanol in dichloromethane. The clean fractions were combined and concentrated. The resulting solid was recrystallized from acetonitrile to provide 160 mg of 1-{4-amino-2-ethoxymethyl-7-[3-(pyridin-3-yl)propoxy]-1H-imidazo[4,5-c]quinolin-1-yl}-2-methylpropan-2-ol as off white crystals, mp 160.0-161.0° C.

MS (APCI) m/z 450 (M+H)$^+$;

Anal. Calcd. for $C_{25}H_{31}N_5O_3$: % C, 66.79; % H, 6.95; % N, 15.58. Found: % C, 66.79; % H, 6.81; % N, 15.76.

Example 123

1-{4-Amino-7-[3-(3-aminophenyl)propoxy]-2-ethoxymethyl-1H-imidazo[4,5-c]quinolin-1-yl}-2-methylpropan-2-ol

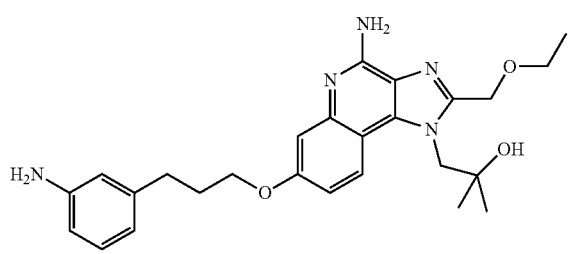

Part A

1-[4-Amino-2-ethoxymethyl-7-(prop-2-ynyloxy)-1H-imidazo[4,5-c]quinolin-1-yl]-2-methylpropan-2-ol (0.5 g, 1.35 mmol), 1-iodo-3-nitropyridine (565 mg, 2.27 mmol), 0.28 mL of anhydrous triethylamine, PdCl$_2$(PPh$_3$)$_2$ (21 mg, 0.03 mmol), copper (I) iodide (12 mg, 0.066 mmol), and DMF (15 mL) were combined. The reaction mixture was heated at 75° C. for 4 hours. The reaction was poured into 250 mL of saturated aqueous NaCl and stirred for 24 hours. The resulting brown precipitate was dissolved in dichloromethane and filtered through a plug of silica gel using 20% methanol in dichloromethane as the eluent. The filtrate was concentrated under reduced pressure to provide 1-{4-amino-2-ethoxymethyl-7-[3-(3-nitrophenyl)prop-2-ynyloxy]]-1H-imidazo[4, 5-c]quinolin-1-yl}-2-methylpropan-2-ol as a solid.

Part B

The product from Part A was combined with ethanol (100 mL), methanol (100 mL) and 200 mg of 10% palladium on carbon. The mixture was shaken under 50 psi (3.4×10$^5$ Pa) of hydrogen overnight. Additional palladium catalyst was added and the reaction was shaken for an additional 6 hours under 35 psi (2.4×10$^5$ Pa) of hydrogen. The catalyst was removed by filtration and the filtrate was concentrated under reduced pressure to give a solid. This material was purified using flash column chromatography on silica gel, eluting with a gradient of 0-8% methanol in dichloromethane. The clean fractions were combined and concentrated. The recovered solid was again purified by flash column chromatography on silica gel eluting with CMA:dichloromethane. A final recrystallization from acetonitrile provided 141 mg of 1-{4-amino-7-[3-(3-aminophenyl)propoxy]-2-ethoxymethyl-1H-imidazo[4,5-c]quinolin-1-yl}-2-methylpropan-2-ol as an off white solid, mp 164.0-166.0° C.

MS (APCI) m/z 464 (M+H)$^+$;

Anal. Calcd. for $C_{26}H_{33}N_5O_3 \cdot H_2O$: % C, 66.85; % H, 7.32; % N, 14.54. Found: % C, 64.74; % H, 7.67; % N, 14.71.

Examples 124-130

The general method described for Examples 7-20 was followed, substituting N-[2-(4-amino-2-ethoxymethyl-7-hydroxy-1H-imidazo[4,5-c]quinolin-1-yl)-1,1-dimethylethyl]methanesulfonamide for 4-amino-1-(2-methylpropyl)-2-propyl-1H-imidazo[4,5-c]quinolin-7-ol. The halides used are presented in the table below. For each example, the purification and characterization of the product is described below the table.

| Example | Halide | R |
|---|---|---|
| 124 | 3-methoxybenzyl bromide | 3-methoxybenzyl |
| 125 | 2-chlorobenzyl bromide | 2-chlorobenzyl |
| 126 | 4-fluorobenzyl bromide | 4-fluorobenzyl |
| 127 | 3-methylbenzyl bromide | 3-methylbenzyl |
| 128 | 2-(bromomethyl)-1,2-benzothiazole | 2-benzothiazolylmethyl |
| 129 | 2-(bromomethyl)-5-(trifluoromethyl)furan | 5-(trifluoromethyl)furan-2-ylmethyl |
| 130 | 5-chloromethyl-2-furancarboxylic acid ethyl ester | ethyl 5-methylfuran-2-carboxylate |

Example 124

N-{2-[4-Amino-2-ethoxymethyl-7-(3-methoxybenzyloxy)-1H-imidazo[4,5-c]quinolin-1-yl]-1,1-dimethylethyl}methanesulfonamide Upon precipitation of the product from water, 20 g of solid sodium carbonate was added to the precipitate/water mixture followed by stirring for 30 minutes. The precipitate was recovered by filtration and the solid was purified by flash column chromatography on silica gel eluting with a gradient of 1-5% methanol in dichloromethane. Clean fractions were concentrated and the product was recrystallized from acetonitrile to provide 550 mg of N-{2-[4-amino-2-ethoxymethyl-7-(3-methoxybenzyloxy)-1H-imidazo[4,5-c]quinolin-1-yl]-1,1-dimethylethyl}methanesulfonamide as a white solid, mp 221.0-222.0° C.

MS (APCI) m/z 528 (M+H)$^+$;

Anal. Calcd. for $C_{26}H_{33}N_5O_5S$: % C, 59.19; % H, 6.30; % N, 13.27. Found: % C, 59.00; % H, 6.44; % N, 13.22.

Example 125

N-{2-[4-Amino-7-(2-chlorobenzyloxy)-2-ethoxymethyl-1H-imidazo[4,5-c]quinolin-1-yl]-1,1-dimethylethyl}methanesulfonamide Upon precipitation of the product from water, 20 g of solid sodium carbonate was added to the precipitate/water mixture followed by stirring for 30 minutes. The precipitate was recovered by filtration and the solid was purified by flash column chromatography on silica gel eluting with a gradient of 1-5% methanol in dichloromethane. Clean fractions were concentrated and the product was slurried in hot methanol and then refluxed for several hours. The solution was concentrated to a smaller volume of methanol and allowed to cool, upon which a solid precipitated. The solid was filtered and dried to give 325 mg of N-{2-[4-amino-7-(2-chlorobenzyloxy)-2-ethoxymethyl-1H-imidazo[4,5-c]quinolin-1-yl]-1,1-dimethylethyl}methanesulfonamide as a white solid, mp 253.0-255.0° C.

MS (APCI) m/z 533 (M+H)$^+$;

Anal. Calcd. for $C_{25}H_{30}ClN_5O_4S$: % C, 56.44; % H, 5.68; % N, 13.16. Found: % C, 56.20; % H, 5.29; % N, 12.89.

Example 126

N-{2-[4-Amino-2-ethoxymethyl-7-(4-fluorobenzyloxy)-1H-imidazo[4,5-c]quinolin-1-yl]-1,1-dimethylethyl}methanesulfonamide Upon precipitation of the product from water, 20 g of solid sodium carbonate was added to the precipitate/water mixture followed by stirring for 30 minutes. The precipitate was filtered and the product was purified by column chromatography on silica gel, eluting with a gradient of 1-5% methanol in dichloromethane. Clean fractions were concentrated and the product was slurried in hot acetonitrile. The solid was filtered and dried to give 325 mg of N-{2-[4-amino-2-ethoxymethyl-7-(4-fluorobenzyloxy)-1H-imidazo[4,5-c]quinolin-1-yl]-1,1-dimethylethyl}methanesulfonamide as a white solid, mp 251.0-253.0° C.

MS (APCI) m/z 516 (M+H)$^+$;

Anal. Calcd. for $C_{25}H_{30}FN_5O_4S$: % C, 58.24; % H, 5.86; % N, 13.58. Found: % C, 57.94; % H, 6.21; % N, 13.34.

Example 127

N-{2-[4-Amino-2-ethoxymethyl-7-(3-methylbenzyloxy)-1H-imidazo[4,5-c]quinolin-1-yl]-1,1-dimethylethyl}methanesulfonamide Upon precipitation of the product from water, 20 g of solid sodium carbonate was added to the precipitate/water mixture followed by stirring for 30 minutes. The precipitate was recovered by filtration and the solid was purified by flash column chromatography on silica gel, eluting with a gradient of methanol:dichloromethane increasing from 1-5%. Clean fractions were concentrated and the product was slurried in hot acetonitrile. The solid was filtered and dried to give 600 mg of N-{2-[4-amino-2-ethoxymethyl-7-(3-methylbenzyloxy)-1H-imidazo[4,5-c]quinolin-1-yl]-1,1-dimethylethyl}methanesulfonamide as a white solid, mp 252.0-254.0° C.

MS (APCI) m/z 512 (M+H)$^+$;

Anal. Calcd. for $C_{26}H_{33}N_5O_4S$: % C, 61.04; % H, 6.50; % N, 13.69. Found: % C, 60.85; % H, 6.66; % N, 13.54.

Example 128

N-{2-[4-Amino-7-(benzthiazol-2-ylmethoxy)-2-ethoxymethyl-1H-imidazo[4,5-c]quinolin-1-yl]-1,1-dimethylethyl}methanesulfonamide The precipitate was purified by flash column chromatography on silica gel eluting with a gradient of 1-5% methanol in dichloromethane. Clean fractions were concentrated and the solid was recrystallized from acetonitrile to give 300 mg of N-{2-[4-amino-7-(benzthiazol-2-ylmethoxy)-2-ethoxymethyl-1H-imidazo[4,5-c]quinolin-1-yl]-1,1-dimethylethyl}methanesulfonamide as a white solid, mp 258.0-259.0° C.

MS (APCI) m/z 555 (M+H)$^+$;

Anal. Calcd. for $C_{26}H_{30}N_6O_4S_2$: % C, 56.30; % H, 5.45; % N, 15.15. Found: % C, 56.03; % H, 5.78; % N, 14.99.

Example 129

N-{2-[4-Amino-2-ethoxymethyl-7-(5-trifluoromethylfuran-2-ylmethoxy)-1H-imidazo[4,5-c]quinolin-1-yl]-1,1-dimethylethyl}methanesulfonamide The precipitate was purified by flash column chromatography on silica gel eluting with a gradient of 1-5% methanol in dichloromethane. Clean fractions were concentrated and the solid was recrystallized from acetonitrile to give 200 mg of N-{2-[4-amino-2-ethoxymethyl-7-(5-trifluoromethylfuran-2-ylmethoxy)-1H-imidazo[4,5-c]quinolin-1-yl]-1,1-dimethyl-ethyl}methanesulfonamide as a white solid, mp 186.0-188.0° C.

MS (APCI) m/z 556 (M+H)$^+$;

Anal. Calcd. for $C_{24}H_{28}F_3N_5O_5S$: % C, 51.89; % H, 5.08; % N, 12.61. Found: % C, 51.95; % H, 4.89; % N, 12.53.

Example 130

Ethyl 5-[4-Amino-2-ethoxymethyl-1-(2-methanesulfonylamino-2-methylpropyl)-1H-imidazo[4,5-c]quinolin-7-yloxymethyl]furan-2-carboxylate The precipitate was purified by flash column chromatography on silica gel eluting with a gradient of 1-5% methanol in dichloromethane. Clean fractions were concentrated and slurried in ice cold acetonitrile. The solid was filtered and dried to give 125 mg of ethyl 5-[4-amino-2-ethoxymethyl-1-(2-methanesulfonylamino-2-methylpropyl)-1H-imidazo[4,5-c]quinolin-7-yloxymethyl]furan-2-carboxylate as a white powder, mp 122.0-123.0° C.

MS (APCI) m/z 560 (M+H)+;

Anal. Calcd. for $C_{26}H_{33}N_5O_7S$: % C, 54.48; % H, 6.07; % N, 12.22. Found: % C, 54.54; % H, 5.93; % N, 12.38.

Example 131

1-(2-Methylpropyl)-2-methoxymethyl-8-[3-(pyridin-3-yl)propoxy]-1H-imidazo[4,5-c]quinolin-4-amine

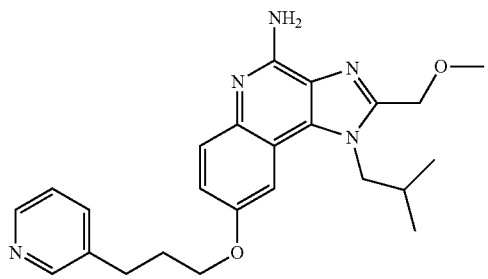

Part A

6-Benzyloxy-$N^4$-(2-methylpropyl)quinoline-3,4-diamine was dissolved in 200 mL of dichloromethane and methoxyacetyl chloride (1.85 g, 17.1 mmol), diluted in 10 mL of dichloromethane, was added dropwise. After 1 hour, the solvent was removed and the resulting solid was dissolved in 250 mL of 3:1 methanol:water. Aqueous potassium carbonate (6M) was added and the reaction was heated at reflux temperature for 3 hours. The solvent was removed and the residue was partitioned between 200 mL of dichloromethane and 100 mL of water. The aqueous fraction was isolated and extracted three times with dichloromethane. The combined organic fractions were dried, filtered, and concentrated under reduced pressure. The resulting material was purified by flash column chromatography on silica gel eluting with a gradient of 0-4% methanol in dichloromethane. The clean fractions were combined and concentrated to give 4.2 g of 8-benzyloxy-1-(2-methylpropyl)-2-methoxymethyl-1H-imidazo[4,5-c]quinoline as a light brown solid.

Part B

3-Chloroperoxybenzoic acid (60% pure, 3.5 g, 12.3 mmol) was added portionwise to a solution of 8-benzyloxy-1-(2-methylpropyl)-2-methoxymethyl-1H-imidazo[4,5-c]quinoline (4.2 g, 11.19 mmol) in 200 mL of dichloromethane. The reaction was stirred at ambient temperature for 2 hours, and then 100 mL of 2% aqueous sodium carbonate was added. The aqueous layer was extracted with two 100 mL portions of dichloromethane and the organic fractions were combined, dried, and concentrated to give 4.3 g of crude 8-benzyloxy-1-(2-methylpropyl)-2-methoxymethyl-5-oxido-1H-imidazo[4,5-c]quinoline as a light brown solid.

MS (APCI) m/z 392 (M+H)+.

Part C

Phosphorous oxychloride (1.78 g, 11.6 mmol) was added dropwise to a solution of 8-benzyloxy-1-(2-methylpropyl)-2-methoxymethyl-5-oxido-1H-imidazo[4,5-c]quinoline in 10 mL of DMF. After 1 hour, the reaction was poured onto 700 mL of ice and stirred overnight. Solid potassium carbonate was then added until the pH of the reached 10. After 30 minutes of stirring, the mixture was filtered. The resulting solid was washed with water and dried under a stream of air to give 3.75 g of 8-benzyloxy-4-chloro-1-(2-methylpropyl)-2-methoxymethyl-1H-imidazo[4,5-c]quinoline as a yellow-tan solid.

MS (APCI) m/z 410 (M+H)+.

Part D

8-Benzyloxy-4-chloro-1-(2-methylpropyl)-2-methoxymethyl-1H-imidazo[4,5-c]quinoline (2.73 g, 6.65 mmol) was stirred for 1 hour in 25 mL of 30% hydrogen bromide in acetic acid at 65° C. The reaction was cooled in an ice bath and aqueous NaOH (50%) was added to adjust the pH to 7. The precipitate was recovered by filtration and air dried to provide 2.75 g of 4-bromo-1-(2-methylpropyl)-2-methoxymethyl-1H-imidazo[4,5-c]quinolin-8-ol as a brown solid.

Part E

A slurry of 4-bromo-1-(2-methylpropyl)-2-methoxymethyl-1H-imidazo[4,5-c]quinolin-8-ol (600 mg, 1.64 mmol) in 15 mL of 7N methanolic ammonia was heated to 120° C. for 9 hours in a Parr bomb apparatus. After additional heating to 150° C. for 36 hours, the reaction was cooled and concentrated to dryness. The crude 4-amino-1-(2-methypropyl)-2-methoxymethyl-1H-imidazo[4,5-c]quinolin-8-ol was dissolved in 10 mL of DMF and cesium carbonate (800 mg, 2.64 mmol) was added. After 10 minutes, propargyl bromide (80% in toluene, 268 mg, 1.80 mmol) was added and the reaction was stirred overnight. The reaction was then poured into 250 mL of water and solid potassium carbonate was added to keep the mixture basic. A precipitate formed which was filtered and dried under a flow of air to give 450 mg of 1-(2-methylpropyl)-2-methoxymethyl-8-(prop-2-ynloxy)-1H-imidazo[4,5-c]quinolin-4-amine, MS (ESI) m/z 339 (M+H)+.

Part F

A mixture of 1-(2-methylpropyl)-2-methoxymethyl-8-(prop-2-ynloxy)-1H-imidazo[4,5-c]quinolin-4-amine (300 mg, 0.88 mmol), 3-iodopyridine (200 mg, 0.98 mmol), anhydrous triethylamine (0.3 mL, 2.22 mmol), Pd $Cl_2(PPh_3)_2$ (12 mg, 0.01 mmol), and copper (I) iodide (6 mg, 0.03 mmol) in 10 mL of DMF was heated to 60° C. After 4 hours, the reaction was cooled to ambient temperature and stirred overnight. The reaction mixture was poured into 200 mL of water and 30 mL of saturated potassium carbonate and stirred overnight. The resulting black precipitate was filtered and purified by flash column chromatography on silica gel, eluting with a gradient of 0-7% methanol in dichloromethane. The clean fractions were combined and concentrated to give 160 mg of 1-(2-methylpropyl)-2-methoxymethyl-8-[(3-pyridin-3-yl)prop-2-ynloxy]-1H-imidazo[4,5-c]quinolin-4-amine as a glass-like solid.

MS (ESI) m/z 416 (M+H)+.

Part G 1-(2-Methylpropyl)-2-methoxymethyl-8-[(3-pyridin-3-yl)prop-2-ynloxy]-1H-imidazo[4,5-c]quinolin-4-amine (150 mg, 0.36 mmol) was dissolved in a minimal amount of 1:1 ethanol:methanol and 200 mg of 10% palladium on carbon was added. The mixture was shaken for 2 days under 50 psi (3.4×10⁵ Pa) of hydrogen. The reaction was filtered and concentrated to dryness. The solid material was purified by flash column chromatography on silica gel eluting with a gradient of 0-30% CMA in chloroform. The clean fractions were combined, concentrated, and recrystallized from acetonitrile to give 25 mg of 1-(2-methylpropyl)-2-methoxymethyl-8-[3-(pyridin-3-yl)propoxy]-1H-imidazo[4,5-c]quinolin-4-amine as off-white crystals, mp 158.0-159.0.

MS (APCI) m/z 420 (M+H)+;

Anal. Calcd. for $C_{24}H_{29}N_5O_2$: % C, 68.71; % H, 6.97; % N, 16.69. Found: % C, 68.48; % H, 7.12; % N, 16.62.

Example 132

1-[4-Amino-2-ethoxymethyl-7-[3-(pyrazin-2-yl) propoxy]-1H-imidazo[4,5-c]quinolin-1-yl]-2-methylpropan-2-ol

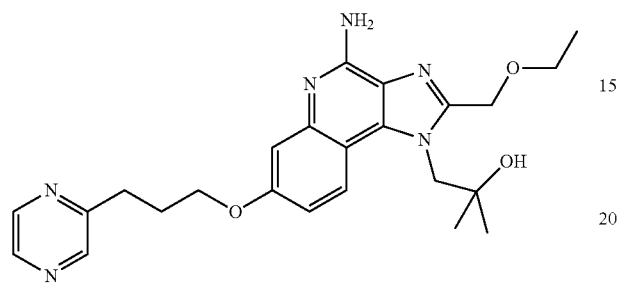

Part A 1-(4-Amino-2-ethoxymethyl-7-(prop-2-ynyloxy)-1H-imidazo[4,5-c]quinolin-1-yl)-2-methylpropan-2-ol (800 mg, 2.17 mmol) was combined in 40 mL of DMF with iodopyrazine (492 mg, 2.39 mmol), anhydrous triethylamine (0.786 mL, 5.64 mmol), PdCl$_2$(PPh$_3$)$_2$ (30 mg, 0.04 mmol), and copper(I) iodide (17 mg, 0.09 mmol). The mixture was heated to 60° C. overnight. Additional reagents were added, and after 5 days, the reaction was cooled to ambient temperature and stirred overnight. The reaction mixture was then poured into 400 mL of 50% aqueous potassium carbonate, upon which a milky brown precipitate formed. The aqueous solution was decanted and the solids were dissolved in dichloromethane, dried, and filtered. The filtrate was purified using silica gel chromatography eluting with a gradient of 0-8% methanol in dichloromethane. The purified fractions were concentrated to give 1-[4-amino-2-ethoxymethyl-7-[3-(pyrazin-2-yl)prop-2-ynloxy]-1H-imidazo[4,5-c]quinolin-1-yl]-2-methylpropan-2-ol as a white solid.

MS (APCI) m/z 447 (M+H)$^+$.

Part B

1-[4-Amino-2-ethoxymethyl-7-[3-(pyrazin-2-yl)prop-2-ynloxy]-1H-imidazo[4,5-c]quinolin-1-yl]-2-methylpropan-2-ol (400 mg, 0.89 mmol) was dissolved in a minimal amount of 1:1 methanol:ethanol and shaken with 10% palladium on carbon (400 mg) under 45 psi (3.1×10$^5$ Pa) of hydrogen for 18 hours. The mixture was filtered through a PTFE filter and the filtrate concentrated under reduced pressure. The resulting dark oil was purified by flash column chromatography eluting with a gradient of 0-6% methanol in dichloromethane. Clean fractions were concentrated. The solid was recrystallized from acetonitrile to provide 1-[4-amino-2-ethoxymethyl-7-[3-(pyrazin-2-yl)propoxy]-1H-imidazo[4,5-c]quinolin-1-yl]-2-methylpropan-2-ol (57 mg) as a white solid, mp 166.0-167.0.

MS (APCI) m/z 451 (M+H)$^+$;

Anal. Calcd. for $C_{24}H_{30}N_6O_3$: % C, 63.98; % H, 6.71; % N, 18.65. Found: % C, 63.66; % H, 6.54; % N, 18.62.

Example 133

2-Ethoxymethyl-1-propyl-8-(pyridin-3-ylmethoxy)-1H-imidazo[4,5-c]quinolin-4-amine

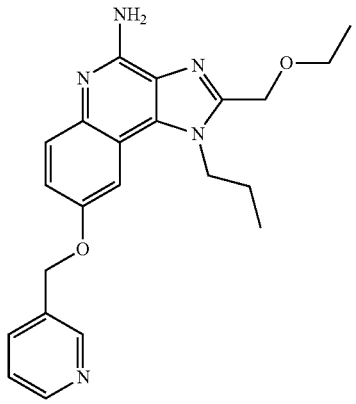

Part A

2-Ethoxymethyl-1-propyl-1H-imidazo[4,5-c]quinolin-8-ol was prepared by treating 8-benzyloxy-2-ethoxymethyl-1-propyl-1H-imidazo[4,5-c]quinoline, prepared in Parts A-F of Example 150, according to the method described in Example 5.

2-Ethoxymethyl-1-propyl-1H-imidazo[4,5-c]quinolin-8-ol (680 mg, 2.38 mmol) was dissolved in dichloromethane and mCPBA (60%, 750 mg, 2.62 mmol) was added. The reaction was monitored by TLC and when all of the starting material was determined to be consumed, 20 mL of 2% aqueous sodium carbonate was added. The organic layer was extracted with 2 additional portions of 2% sodium carbonate. The aqueous fractions were combined and concentrated hydrochloric acid was added dropwise until the pH reached 1. The pH was then adjusted to 5 with the portionwise addition of 2% sodium carbonate. A precipitate formed and was collected by filtration to give crude 2-ethoxymethyl-5-oxido-1-propyl-1H-imidazo[4,5-c]quinolin-8-ol as an off-white powder. The solid was combined in 50 mL of anhydrous THF with triphenylphosphine (1.2 g, 4.76 mmol) and pyridine-3-methanol (390 mg, 3.57 mmol). Diisopropyl azodicarboxylate (1.2 g, 5.95 mmol) was added dropwise. After 4 hours, additional portions of triphenyphosphine and pyridine-3-methanol followed by diisopropyldicarboxylate were added and the reaction was stirred for one hour. Water (1 mL) was added and the reaction stirred overnight. The reaction mixture was concentrated under reduced pressure and the resulting solid was dissolved in dichloromethane and washed 3 times with 50 mL portions of 2% aqueous sodium carbonate. The aqueous fractions were combined and extracted with chloroform. The organic fractions were combined, dried over magnesium sulfate, filtered, and concentrated to give crude 2-ethoxymethyl-5-oxido-1-propyl-8-(pyridin-3-ylmethoxy)-1H-imidazo[4,5-c]quinoline.

Part B

The crude 2-ethoxymethyl-5-oxido-1-propyl-8-(pyridin-3-ylmethoxy)-1H-imidazo[4,5-c]quinoline from Part A was dissolved in 50 mL of dichloromethane and trichloroacetyl isocyanate (540 mg, 2.85 mmol) was added dropwise. The reaction was monitored by thin layer chromatography and once the starting material was consumed, 2 mL of concentrated ammonium hydroxide was added. The reaction was stirred for 30 minutes and then passed through a column containing cation-exchange resin. The column was washed with methanol to remove impurities followed by elution of the desired product from the column with 2M ammonia in methanol. The volatiles were removed under reduced pressure. The resulting residue was dissolved in dichloromethane and purified by column chromatography on a HORIZON HPFC system. A silica gel cartridge was used eluting with a gradient of 0-8% methanol in dichloromethane. The solid was further purified by recrystallization from acetonitrile to give 2-ethoxymethyl-1-propyl-8-(pyridin-3-ylmethoxy)-1H-imidazo[4,5-c]quinolin-4-amine as light amber crystals, mp 190.0-191.0° C.

Anal. Calcd. for $C_{22}H_{25}N_5O_2$: % C, 67.50; % H, 6.44; % N, 17.89. Found: % C, 67.24; % H, 6.35; % N, 17.96.

Example 134

1-[4-Amino-2-(2-methoxyethyl)-7-[2-(pyrrol-1-yl)ethoxy]-1H-imidazo[4,5-c]quinolin-1-yl]-2-methylpropan-2-ol

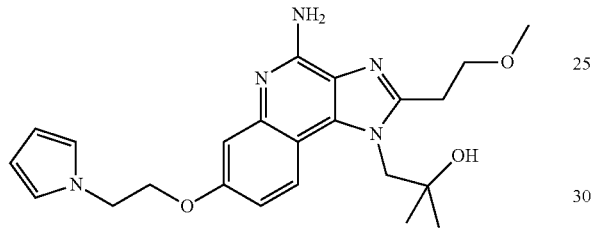

4-Amino-1-(2-hydroxy-2-methylpropyl)-2-(2-methoxyethyl)-1H-imidazo[4,5-c]quinolin-7-ol was alkylated as described in the general procedure for Examples 7-20, using 2 equivalents of cesium carbonate and 1.1 equivalents of 1-(2-bromoethyl)pyrrole. The reaction was heated overnight at 50° C. and then heated to 80° C. for an additional four hours. The reaction was cooled and poured into water containing 20 g of sodium chloride. The resulting precipitate was filtered and purified using column chromatography eluting with a gradient of 0-8% methanol in dichloromethane. The clean fractions were combined, concentrated, and recrystallized from acetonitrile to give 160 mg of 1-[4-amino-2-(2-methoxyethyl)-7-[2-(pyrrol-1-yl)ethoxy]-1H-imidazo[4,5-c]quinolin-1-yl]-2-methylpropan-2-ol as an off-white solid, mp 168.0-169.0° C.

MS (APCI) m/z 424 (M+H)$^+$;

Anal. Calcd. for $C_{23}H_{29}N_5O_3$: % C, 65.23; % H, 6.90; % N, 16.54. Found: % C, 65.16; % H, 7.16; % N, 16.69.

Example 135

1-(4-Amino-2-ethoxymethyl-7-[2-(1H-indol-3-yl)ethoxy]-1H-imidazo[4,5-c]quinolin-1-yl)-2-methylpropan-2-ol

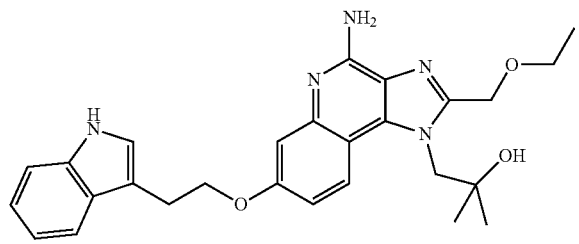

4-Amino-2-ethoxymethyl-1-(2-hydroxy-2-methylpropyl)-1H-imidazo[4,5-c]quinolin-7-ol (500 mg, 1.51 mmol), cesium carbonate (980 mg, 3.02 mmol), 3-(2-bromoethyl)indole (375 mg, 1.66 mmol), and DMF (10 mL) were combined and stirred at ambient temperature overnight followed by heating at 80° C. for 4 hours. The reaction mixture was cooled to ambient temperature and poured into 200 mL of water containing 20 g of sodium chloride. The resulting precipitate was filtered, dissolved in dichloromethane, and purified by flash column chromatography on silica gel, eluting with a gradient of 0-8% methanol in dichloromethane. Clean fractions were combined and concentrated. The solid was slurried in hot acetonitrile, filtered, and dried under reduced pressure to yield 305 mg of 1-(4-amino-2-ethoxymethyl-7-[2-(1H-indol-3-yl)ethoxy]-1H-imidazo[4,5-c]quinolin-1-yl)-2-methylpropan-2-ol as an off-white solid, mp 220.0-222.0° C.

MS (APCI) m/z 474 (M+H)$^+$;

Anal. Calcd. for $C_{27}H_{31}N_5O_3$: % C, 68.48; % H, 6.60; % N, 14.79. Found: % C, 68.27; % H, 6.80; % N, 14.87.

Example 136

1-[4-Amino-2-(2-methoxyethyl)-7-(5-methylisoxazol-3-ylmethoxy)-1H-imidazo[4,5-c]quinolin-1-yl]-2-methylpropan-2-ol

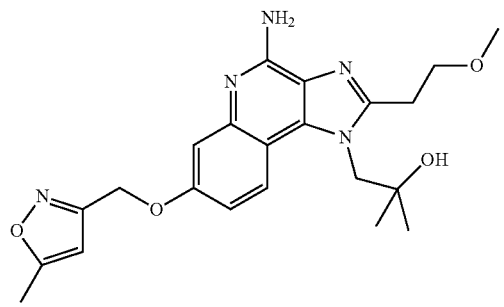

4-Amino-1-(2-hydroxy-2-methylpropyl)-2-(2-methoxyethyl)-1H-imidazo[4,5-c]quinolin-7-ol was alkylated as described in the general procedure for Examples 7-20, using 2 equivalents of cesium carbonate and 1.1 eq of 3-(bromomethyl)-5-methylisoxazole. After stirring overnight at room temperature, the reaction mixture was poured into 200 mL of water containing 20 g of sodium chloride. The resulting precipitate was filtered, dissolved in dichloromethane, and purified by flash column chromatography on silica gel, eluting with a gradient of 0-8% methanol in dichloromethane. The clean fractions were combined and concentrated. The resulting solid was slurried in cold acetonitrile, filtered, and dried under reduced pressure to yield 315 mg of 1-[4-amino-2-(2-methoxyethyl)-7-(5-methylisoxazol-3-ylmethoxy)-1H-imidazo[4,5-c]quinolin-1-yl]-2-methylpropan-2-ol as an off-white solid, mp 169.0-170.0.

MS (APCI) m/z 426 (M+H)$^+$;

Anal. Calcd. for $C_{22}H_{27}N_5O_4 \cdot 0.5 \, H_2O$: % C, 60.81; % H, 6.50; % N, 16.12. Found: % C, 61.05; % H, 6.36; % N, 16.26.

Example 137

1-[4-Amino-2-ethoxymethyl-7-(thiazol-4-yl-methoxy)-1H-imidazo[4,5-c]quinolin-1-yl]-2-methylpropan-2-ol

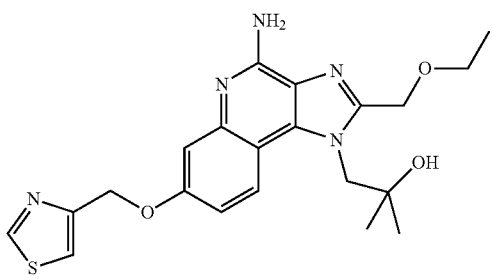

4-Amino-2-ethoxymethyl-1-(2-hydroxy-2-methylpropyl)-1H-imidazo[4,5-c]quinolin-7-ol (100 mg, 0.3 mmol), cesium carbonate (488 mg, 1.5 mmol), 4-(chloromethyl)thiazole.HCl (102 mg, 0.6 mmol), tetrabutylammonium bromide (96 mg, 0.3 mmol), triethylamine (0.5 ml), and DMF (10 mL) were combined and stirred at ambient temperature overnight. The reaction was concentrated under reduced pressure and dichloromethane was added to the residue. Undissolved solids were removed by filtration. The filtrate was concentrated under reduced pressure and subsequently purified by flash column chromatography on silica gel, eluting with a gradient of 0-4% methanol in dichloromethane. The clean fractions were combined and concentrated under reduced pressure. The resulting solid was recrystallized from acetonitrile to yield 62 mg of 1-[4-amino-2-ethoxymethyl-7-(thiazol-4-ylmethoxy)-1H-imidazo[4,5-c]quinolin-1-yl]-2-methylpropan-2-ol as a white powder, mp 190.0-191.0° C.

MS (APCI) m/z 428 $(M+H)^+$;

Anal. Calcd. for $C_{21}H_{25}N_5O_3S$: % C, 59.00; % H, 5.89; % N, 16.38. Found: % C, 58.94; % H, 5.90; % N, 16.59.

Example 138

1-[4-Amino-2-ethoxymethyl-7-(2-methylthiazol-4-ylmethoxy)-1H-imidazo[4,5-c]quinolin-1-yl]-2-methylpropan-2-ol

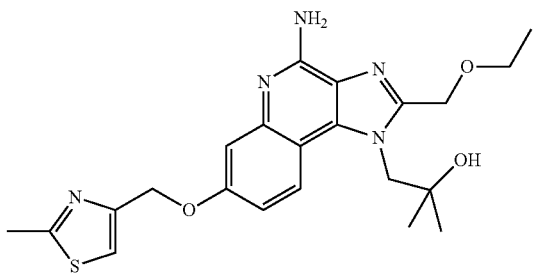

4-Amino-2-ethoxymethyl-1-(2-hydroxy-2-methylpropyl)-1H-imidazo[4,5-c]quinolin-7-ol (100 mg, 0.3 mmol), cesium carbonate (488 mg, 1.5 mmol), 4-(chloromethyl)-2-methylthiazole.HCl (110 mg, 0.6 mmol), tetrabutylammonium bromide (96 mg, 0.3 mmol), triethylamine (0.5 ml), and DMF (10 mL) were combined and stirred at ambient temperature overnight. The reaction was concentrated under reduced pressure and dichloromethane was added to the residue. Undissolved solids were removed by filtration. The filtrate was concentrated under reduced pressure and subsequently purified by flash column chromatography on silica gel, eluting with a gradient of 0-5% methanol in dichloromethane. The clean fractions were combined and concentrated under reduced pressure. The resulting solid was recrystallized from acetonitrile to yield 77 mg of 1-[4-amino-2-ethoxymethyl-7-(2-methylthiazol-4-ylmethoxy)-1H-imidazo[4,5-c]quinolin-1-yl]-2-methylpropan-2-ol as a white powder, mp 200.0-201.0° C.

MS (APCI) m/z 442 $(M+H)^+$;

Anal. Calcd. for $C_{22}H_{27}N_5O_3S$: % C, 59.84; % H, 6.16; % N, 15.86. Found: % C, 59.86; % H, 6.39; % N, 15.98.

Example 139

1-[4-Amino-2-ethoxymethyl-7-[2-(thiophen-2-yl)thiazol-4-ylmethoxy]-1H-imidazo[4,5-c]quinolin-1-yl]-2-methylpropan-2-ol

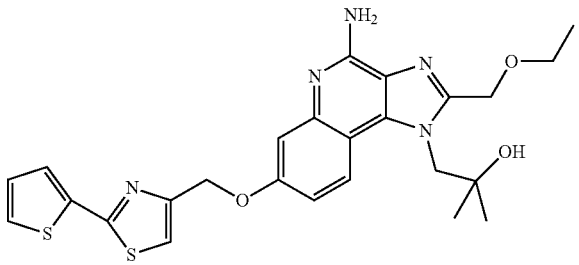

4-Amino-2-ethoxymethyl-1-(2-hydroxy-2-methylpropyl)-1H-imidazo[4,5-c]quinolin-7-ol (100 mg, 0.3 mmol), cesium carbonate (195 mg, 0.6 mmol), 4-(chloromethyl)-2-(2-thienyl)-1,3-thiazole (71 mg, 0.33 mmol), tetrabutylammonium bromide (10 mg, 0.03 mmol), triethylamine (0.5 ml), and acetonitrile (10 mL) were combined and stirred at ambient temperature overnight. The reaction was concentrated under reduced pressure and dichloromethane was added to the residue. Undissolved solids were removed by filtration. The filtrate was concentrated under reduced pressure and subsequently purified by flash column chromatography on silica gel, eluting with a gradient of 0-5% methanol in dichloromethane. The clean fractions were combined and concentrated under reduced pressure. The solid was recrystallized from acetonitrile to yield 82 mg of 1-[4-amino-2-ethoxymethyl-7-[2-(thiophen-2-yl)thiazol-4-ylmethoxy]-1H-imidazo[4,5-c]quinolin-1-yl]-2-methylpropan-2-ol as an off white powder, mp 192.0-194.0° C.

MS (APCI) m/z 510 $(M+H)^+$;

Anal. Calcd. for $C_{25}H_{27}N_5O_3S_2$: % C, 58.92; % H, 5.34; % N, 13.74. Found: % C, 58.68; % H, 5.24; % N, 13.82.

Example 140

1-[4-Amino-2-ethoxymethyl-7-[3-(thiophen-2-yl)-[1,2,4]oxadiazol-5-ylmethoxy]-1H-imidazo[4,5-c]quinolin-1-yl]-2-methyl-propan-2-ol

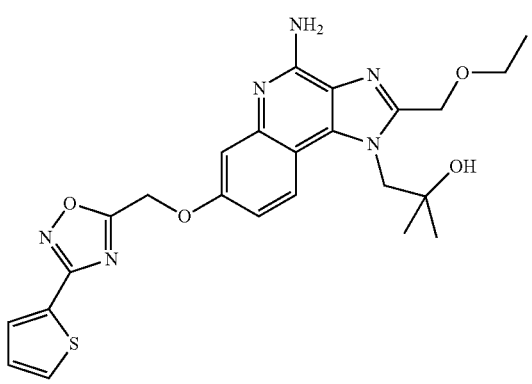

4-Amino-2-ethoxymethyl-1-(2-hydroxy-2-methylpropyl)-1H-imidazo[4,5-c]quinolin-7-ol (100 mg, 0.3 mmol), cesium carbonate (195 mg, 0.6 mmol), 5-(chloromethyl)-3-(2-thienyl)-1,2,4-oxadiazole (71 mg, 0.33 mmol), tetrabutylammonium bromide (10 mg, 0.03 mmol), triethylamine (0.5 ml), and acetonitrile (10 mL) were combined and stirred at ambient temperature overnight. The reaction was concentrated under reduced pressure and dichloromethane was added to the residue. Undissolved solids were removed by filtration. The filtrate was concentrated under reduced pressure and subsequently purified by flash column chromatography on silica gel, eluting with a gradient of 0-5% methanol in dichloromethane. The clean fractions were combined and concentrated under reduced pressure. The solid was recrystallized from acetonitrile to yield 71 mg of 1-[4-amino-2-ethoxymethyl-7-[3-(thiophen-2-yl)-[1,2,4]oxadiazol-5-ylmethoxy]-1H-imidazo[4,5-c]quinolin-1-yl]-2-methylpropan-2-ol as a white solid, mp 173.0-175.0° C.
MS (APCI) m/z 495 (M+H)$^+$;
Anal. Calcd. for $C_{24}H_{26}N_6O_4S_2$: % C, 58.29; % H, 5.30; % N, 16.99. Found: % C, 58.31; % H, 5.40; % N, 17.15.

Example 141

1-[4-Amino-2-ethoxymethyl-7-(1-methyl-1H-imidazol-2-ylmethoxy)-1H-imidazo[4,5-c]quinolin-1-yl]-2-methylpropan-2-ol

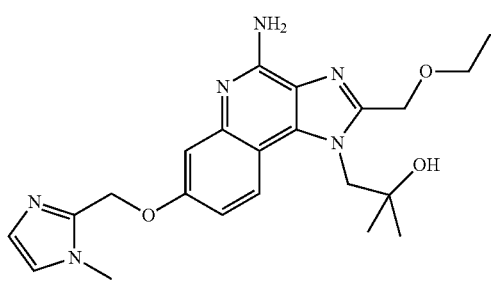

4-Amino-2-ethoxymethyl-1-(2-hydroxy-2-methylpropyl)-1H-imidazo[4,5-c]quinolin-7-ol (100 mg, 0.3 mmol), cesium carbonate (488 mg, 1.5 mmol), 2-chloromethyl-1-methyl-1H-imidazole.HCl (100 mg, 0.6 mmol), tetrabutylammonium bromide (96 mg, 0.3 mmol), triethylamine (0.5 ml), and DMF (10 mL) were combined and stirred at ambient temperature overnight. The reaction was concentrated under reduced pressure and dichloromethane was added to the residue. Undissolved solids were removed by filtration. The filtrate was concentrated under reduced pressure and subsequently purified by flash column chromatography on silica gel, eluting with a gradient of 0-5% methanol in dichloromethane. The clean fractions were combined and concentrated under reduced pressure. The resulting solid was recrystallized from isopropanol/diethylether to yield 40 mg of 1-[4-amino-2-ethoxymethyl-7-(1-methyl-1H-imidazol-2-ylmethoxy)-1H-imidazo[4,5-c]quinolin-1-yl]-2-methylpropan-2-ol as an off white solid, mp 200.0-202.0° C.
MS (APCI) m/z 425 (M+H)$^+$;
Anal. Calcd. for $C_{22}H_{28}N_6O_3$: % C, 62.25; % H, 6.65; % N, 19.80. Found: % C, 62.03; % H, 6.83; % N, 19.48.

Example 142

N-[2-(4-Amino-7-benzyloxy-2-ethoxymethyl-1H-imidazo[4,5-c]quinolin-1-yl)-1,1-dimethylethyl]acetamide

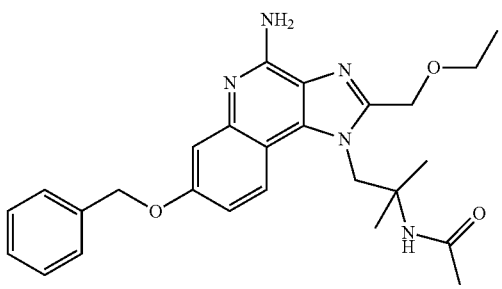

Part A (2-Amino-2-methylpropyl)-(7-benzyloxy-3-nitroquinolin-4-yl)amine (5.29 g, 14.44 mmol) was stirred in 100 mL of THF and sodium hydroxide (0.64 g in 50 mL of water) was added. Next, 3.82 g of di-tert-butyl dicarbonate in 50 mL of THF was added dropwise and the reaction was stirred for 24 hours at ambient temperature. Analysis of the reaction by TLC indicated that starting material was still present. An additional 0.55 g of di-tert-butyl dicarbonate in 20 mL of THF was added and the reaction was stirred for another 24 hours. The THF was removed under reduced pressure and dichloromethane was added. The organic fraction was separated from the aqueous fraction. The organic fraction was then sequentially washed with water followed by brine; dried over magnesium sulfate; filtered; and concentrated under reduced pressure to yield 7.04 g of tert-butyl[2-(7-benzyloxy-3-nitroquinolin-4-ylamino)-1,1-dimethylethyl]carbamate as a yellow foam.

Part B tert-Butyl[2-(7-benzyloxy-3-nitroquinolin-4-ylamino)-1,1-dimethylethyl]carbamate (6.74 g), 5% platinum on carbon (1.02 g), and acetonitrile (125 mL) were combined. The mixture was shaken overnight under 50 psi (3.4×10$^5$ Pa) of hydrogen. The reaction was filtered through CELITE filter agent and the filtrate was concentrated under reduced pressure to give 6.04 g of tert-butyl[2-(3-amino-7-benzyloxyquinolin-4-ylamino)-1,1-dimethylethyl]carbamate as an orange foam.

Part C

Ethoxyacetyl chloride (1.82 mL, 16.60 mmol) was added to a chilled (0° C.) solution of tert-butyl[2-(3-amino-7-benzyloxyquinolin-4-ylamino)-1,1-dimethylethyl]carbamate (6.04 g, 13.8 mmol) and triethylamine (3.86 mL, 27.68 mmol) in 150 mL of anhydrous dichloromethane. After stirring for 30 minutes, the cooling bath was removed and the reaction was stirred for 24 hours at ambient temperature. The volatiles were removed under reduced pressure and the resulting residue was dissolved in ethanol, followed by the addition of 3.86 mL of triethylamine. The reaction was heated at reflux for 2.5 days and then cooled to ambient temperature. The solvent was removed under reduced pressure and dichloromethane was added. The solution was sequentially washed with aqueous sodium bicarbonate followed by brine; dried over sodium sulfate; filtered; and concentrated under reduced pressure. The residue was purified using flash column chromatography on silica gel, eluting with 5% methanol in dichloromethane. Clean fractions were concentrated; while fractions containing both the product and the starting material were resubmitted to the reaction conditions and repurified as described above. The combined lots provided a total of 5.07 g of tert-butyl[2-(7-benzyloxy-2-ethoxymethyl-1H-imidazo[4,5-e]quinolin-1-yl)-1,1-dimethylethyl]carbamate was obtained as an orange foam.

Part D

HCl in ethanol (3M, 75 mL) was added to tert-butyl[2-(7-benzyloxy-2-ethoxymethyl-1H-imidazo[4,5-e]quinolin-1-yl)-1,1-dimethylethyl]carbamate (5.07 g, 10.04 mmol) and the solution was heated at reflux for 15 minutes. The volatiles were removed under reduced pressure and the orange residue was partitioned between dilute aqueous hydrochloric acid and dichloromethane. The aqueous layer was washed with 2 portions of dichloromethane and then made basic with the addition of aqueous ammonium hydroxide. The aqueous fraction was then extracted with three portions of dichloromethane. The combined organic fractions were washed with brine, dried over sodium sulfate, filtered, and concentrated to yield 3.77 g of 2-(7-benzyloxy-2-ethoxymethyl-1H-imidazo[4,5-e]quinolin-1-yl)-1,1-dimethylethylamine as a brown oil.

Part E 2-(7-Benzyloxy-2-ethoxymethyl-1H-imidazo[4,5-e]quinolin-1-yl)-1,1-dimethylethylamine (1.88 g, 4.65 mmol), triethylamine (1.3 mL, 9.3 mmol), and dichloromethane (50 mL) were combined and cooled to 0° C. Acetyl chloride (0.36 mL, 5.11 mmol) was added and the reaction was stirred for 30 minutes. The cooling bath was removed and the reaction was stirred for an additional 3.5 hours. Water was added and the layers were separated. The organic fraction was sequentially washed with brine; dried over sodium sulfate; filtered; and concentrated under reduced pressure to provide a tan solid. The solid was purified by flash column chromatography on silica gel (eluting with a gradient of 6-7.5% methanol in dichloromethane) to yield 1.71 g of N-[2-(7-benzyloxy-2-ethoxymethyl-1H-imidazo[4,5-c]quinolin-1-yl)-1,1-dimethylethyl]acetamide as a cream colored solid.

Part F mCPBA (60% pure, 1.70 g,) was added to a solution of N-[2-(7-benzyloxy-2-ethoxymethyl-1H-imidazo[4,5-c]quinolin-1-yl)-1,1-dimethylethyl]acetamide (1.71 g, 3.83 mmol) in chloroform (100 mL). The reaction was stirred for 4 hours and then an additional 0.57 g of mCPBA was added. The reaction was stirred for 2 more hours and then quenched by adding aqueous 1% sodium carbonate. The layers were separated and the aqueous fraction was extracted with five portions of chloroform. The combined organic fractions were washed with brine, dried over sodium sulfate, filtered, and concentrated to give 1.78 g of crude N-[2-(7-benzyloxy-2-ethoxymethyl-5-oxido-1H-imidazo[4,5-c]quinolin-1-yl)-1,1-dimethylethyl]acetamide as an orange foam.

Part G

N-[2-(7-Benzyloxy-2-ethoxymethyl-5-oxido-1H-imidazo[4,5-c]quinolin-1-yl)-1,1-dimethylethyl]acetamide (1.77 g, 3.83 mmol) was dissolved in dichloromethane (100 mL) and aqueous ammonium hydroxide (10 mL) was added, followed by para-toluenesulfonyl chloride (0.73 g, 3.83 mmol). After stirring for 5 hours, the organic and aqueous phases were separated and the organic fraction was washed twice with saturated sodium bicarbonate and then once with brine. The organic fraction was then dried over sodium sulfate, filtered, and concentrated to give a dark orange solid. The solid was purified by flash column chromatography on silica gel (eluting with a gradient of 6-7.5% methanol in dichloromethane) followed by recrystallization from acetonitrile to provide 1.27 g of N-[2-(4-amino-7-benzyloxy-2-ethoxymethyl-1H-imidazo[4,5-c]quinolin-1-yl)-1,1-dimethylethyl]acetamide as a white powder, mp 202.0-205.0° C.

$^1$H NMR (300 MHz, DMSO-$d_6$) δ 8.23 (d, J=9.04 Hz, 1H), 7.01 (s, 1H), 7.48 (m, 2H), 7.41-7.31 (m, 3H), 7.10 (d, J=2.6 Hz, 1H), 6.92 (dd, J=9.0, 2.6 Hz, 1H), 6.54 (s, 2H), 5.19 (s, 2H), 4.93 (s, 2H), 4.69 (s, 2H), 3.49 (q, J=7.0 Hz, 2H), 1.80 (s, 3H), 1.18 (s, 6H), 1.11 (t, J=7.0 Hz, 3H);

$^{13}$C NMR (75 MHz, DMSO-$d_6$) δ 167.8, 155.0, 150.2, 147.4, 145.0, 135.1, 132.5, 126.3, 125.6, 125.5, 122.9, 120.1, 109.1, 107.3, 106.5, 66.9, 63.2, 62.1, 52.5, 48.6, 23.4, 21.5, 12.8;

MS (APCI) m/z 462 (M+H)$^+$;

Anal. Calcd. for $C_{26}H_{31}N_5O_3 \cdot 0.37 H_2O$: C, 66.70; H, 6.83; N, 14.96. Found: C, 67.05; H, 6.83; N, 15.08.

Example 143

N-[2-(4-Amino-2-ethoxymethyl-7-hydroxy-1H-imidazo[4,5-c]quinolin-1-yl)-1,1-dimethylethyl]acetamide

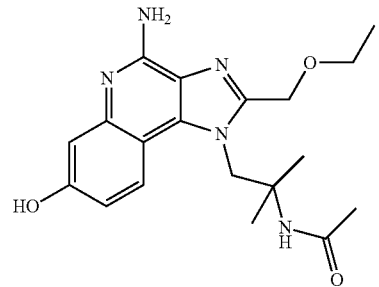

N-[2-(4-Amino-7-benzyloxy-2-ethoxymethyl-1H-imidazo[4,5-c]quinolin-1-yl)-1,1-dimethylethyl]acetamide (0.72 g, 1.56 mmol) was dissolved in 200 mL of warm ethanol. 10% Palladium on carbon (0.33 g) was added and the mixture was shaken overnight under 50 psi (3.4×10$^5$ Pa) of hydrogen. The reaction was filtered through CELITE filter agent, and the filtrate was removed under reduced pressure. The resulting brown solid was purified by flash column chromatography on silica gel, eluting with 14% methanol in dichloromethane. The fractions containing the desired product were combined and further purified by column chromatography on a HORIZON HPFC system. A silica gel cartridge was used with the eluent being a gradient of 30-50% CMA in chloroform. The clean fractions were combined and concentrated under reduced pressure to provide 0.23 g of N-[2-(4-amino-2-ethoxymethyl-7-hydroxy-1H-imidazo[4,5-c]quinolin-1-yl)-1,1-dimethylethyl]acetamide as an off-white solid, m.p. 140° C.

$^1$H NMR (300 MHz, DMSO-$d_6$) δ 9.50 (s, 1H), 8.15 (d, J=8.9 Hz, 1H), 7.72 (s, 1H), 6.93 (d, J=2.5 Hz, 1H), 6.75 (dd, J=8.9, 2.5 Hz, 1H), 6.46 (s, 2H), 4.93 (s, 2H), 4.70 (s, 2H), 3.50 (q, J=7.0 Hz, 2H), 1.82 (s, 3H), 1.20 (s, 6H), 1.12 (t, J=7.0 Hz, 3H);

$^{13}$C NMR (75 MHz, DMSO-$d_6$) δ 170.3, 156.7, 152.5, 149.4, 147.8, 135.2, 125.1, 122.5, 111.7, 110.1, 108.8, 65.7, 64.6, 55.1, 51.0, 25.9, 24.0, 15.3;

MS (APCI) m/z 372 (M+H)$^+$;

Anal. Calcd. for $C_{19}H_{25}N_5O_3 \cdot 0.32\ H_2O$: C, 60.50; H, 6.85; N, 18.57. Found: C, 60.30; H, 6.66; N, 18.42.

Example 144

N-[2-(4-Amino-7-benzyloxy-2-ethoxymethyl-1H-imidazo[4,5-c]quinolin-1-yl)-1,1-dimethylethyl]-N'-isopropylurea

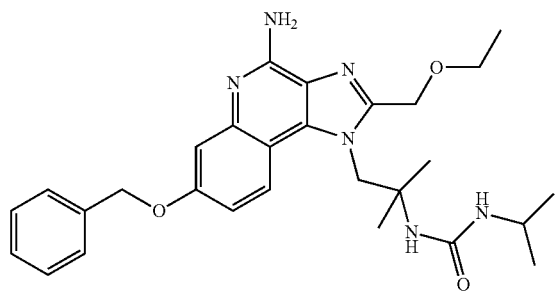

Part A 2-(7-Benzyloxy-2-ethoxymethyl-1H-imidazo[4,5-c]quinolin-1-yl)-1,1-dimethylethylamine (1.88 g, 4.65 mmol) and dichloromethane (50 mL) were combined and cooled to 0° C. Isopropyl isocyanate (0.50 mL, 5.11 mmol) was added and the reaction was stirred for 30 minutes. The cooling bath was removed and the reaction was stirred overnight. The volatiles were removed under reduced pressure to give a brown solid. The solid was purified by flash column chromatography on silica gel (eluting with 6% methanol in dichloromethane) to yield 1.96 g of N-[2-(7-benzyloxy-2-ethoxymethyl-1H-imidazo[4,5-c]quinolin-1-yl)-1,1-dimethylethyl]-N'-isopropylurea as a cream colored solid.

Part B mCPBA (60% pure, 1.18 g) was added to a solution of N-[2-(7-benzyloxy-2-ethoxymethyl-1H-imidazo[4,5-c]quinolin-1-yl)-1,1-dimethylethyl]-N'-isopropylurea (1.96 g, 4.0 mmol) in chloroform (50 mL). The reaction was stirred for 3 hours and then an additional 0.53 g of mCPBA was added. The reaction was stirred for 2 more hours and then quenched with aqueous 1% sodium carbonate. The layers were separated and the aqueous fraction was extracted with dichloromethane. The combined organic fractions were washed with brine, dried over sodium sulfate, filtered, and concentrated under reduced pressure to yield 2.2 g of crude N-[2-(7-benzyloxy-2-ethoxymethyl-5-oxido-1H-imidazo[4,5-c]quinolin-1-yl)-1,1-dimethylethyl]-N'-isopropylurea as an orange foam.

Part C

N-[2-(7-Benzyloxy-2-ethoxymethyl-5-oxido-1H-imidazo[4,5-c]quinolin-1-yl)-1,1-dimethylethyl]-N'-isopropylurea (2.02 g, 4.0 mmol) was dissolved in dichloromethane (50 mL) and aqueous ammonium hydroxide (10 mL) was added, followed by para-toluenesulfonylchloride (0.76 g, 4.0 mmol). After stirring for 4 hours, the organic and aqueous phases were separated and the organic fraction was washed twice with saturated sodium bicarbonate and then once with brine. The organic fraction was then dried over sodium sulfate, filtered, and concentrated to give 2.03 g of an orange solid. The solid was recrystallized from acetonitrile. Residual acetonitrile was removed from the product by dissolving the solid in 1:1 dichloromethane/methanol and removing the solvents under reduced pressure. 1.28 g of N-[2-(4-amino-7-benzyloxy-2-ethoxymethyl-1H-imidazo[4,5-c]quinolin-1-yl)-1,1-dimethylethyl]-N'-isopropylurea was recovered as a cream colored solid, mp 110° C.

$^1$H NMR (300 MHz, DMSO-$d_6$) δ 8.23 (d, J=9.10 Hz, 1H), 7.47 (m, 2H), 7.41-7.31 (m, 3H), 7.10 (d, J=2.63 Hz, 1H), 6.92 (dd, J=9.02, 2.63 Hz, 1H), 6.54 (s, 2H), 5.66 (m, 2H), 5.18 (s, 2H), 4.92 (s, 2H), 4.70 (br s, 2H), 3.71 (m, 1H), 3.49 (q, J=6.98 Hz, 2H), 1.15 (br s, 6H), 1.11 (t, J=6.98 Hz, 3H), 1.04 (d, J=6.50, 6H);

$^{13}$C NMR (75 MHz, DMSO-$d_6$) δ 157.5, 157.2, 152.7, 150.2, 147.5, 137.6, 134.9, 128.8, 128.1, 127.9, 125.4, 122.6, 111.7, 109.9, 108.9, 69.4, 65.7, 64.4, 54.2, 51.9, 40.9, 26.4, 23.6, 15.3;

MS (APCI) m/z 505 (M+H)$^+$;

Anal. Calcd. for $C_{28}H_{36}N_6O_3 \cdot 0.45\ H_2O$: C, 65.59; H, 7.25; N, 16.39. Found: C, 65.83; H, 7.65; N, 16.50.

Example 145

N-[2-(4-Amino-2-ethoxymethyl-7-hydroxy-1H-imidazo[4,5-c]quinolin-1-yl)-1,1-dimethylethyl]-N'-isopropylurea

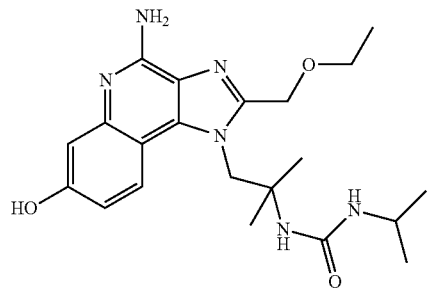

N-[2-(4-Amino-7-benzyloxy-2-ethoxymethyl-1H-imidazo[4,5-c]quinolin-1-yl)-1,1-dimethylethyl]-N'-isopropylurea (0.94 g, 1.66 mmol) was dissolved in 100 mL of warm ethanol and then cooled back to ambient temperature. 10% Palladium on carbon (0.35 g) was added and the mixture was shaken overnight under 50 psi ($3.4 \times 10^5$ Pa) of hydrogen. The reaction was filtered through CELITE filter agent, and the filter pad was washed sequentially with ethanol and methanol. The filtrate was concentrated under reduced pressure. The resulting off white solid was purified by flash column chromatography on silica gel (eluting with 90:10:1 dichloromethane/methanol/aqueous ammonium hydroxide) to provide 0.53 g of N-[2-(4-amino-2-ethoxymethyl-7-hydroxy-1H-imidazo[4,5-c]quinolin-1-yl)-1,1-dimethylethyl]-N'-isopropylurea as an off-white powder, m.p. 163-168° C.

$^1$H NMR (300 MHz, DMSO-d$_6$) δ 9.48 (s, 1H), 8.13 (d, J=8.9 Hz, 1H), 6.93 (d, J=2.6 Hz, 1H), 6.75 (dd, J=8.6, 2.6 Hz, 1H), 6.44 (s, 2H), 5.70 (s, 1H), 5.67 (d, J=7.6 Hz, 1H), 4.91 (s, 2H), 4.70 (br s, 2H), 6.72 (m, 1H), 3.50 (q, J=7.0 Hz, 2H), 1.12 (t, J=7.0 Hz, 3H), 1.10 (br s, 6H), 1.06 (d, J=6.5 Hz, 6H);

$^{13}$C NMR (75 MHz, DMSO-d$_6$) δ 157.2, 156.6, 152.5, 149.7, 147.7, 135.1, 125.0, 122.5, 111.7, 110.1, 108.9, 65.6, 64.4, 54.2, 51.9, 40.9, 26.4, 23.6, 15.3;

MS (APCI) m/z 415 (M+H)$^+$;

Anal. Calcd. for C$_{21}$H$_{30}$N$_6$O$_3$.0.45 H$_2$O: C, 59.68; H, 7.37; N, 19.89. Found: C, 59.84; H, 7.27; N, 19.54.

Example 146

N-[2-(4-Amino-8-benzyloxy-2-ethoxymethyl-1H-imidazo[4,5-c]quinolin-1-yl)-1,1-dimethylethyl]methanesulfonamide

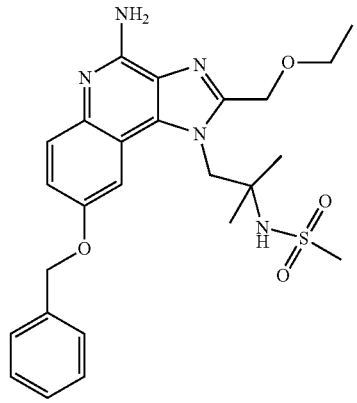

Part A (2-Amino-2-methylpropyl)-(6-benzyloxy-3-nitroquinolin-4-yl)amine was prepared according to the method described in Part A of Example 52, using 6-benzyloxy-4-chloro-3-nitroquinoline in lieu of 7-benzyoxy-4-chloro-3-nitroquinoline.

(2-Amino-2-methylpropyl)(6-benzyloxy-3-nitroquinolin-4-yl)amine (24.33 g, 66.4 mmol) was stirred in 400 mL of THF and sodium hydroxide (2.92 g in 100 mL of water) was added. Next, 17.40 g of di-tert-butyl dicarbonate in 100 mL of THF was added dropwise and the reaction was stirred overnight at ambient temperature. The THF was removed under reduced pressure and dichloromethane and water were added. The organic fraction was separated from the aqueous fraction. The organic fraction was then sequentially washed with water followed by brine; dried over sodium sulfate and magnesium sulfate; filtered; and concentrated under reduced pressure to yield 31.05 g of crude tert-butyl[2-(6-benzyloxy-3-nitroquinolin-4-ylamino)-1,1-dimethylethyl]carbamate as a brown foam.

Part B tert-Butyl[2-(6-benzyloxy-3-nitroquinolin-4-ylamino)-1,1-dimethylethyl]carbamate (13.75 g), 5% platinum on carbon (1.03 g), and acetonitrile (250 mL) were combined. The mixture was shaken overnight under 50 psi (3.4×10$^5$ Pa) of hydrogen. The reaction was filtered through CELITE filter agent, and the filter pad was rinsed with acetonitrile. The filtrate was concentrated under reduced pressure. Residual water was removed by an azeotrope with toluene. Removal of all volatiles under reduced pressure provided 13.34 g of crude tert-butyl[2-(3-amino-6-benzyloxyquinolin-4-ylamino)-1,1-dimethylethyl]carbamate as a brown foam.

Part C

Ethoxyacetyl chloride (3.5 mL, 32.0 mmol) was added to a solution of tert-butyl[2-(3-amino-6-benzyloxyquinolin-4-ylamino)-1,1-dimethylethyl]carbamate (12.71 g, 29.1 mmol) and triethylamine (8.1 mL, 58.2 mmol) in approximately 250 mL of anhydrous dichloromethane. After stirring for 2 hours, the volatiles were removed under reduced pressure and the resulting brown residue was dissolved in ethanol, followed by the addition of 8.1 mL of triethylamine. The reaction was heated at reflux for 2.5 days and then cooled to ambient temperature. The solvent was removed under reduced pressure and dichloromethane was added. The solution was sequentially washed with aqueous sodium bicarbonate (2×) followed by brine; dried over sodium sulfate; filtered, and concentrated under reduced pressure. The residue was purified by column chromatography on a HORIZON HPFC system. A silica gel cartridge was used eluting with a gradient of 0-15% CMA in chloroform to provide 8.4 g of tert-butyl[2-(8-benzyloxy-2-ethoxymethyl-1H-imidazo[4,5-c]quinolin-1-yl)-1,1-dimethylethyl]carbamate as an orange foam.

Part D

A 50 mL solution of HCl in ethanol (4.3 M) was added to a solution of tert-butyl[2-(8-benzyloxy-2-ethoxymethyl-1H-imidazo[4,5-c]quinolin-1-yl)-1,1-dimethylethyl]carbamate (8.4 g, 16.6 mmol) in ethanol (50 mL) and heated at reflux temperature for 1 hour. The reaction was cooled to ambient temperature and nitrogen was bubbled through the solution. The solvent was removed under reduced pressure and water was added to the residue. The solution was made basic and then extracted with three portions of dichloromethane. The combined organic fractions were washed with brine, dried over sodium sulfate, filtered, and concentrated to yield 6.26 g of 2-(8-benzyloxy-2-ethoxymethyl-1H-imidazo[4,5-c]quinolin-1-yl)-1,1-dimethylethylamine as a brown solid.

Part E 2-(8-Benzyloxy-2-ethoxymethyl-1H-imidazo[4,5-c]quinolin-1-yl)-1,1-dimethylethylamine (2.19 g, 5.4 mmol), triethylamine (1.5 mL, 10.8 mmol), and dichloromethane (50 mL) were combined. Methanesulfonic anhydride (1.04 g, 6.0 mmol) was added and the reaction was stirred overnight. Analysis by thin layer chromatography indicated that the reaction was not complete. An additional 0.2 g of methanesulfonic anhydride was added and the reaction was stirred for 2 more hours. Saturated sodium bicarbonate was added and the layers were separated. The organic fraction was sequentially washed with a second portion of saturated sodium bicarbonate and then brine; dried over sodium sulfate; filtered; and concentrated under reduced pressure to provide an orange foam. The residue was purified by column chromatography on a HORIZON HPFC system. A silica gel cartridge was used eluting with a gradient of 0-20% CMA in chloroform to provide 2.37 g of N-[2-(8-benzyloxy-2-ethoxymethyl-1H-imidazo[4,5-c]quinolin-1-yl)-1,1-dimethylethyl]methanesulfonamide as a white solid.

Part F mCPBA (60% pure, 1.45 g,) was added to a solution of N-[2-(8-benzyloxy-2-ethoxymethyl-1H-imidazo[4,5-c]quinolin-1-yl)-1,1-dimethylethyl]methanesulfonamide (2.37 g, 4.91 mmol) in chloroform (100 mL). The reaction was stirred for 2 hours and quenched by adding 50 mL of aqueous 2% sodium carbonate. The layers were separated and the aqueous fraction was extracted with two portions of chloroform. The combined organic fractions were washed with brine, dried over sodium sulfate, filtered, and concentrated to give 2.29 g of crude N-[2-(8-benzyloxy-2-ethoxymethyl-5- oxido-1H-imidazo[4,5-c]quinolin-1-yl)-1,1-dimethylethyl]methanesulfonamide as an orange foam.

Part G

N-[2-(8-Benzyloxy-2-ethoxymethyl-5-oxido-1H-imidazo[4,5-c]quinolin-1-yl)-1,1-dimethylethyl]methanesulfonamide (2.29 g, 4.59 mmol) was suspended in dichloromethane (75 mL) and trichloroacetyl isocyanate (0.71 mL, 5.97 mmol) was added dropwise. After stirring for 1 hour, the volatiles were removed under reduced pressure. The resulting orange residue was dissolved in methanol (75 mL) and 6 mL of sodium methoxide (21% in methanol) was added. The reaction was stirred for two additional hours and then the methanol was removed under reduced pressure. The residue was dissolved in dichloromethane and washed with water followed by brine. The organic fraction was dried over sodium sulfate, filtered and concentrated under reduced pressure to give an orange foam. The residue was purified by column chromatography on a HORIZON HPFC system. A silica gel cartridge was used eluting with a gradient of 10-30% CMA in chloroform to provide 1.88 g of N-[2-(4-amino-8-benzyloxy-2-ethoxymethyl-1H-imidazo[4,5-c]quinolin-1-yl)-1,1-dimethylethyl]methanesulfonamide as a white powder, mp 90° C.

Anal. Calcd. for $C_{25}H_{31}N_5O_4S \cdot 0.30\ H_2O$: C, 59.70; H, 6.33; N, 13.92. Found: C, 59.52; H, 6.24; N, 13.89.

Example 147

N-[2-(4-Amino-2-ethoxymethyl-8-hydroxy-1H-imidazo[4,5-c]quinolin-1-yl)-1,1-dimethylethyl]methanesulfonamide

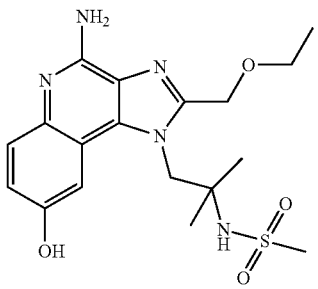

N-[2-(4-Amino-8-benzyloxy-2-ethoxymethyl-1H-imidazo[4,5-c]quinolin-1-yl)-1,1-dimethylethyl]methanesulfonamide (1.16 g, 2.33 mmol) was dissolved in 50 mL of ethanol and 10% palladium on carbon (0.46 g) was added. The mixture was shaken overnight under 50 psi ($3.4 \times 10^5$ Pa) of hydrogen. Dichloromethane (100 mL) and methanol (100 mL) were added and reaction was filtered through CELITE filter agent. The filter cake was washed with 200 mL of 1:1 dichloromethane:methanol. The filtrate was concentrated under reduced pressure to give a white solid. The solid was precipitated from a minimum amount of ethanol and then redissolved in dichloromethane containing a minimum amount of methanol. Aqueous ammonium hydroxide was added. The two phases were mixed by shaking and then separated. The organic fraction was discarded and the aqueous fraction was extracted with four portions of dichloromethane followed by two portions of ethyl acetate. The combined organic fractions were concentrated. The volume of the aqueous fraction was reduced, and a precipitate formed. The aqueous fraction was made basic by the addition of aqueous ammonium hydroxide and the resulting precipitate was recovered by filtration. The solid precipitate was combined with the residue from the organic fraction to give 0.75 g of crude product. This material was purified by column chromatography on a HORIZON HPFC system. A silica gel cartridge was used with the eluent being a gradient of 30-50% CMA in chloroform to provide 0.57 g of N-[2-(4-amino-2-ethoxymethyl-8-hydroxy-1H-imidazo[4,5-c]quinolin-1-yl)-1,1-dimethylethyl]methanesulfonamide as a white powder, m.p. 252-254° C.

$^1$H NMR (300 MHz, DMSO-$d_6$) δ 9.35 (s, 1H), 7.47 (m, 2H), 7.25 (s, 1H), 6.97 (dd, J=8.9, 2.4 Hz, 1H), 6.23 (s, 2H), 4.90 (br s, 2H), 4.77 (s, 2H), 3.54 (q, J=6.9 Hz, 2H), 3.00 (s, 3H), 1.32 (br s, 6H), 1.13 (t, J=7.0 Hz, 3H);

$^{13}$C NMR (125 MHz, DMSO-$d_6$) δ 151.8, 150.8, 150.3, 139.7, 133.9, 128.1, 127.2, 117.5, 115.9, 104.8, 65.7, 65.1, 57.6, 54.8, 44.7, 25.7, 15.3; MS (APCI) m/z 408 (M+H)$^+$;

Anal. Calcd. for $C_{18}H_{25}N_5O_4S \cdot 0.12\ H_2O$: C, 52.78; H, 6.21; N, 17.10; S, 7.83. Found: C, 52.48; H, 6.37; N, 16.92; S, 7.84.

Example 148

N-{2-[4-Amino-8-(benzyloxy)-2-(ethoxymethyl)-1H-imidazo[4,5-c]quinolin-1-yl]-1,1-dimethylethyl}cyclohexanecarboxamide

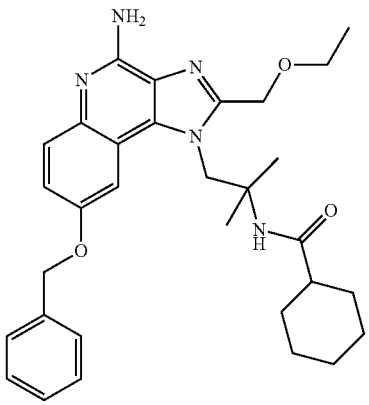

Part A 2-(8-Benzyloxy-2-ethoxymethyl-1H-imidazo[4,5-c]quinolin-1-yl)-1,1-dimethylethylamine (2.19 g, 5.4 mmol), triethylamine (1.5 mL, 10.8 mmol), and dichloromethane (50 mL) were combined. Cyclohexanecarbonyl chloride (0.95 mL, 6.0 mmol) was added and the reaction was stirred overnight. Saturated sodium bicarbonate was added and the layers were separated. The organic fraction was sequentially washed with a second portion of saturated sodium bicarbonate and then brine; dried over sodium sulfate; filtered; and concentrated under reduced pressure to provide an orange foam. The residue was purified by column chromatography on a HORIZON HPFC system. A silica gel cartridge was used eluting with a gradient of 0-20% CMA in chloroform to provide 2.34 g of N-{2-[8-(benzyloxy)-2-(ethoxymethyl)-1H-imidazo[4,5-c]quinolin-1-yl]-1,1-dimethylethyl}cyclohexanecarboxamide as a tan solid.

Part B mCPBA (60% pure, 1.34 g) was added to a solution of N-{2-[8-(benzyloxy)-2-(ethoxymethyl)-1H-imidazo[4,5-c]quinolin-1-yl]-1,1-dimethylethyl}cyclohexanecarboxamide (2.34 g, 4.55 mmol) in chloroform (100 mL). The reaction was stirred for 2 hours and quenched by adding 50 mL of aqueous 2% sodium carbonate. The layers were separated and the aqueous fraction was extracted with two portions of chloroform. The combined organic fractions were washed with brine, dried over sodium sulfate, filtered, and concentrated to give 2.68 g of crude N-{2-[8-(benzyloxy)-2-(ethoxymethyl)-5-oxido-1H-imidazo[4,5-c]quinolin-1-yl]-1,1-dimethylethyl}cyclohexanecarboxamide as an orange foam.

Part C

N-{2-[8-(benzyloxy)-2-(ethoxymethyl)-5-oxido-1H-imidazo[4,5-c]quinolin-1-yl]-1,1-dimethylethyl}cyclohexanecarboxamide (2.41 g, 4.55 mmol) was suspended in dichloromethane (75 mL) and trichloroacetyl isocyanate (0.70 mL, 5.92 mmol) was added dropwise. After stirring for 1 hour, the volatiles were removed under reduced pressure. The resulting orange residue was dissolved in methanol (75 mL) and 6 mL of sodium methoxide (21% in methanol) was added. The reaction was stirred overnight and then the methanol was removed under reduced pressure. The residue was dissolved in dichloromethane and washed with water followed by brine. The organic fraction was dried over sodium sulfate, filtered and concentrated under reduced pressure to give an orange foam. The residue was purified by column chromatography on a HORIZON HPFC system. A silica gel cartridge was used eluting with a gradient of 10-20% CMA in chloroform to yield 1.51 g of N-{2-[4-amino-8-(benzyloxy)-2-(ethoxymethyl)-1H-imidazo[4,5-c]quinolin-1-yl]-1,1-dimethylethyl}cyclohexanecarboxamide as a tan solid. A second purification of the product by column chromatography using the conditions described above provided an analytical sample, mp 90° C.

Anal. Calcd. for $C_{31}H_{39}N_5O_3 \cdot 0.20 H_2O$: C, 69.82; H, 7.45; N, 13.13. Found: C, 69.44; H, 6.62; N, 13.06.

Example 149

N-{2-[4-Amino-8-hydroxy-2-(ethoxymethyl)-1H-imidazo[4,5-c]quinolin-1-yl]-1,1-dimethylethyl}cyclohexanecarboxamide

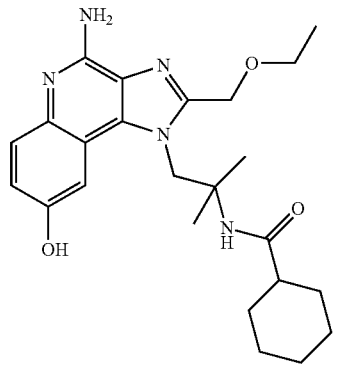

N-{2-[4-Amino-8-(benzyloxy)-2-(ethoxymethyl)-1H-imidazo[4,5-c]quinolin-1-yl]-1,1-dimethylethyl}cyclohexanecarboxamide (1.25 g, 2.36 mmol) was dissolved in 40 mL of ethanol and 10% palladium on carbon (0.58 g) was added. The mixture was shaken overnight under 50 psi ($3.4 \times 10^5$ Pa) of hydrogen. An additional 0.21 g of 10% palladium on carbon was added and the reaction was shaken under 50 psi ($3.4 \times 10^5$ Pa) of hydrogen for three more hours. The reaction was filtered through CELITE filter agent, and the filter cake was washed with 100 mL of ethanol. The filtrate was concentrated under reduced pressure. The resulting off white solid was purified by column chromatography on a HORIZON HPFC system. A silica gel cartridge was used eluting with a gradient of 10-30% CMA in chloroform to provide 0.56 g of N-{2-[4-amino-8-hydroxy-2-(ethoxymethyl)-1H-imidazo[4,5-c]quinolin-1-yl]-1,1-dimethylethyl}cyclohexanecarboxamide as a white powder, m.p. 231-232° C.

$^1$H NMR (300 MHz, DMSO-$d_6$) δ 9.34 (s, 1H), 7.50 (d, J=2.4 Hz, 1H), 7.46 (m, 2H), 6.97 (dd, J=8.9, 2.4 Hz, 1H), 6.22 (s, 2H), 4.90 (br s, 2H), 4.68 (br s, 2H), 3.50 (q, J=7.0 Hz, 2H), 2.12 (m, 1H), 1.71 (m, 6H), 1.35-1.13 (m, 10H), 1.09 (t, J=7.0 Hz, 3H); $^{13}$C NMR (125 MHz, DMSO-$d_6$) δ 176.4, 151.8, 150.6, 150.3, 139.6, 134.0, 128.0, 127.2, 117.5, 116.0, 104.8, 65.7, 64.5, 54.9, 51.3, 44.7, 29.5, 25.8, 25.7, 15.3;

MS (APCI) m/z 440 (M+H)$^+$;

Anal. Calcd. for $C_{24}H_{33}N_5O_3 \cdot 0.20 H_2O$: C, 65.05; H, 7.60; N, 15.80. Found: C, 64.69; H, 7.63; N, 15.71.

Example 150

8-Benzyloxy-2-ethoxymethyl-1-propyl-1H-imidazo[4,5-c]quinolin-4-amine

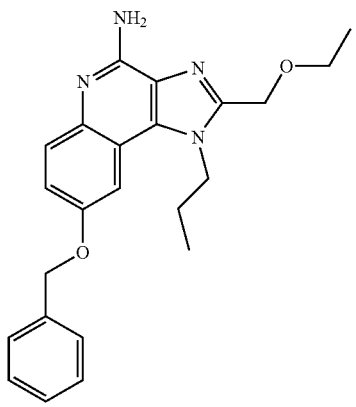

Part A

A mixture of triethyl orthoformate (170 mL, 1.0 mol) and 2,2-dimethyl-[1,3]-dioxane-4,6-dione (53.5 g, 0.37 mol) (Meldrum's acid) was heated at 55° C. for 90 minutes. A solution of 4-benzyloxyaniline (84.8 g, 0.43 mol) in methanol (150 mL) was slowly added to the reaction over a period 1 hour while maintaining the reaction temperature between 57-60° C. The reaction was cooled to 45° C. and stirred vigorously for 1.5 hours, allowed to cool to room temperature, and then stirred overnight. The reaction mixture was cooled to 1° C., and the product was isolated by filtration. The solid was washed with cold ethanol (~400 mL) until the filtrate was colorless. 5-{[(4-Benzyloxy)phenylimino]methyl}-2,2-dimethyl-[1,3]-dioxane-4,6-dione (142.4 g, wet with residual solvent) was isolated as a tan powder.

Part B

A solution of 5-{[(4-benzyloxy)phenylimino)]methyl}-2,2-dimethyl-[1,3]-dioxane-4,6-dione (127.2 g) and DOWTHERM A (500 mL) heat transfer fluid was heated to 100° C. and then slowly added to a flask containing DOWTHERM A heat transfer fluid (1 L, heated at 250° C.) over a period of 90 minutes. During the addition, the reaction temperature was not allowed to fall below 245° C. Following the addition, the reaction was stirred at 250° C. for 30 minutes, and then allowed to cool to ambient temperature. A precipitate formed, which was isolated by filtration, washed with diethyl ether (1 L) and acetone (250 mL), and dried for two hours under vacuum to provide 65.7 g of 6-benzyloxyquinolin-4-ol as a yellow powder.

Part C

A mixture of 6-benzyloxyquinolin-4-ol (65.7 g) and propionic acid (660 mL) was heated at 110° C. with vigorous stirring. Nitric acid (19.2 mL of 16 M) was slowly added over a period of 30 minutes while maintaining the reaction temperature below 120° C. After the addition, the reaction was allowed to cool to ambient temperature. The resulting solid was isolated by filtration, washed sequentially with propionic acid, isopropanol, and diethyl ether. The material was dried in a vacuum dessicator for 2 days to provide 46.0 g of 6-benzyloxy-3-nitroquinolin-4-ol as a tan powder.

The powder was suspended in DMF (300 mL). A preformed solution of phosphorous oxychloride in DMF (prepared as described in Part D of Example 1) was added dropwise to the reaction. Following the addition, the reaction was heated at 100° C. for 5 minutes; cooled to ambient temperature; and poured into ice water with stirring. A tan precipitate formed, which was isolated by filtration and dissolved in dichloromethane. The resulting solution was dried over magnesium sulfate, filtered, and concentrated under reduced pressure to yield 39.1 g of 6-benzyloxy-4-chloro-3-nitroquinoline as a tan solid.

The solid was dissolved in dichloromethane (790 ml) and triethylamine (38.5 mL, 0.28 mol) was added. n-Propylamine (19.5 mL, 0.24 mol) was then added over a period of 25 minutes, and the reaction was stirred for 18 hours. The reaction was diluted with dichloromethane (500 mL); washed sequentially with water and brine; dried over magnesium sulfate; filtered; and concentrated under reduced pressure. The crude product was recrystallized from 2-propanol to provide 39.1 g of (6-benzyloxy-3-nitroquinolin-4-yl)propylamine as fine, yellowish-brown needles.

Part D (6-Benzyloxy-3-nitroquinolin-4-yl)propylamine (26.2 g, 77.7 mmol), 5% platinum on carbon (5.2 g), toluene (600 mL) and 2-propanol (75 mL) were added to a Parr vessel. The vessel was purged with nitrogen and then placed under hydrogen pressure (30 psi, $2.1 \times 10^5$ Pa) and shaken for 20 minutes. The reaction mixture was filtered through a layer of CELITE filter aid, and the filter cake was washed sequentially with toluene (1 L) and 2-propanol (1 L). The orange filtrate was concentrated under reduced pressure. Heptane was added to the residue and subsequently removed under reduced pressure. The residue was dried under vacuum (0.1 torr, 13.3 Pa) for 30 minutes to provide 24.3 g of 6-benzyloxy-$N^4$-propylquinoline-3,4-diamine as a viscous, brown oil containing some toluene.

Part E

A solution of ethoxyacetyl chloride (10.46 g, 85.4 mmol) in dichloromethane (65 mL) was added dropwise to a solution of the crude product from Part D in dichloromethane (200 mL), and the reaction was stirred for 16 hours. A precipitate formed. The solid was isolated by filtration; washed with cold hexanes; and dried for 30 minutes under reduced pressure to yield 25.4 g of N-(6-benzyloxy-4-propylaminoquinolin-3-yl)-2-ethoxyacetamide hydrochloride as a tan powder.

Part F

Triethylamine (32.9 mL, 0.24 mol) was added to a solution of N-(6-benzyloxy-4-propylaminoquinolin-3-yl)-2-ethoxyacetamide hydrochloride (25.4 g) in ethanol (250 mL), and the reaction mixture was heated at reflux for 3 hours. The reaction mixture was allowed to cool to ambient temperature. The ethanol was removed under reduced pressure and the residue was dissolved in chloroform. The solution was washed sequentially with water and brine; dried over magnesium sulfate; filtered; and concentrated under reduced pressure. The resulting oil was dissolved in acetonitrile and concentrated under reduced pressure to yield 22.3 g of 8-benzyloxy-2-ethoxymethyl-1-propyl-1H-imidazo[4,5-c]quinoline as a brown, crystalline solid.

Part G

8-Benzyloxy-2-ethoxymethyl-1-propyl-1H-imidazo[4,5-c]quinoline (2.0 g, 5.3 mmol) was dissolved in chloroform (20 mL). 3-Chloroperoxybenzoic acid (60% pure, 1.53 g, 5.3 mmol) was added in one portion and the mixture was stirred for 25 minutes. Ammonium hydroxide (20 mL) was added and the biphasic mixture was stirred for 10 minutes. p-Toluenesulfonyl chloride (1.0 g, 5.3 mmol) was added in one portion and the reaction was stirred for an additional 1 hour. The layers were separated and the aqueous fraction was extracted with dichloromethane. The organic fractions were combined and washed successively with 5% aqueous sodium carbonate, water and saturated aqueous sodium chloride. The organic fraction was dried over anhydrous sodium sulfate, filtered and concentrated under reduced pressure. The residue was purified by flash column chromatography. The purification was carried out eluting with chloroform:CMA in a gradient from 99:1 to 93:7 to provide a red-brown solid. The solid was recrystallized from acetonitrile to yield 1.1 g of 8-benzyloxy-2-ethoxymethyl-1-propyl-1H-imidazo[4,5-c]quinolin-4-amine as red brown crystals, mp 152.5-154.0° C.

$^1$H NMR (300 MHz, DMSO-$d_6$) δ 7.60 (d, J=9.1 Hz, 1H), 7.50-7.31 (m, 6H), 7.21 (dd, J=9.1, 2.7 Hz, 1H), 6.35 (s, 2H), 5.26 (s, 2H), 4.76 (s, 2H), 4.51-4.45 (m, 2H), 3.55 (q, J=7.0 Hz, 2H), 1.88-1.76 (m, 2H), 1.16 (t, J=7.0 Hz, 3H), 0.96 (d, J=7.4 Hz, 3H);

$^{13}$C NMR (75 MHz, DMSO-$d_6$) δ 152.8, 150.6, 149.0, 140.1, 137.2, 132.7, 128.4, 127.7, 127.6, 127.4, 126.6, 117.3, 114.6, 103.0, 69.6, 65.3, 64.2, 46.7, 23.2, 14.9, 10.7;

MS (ESI) m/z 391.2143 (391.2134 calcd for $C_{23}H_{26}N_4O_2$, M+H);

Anal. Calcd. for $C_{23}H_{26}N_4O_2$: % C, 70.75; % H, 6.71; % N, 14.35. Found: % C, 70.49; % H, 6.87; % N, 14.28.

Example 151

7-Benzyloxy-1-[4-(1,1-dioxoisothiazolidin-2-yl)butyl]-2-ethoxymethyl-1H-imidazo[4,5-c]quinolin-4-amine

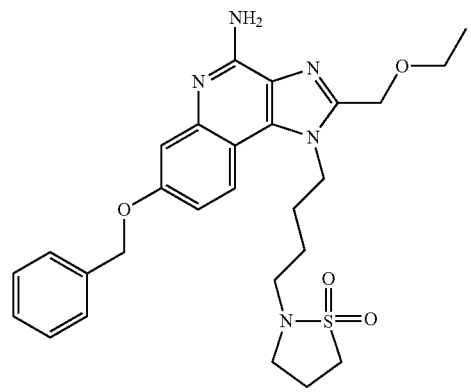

Part A tert-Butyl{4-[3-amino-7-(benzyloxy)quinolin-4-ylamino]butyl}carbamate (28.1 g, 64.3 mmol) was dissolved in dichloromethane (319 mL). Ethoxyacetyl chloride (7.87 g, 64.5 mmol) was added dropwise via an addition funnel and the mixture was stirred for 1 hour. The dichloromethane was removed under reduced pressure and the resulting residue was dissolved in a solution of triethylamine (35.84 mL, 0.26 mol) and ethanol (319 mL). The reaction was heated at reflux for 4 hours, and then allowed to cool overnight. The solvent was evaporated under reduced pressure and the residue was dissolved in dichloromethane. The organic fraction was washed sequentially with water and saturated aqueous sodium chloride; dried over anhydrous sodium sulfate; filtered; and concentrated under reduced pressure. The oily residue was dissolved in acetonitrile. The acetonitrile was subsequently removed under reduced pressure to provide 30 g of tert-butyl[4-(7-benzyloxy-2-ethoxymethyl-1H-imidazo[4,5-c]quinolin-1-yl)butyl]carbamate as a brown solid.

Part B tert-Butyl[4-(7-benzyloxy-2-ethoxymethyl-1H-imidazo[4,5-c]quinolin-1-yl)butyl]carbamate (21.0 g) was dissolved in ethanol (100 mL) and concentrated hydrochloric acid (13.0 mL). The reaction was heated at reflux for 1 hour and then cooled to ambient temperature. A tan precipitate formed. The solid was filtered and dried under vacuum for 16 hours to yield 12.1 g of 4-(7-benzyloxy-2-ethoxymethyl-1H-imidazo[4,5-c]quinolin-1-yl)butylamine dihydrochloride as a beige solid.

The solid was dissolved in a solution of dichloromethane (168 mL) and triethylamine (14.0 mL, 0.1 mol). 3-Chloropropanesulfonyl chloride (4.58 mL, 37.5 mmol) was added dropwise to the solution and the reaction was stirred for an additional 1.5 hours. The reaction mixture was treated with 5% aqueous sodium carbonate and the fractions were separated. The organic fraction was sequentially washed with water and saturated aqueous sodium chloride; dried over anhydrous sodium sulfate; filtered; and concentrated under reduced pressure to yield an oil.

The oil was dissolved in DMF. 1,8-Diazabicyclo[5.4.0]undec-7-ene, DBU, (5.70 mL, 38.0 mmol) was added and the reaction was stirred for 44 hours. The solvent was removed under reduced pressure. The residue was dissolved in dichloromethane and washed with water (3×). The organic fraction was dried over anhydrous sodium sulfate, filtered and concentrated under reduced pressure to yield 13.1 g of 7-benzyloxy-1-[4-(1,1-dioxoisothiazolidin-2-yl)butyl]-2-ethoxymethyl-1H-imidazo[4,5-c]quinoline as a viscous brown oil.

Part C

7-Benzyloxy-1-[4-(1,1-dioxoisothiazolidin-2-yl)butyl]-2-ethoxymethyl-1H-imidazo[4,5-c]quinoline (2.83 g) was dissolved in chloroform (30 mL). 3-Chloroperoxybenzoic acid (60% pure, 2.21 g, 7.7 mmol) was added in one portion and the mixture was stirred for 1 hour Ammonium hydroxide (30 mL) was added and the biphasic mixture was stirred for 20 minutes. p-Toluenesulfonyl chloride (1.07 g, 5.6 mmol) was added in one portion and the reaction was stirred for 16 hours. A white precipitate formed. The mixture was diluted with dichloromethane (solid remains in the organic fraction) and the layers were separated. The organic fraction was washed with 5% aqueous sodium bicarbonate (solid moves to the aqueous fraction). The layers were separated, followed by filtration of the solid from the aqueous fraction. The solid was sequentially washed with water and diethyl ether; slurried in acetonitrile; filtered; and dried to yield 1.5 g of 7-benzyloxy-1-[4-(1,1-dioxoisothiazolidin-2-yl)butyl]-2-ethoxymethyl-1H-imidazo[4,5-c]quinolin-4-amine as an off-white solid, mp 225-227° C.

$^1$H NMR (300 MHz, DMSO-d$_6$) δ 7.95 (d, J=9.0 Hz, 1H), 7.51-7.48 (m, 2H), 7.43-7.30 (m, 3H), 7.14 (d, J=2.6 Hz, 1H), 6.99 (dd, J=9.0, 2.6 Hz, 1H), 6.54 (s, 2H), 5.21 (s, 2H), 4.74 (s, 2H), 4.55-4.50 (m, 2H), 3.55 (q, J=7.0 Hz, 2H), 3.18-3.13 (m, 4H), 2.93 (t, J=6.7 Hz, 2H), 2.23-2.13 (m, 2H), 1.94-1.79 (m, 2H), 1.77-1.64 (m, 2H), 1.16 (t, J=7.0 Hz, 3H);

$^{13}$C NMR (75 MHz, DMSO-d$_6$) δ 157.3, 152.3, 148.0, 146.9, 137.2, 133.3, 128.4, 127.7, 127.5, 124.9, 121.4, 111.9, 108.8, 108.7, 69.1, 65.3, 64.1, 46.5, 46.1, 44.9, 27.1, 24.3, 18.3, 14.9;

MS (ESI) m/z 524.2347 (524.2332 calcd for $C_{27}H_{33}N_5O_4S$, M+H);

Anal. Calcd. for $C_{27}H_{33}N_5O_4S$: % C, 61.93; % H, 6.35; % N, 13.37; % S, 6.12. Found: % C, 61.11; % H, 6.28; % N, 13.15; % S, 6.07.

Example 152

7-Benzyloxy-1-[(2,2-dimethyl-[1,3]dioxolan-4-yl)methyl]-2-ethoxymethyl-1H-imidazo[4,5-c]quinolin-4-amine)

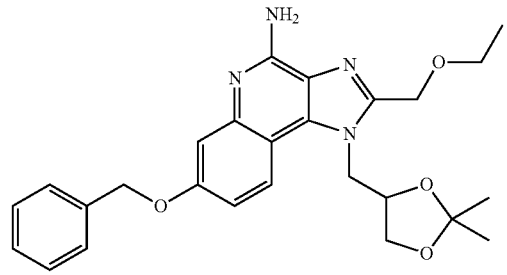

Part A

Triethylamine (31.88 mL, 228.77 mmol, 1.5 eq) was added to a solution of 7-benzyloxy-4-chloro-3-nitroquinoline (48.00 g, 152.51 mmol, 1 eq) in dichloromethane (400 mL). Dropwise addition of 2,2-dimethyl-1,3-dioxolan-4-methanamine (20.0 g, 152.51 mmol, 1 eq) to the reaction mixture followed, which was then stirred at ambient temperature for 6 hours. The crude reaction mixture was concentrated under reduced pressure, and the resulting solid was triturated with water and then stirred for 1 hour. The precipitate was collected by filtration, washed with water, dried, suspended in diethyl ether (400 mL), sonicated, and the resulting precipitate material was collected by filtration. The product was dried under vacuum at 40° C. for 12 hours to afford 60.1 g of (7-benzyloxy-3-nitro-quinolin-4-yl)[(2,2-dimethyl[1,3]dioxolan-4-yl)methyl]amine as a yellow solid, mp 154-155° C. $^1$H-NMR (300 MHz, CDCl$_3$) δ 9.74-9.62 (br m, 1H), 9.32 (s, 1H), 8.15 (d, J=9.4 Hz, 1H), 7.51-7.31 (m, 6H), 7.15 (dd, J=9.4, 2.7 Hz, 1H), 5.21 (s, 2H), 4.48-4.37 (m, 1H), 4.16-4.05 (m, 2H), 4.04-3.93 (m, 1H), 3.74 (dd, J=8.5, 5.9 Hz, 1H), 1.54 (s, 3H), 1.40 (s, 3H); MS (APCI) m/z 410.1 (M+H)$^+$.

Part B

A solution of sodium dithionate (85% pure, 135.07 g, 659.42 mmol) and potassium carbonate (101.27 g, 732.73 mmol) in water (450 mL) was added dropwise to a mechanically stirred mixture of ethyl viologen dibromide (1.1 g, 2.93 mmol) and (7-benzyloxy-3-nitro-quinolin-4-yl)[(2,2-dimethyl[1,3]dioxolan-4-yl)methyl]amine (60.0 g, 146.54 mmol) in dichloromethane (500 mL) and water (50 mL). The reaction mixture was stirred at ambient temperature overnight and then diluted with water (600 mL) and stirred for an additional 10 minutes. The organic phase was separated and the aqueous layer was reextracted with dichloromethane (400 mL). The combined organic layers were washed with water (800 mL) and brine (800 mL), dried over sodium sulfate, and concentrated under reduced pressure to afford 55.60 g of 7-benzyloxy-N⁴-[(2,2-dimethyl[1,3]dioxolan-4-yl)methyl]quinoline-3,4-diamine as a brown foam. ¹H-NMR (300 MHz, CDCl₃) δ 8.38 (s, 1H), 7.83 (d, J=9.3 Hz, 1H), 7.51-7.28 (m, 6H), 7.18 (dd, J=9.2, 2.5 Hz, 1H), 5.16 (s, 2H), 4.35 (br s, 1H), 4.30-4.18 (m, 1H), 4.02 (dd, J=8.3, 6.5 Hz, 1H), 3.81 (br s, 2H), 3.68 (dd, J=8.3, 6.1 Hz, 1H), 3.60-3.46 (m, 1H), 3.40-3.25 (m, 1H), 1.52 (s, 3H), 1.37 (s, 3H); MS (APCI) m/z 380.0 (M+H)⁺.

Part C

Triethylamine (25.53 mL, 183.17 mmol) was added to a solution of 7-benzyloxy-N⁴-[(2,2-dimethyl[1,3]dioxolan-4-yl)methyl]quinoline-3,4-diamine (55.60 g, 146.54 mmol) in dichloromethane (500 mL) at 0° C. Dropwise addition of ethoxyacetyl chloride (22.45 g, 183.17 mmol) to the reaction mixture followed, and the reaction mixture was allowed to stir for 4 hours at ambient temperature. The reaction mixture was concentrated under reduced pressure and the residue was added to a mixture of triethylamine (61.26 mL, 439.54 mmol) in ethanol (350 mL) and heated to reflux for 16 hours. The reaction mixture was concentrated under reduced pressure, extracted with dichloromethane (3×300 mL), washed with water (300 mL) and brine (300 mL) and dried over sodium sulfate. The crude material was purified by flash column chromatography on silica gel (with a 95:5 mixture of chloroform: CMA) serving as eluent) and concentrated under reduced pressure to give 42.5 g of material as a brown solid. The material was recrystallized from diethyl ether to afford 37.5 g of 7-benzyloxy-1-[(2,2-dimethyl[1,3]dioxolan-4-yl)methyl]-2-ethoxymethyl-1H-imidazo[4,5-c]quinoline as a white crystalline solid, mp 110-111° C.

¹H-NMR (300 MHz, CDCl₃) δ 9.23 (s, 1H), 8.16 (d, J=9.2 Hz, 1H), 7.75 (d, J=2.7 Hz, 1H), 7.55-7.31 (m, 6H), 5.25 (s, 2H), 5.00 (d, J=12.7 Hz, 1H), 4.93-4.75 (m, 3H), 4.72-4.60 (m, 1H), 4.18 (dd, J=8.6, 6.2 Hz, 1H), 3.87 (dd, J=8.7, 6.2 Hz, 1H), 3.63 (q, J=7.0 Hz, 2H), 1.45 (s, 3H), 1.29 (s, 3H), 1.25 (t, J=7.0 Hz, 3H); ¹³C-NMR (75 MHz, CDCl₃) δ 157.8, 150.9, 146.9, 145.7, 136.5, 135.4, 134.9, 128.7, 128.2, 127.7, 121.2, 118.9, 112.4, 111.5, 110.3, 74.7, 70.2, 66.8, 66.4, 65.5, 48.4, 26.6, 25.1, 15.0; MS (APCI) m/z 448.1 (M+H)⁺; Anal. calcd for C₂₆H₂₉N₃O₄: C, 69.78; H, 6.53; N, 9.39. Found: C, 69.82; H, 6.74; N, 9.34.

Part D

3-Chloroperoxybenozic acid (mCPBA) (75% pure, 11.57 g, 50.27 mmol, 1.5 eq) was added to a solution of 7-benzyloxy-1-[(2,2-dimethyl[1,3]dioxolan-4-yl)methyl]-2-ethoxymethyl-1H-imidazo[4,5-c]quinoline (15.00 g, 33.52 mmol, 1 eq) in dichloromethane (200 mL), and the reaction mixture was stirred for two hours. Analysis by thin layer chromatography indicated the reaction was incomplete and additional mCPBA (1.2 g) was added and the reaction was stirred overnight. The reaction mixture was diluted with dichloromethane (300 mL), washed sequentially with 4% aqueous sodium carbonate solution (2×300 mL) and brine (300 mL), and concentrated under reduced pressure to afford a residue. Concentrated ammonium hydroxide (75 mL) was then added to a mixture of the residue in dichloromethane (200 mL) and cooled to 4° C. p-Toluenesulfonyl chloride (2.75 g, 14.44 mmol, 1.1 eq) was added in portions to the reaction mixture and stirred at ambient temperature for 16 hours. The reaction mixture was then diluted with dichloromethane (200 mL), washed with 4M aqueous sodium carbonate solution and separated. The aqueous layer was re-extracted with dichloromethane (200 mL) and the combined organic layers were washed with brine, dried over sodium sulfate, filtered and concentrated under reduced pressure to afford a brown solid. The crude material was purified by crystallization from diethyl ether to provide 9.8 g of 7-benzyloxy-1-[(2,2-dimethyl[1,3]dioxolan-4-yl)methyl]-2-ethoxymethyl-1H-imidazo[4,5-c]quinolin-4-ylamine as white plates of solid, mp 186-187° C. ¹H-NMR (300 MHz, CDCl₃) δ 7.89 (d, J=9.1 Hz, 1H), 7.53-7.29 (m, 6H), 7.05 (dd, J=9.0, 2.6 Hz, 1H), 5.42 (br s, 2H), 5.18 (s, 2H), 4.94 (d, J=12.6 Hz, 1H), 4.83-4.69 (m, 3H), 4.68-4.58 (m, 1H), 4.15 (dd, J=8.6, 6.2 Hz, 1H), 3.86 (dd, J=8.6, 6.1 Hz, 1H), 3.62 (q, J=7.0 Hz, 2H), 1.45 (s, 3H), 1.29 (s, 3H), 1.25 (t, J=7.0 Hz, 3H); ¹³C-NMR (75 MHz, CDCl₃) δ 158.3, 151.7, 149.0, 147.1, 136.8, 134.7, 128.6, 128.0, 127.6, 125.4, 120.9, 113.8, 110.2, 109.7, 108.9, 74.6, 70.0, 66.7, 66.3, 65.3, 48.2, 26.7, 25.1, 15.0; MS (APCI) m/z 463.1 (M+H)⁺; Anal. calcd for C₂₆H₃₀N₄O₄: C, 67.51; H, 6.54; N, 12.11. Found: C, 67.29; H, 6.33; N, 12.03.

Example 153

4-Amino-1-[(2,2-dimethyl[1,3]dioxolan-4-yl)methyl]-2-ethoxymethyl-1H-imidazo[4,5-c]quinolin-7-ol

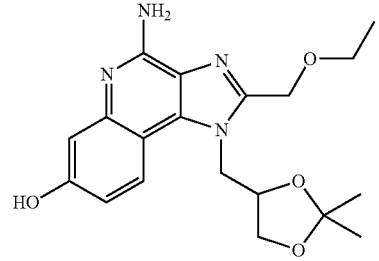

Palladium hydroxide (Pearlman's catalyst) (20% palladium w/w on carbon, 900 mg) was added to a solution of 7-benzyloxy-1-[(2,2-dimethyl[1,3]dioxolan-4-yl)methyl]-2-ethoxymethyl-1H-imidazo[4,5-c]quinolin-4-ylamine (9.00 g, 19.46 mmol, 1 eq), prepared as described in Example 152, in acetonitrile (300 mL) and methanol (300 mL) in a sealed vessel and the reaction mixture was placed under hydrogen pressure (30 psi, 2.1×10⁵ Pa) for 24 hours. The crude reaction mixture was filtered through a layer of CELITE filter aid and the filtrate was concentrated under reduced pressure and triturated with acetonitrile. The resulting crystalline material was collected by filtration and washed with acetonitrile to afford 3.66 of 4-amino-1-[(2,2-dimethyl[1,3]dioxolan-4-yl)methyl]-2-ethoxymethyl-1H-imidazo[4,5-c]quinolin-7-ol as an off-white solid. Additional product (0.36 g) was isolated from the filtrate of the initial trituration by concentration under reduced pressure, trituration with acetonitrile, and filtration for a total yield of 4.02 g of 4-amino-1-[(2,2-dimethyl[1,3]dioxolan-4-yl)methyl]-2-ethoxymethyl-1H-imidazo[4,5-c]quinolin-7-ol, isolated as an off-white solid, mp 240-242° C. ¹H-NMR (300 MHz, DMSO) δ 9.51 (br s, 1H), 7.96 (d, J=8.9 Hz, 1H), 6.95 (d, J=2.5 Hz, 1H), 6.76 (dd, J=8.9, 2.6 Hz, 1H), 6.46 (br s, 2H), 4.92-4.60 (m, 4H), 4.57-4.45 (m, 1H), 4.18 (dd, J=8.6, 6.4 Hz, 1H), 3.83 (dd, J=8.6, 6.5 Hz, 1H), 3.54 (q, J=7.0 Hz, 2H), 1.34 (s, 3H), 1.19 (s, 3H), 1.15 (t, J=7.0 Hz, 3H); ¹³C-NMR (75 MHz, DMSO) δ 156.41, 152.0, 148.1, 147.2, 133.9, 124.4, 121.7, 111.7, 109.7, 109.0, 107.9, 74.4, 66.0, 65.2, 64.3, 47.6, 26.2, 24.9, 14.8; MS (APCI) m/z 373.0

(M+H)+; Anal. calcd for $C_{19}H_{24}N_4O_4$: C, 61.28; H, 6.50; N, 15.04. Found: C, 61.12; H, 6.53; N, 14.98.

Examples 155-173

An alkylating reagent (0.125 mmol, 1.0 eq) from the table below was added to a test tube containing 4-amino-1-[(2,2-dimethyl[1,3]dioxolan-4-yl)methyl]-2-ethoxymethyl-1H-imidazo[4,5-c]quinolin-7-ol (73 mg, 0.2 mmol, 1.6 eq) and potassium carbonate (55 mg, 2 eq) in DMF (1 mL). The test tubes were capped and shaken overnight at ambient temperature. Each reaction mixture was then filtered and one drop of water was added to each mixture. Each mixture was then diluted with methanol (5 mL) and half of each solution was removed for use in Examples 174-181 below. The remaining solution from each reaction was concentrated by vacuum centrifugation. The compounds were purified by prep HPLC using a Waters Fraction Lynx automated purification system. The prep HPLC fractions were analyzed using a Micromass LC/TOF-MS, and the appropriate fractions were centrifuge evaporated to provide the trifluoroacetate salt of the desired compound. Column: ZORBAX BonusRP, 21.2×50 millimeters (mm), 5 micron particle size; non-linear gradient elution from 5-95% B where A is 0.05% trifluoroacetic acid/water and B is 0.05% trifluoroacetic acid/acetonitrile; fraction collection by mass-selective triggering. The table below shows the reagent added to each test tube, the structure of the resulting compound, and the observed accurate mass for the isolated trifluoroacetate salt.

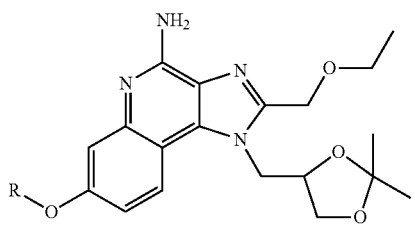

| Example | Reagent | R | Measured Mass (M + H) |
|---|---|---|---|
| 155 | α-Bromo-p-xylene | (4-methylbenzyl) | 477.2498 |
| 156 | 4-Cyanobenzyl bromide | (4-cyanobenzyl) | 488.2280 |
| 157 | 1-(Bromoethyl)benzene | (1-phenylethyl) | 477.2498 |
| 158 | 2-Cyanobenzyl bromide | (2-cyanobenzyl) | 488.2310 |
| 159 | α-Bromo-m-tolunitrile | (3-cyanobenzyl) | 488.2286 |
| 160 | 3-Methoxybenzyl bromide | (3-methoxybenzyl) | 493.2431 |
| 161 | 3-Chlorobenzyl bromide | (3-chlorobenzyl) | 497.1946 |
| 162 | 2,3-Difluorobenzyl bromide | (2,3-difluorobenzyl) | 499.2141 |
| 163 | 2,4-Difluorobenzyl bromide | (2,4-difluorobenzyl) | 499.2134 |

-continued

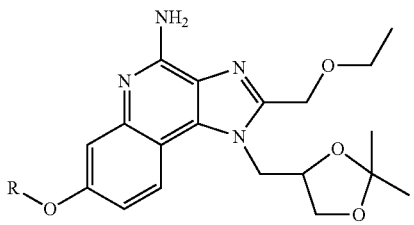

| Example | Reagent | R | Measured Mass (M + H) |
|---|---|---|---|
| 164 | 2,6-Difluorobenzyl bromide | 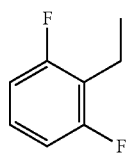 | 499.2162 |
| 165 | Methyl 4-(bromomethyl) benzoate | 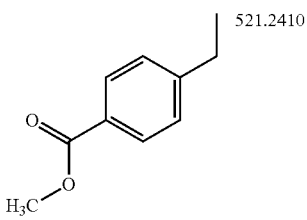 | 521.2410 |
| 166 | Methyl 3-(bromomethyl) benzoate | 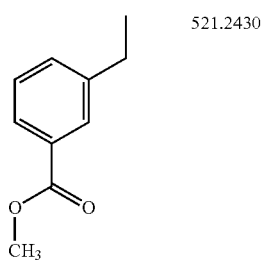 | 521.2430 |
| 167 | 4-(Trifluoromethyl) benzyl bromide | 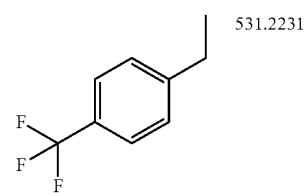 | 531.2231 |
| 168 | 2-(Trifluoromethyl) benzyl bromide | 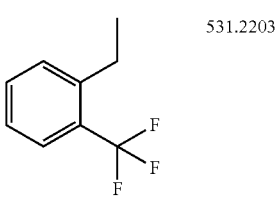 | 531.2203 |
| 169 | 3-(Trifluoromethyl) benzyl bromide | 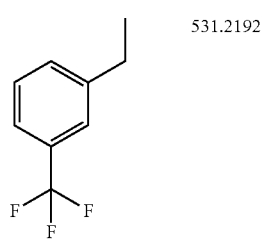 | 531.2192 |

-continued

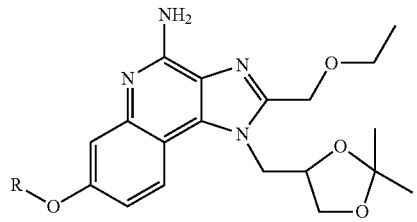

| Example | Reagent | R | Measured Mass (M + H) |
|---|---|---|---|
| 170 | 2,6-Dichlorobenzyl bromide | 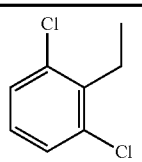 | 531.1617 |
| 171 | 3-(Trifluoromethoxy) benzyl bromide | 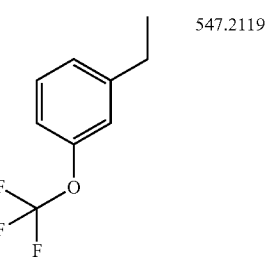 | 547.2119 |
| 172 | 4-(Trifluoromethoxy) benzyl bromide | 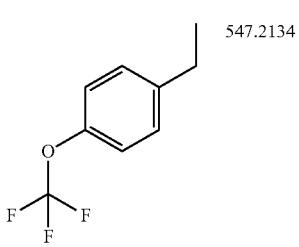 | 547.2134 |
| 173 | 4-(Bromomethyl) benzophenone | 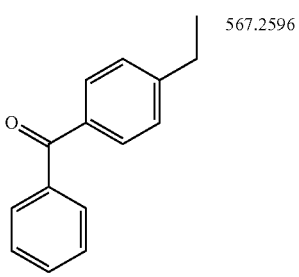 | 567.2596 |

Examples 174-191

The ketals of Examples 154-173 were hydrolyzed. 1N Aqueous hydrochloric acid (0.50 mL) and THF (0.50 mL) were added to each test tube containing a solution from Examples 154-173. The test tubes were capped and shaken for 56 hours at ambient temperature. Each reaction mixture was then concentrated by vacuum centrifugation. The compounds were purified by prep HPLC using a Waters Fraction Lynx automated purification system. The prep HPLC fractions were analyzed using a Micromass LC/TOF-MS, and the appropriate fractions were centrifuge evaporated to provide the trifluoroacetate salt of the desired compound. Column: ZORBAX BonusRP, 21.2×50 millimeters (mm), 5 micron particle size; non-linear gradient elution from 5-95% B where A is 0.05% trifluoroacetic acid/water and B is 0.05% trifluoroacetic acid/acetonitrile; fraction collection by mass-selective triggering. The table below shows the alkylating reagent used to prepare the ketal starting material, the structure of the resulting compound, and the observed accurate mass for the isolated trifluoroacetate salt.

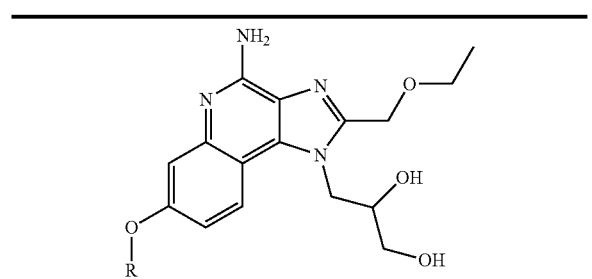

| Example | Reagent | R | Measured Mass (M + H) |
|---|---|---|---|
| 174 | Benzyl bromide | (phenyl) | 423.2039 |
| 175 | α-Bromo-p-xylene | (4-methylphenyl) | 437.2176 |
| 176 | 4-Cyanobenzyl bromide | (4-cyanophenyl) | 448.1973 |
| 177 | α-Bromo-m-nitrile | (3-cyanophenyl) | 448.1969 |
| 178 | 3-Methoxybenzyl bromide | (3-methoxyphenyl) | 453.2149 |
| 179 | 4-Chlorobenzyl bromide | (4-chlorophenyl) | 457.1664 |

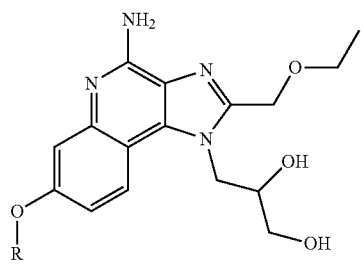

| Example | Reagent | R | Measured Mass (M + H) |
|---|---|---|---|
| 180 | 3-Chlorobenzyl bromide | (3-chlorophenyl) | 457.1636 |
| 181 | 2,3-Difluorobenzyl bromide | (2,3-difluorophenyl) | 459.1832 |
| 182 | 2,4-Difluorobenzyl bromide | (2,4-difluorophenyl) | 459.1819 |
| 183 | 3,4-Difluorobenzyl bromide | (3,4-difluorophenyl) | 459.1840 |
| 184 | Methyl 4-(bromomethyl)benzoate | (4-methoxycarbonylphenyl) | 481.2097 |
| 185 | 2-(Trifluoromethyl)benzyl bromide | (2-trifluoromethylphenyl) | 491.1869 |

-continued

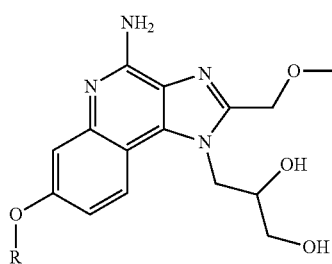

| Example | Reagent | R | Measured Mass (M + H) |
|---|---|---|---|
| 186 | 3-(Trifluoromethyl) benzyl bromide | 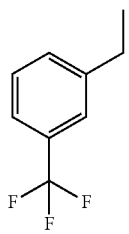 | 491.1912 |
| 187 | 2,6-Dichlorobenzyl bromide | 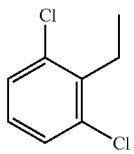 | 491.1268 |
| 188 | 3,4-Dichlorobenzyl bromide | 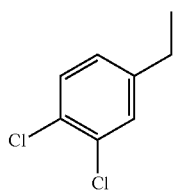 | 491.1273 |
| 189 | 3-(Trifluoromethoxy) benzyl bromide | 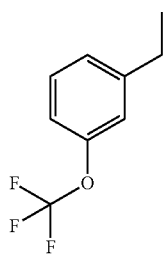 | 507.1851 |
| 190 | 4-(Trifluoromethoxy) benzyl bromide | 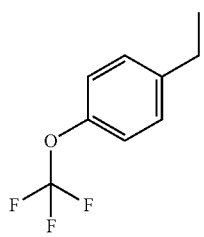 | 507.1827 |

-continued

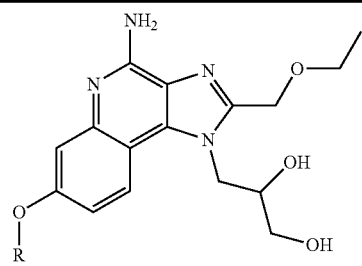

| Example | Reagent | R | Measured Mass (M + H) |
|---|---|---|---|
| 191 | 4-(Bromomethyl) benzophenone | | 527.2290 |

Examples 192-225

Part A

Triethylamine (58.9 mL, 422.4 mmol, 1.5 eq) and tert-butyl N-(2-aminoethyl) carbamate (54.1 g, 337.9 mmol, 1.2 eq) were added sequentially to a solution of 7-benzyloxy-4-chloro-3-nitroquinoline (88.63 g, 281.6 mmol) in DMF (800 mL) and stirred for 4 hours at ambient temperature. The crude reaction mixture was poured into hot water with continuous stirring to afford bright a yellow precipitate. The yellow solid was filtered and dried under reduced pressure at 65° C. to afford 123.65 g of tert-butyl2-[(7-benzyloxy-3-nitroquinolin-4-yl)amino]ethylcarbamate.

Part B tert-Butyl 2-[(7-benzyloxy-3-nitroquinolin-4-yl)amino] ethylcarbamate (40.0 g, 91.22 mmol) was dissolved in ethyl acetate (550 mL) and transferred to a Parr hydrogenation vessel charged with 5% platinum on carbon (10.68 g, 54.73 mmol, 0.03 eq). The vessel was purged with nitrogen gas and placed under hydrogen pressure (30 psi, $2.07 \times 10^5$ Pa) overnight. The catalyst was removed by filtration through a layer of CELITE filter aid and the filter cake was rinsed with methanol and dichloromethane. The filtrate was concentrated under reduced pressure to provide 35.25 g tert-butyl 2-[(3-amino-7-benzyloxyquinolin-4-yl)amino]ethylcarbamate.

Part C

Triethylamine (24.0 mL, 172.58 mmol) was added to a solution of tert-butyl 2-[(3-amino-7-benzyloxyquinolin-4-yl) amino]ethylcarbamate (35.25 g, 86.29 mmol) in dichloromethane (400 mL) and stirred at ambient temperature. Chloroacetyl chloride (6.87 mL, 86.29 mmol) was quickly added at ambient temperature to avoid splashing and was stirred for 10 minutes. The reaction mixture was concentrated under reduced pressure, dissolved in ethanol (500 mL), and stirred for 2 days at ambient temperature. The mixture was concentrated under reduced pressure and the residue was recrystallized from dichloromethane to afford 6.23 g of tert-butyl 2-(7-benzyloxy-2-chloromethyl-1H-imidazo[4,5-c] quinolin-1-yl)ethylcarbamate.

Part D

3-Chloroperoxybenozic acid (mCPBA) (77% pure, 3.53 g, 15.76 mmol, 1.2 eq) was added to a solution of tert-butyl 2-(7-benzyloxy-2-chloromethyl-1H-imidazo[4,5-c]quinolin-1-yl)ethylcarbamate (6.13 g, 13.13 mmol, 1 eq) in chloroform (60 mL), and the reaction mixture was stirred for one hour Ammonium hydroxide (25 mL, excess eq) was then added to the reaction mixture, which was stirred for 5 minutes. p-Toluenesulfonyl chloride (2.75 g, 14.44 mmol, 1.1 eq) was added and the reaction mixture was stirred overnight. Analysis by liquid chromatography mass spectrometry indicated the reaction was incomplete.

The crude product was diluted with chloroform and water and the phases were separated. The aqueous layer was extracted with additional chloroform and the combined organic layers were concentrated under reduced pressure. Chromatographic purification on a HORIZON HPFC system afforded a residue, which was dissolved in methanol (60 mL) and saturated with ammonia by bubbling ammonia gas throughout the reaction mixture for 30 minutes. The reaction mixture was then stirred overnight at ambient temperature. The crude product was concentrated under reduced pressure and purified by column chromatography to yield 2.32 g of tert-butyl 2-(4-amino-2-aminomethyl-7-benzyloxy-1H-imidazo[4,5-c]quinolin-1-yl)ethylcarbamate.

Part E

Methyl isocyanate (322.9 mg, 5.66 mmol, 1.1 eq) was added to a solution of tert-butyl 2-(4-amino-2-aminomethyl-7-benzyloxy-1H-imidazo[4,5-c]quinolin-1-yl)ethylcarbamate (2.38 g, 5.14 mmol, 1 eq) in DMF and stirred at ambient temperature for 2 days. The crude reaction mixture was concentrated under reduced pressure and purified by flash column chromatography (on silica gel, 0-6% methanol in dichloromethane) and concentrated under reduced pressure to yield 2.73 g of tert-butyl 2-{4-amino-7-benzyloxy-2-[(3-methylureido)methyl]-1H-imidazo[4,5-c]quinolin-1-yl}ethylcarbamate.

Part F tert-Butyl 2-[4-amino-7-benzyloxy-2-[3-methylureido)methyl]-1H-imidazo[4,5-c]quinolin-1-yl]ethylcarbamate (2.73 g, 5.25 mmol, 1 eq) was dissolved in dichloromethane (100 mL). 4N Hydrochloric acid in 1,4-dioxane (100 mL) was added to the reaction mixture and stirred for 30 minutes. The reaction mixture was concentrated under reduced pressure and the residue was dissolved in methanol. The solution was then poured into diethyl ether (300 mL) to produce a precipitate. The precipitate was isolated by filtration to yield 2.63 g of the hydrochloride salt of 1-1-{[4-amino-1-(2-aminoethyl)-7-benzyloxy-1H-imidazo[4,5-c]quinolin-2-yl]methyl}-3-methylurea.

Part G

A reagent (0.14 mmol, 1.1 eq) from the table below was added to a test tube containing 1-{[4-amino-1-(2-aminoethyl)-7-benzyloxy-1H-imidazo[4,5-c]quinolin-2-yl]methyl}-3-methylurea (54 mg, 0.13 mmol, 1.0 eq) and triethylamine (0.080 mL, 6.0 eq) in chloroform (1 mL). The test tubes were capped and shaken overnight at ambient temperature. Two drops of water were added to each reaction mixture and then the mixture was concentrated by vacuum centrifugation. The compounds were purified by prep HPLC using a Waters Fraction Lynx automated purification system. The prep HPLC fractions were analyzed using a Micromass LC/TOF-MS, and the appropriate fractions were centrifuge evaporated to provide the trifluoroacetate salt of the desired compound. Column. ZORBAX BonusRP, 21.2×50 millimeters (mm), 5 micron particle size; non-linear gradient elution from 5-95% B where A is 0.05% trifluoroacetic acid/water and B is 0.05% trifluoroacetic acid/acetonitrile; fraction collection by mass-selective triggering. The table below shows the reagent added to each test tube, the structure of the resulting compound, and the observed accurate mass for the isolated trifluoroacetate salt.

| Example | Reagent | R | Measured Mass (M + H) |
|---|---|---|---|
| 192 | Propionyl chloride | | 476.2423 |
| 193 | Cyclopropanecarbonyl chloride | | 488.2415 |
| 194 | Butryl chloride | | 490.2578 |
| 195 | Methoxyacetyl chloride | | 492.2379 |
| 196 | Cyclobutanecarbonyl chloride | | 502.2534 |
| 197 | 3-Furoyl chloride | | 514.2200 |

179
-continued

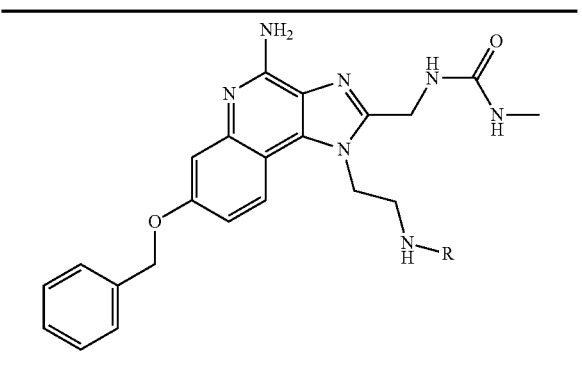

| Example | Reagent | R | Measured Mass (M + H) |
|---|---|---|---|
| 198 | Benzoyl chloride |  | 524.2427 |
| 199 | Thiophene-2-carbonyl chloride |  | 530.1956 |
| 200 | Hydrocinnamoyl chloride |  | 552.2740 |
| 201 | 3-Methoxybenzoyl chloride |  | 554.2499 |
| 202 | Nicotinoyl chloride hydrochloride |  | 525.2355 |
| 203 | 3-Dimethylaminobenzoyl chloride | | 567.2850 |

180
-continued

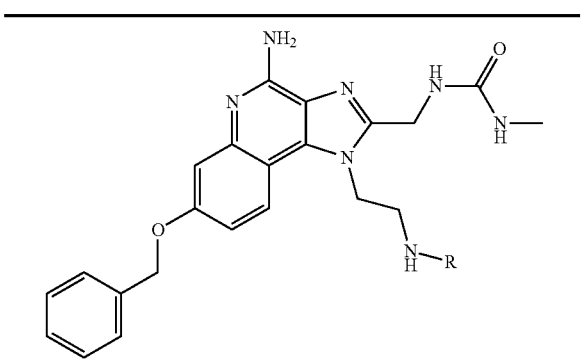

| Example | Reagent | R | Measured Mass (M + H) |
|---|---|---|---|
| 204 | Methanesulfonyl chloride | 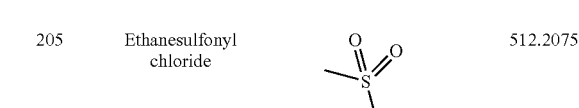 | 498.1945 |
| 205 | Ethanesulfonyl chloride |  | 512.2075 |
| 206 | Dimethylsulfamoyl chloride | 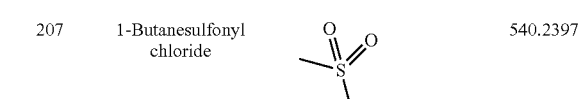 | 527.2189 |
| 207 | 1-Butanesulfonyl chloride |  | 540.2397 |
| 208 | Trifluoromethane-sulfonyl chloride |  | 552.1658 |
| 209 | Benzenesulfonyl chloride | 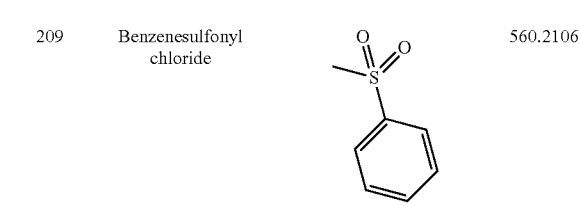 | 560.2106 |
| 210 | 2-Thiophenesulfonyl chloride | | 566.1672 |

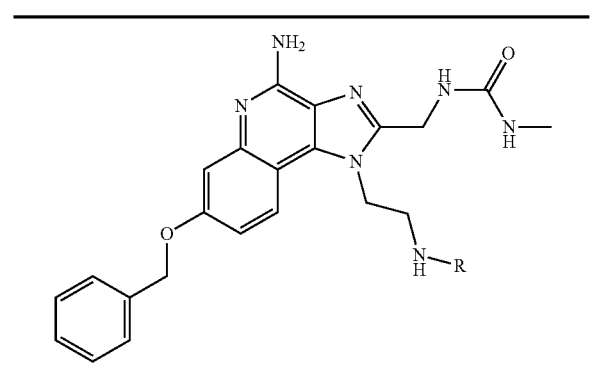

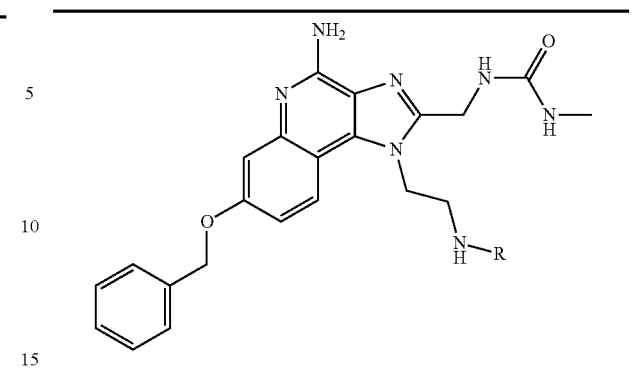

| Example | Reagent | R | Measured Mass (M + H) |
|---|---|---|---|
| 211 | 3-Methylbenzenesulfonyl chloride | | 574.2250 |
| 212 | α-Toluenesulfonyl chloride | | 574.2256 |
| 213 | 2-Fluorobenzenesulfonyl chloride | | 578.2001 |
| 214 | 3-Fluorobenzenesulfonyl chloride | | 578.2015 |
| 215 | Methyl isocyanate | | 477.2389 |
| 216 | Ethyl isocyanate | | 491.2544 |

| Example | Reagent | R | Measured Mass (M + H) |
|---|---|---|---|
| 217 | Isopropyl isocyanate | | 505.2675 |
| 218 | Isopropyl isothiocyanate | | 521.2446 |
| 219 | Cyclopropylmethyl isothiocyanate | | 533.2486 |
| 220 | Phenyl isocyanate | | 539.2513 |
| 221 | Cyclohexyl isocyanate | | 545.2973 |
| 222 | m-Tolyl isocyanate | | 553.2718 |
| 223 | 3-Pyridyl isothiocyanate | | 556.2243 |

183 -continued

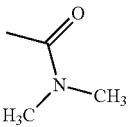

| Example | Reagent | R | Measured Mass (M + H) |
|---|---|---|---|
| 224 | N,N-Dimethylcarbamoyl chloride | 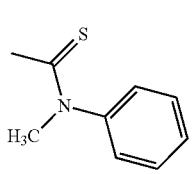 | 491.2545 |
| 225 | N-Methyl-N-phenylthiocarbamoyl chloride | 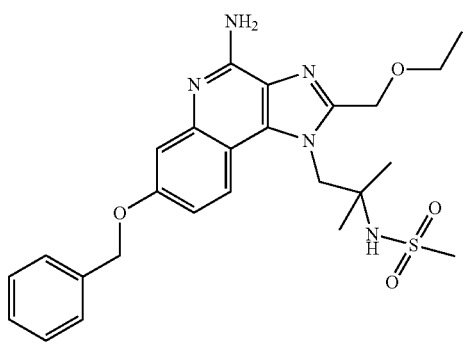 | 569.2408 |

Example 226

N-{2-[4-Amino-7-(benzyloxy)-2-(ethoxymethyl)-1H-imidazo[4,5-c]quinolin-1-yl]-1,1-dimethylethyl}methanesulfonamide

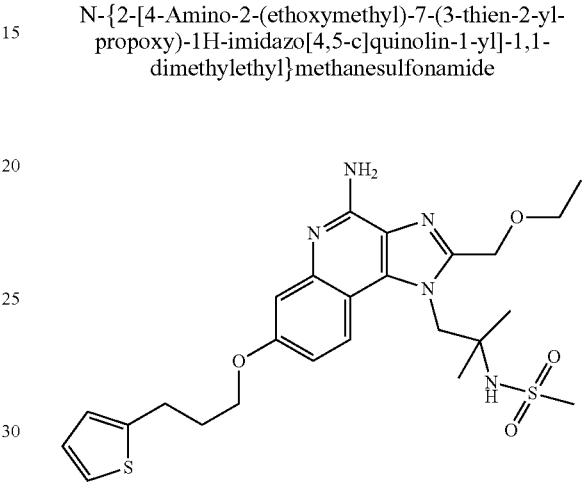

mCPBA (11.2 g, 39.2 mmol) was added to a solution of N-[2-(7-benzyloxy-2-ethoxymethyl-1H-imidazo[4,5-c]quinolin-1-yl)-1,1-dimethylethyl]methanesulfonamide (prepared as described in Parts A-D of Example 52, 17.2 g, 35.6 mmol) in dichloromethane (350 mL). The solution was stirred overnight and additional mCPBA (approximately 1-2 g) was added. After 20 minutes, concentrated ammonium hydroxide (150 mL) was added. The mixture was stirred for 10 minutes and p-toluenesulfonyl chloride (8.20 g, 42.8 mmol) was added in portions. The mixture was stirred at ambient temperature for 2 days, then was filtered. A white solid was obtained, which was slurried in water, filtered, and dried to yield 11.7 g of N-{2-[4-amino-7-(benzyloxy)-2-(ethoxymethyl)-1H-imidazo[4,5-c]quinolin-1-yl]-1,1-dimethylethyl}methanesulfonamide. A small sample, 500 mg, was purified to yield 300 mg of analytically pure N-{2-[4-amino-7-(benzyloxy)-2-(ethoxymethyl)-1H-imidazo[4,5-c]quinolin-1-yl]-1,1-dimethylethyl}methanesulfonamide as a white solid, mp 264-266° C.

MS (APCI) m/z 498 (M+H)$^+$;

Anal. calcd for $C_{25}H_{31}N_5O_4S$: C, 60.34; H, 6.28; N, 14.07. Found: C, 60.10; H, 6.34; N, 13.98.

Example 227

N-{2-[4-Amino-2-(ethoxymethyl)-7-(3-thien-2-yl-propoxy)-1H-imidazo[4,5-c]quinolin-1-yl]-1,1-dimethylethyl}methanesulfonamide Part A Propargyl bromide (1.30 g, 9.19 mmol) was added to a mixture of N-[2-(4-amino-2-ethoxymethyl-7-hydroxy-1H-imidazo[4,5-c]quinolin-1-yl)-1,1-dimethylethyl]methanesulfonamide (2.5 g, 6.13 mmol) and cesium carbonate (5.00 g, 12.3 mmol) in DMF. The mixture was stirred overnight and then was poured into water (600 mL). The mixture was stirred overnight and a gummy solid was isolated by filtration. The solid was dissolved in dichloromethane and the resulting solution was dried over magnesium sulfate, filtered, and concentrated under reduced pressure. The crude product was purified by flash chromatography (silica gel, gradient elution with 0-30% of a 1:5 methanol/dichloromethane solution in dichloromethane) to provide 675 mg of N-{2-[4-amino-2-(ethoxymethyl)-7-(prop-2-ynyloxy)-1H-imidazo[4,5-c]quinolin-1-yl]-1,1-dimethylethyl}methanesulfonamide as an off-white solid. A small portion was recrystallized from methanol to yield an off-white solid, mp 175.0-176.0° C.

MS (APCI) m/z 446 (M+H)$^+$;

Anal. calcd for $C_{21}H_{27}N_5O_4S \cdot H_2O$: C, 54.41; H, 6.31; N, 15.11. Found: C, 54.67; H, 6.57; N, 14.80.

Part B

N-{2-[4-Amino-2-(ethoxymethyl)-7-(prop-2-ynyloxy)-1H-imidazo[4,5-c]quinolin-1-yl]-1,1-dimethylethyl}methanesulfonamide (600 mg, 1.34 mmol), 2-iodothiophene (565 mg, 2.69 mmol), triethylamine (0.50 mL, 3.5 mmol), dichlorobis(triphenylphosphine)palladium (II) (19 mg, 0.03 mmol), copper(I) iodide (10 mg, 0.05 mmol), and DMF (10 mL) were combined and heated at 60° C. overnight. After cooling to ambient temperature, the reaction was poured into water (200 mL) and a fine precipitate formed. After the mixture was stirred for 1 hour, the solid was isolated by filtration. The solid was dissolved in dichloromethane and methanol and was passed through a plug of silica gel, which was rinsed with 20% methanol in dichloromethane. The filtrate was concentrated under reduced pressure to yield approximately 900 mg of N-(2-{4-amino-2-(ethoxymethyl)-7-[(3-thien-2-ylprop-2-ynyl)oxy]-1H-imidazo[4,5-c]quinolin-1-yl}-1,1-dimethylethyl)methanesulfonamide as a dark brown semi-solid that was used without further purification in the next step.

Part C

The material from Part B (approximately 1.34 mmol) was dissolved in 1:1 ethanol/methanol and 10% palladium on carbon (150 mg) was added. The mixture was hydrogenated on a Parr apparatus overnight at 50 psi (3.4×10$^5$ Pa). Additional 10% palladium on carbon (100 mg) was added carefully, and the mixture was hydrogenated an additional 4 hours. The mixture was filtered through CELITE filter agent and the filtrate was concentrated. The crude product was purified by chromatography on silica gel multiple times with different solvent systems (methanol/dichloromethane or CMA/chloroform) and was recrystallized multiple times from acetonitrile and butyl acetate to provide 90 mg of N-{2-[4-amino-2-(ethoxymethyl)-7-(3-thien-2-ylpropoxy)-1H-imidazo[4,5-c]quinolin-1-yl]-1,1-dimethylethyl}methanesulfonamide as a white solid that contained some minor impurities, mp. 202.0-203.0° C.

MS (APCI) m/z 532 (M+H)$^+$;

Anal. calcd for $C_{25}H_{33}N_5O_4S_2$: C, 56.48; H, 6.26; N, 13.17. Found: C, 56.41; H, 6.46; N, 13.28.

Examples 228-235

Part A

Ammonium hydroxide (1 L) was added to a solution of methyl tetrahydro-2H-pyran-4-carboxylate (20 mL, 150 mmol) in methanol (500 mL), and the reaction was stirred overnight at ambient temperature. Additional ammonium hydroxide (500 mL) was added, and the reaction was stirred for four additional days. The methanol was removed under reduced pressure. Solid sodium chloride was added to the aqueous layer, which was extracted with chloroform (3×150 mL). The combined extracts were dried over sodium sulfate, filtered, and concentrated under reduced pressure to provide 11.4 g of tetrahydro-2H-pyran-4-carboxamide as a white solid.

Part B

A solution of tetrahydro-2H-pyran-4-carboxamide (11.4 g, 88.3 mmol) in THF (441 mL) was cooled to 0° C. Lithium aluminum hydride (10.0 g, 265 mmol) was added in six portions over a period of ten minutes. The reaction flask was purged with nitrogen between the additions. When the reaction mixture was no longer bubbling, it was heated at reflux for six hours. The reaction was then cooled to 0° C., and ethyl acetate was added dropwise until bubbling ceased. Methanol was then added dropwise until bubbling ceased. Water (10 mL), 15% aqueous sodium hydroxide (10 mL), and water (30 mL) were sequentially added. The organic fraction was decanted off, and the remaining gray solid was washed with chloroform. The combined organic fractions were dried over sodium sulfate, filtered, and concentrated under reduced pressure to provide tetrahydro-2H-pyran-4-ylmethylamine Part C The method described in Part E of Example 1 can be used to treat 7-benzyloxy-4-chloro-3-nitroquinoline with tetrahydro-2H-pyran-4-ylmethylamine to provide (7-benzyloxy-3-nitroquinolin-4-yl)(tetrahydro-2H-pyran-4-ylmethyl)amine. The same method can be used to treat 6-benzyloxy-4-chloro-3-nitroquinoline with tetrahydro-2H-pyran-4-ylmethylamine to provide (6-benzyloxy-3-nitroquinolin-4-yl)(tetrahydro-2H-pyran-4-ylmethyl)amine.

Part D

The method described in Part F of Example 1 can be used to reduce (7-benzyloxy-3-nitroquinolin-4-yl)(tetrahydro-2H-pyran-4-ylmethyl)amine or (6-benzyloxy-3-nitroquinolin-4-yl)(tetrahydro-2H-pyran-4-ylmethyl)amine to 7-benzyloxy-N$^4$-(tetrahydro-2H-pyran-4-ylmethyl)quinoline-3,4-diamine or 6-benzyloxy-N$^4$-(tetrahydro-2H-pyran-4-ylmethyl)quinoline-3,4-diamine, respectively.

Part E

For Examples 228 and 230, 7-benzyloxy-N$^4$-(tetrahydro-2H-pyran-4-ylmethyl)quinoline-3,4-diamine (Example 228) or 6-benzyloxy-N$^4$-(tetrahydro-2H-pyran-4-ylmethyl)quinoline-3,4-diamine (Example 230) can be treated with ethoxyacetyl chloride according to the method described in Part C of Example 50 to provide 7-benzyloxy-2-ethoxymethyl-1-(tetrahydro-2H-pyran-4-ylmethyl)-1H-imidazo[4,5-c]quinoline (Example 228) or 8-benzyloxy-2-ethoxymethyl-1-(tetrahydro-2H-pyran-4-ylmethyl)-1H-imidazo[4,5-c]quinoline (Example 230).

For examples 229 and 231, 7-benzyloxy-N$^4$-(tetrahydro-2H-pyran-4-ylmethyl)quinoline-3,4-diamine (Example 229) or 6-benzyloxy-N$^4$-(tetrahydro-2H-pyran-4-ylmethyl)quinoline-3,4-diamine (Example 231) can be treated with triethyl orthopropionate according to the general method described in Part G of Example 1 to provide 7-benzyloxy-2-ethyl-1-(tetrahydro-2H-pyran-4-ylmethyl)-1H-imidazo[4,5-c]quinoline (Example 229) or 8-benzyloxy-2-ethyl-1-(tetrahydro-2H-pyran-4-ylmethyl)-1H-imidazo[4,5-c]quinoline (Example 231).

Part F

The methods described in Parts H and I of Example 1 can be used to oxidize and aminate the products from Part E to provide the compounds shown in the table below. The table indicates the product from Part E that can be used as the starting material for each example as well as the structure of the product.

Examples 228-231

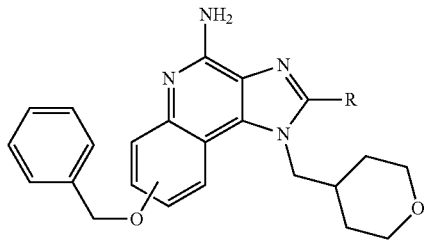

| Example | Product from Part E | Benzyloxy position | R |
|---|---|---|---|
| 228 | 7-benzyloxy-2-ethoxymethyl-1-(tetrahydropyran-4-ylmethyl)-1H-imidazo[4,5-c]quinoline | 7-benzyloxy | —CH$_2$OCH$_2$CH$_3$ |
| 229 | 7-benzyloxy-2-ethyl-1-(tetrahydropyran-4-ylmethyl)-1H-imidazo[4,5-c]quinoline | 7-benzyloxy | —CH$_2$CH$_3$ |
| 230 | 8-benzyloxy-2-ethoxymethyl-1-(tetrahydropyran-4-ylmethyl)-1H-imidazo[4,5-c]quinoline | 8-benzyloxy | —CH$_2$OCH$_2$CH$_3$ |
| 231 | 8-benzyloxy-2-ethyl-1-(tetrahydropyran-4-ylmethyl)-1H-imidazo[4,5-c]quinoline | 8-benzyloxy | —CH$_2$CH$_3$ |

Part G

The method described in Example 5 can be used to reduce Examples 228 to 231 to provide the compounds shown in the following table.

Examples 232-235

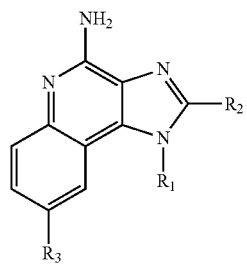

| Example | Starting Material | Hydroxy position | R |
|---|---|---|---|
| 232 | 228 | 7-hydroxy | —CH$_2$OCH$_2$CH$_3$ |
| 233 | 229 | 7-hydroxy | —CH$_2$CH$_3$ |
| 234 | 230 | 8-hydroxy | —CH$_2$OCH$_2$CH$_3$ |
| 235 | 231 | 8-hydroxy | —CH$_2$CH$_3$ |

Exemplary Compounds

Certain exemplary compounds, including some of those described above in the Examples, have the following Formula (IV) or (V) and the following R$_1$, R$_2$, and R$_3$ substituents, wherein each line of the table is matched with each of Formula IV or Formula V to represent a specific embodiment of the invention.

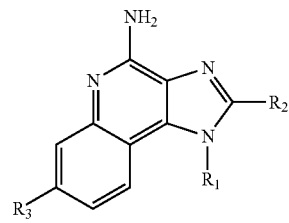

IV

V

| R$_1$ | R$_2$ | R$_3$ |
|---|---|---|
| 2-hydroxy-2-methylpropyl | ethyl | hydroxy |
| 2-hydroxy-2-methylpropyl | ethyl | pyridin-3-ylmethoxy |
| 2-hydroxy-2-methylpropyl | ethyl | (4-chlorobenzyl)oxy |
| 2-hydroxy-2-methylpropyl | ethyl | (4-fluorobenzyl)oxy |
| 2-hydroxy-2-methylpropyl | ethyl | 3-pyridin-3-ylpropoxy |
| 2-hydroxy-2-methylpropyl | propyl | hydroxy |
| 2-hydroxy-2-methylpropyl | propyl | pyridin-3-ylmethoxy |
| 2-hydroxy-2-methylpropyl | propyl | (4-chlorobenzyl)oxy |
| 2-hydroxy-2-methylpropyl | propyl | (4-fluorobenzyl)oxy |
| 2-hydroxy-2-methylpropyl | propyl | 3-pyridin-3-ylpropoxy |
| 2-hydroxy-2-methylpropyl | methoxymethyl | hydroxy |
| 2-hydroxy-2-methylpropyl | methoxymethyl | pyridin-3-ylmethoxy |
| 2-hydroxy-2-methylpropyl | methoxymethyl | (4-chlorobenzyl)oxy |
| 2-hydroxy-2-methylpropyl | methoxymethyl | (4-fluorobenzyl)oxy |
| 2-hydroxy-2-methylpropyl | methoxymethyl | 3-pyridin-3-ylpropoxy |
| 2-hydroxy-2-methylpropyl | ethoxymethyl | pyridin-3-ylmethoxy |
| 2-hydroxy-2-methylpropyl | ethoxymethyl | (4-chlorobenzyl)oxy |
| 2-hydroxy-2-methylpropyl | ethoxymethyl | (4-fluorobenzyl)oxy |
| 2-hydroxy-2-methylpropyl | ethoxymethyl | 3-pyridin-3-ylpropoxy |
| 2-hydroxy-2-methylpropyl | 2-methoxyethyl | hydroxy |
| 2-hydroxy-2-methylpropyl | 2-methoxyethyl | pyridin-3-ylmethoxy |
| 2-hydroxy-2-methylpropyl | 2-methoxyethyl | (4-chlorobenzyl)oxy |
| 2-hydroxy-2-methylpropyl | 2-methoxyethyl | (4-fluorobenzyl)oxy |
| 2-hydroxy-2-methylpropyl | 2-methoxyethyl | 3-pyridin-3-ylpropoxy |
| 2-methylpropyl | ethyl | hydroxy |
| 2-methylpropyl | ethyl | pyridin-3-ylmethoxy |
| 2-methylpropyl | ethyl | (4-chlorobenzyl)oxy |
| 2-methylpropyl | ethyl | (4-fluorobenzyl)oxy |
| 2-methylpropyl | ethyl | 3-pyridin-3-ylpropoxy |
| 2-methylpropyl | propyl | hydroxy |
| 2-methylpropyl | propyl | pyridin-3-ylmethoxy |
| 2-methylpropyl | propyl | (4-chlorobenzyl)oxy |
| 2-methylpropyl | propyl | (4-fluorobenzyl)oxy |
| 2-methylpropyl | propyl | 3-pyridin-3-ylpropoxy |
| 2-methylpropyl | methoxymethyl | hydroxy |
| 2-methylpropyl | methoxymethyl | pyridin-3-ylmethoxy |
| 2-methylpropyl | methoxymethyl | (4-chlorobenzyl)oxy |
| 2-methylpropyl | methoxymethyl | (4-fluorobenzyl)oxy |
| 2-methylpropyl | methoxymethyl | 3-pyridin-3-ylpropoxy |
| 2-methylpropyl | ethoxymethyl | pyridin-3-ylmethoxy |
| 2-methylpropyl | ethoxymethyl | (4-chlorobenzyl)oxy |
| 2-methylpropyl | ethoxymethyl | (4-fluorobenzyl)oxy |
| 2-methylpropyl | ethoxymethyl | 3-pyridin-3-ylpropoxy |
| 2-methylpropyl | 2-methoxyethyl | hydroxy |
| 2-methylpropyl | 2-methoxyethyl | pyridin-3-ylmethoxy |
| 2-methylpropyl | 2-methoxyethyl | (4-chlorobenzyl)oxy |

-continued

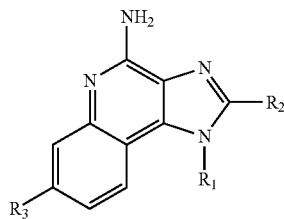

IV

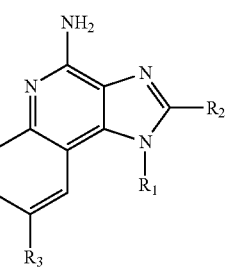

V

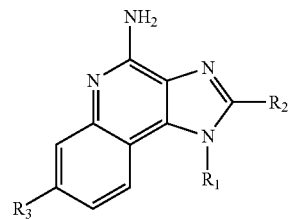

IV

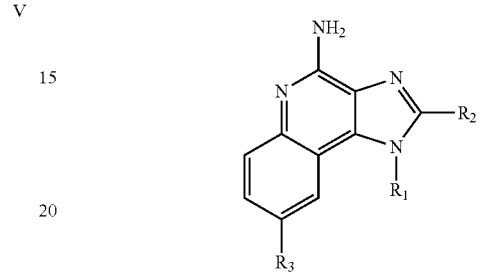

V

| R₁ | R₂ | R₃ |
|---|---|---|
| 2-methylpropyl | 2-methoxyethyl | (4-fluorobenzyl)oxy |
| 2-methylpropyl | 2-methoxyethyl | 3-pyridin-3-ylpropoxy |
| propyl | ethyl | hydroxy |
| propyl | ethyl | pyridin-3-ylmethoxy |
| propyl | ethyl | (4-chlorobenzyl)oxy |
| propyl | ethyl | (4-fluorobenzyl)oxy |
| propyl | ethyl | 3-pyridin-3-ylpropoxy |
| propyl | propyl | hydroxy |
| propyl | propyl | pyridin-3-ylmethoxy |
| propyl | propyl | (4-chlorobenzyl)oxy |
| propyl | propyl | (4-fluorobenzyl)oxy |
| propyl | propyl | 3-pyridin-3-ylpropoxy |
| propyl | methoxymethyl | hydroxy |
| propyl | methoxymethyl | pyridin-3-ylmethoxy |
| propyl | methoxymethyl | (4-chlorobenzyl)oxy |
| propyl | methoxymethyl | (4-fluorobenzyl)oxy |
| propyl | methoxymethyl | 3-pyridin-3-ylpropoxy |
| propyl | ethoxymethyl | hydroxy |
| propyl | ethoxymethyl | pyridin-3-ylmethoxy |
| propyl | ethoxymethyl | (4-chlorobenzyl)oxy |
| propyl | ethoxymethyl | (4-fluorobenzyl)oxy |
| propyl | ethoxymethyl | 3-pyridin-3-ylpropoxy |
| propyl | 2-methoxyethyl | hydroxy |
| propyl | 2-methoxyethyl | pyridin-3-ylmethoxy |
| propyl | 2-methoxyethyl | (4-chlorobenzyl)oxy |
| propyl | 2-methoxyethyl | (4-fluorobenzyl)oxy |
| propyl | 2-methoxyethyl | 3-pyridin-3-ylpropoxy |
| 2,3-dihydroxypropyl | ethyl | hydroxy |
| 2,3-dihydroxypropyl | ethyl | pyridin-3-ylmethoxy |
| 2,3-dihydroxypropyl | ethyl | (4-chlorobenzyl)oxy |
| 2,3-dihydroxypropyl | ethyl | (4-fluorobenzyl)oxy |
| 2,3-dihydroxypropyl | ethyl | 3-pyridin-3-ylpropoxy |
| 2,3-dihydroxypropyl | propyl | hydroxy |
| 2,3-dihydroxypropyl | propyl | pyridin-3-ylmethoxy |
| 2,3-dihydroxypropyl | propyl | (4-chlorobenzyl)oxy |
| 2,3-dihydroxypropyl | propyl | (4-fluorobenzyl)oxy |
| 2,3-dihydroxypropyl | propyl | 3-pyridin-3-ylpropoxy |
| 2,3-dihydroxypropyl | methoxymethyl | hydroxy |
| 2,3-dihydroxypropyl | methoxymethyl | pyridin-3-ylmethoxy |
| 2,3-dihydroxypropyl | methoxymethyl | (4-chlorobenzyl)oxy |
| 2,3-dihydroxypropyl | methoxymethyl | (4-fluorobenzyl)oxy |
| 2,3-dihydroxypropyl | methoxymethyl | 3-pyridin-3-ylpropoxy |
| 2,3-dihydroxypropyl | ethoxymethyl | hydroxy |
| 2,3-dihydroxypropyl | ethoxymethyl | pyridin-3-ylmethoxy |
| 2,3-dihydroxypropyl | ethoxymethyl | (4-chlorobenzyl)oxy |
| 2,3-dihydroxypropyl | ethoxymethyl | (4-fluorobenzyl)oxy |
| 2,3-dihydroxypropyl | ethoxymethyl | 3-pyridin-3-ylpropoxy |
| 2,3-dihydroxypropyl | 2-methoxyethyl | hydroxy |
| 2,3-dihydroxypropyl | 2-methoxyethyl | pyridin-3-ylmethoxy |
| 2,3-dihydroxypropyl | 2-methoxyethyl | (4-chlorobenzyl)oxy |
| 2,3-dihydroxypropyl | 2-methoxyethyl | (4-fluorobenzyl)oxy |
| 2,3-dihydroxypropyl | 2-methoxyethyl | 3-pyridin-3-ylpropoxy |
| 4-[(methylsulfonyl)amino]butyl | ethyl | hydroxy |
| 4-[(methylsulfonyl)amino]butyl | ethyl | pyridin-3-ylmethoxy |
| 4-[(methylsulfonyl)amino]butyl | ethyl | (4-chlorobenzyl)oxy |
| 4-[(methylsulfonyl)amino]butyl | ethyl | (4-fluorobenzyl)oxy |
| 4-[(methylsulfonyl)amino]butyl | ethyl | 3-pyridin-3-ylpropoxy |
| 4-[(methylsulfonyl)amino]butyl | propyl | hydroxy |
| 4-[(methylsulfonyl)amino]butyl | propyl | pyridin-3-ylmethoxy |
| 4-[(methylsulfonyl)amino]butyl | propyl | (4-chlorobenzyl)oxy |
| 4-[(methylsulfonyl)amino]butyl | propyl | (4-fluorobenzyl)oxy |
| 4-[(methylsulfonyl)amino]butyl | propyl | 3-pyridin-3-ylpropoxy |
| 4-[(methylsulfonyl)amino]butyl | methoxymethyl | hydroxy |
| 4-[(methylsulfonyl)amino]butyl | methoxymethyl | pyridin-3-ylmethoxy |
| 4-[(methylsulfonyl)amino]butyl | methoxymethyl | (4-chlorobenzyl)oxy |
| 4-[(methylsulfonyl)amino]butyl | methoxymethyl | (4-fluorobenzyl)oxy |
| 4-[(methylsulfonyl)amino]butyl | methoxymethyl | 3-pyridin-3-ylpropoxy |
| 4-[(methylsulfonyl)amino]butyl | ethoxymethyl | hydroxy |
| 4-[(methylsulfonyl)amino]butyl | ethoxymethyl | pyridin-3-ylmethoxy |
| 4-[(methylsulfonyl)amino]butyl | ethoxymethyl | (4-chlorobenzyl)oxy |
| 4-[(methylsulfonyl)amino]butyl | ethoxymethyl | (4-fluorobenzyl)oxy |
| 4-[(methylsulfonyl)amino]butyl | ethoxymethyl | 3-pyridin-3-ylpropoxy |
| 4-[(methylsulfonyl)amino]butyl | 2-methoxyethyl | hydroxy |
| 4-[(methylsulfonyl)amino]butyl | 2-methoxyethyl | pyridin-3-ylmethoxy |
| 4-[(methylsulfonyl)amino]butyl | 2-methoxyethyl | (4-chlorobenzyl)oxy |
| 4-[(methylsulfonyl)amino]butyl | 2-methoxyethyl | (4-fluorobenzyl)oxy |
| 4-[(methylsulfonyl)amino]butyl | 2-methoxyethyl | 3-pyridin-3-ylpropoxy |
| 2-methyl-2-[(methylsulfonyl)amino]propyl | ethyl | hydroxy |
| 2-methyl-2-[(methylsulfonyl)amino]propyl | ethyl | pyridin-3-ylmethoxy |
| 2-methyl-2-[(methylsulfonyl)amino]propyl | ethyl | (4-chlorobenzyl)oxy |
| 2-methyl-2-[(methylsulfonyl)amino]propyl | ethyl | (4-fluorobenzyl)oxy |
| 2-methyl-2-[(methylsulfonyl)amino]propyl | ethyl | 3-pyridin-3- |

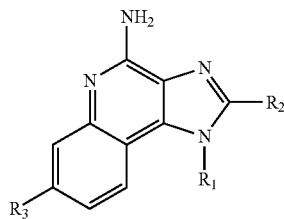

IV

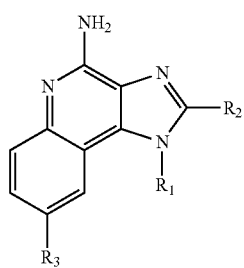

V

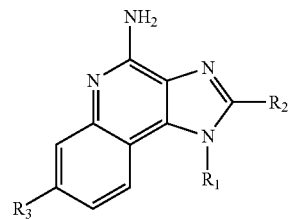

IV

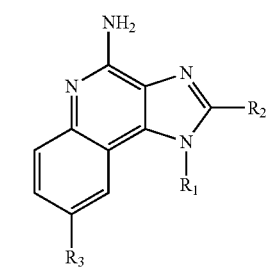

V

| R₁ | R₂ | R₃ |
|---|---|---|
| 2-methyl-2-[(methylsulfonyl)amino]propyl | propyl | 3-pyridin-3-ylpropoxy |
| 2-methyl-2-[(methylsulfonyl)amino]propyl | propyl | hydroxy |
| 2-methyl-2-[(methylsulfonyl)amino]propyl | propyl | pyridin-3-ylmethoxy |
| 2-methyl-2-[(methylsulfonyl)amino]propyl | propyl | (4-chlorobenzyl)oxy |
| 2-methyl-2-[(methylsulfonyl)amino]propyl | propyl | (4-fluorobenzyl)oxy |
| 2-methyl-2-[(methylsulfonyl)amino]propyl | propyl | 3-pyridin-3-ylpropoxy |
| 2-methyl-2-[(methylsulfonyl)amino]propyl | methoxymethyl | hydroxy |
| 2-methyl-2-[(methylsulfonyl)amino]propyl | methoxymethyl | pyridin-3-ylmethoxy |
| 2-methyl-2-[(methylsulfonyl)amino]propyl | methoxymethyl | (4-chlorobenzyl)oxy |
| 2-methyl-2-[(methylsulfonyl)amino]propyl | methoxymethyl | (4-fluorobenzyl)oxy |
| 2-methyl-2-[(methylsulfonyl)amino]propyl | methoxymethyl | 3-pyridin-3-ylpropoxy |
| 2-methyl-2-[(methylsulfonyl)amino]propyl | ethoxymethyl | hydroxy |
| 2-methyl-2-[(methylsulfonyl)amino]propyl | ethoxymethyl | pyridin-3-ylmethoxy |
| 2-methyl-2-[(methylsulfonyl)amino]propyl | ethoxymethyl | (4-chlorobenzyl)oxy |
| 2-methyl-2-[(methylsulfonyl)amino]propyl | ethoxymethyl | (4-fluorobenzyl)oxy |
| 2-methyl-2-[(methylsulfonyl)amino]propyl | ethoxymethyl | 3-pyridin-3-ylpropoxy |
| 2-methyl-2-[(methylsulfonyl)amino]propyl | 2-methoxyethyl | hydroxy |
| 2-methyl-2-[(methylsulfonyl)amino]propyl | 2-methoxyethyl | pyridin-3-ylmethoxy |
| 2-methyl-2-[(methylsulfonyl)amino]propyl | 2-methoxyethyl | (4-chlorobenzyl)oxy |
| 2-methyl-2-[(methylsulfonyl)amino]propyl | 2-methoxyethyl | (4-fluorobenzyl)oxy |
| 2-methyl-2-[(methylsulfonyl)amino]propyl | 2-methoxyethyl | 3-pyridin-3-ylpropoxy |
| 2-[(cyclohexylcarbonyl)amino]-2-methylpropyl | ethyl | hydroxy |
| 2-[(cyclohexylcarbonyl)amino]-2-methylpropyl | ethyl | pyridin-3-ylmethoxy |
| 2-[(cyclohexylcarbonyl)amino]-2-methylpropyl | ethyl | (4-chlorobenzyl)oxy |
| 2-[(cyclohexylcarbonyl)amino]-2-methylpropyl | ethyl | (4-fluorobenzyl)oxy |
| 2-[(cyclohexylcarbonyl)amino]-2-methylpropyl | ethyl | 3-pyridin-3-ylpropoxy |

| R₁ | R₂ | R₃ |
|---|---|---|
| 2-[(cyclohexylcarbonyl)amino]-2-methylpropyl | propyl | hydroxy |
| 2-[(cyclohexylcarbonyl)amino]-2-methylpropyl | propyl | pyridin-3-ylmethoxy |
| 2-[(cyclohexylcarbonyl)amino]-2-methylpropyl | propyl | (4-chlorobenzyl)oxy |
| 2-[(cyclohexylcarbonyl)amino]-2-methylpropyl | propyl | (4-fluorobenzyl)oxy |
| 2-[(cyclohexylcarbonyl)amino]-2-methylpropyl | propyl | 3-pyridin-3-ylpropoxy |
| 2-[(cyclohexylcarbonyl)amino]-2-methylpropyl | methoxymethyl | hydroxy |
| 2-[(cyclohexylcarbonyl)amino]-2-methylpropyl | methoxymethyl | pyridin-3-ylmethoxy |
| 2-[(cyclohexylcarbonyl)amino]-2-methylpropyl | methoxymethyl | (4-chlorobenzyl)oxy |
| 2-[(cyclohexylcarbonyl)amino]-2-methylpropyl | methoxymethyl | (4-fluorobenzyl)oxy |
| 2-[(cyclohexylcarbonyl)amino]-2-methylpropyl | methoxymethyl | 3-pyridin-3-ylpropoxy |
| 2-[(cyclohexylcarbonyl)amino]-2-methylpropyl | ethoxymethyl | hydroxy |
| 2-[(cyclohexylcarbonyl)amino]-2-methylpropyl | ethoxymethyl | pyridin-3-ylmethoxy |
| 2-[(cyclohexylcarbonyl)amino]-2-methylpropyl | ethoxymethyl | (4-chlorobenzyl)oxy |
| 2-[(cyclohexylcarbonyl)amino]-2-methylpropyl | ethoxymethyl | (4-fluorobenzyl)oxy |
| 2-[(cyclohexylcarbonyl)amino]-2-methylpropyl | ethoxymethyl | 3-pyridin-3-ylpropoxy |
| 2-[(cyclohexylcarbonyl)amino]-2-methylpropyl | 2-methoxyethyl | hydroxy |
| 2-[(cyclohexylcarbonyl)amino]-2-methylpropyl | 2-methoxyethyl | pyridin-3-ylmethoxy |
| 2-[(cyclohexylcarbonyl)amino]-2-methylpropyl | 2-methoxyethyl | (4-chlorobenzyl)oxy |
| 2-[(cyclohexylcarbonyl)amino]-2-methylpropyl | 2-methoxyethyl | (4-fluorobenzyl)oxy |
| 2-[(cyclohexylcarbonyl)amino]-2-methylpropyl | 2-methoxyethyl | 3-pyridin-3-ylpropoxy |
| 4-(1,1-dioxidoisothiazolidin-2-yl)butyl | ethyl | hydroxy |
| 4-(1,1-dioxidoisothiazolidin-2-yl)butyl | ethyl | pyridin-3-ylmethoxy |
| 4-(1,1-dioxidoisothiazolidin-2-yl)butyl | ethyl | (4-chlorobenzyl)oxy |
| 4-(1,1-dioxidoisothiazolidin-2-yl)butyl | ethyl | (4-fluorobenzyl)oxy |
| 4-(1,1-dioxidoisothiazolidin-2-yl)butyl | ethyl | 3-pyridin-3-ylpropoxy |

-continued

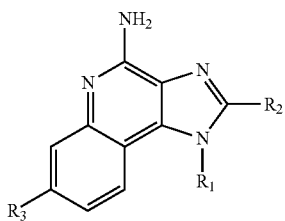

IV

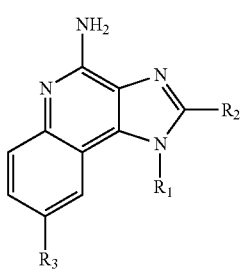

V

| R₁ | R₂ | R₃ |
|---|---|---|
| 4-(1,1-dioxidoisothiazolidin-2-yl)butyl | propyl | hydroxy |
| 4-(1,1-dioxidoisothiazolidin-2-yl)butyl | propyl | pyridin-3-ylmethoxy |
| 4-(1,1-dioxidoisothiazolidin-2-yl)butyl | propyl | (4-chlorobenzyl)oxy |
| 4-(1,1-dioxidoisothiazolidin-2-yl)buty | propyl | (4-fluorobenzyl)oxy |
| 4-(1,1-dioxidoisothiazolidin-2-yl)butyl | propyl | 3-pyridin-3-ylpropoxy |
| 4-(1,1-dioxidoisothiazolidin-2-yl)butyl | methoxymethyl | hydroxy |
| 4-(1,1-dioxidoisothiazolidin-2-yl)butyl | methoxymethyl | pyridin-3-ylmethoxy |
| 4-(1,1-dioxidoisothiazolidin-2-yl)butyl | methoxymethyl | (4-chlorobenzyl)oxy |
| 4-(1,1-dioxidoisothiazolidin-2-yl)butyl | methoxymethyl | (4-fluorobenzyl)oxy |
| 4-(1,1-dioxidoisothiazolidin-2-yl)butyl | methoxymethyl | 3-pyridin-3-ylpropoxy |
| 4-(1,1-dioxidoisothiazolidin-2-yl)butyl | ethoxymethyl | hydroxy |
| 4-(1,1-dioxidoisothiazolidin-2-yl)butyl | ethoxymethyl | pyridin-3-ylmethoxy |
| 4-(1,1-dioxidoisothiazolidin-2-yl)butyl | ethoxymethyl | (4-chlorobenzyl)oxy |
| 4-(1,1-dioxidoisothiazolidin-2-yl)butyl | ethoxymethyl | (4-fluorobenzyl)oxy |
| 4-(1,1-dioxidoisothiazolidin-2-yl)butyl | ethoxymethyl | 3-pyridin-3-ylpropoxy |
| 4-(1,1-dioxidoisothiazolidin-2-yl)butyl | 2-methoxyethyl | hydroxy |
| 4-(1,1-dioxidoisothiazolidin-2-yl)butyl | 2-methoxyethyl | pyridin-3-ylmethoxy |
| 4-(1,1-dioxidoisothiazolidin-2-yl)butyl | 2-methoxyethyl | (4-chlorobenzyl)oxy |
| 4-(1,1-dioxidoisothiazolidin-2-yl)butyl | 2-methoxyethyl | (4-fluorobenzyl)oxy |
| 4-(1,1-dioxidoisothiazolidin-2-yl)butyl | 2-methoxyethyl | 3-pyridin-3-ylpropoxy |

Compounds of the invention were found to induce cytokine biosynthesis when tested using the method described below.

Cytokine Induction in Human Cells

An in vitro human blood cell system is used to assess cytokine induction. Activity is based on the measurement of interferon (α) and tumor necrosis factor (α) (IFN and TNF, respectively) secreted into culture media as described by Testerman et. al. in "Cytokine Induction by the Immunomodulators Imiquimod and S-27609," *Journal of Leukocyte Biology*, 58, 365-372 (September, 1995).

Blood Cell Preparation for Culture

Whole blood from healthy human donors is collected by venipuncture into EDTA vacutainer tubes. Peripheral blood mononuclear cells (PBMC) are separated from whole blood by density gradient centrifugation using HISTOPAQUE-1077. Blood is diluted 1:1 with Dulbecco's Phosphate Buffered Saline (DPBS) or Hank's Balanced Salts Solution (HBSS). The PBMC layer is collected and washed twice with DPBS or HBSS and resuspended at $4 \times 10^6$ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 micromolar (μM).

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (30-0.014 μM). The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed with a sterile polypropylene pipet and transferred to sterile polypropylene tubes. Samples are maintained at −30° C. to −70° C. until analysis. The samples are analyzed for interferon (α) by ELISA and for tumor necrosis factor (α) by ELISA or IGEN Assay.

Interferon (α) and Tumor Necrosis Factor (α) Analysis by ELISA

Interferon (α) concentration is determined by ELISA using a Human Multi-Species kit from PBL Biomedical Laboratories, New Brunswick, N.J. Results are expressed in pg/mL.

Tumor necrosis factor (α) (TNF) concentration is determined using ELISA kits available from Biosource International, Camarillo, Calif. Alternately, the TNF concentration can be determined by ORIGEN M-Series Immunoassay and read on an IGEN M-8 analyzer from IGEN International, Gaithersburg, Md. The immunoassay uses a human TNF capture and detection antibody pair from Biosource International, Camarillo, Calif. Results are expressed in pg/mL.

Certain compounds of the invention may inhibit the production of TNF-α when tested using the method described below.

Cytokine Inhibition in Mouse Cells

The mouse macrophage cell line Raw 264.7 is used to assess the ability of compounds to inhibit tumor necrosis factor-α (TNF-α) production upon stimulation by lipopolysaccharide (LPS).

Single Concentration Assay:
Blood Cell Preparation for Culture

Raw cells (ATCC) are harvested by gentle scraping and then counted. The cell suspension is brought to $3 \times 10^5$ cells/mL in RPMI with 10% fetal bovine serum (FBS). Cell suspension (100 µL) is added to 96-well flat bottom sterile tissues culture plates (Becton Dickinson Labware, Lincoln Park, N.J.). The final concentration of cells is $3 \times 10^4$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 5 µM. LPS (Lipopolysaccharide from *Salmonella typhimurium*, Sigma-Aldrich) is diluted with colorless RPMI to the $EC_{70}$ concentration as measured by a dose response assay.

Incubation

A solution of test compound (1 µl) is added to each well. The plates are mixed on a microtiter plate shaker for 1 minute and then placed in an incubator. Twenty minutes later the solution of LPS (1 µL, $EC_{70}$ concentration~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

Dose Response Assay:
Blood Cell Preparation for Culture

Raw cells (ATCC) are harvested by gentle scraping and then counted. The cell suspension is brought to $4 \times 10^5$ cells/mL in RPMI with 10% FBS. Cell suspension (250 µL) is added to 48-well flat bottom sterile tissues culture plates (Costar, Cambridge, Mass.). The final concentration of cells is $1 \times 10^5$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 0.03, 0.1, 0.3, 1, 3, 5 and 10 µM. LPS (Lipopolysaccharide from *Salmonella typhimurium*, Sigma-Aldrich) is diluted with colorless RPMI to the $EC_{70}$ concentration as measured by dose response assay.

Incubation

A solution of test compound (200 µl) is added to each well. The plates are mixed on a microtiter plate shaker for 1 minute and then placed in an incubator. Twenty minutes later the solution of LPS (200 mL, $EC_{70}$ concentration~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-αconcentration is determined by ELISA using a mouse TNF-α kit (from Biosource International, Camarillo, Calif.). Results are expressed in pg/mL. TNF-α expression upon LPS stimulation alone is considered a 100% response.

The complete disclosures of the patents, patent documents, and publications cited herein are incorporated by reference in their entirety as if each were individually incorporated. The present invention has been described with reference to several embodiments thereof. The foregoing illustrative embodiments and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention is intended to be limited only by the claims that follow.

What is claimed is:

1. A compound of the formula (II):

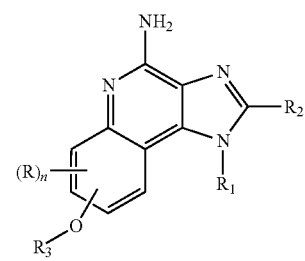

wherein:
R₃ is —Z—Ar,
Z is selected from the group consisting of a bond and alkylene;
Ar is phenyl which is unsubstituted or substituted by one or more substituents independently selected from the group consisting of alkyl, alkoxy, nitro, cyano, halogen, amino, alkylamino, dialkylamino, trifluoromethyl, and trifluoromethoxy;
R is selected from the group consisting of alkyl, alkoxy, hydroxy, halogen, and trifluoromethyl;
n is 0 or 1;
R₁ is —R₄,
R₂ is selected from the group consisting of hydrogen, alkyl, and alkoxyalkylenyl;
R₄ is independently selected from the group consisting of hydrogen, alkyl, alkenyl, alkynyl, aryl, arylalkylenyl, aryloxyalkylenyl, alkylarylenyl, heteroaryl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, and heterocyclyl groups can be unsubstituted or substituted by one or more substituents independently selected from the group consisting of acetyl, alkyl, alkoxy, alkylthio, alkylsulfonyl, alkanoyloxy, alkoxycarbonyl, hydroxyalkyl, haloalkyl, haloalkoxy, halogen, nitro, hydroxy, mercapto, cyano, formyl, aryl, aryloxy, arylthio, arylsulfonyl, arylalkyleneoxy, aroylamino, heteroaryl, heteroaryloxy, heteroarylalkyleneoxy, heterocyclyl, heterocyclylalkylenyl, amino, alkylamino, dialkylamino, (dialkylamino)alkyleneoxy, aminosulfonyl, and in the case of alkyl, alkenyl, alkynyl, and heterocyclyl, oxo;
or a pharmaceutically acceptable salt thereof.

2. The compound or salt of claim 1 wherein n is 0.

3. The compound or salt of claim 1 wherein Z is $C_{1-3}$ alkylene.

4. The compound or salt of claim 1 wherein Z is a bond.

5. The compound or salt of claim 1 wherein R₁ is hydroxyalkyl.

6. The compound or salt of claim 5 wherein R₁ is 2-hydroxy-2-methylpropyl.

7. The compound or salt of claim 1 wherein $R_1$ is alkyl.

8. The compound or salt of claim 1 wherein $R_1$ is alkyl substituted with one or more amino groups.

9. The compound or salt of claim 1 wherein $R_1$ is alkyl substituted with one or more alkylamino groups.

10. The compound or salt of claim 1 wherein $R_2$ is selected from the group consisting of hydrogen, methyl, ethyl, propyl, butyl, ethoxymethyl, methoxymethyl, 2-methoxyethyl, and methylaminocarbonylaminomethyl.

11. The compound or salt of claim 10 wherein $R_2$ is selected from the group consisting of ethyl, propyl, 2-methoxyethyl, ethoxymethyl, and methoxymethyl.

12. The compound or salt of claim 1 wherein Ar is phenyl which is unsubstituted or substituted by one or more amino groups.

13. The compound or salt of claim 1 wherein Ar is phenyl which is unsubstituted or substituted by one or more alkylamino groups.

14. The compound or salt of claim 1 wherein Ar is phenyl which is substituted by one or more amino groups.

15. The compound or salt of claim 1 wherein Ar is phenyl which is substituted by one or more alkylamino groups.

16. The compound of salt of claim 1, wherein $R_3$—O— is at the 7- or 8-position.

17. The compound of salt of claim 16, wherein $R_3$—O— is at the 7-position.

18. The compound of salt of claim 1, wherein the compound is 7-(3-aminobenzyloxy)-1-(2-methylpropyl)-2-propyl-1H-imidazo[4,5-c]quinolin-4-amine.

19. The compound of salt of claim 1, wherein the compound is 7-(3-aminobenzyloxy)-2-ethoxymethyl-1-(2-methylpropyl)-1H-imidazo[4,5-c]quinolin-4-amine.

20. The compound of salt of claim 1, wherein the compound is 2-ethoxymethyl-7-(3-ethylaminobenzyloxy)-1-(2-methylpropyl)-1H-imidazo[4,5-c]quinolin-4-amine.

21. The compound of salt of claim 1, wherein the compound is 7-(4-aminophenoxy)-1-(2-methylpropyl)-2-propyl-1H-imidazo[4,5-c]quinolin-4-amine.

22. The compound of salt of claim 1, wherein the compound is 7-(2-aminophenoxy)-1-(2-methylpropyl)-2-propyl-1H-imidazo[4,5-c]quinolin-4-amine.

23. The compound of salt of claim 1, wherein the compound is 7-(3-ethylaminophenoxy)-1-(2-methylpropyl)-2-propyl-1H-imidazo[4,5-c]quinolin-4-amine.

24. The compound of salt of claim 1, wherein the compound is 1-[4-amino-7-(3-aminobenzyloxy)-2-(2-methoxyethyl)-1H-imidazo [4,5-c]quinolin-1-yl]-2-methylpropan-2-ol.

25. The compound of salt of claim 1, wherein the compound is 1-{4-amino-7-[3-(3 -aminophenyl)propoxy]-2-ethoxymethyl-1H-imidazo[4,5-c]quinolin-1-yl}-2-methylpropan-2-ol.

26. The compound of salt of claim 1, wherein the compound is selected from the group consisting of 1-(4-aminobutyl)-8-benzyloxy-2-ethyl-1H-imidazo[4,5-c]quinolin-4-amine, 1-(4-aminobutyl)-8-benzyloxy-2-methyl-1H-imidazo[4,5-c]quinolin-4-amine, and 1-(4-aminobutyl)-8-benzyloxy-2-ethoxymethyl-1H-imidazo[4,5-c]quinolin-4-amine.

27. A pharmaceutical composition comprising a therapeutically effective amount of a compound or salt of claim 1 in combination with a pharmaceutically acceptable carrier.

* * * * *

UNITED STATES PATENT AND TRADEMARK OFFICE
CERTIFICATE OF CORRECTION

PATENT NO. : 8,263,594 B2  
APPLICATION NO. : 13/008453  
DATED : September 11, 2012  
INVENTOR(S) : Kyle J Lindstrom Page 1 of 8

It is certified that error appears in the above-identified patent and that said Letters Patent is hereby corrected as shown below:

Other Publications

<u>First Page - Column 2</u>  
Line 1, Delete "Permanganatet[1,2]."  
and insert -- Permanganate[1,2]. --, therefor.

Foreign Patent Documents

<u>Page 3 - Column 7</u>  
Line 1, Delete "WO 20050324846 4/2005"  
and insert -- WO 2005032484 4/2005 --, therefor.

Specification

<u>Column 4</u>  
Line 30, Delete "substitutents;"  
and insert -- substituents; --, therefor.

<u>Column 17</u>  
Line 61, Delete "substitutent."  
and insert -- substituent. --, therefor.

<u>Column 19</u>  
Line 17, Delete "—$R_5$;"  
and insert-- —$R_5$. --, therefor.

Signed and Sealed this  
Twenty-sixth Day of February, 2013

Teresa Stanek Rea  
*Acting Director of the United States Patent and Trademark Office*

Column 21

Lines 8-11, Delete "and —V—N⟨(CH₂)ₐ/(CH₂)_b⟩A,"

and insert -- —V—N⟨(CH₂)ₐ/(CH₂)_b⟩A , and --, therefor.

Column 23
Line 57, Delete "and or" and insert
-- and/or --, therefor.

Column 23
Line 62, Delete "TNF-a)."
and insert -- TNF-α). --, therefor.

Column 24
Lines 39-40, Delete "triethylamine The"
and insert -- triethylamine. The --, therefor.

Column 30
Lines 44-45, Delete "C₁—R₇C(O)Cl,"
and insert -- Cl—R₇C(O)Cl, --, therefor.

Column 41
Lines 26-27, Delete "histoplasmonsis,"
and insert -- histoplasmosis, --, therefor.

Lines 28-29, Delete "carnii pneumonia,"
and insert -- carinii pneumonia, --, therefor.

Line 33, Delete "Karposi's"
and insert -- Kaposi's --, therefor.

Line 35, Delete "myelogeous"
and insert -- myelogenous --, therefor.

Line 41, Delete "Ommen's"
and insert -- Omenn's --, therefor.

Column 41 Cont'd
Line 42, Delete "greata,"
and insert -- areata, --, therefor.

Column 42
Line 26, Delete "10 ng/kg"
and insert -- 10 μg/kg --, therefor.

Column 42
Line 32, Delete "10 ng/kg"
and insert -- 10 μg/kg --, therefor.

Column 47
Line 55, Delete "58.11 mmol)"
and insert -- 58.1 mmol) --, therefor.

Column 47
Line 57, Delete "$N^1$"
and insert -- $N^4$ --, therefor.

Column 64
Line 57, Delete "dichloromethane"
and insert -- dichloromethane. --, therefor.

Column 66
Line 1, Delete "minutes"
and insert -- minutes. --, therefor.

Column 74
Line 34, Delete "diamine"
and insert -- diamine. --, therefor.

Column 80
Line 29, Delete "tert-butyl {-4-[3"
and insert -- tert-butyl{4-[3 --, therefor.

Column 80
Line 46, Delete "tert-butyl {-4-[7"
and insert -- tert-butyl{4-[7 --, therefor.

Column 82
Line 52, Delete "amino}-1-2"
and insert -- amino}-2 --, therefor.

Column 82 Cont'd
Line 55, Delete "amino}-1-2"
and insert -- amino}-2 --, therefor.

Column 89
Line 32, Delete "δ53.6,"
and insert -- δ 153.6, --, therefor.

Column 94
Line 45, Delete "δ7.59"
and insert -- δ 7.59 --, therefor.

Column 94
Line 51, Delete "δ53.4,"
and insert -- δ 153.4, --, therefor.

Column 100
Line 14, Delete "dissolve Ammonium"
and insert -- dissolve. Ammonium --, therefor.

Column 105
Line 16, Delete "-N-phenylurea"
and insert -- -N'-phenylurea --, therefor.

Column 113
Line 27, Delete "butyl} methanesulfonamide"
and insert -- butyl}methanesulfonamide --, therefor.

Column 126
Line 53, Delete "tetraazolo"
and insert -- tetrazolo --, therefor.

Column 126
Line 56, Delete "tetraazolo"
and insert -- tetrazolo --, therefor.

Column 126
Line 62, Delete "nitrotetraazolo"
and insert -- nitrotetrazolo --, therefor.

Column 127
Line 1, Delete "nitrotetraazolo"
and insert -- nitrotetrazolo --, therefor.

Line 15, Delete "nitrotetraazolo"
and insert -- nitrotetrazolo --, therefor.

Line 18, Delete "nitrotetraazolo"
and insert -- nitrotetrazolo --, therefor.

Line 28, Delete "tetraazolo"
and insert -- tetrazolo --, therefor.

Lines 33-34, Delete "tetraazolo"
and insert -- tetrazolo --, therefor.

Line 45, Delete "tetraazolo"
and insert -- tetrazolo --, therefor.

Line 52, Delete "tetraazolo"
and insert -- tetrazolo --, therefor.

Line 64, Delete "tetraazolo"
and insert -- tetrazolo --, therefor.

Column 128
Line 3, Delete "tetraazolo"
and insert -- tetrazolo --, therefor.

Line 3, Delete "[1,5-c]"
and insert -- [1,5-a] --, therefor.

Line 18, Delete "tetraazolo"
and insert -- tetrazolo --, therefor.

Line 22, Delete "tetraazolo"
and insert -- tetrazolo --, therefor.

Line 23, Delete "triphenyphosphine"
and insert -- triphenylphosphine --, therefor.

Line 63, Delete "tetraazolo"
and insert -- tetrazolo --, therefor.

Column 128 Cont'd
Line 63, Delete "[1,5-c]"
and insert -- [1,5-a] --, therefor.

Column 129
Line 5, Delete "tetraazolo"
and insert -- tetrazolo --, therefor.

Column 129
Line 5, Delete "[1,5-c]"
and insert -- [1,5-a] --, therefor.

Column 129
Line 10, Delete "tetraazolo"
and insert -- tetrazolo --, therefor.

Column 144
Line 33, Delete "4-amine,"
and insert -- 4-amine. --, therefor.

Column 146
Line 49, Delete "triphenyphosphine"
and insert -- triphenylphosphine --, therefor.

Column 157
Line 42, Delete "benzyoxy"
and insert -- benzyloxy --, therefor.

Column 165
Line 51, Delete "1 hour Ammonium"
and insert -- 1 hour. Ammonium --, therefor.

Column 177
Lines 6-7, Delete "one hour Ammonium"
and insert -- one hour. Ammonium --, therefor.

Line 39, Delete "2-[4-amino"
and insert -- 2-{4-amino --, therefor.

Line 39, Delete "2-[3-methylureido)"
and insert -- 2-[(3-methylureido) --, therefor.

Line 40, Delete "1-yl]"
and insert -- 1-yl} --, therefor.

CERTIFICATE OF CORRECTION (continued)

Column 177 Cont'd
Line 48, Delete "1-1-{[4-amino"
and insert -- 1-{[4-amino --, therefor.

Lines 64-65, Delete "Column."
and insert -- Column: --, therefor.

Column 178
Line 39, Delete "Butryl"
and insert -- Butyryl --, therefor.

Column 185
Line 61, Delete "ylmethylamine"
and insert -- ylmethylamine. --, therefor.

Column 193
Line 31, Delete "2-yl)buty"
and insert -- 2-yl)butyl --, therefor.

Column 195
Line 16, Delete "(Lipopolysaccaride"
and insert -- (Lipopolysaccharide --, therefor Line 49, Delete "(Lipopolysaccaride"
and insert -- (Lipopolysaccharide --, therefor.

Line 56, Delete "(200 mL,"
and insert -- (200 μL, --, therefor.

Line 62, Delete "TNF-αconcentration"
and insert -- TNF-α concentration --, therefor.

Claims

Column 197
Line 23, In Claim 16, delete "of salt"
and insert -- or salt --, therefor.

Line 25, In Claim 17, delete "of salt"
and insert -- or salt --, therefor.

Line 27, In Claim 18, delete "of salt"
and insert -- or salt --, therefor.

Column 197 Cont'd
Line 30, In Claim 19, delete "of salt"
and insert -- or salt --, therefor.

Column 198
Line 1, In Claim 20, delete "of salt"
and insert -- or salt --, therefor.

Line 4, In Claim 21, delete "of salt"
and insert -- or salt --, therefor.

Line 7, In Claim 22, delete "of salt"
and insert -- or salt --, therefor.

Line 10, In Claim 23, delete "of salt"
and insert -- or salt --, therefor.

Line 13, In Claim 24, delete "of salt"
and insert -- or salt --, therefor.

Line 15, In Claim 24, delete "imidazo [4,5-c]"
and insert -- imidazo[4,5-c] --, therefor.

Line 17, In Claim 25, delete "of salt"
and insert -- or salt --, therefor.

Line 21, In Claim 26, delete "of salt"
and insert -- or salt --, therefor.